United States Patent [19]

Magnin et al.

[11] Patent Number: 5,567,841

[45] Date of Patent: Oct. 22, 1996

[54] α-PHOSPHONOSULFONATE SQUALENE SYNTHETASE INHIBITORS AND METHOD

[75] Inventors: David R. Magnin, Hamilton; Scott A. Biller, Ewing; John K. Dickson, Jr., Mount Holly, all of N.J.; R. Michael Lawrence, Yardley, Pa.; Richard B. Sulsky, Franklin Park, N.J.

[73] Assignee: Bristol-Myers Squibb Company, Princeton, N.J.

[21] Appl. No.: 464,226

[22] Filed: Jun. 5, 1995

Related U.S. Application Data

[62] Division of Ser. No. 266,843, Jul. 5, 1994, Pat. No. 5,470,845, which is a division of Ser. No. 104,762, Aug. 20, 1993, abandoned, which is a continuation-in-part of Ser. No. 967,904, Oct. 28, 1992, abandoned.

[51] Int. Cl.$^6$ ........................................ C07F 9/38
[52] U.S. Cl. ................... 562/23; 544/232; 544/243; 544/244; 546/22; 546/23; 548/112; 548/113; 549/218; 549/220
[58] Field of Search ................................. 562/23

[56] References Cited

U.S. PATENT DOCUMENTS

| | | |
|---|---|---|
| 2,965,665 | 12/1960 | Gaertner et al. . |
| 3,595,880 | 7/1971 | Firestone . |
| 3,657,282 | 4/1972 | Christensen et al. . |
| 4,032,521 | 6/1977 | Christensen et al. . |
| 4,254,215 | 3/1981 | Kramp et al. . |
| 4,696,693 | 9/1987 | Swerdloff et al. . |
| 4,795,815 | 1/1989 | Ternansky . |
| 5,011,938 | 4/1991 | Barnett et al. . |

FOREIGN PATENT DOCUMENTS

| | | |
|---|---|---|
| 890344980 | 12/1989 | European Pat. Off. . |
| 0344979A2 | 12/1989 | European Pat. Off. . |
| 3739691A1 | 6/1989 | Germany . |
| WO88/00061 | 1/1988 | WIPO . |
| WO90/07513 | 7/1990 | WIPO . |
| 9324495 | 12/1993 | WIPO . |

OTHER PUBLICATIONS

Burton, D. J., J. Am. Chem. Soc. 1989, 111, 1773–1776.
Su, D. et al, Can. J. Chem. 1989, 67, 1795–1799.
Farrington, G. K., et al, J. Med. Chem. 1985, 28, 1668–1673.
Musicki, B. et al, T. S. Tetrahedron Lett. 1991, 32, 1267–1270.
Carretero, J. C. et al, Tetrahedron 1987, 43, 5125–5134.
Callahan, L. et al, Analytical Biochemistry 1989, 177, 67–71.
Amin, Dilip et al, "Bisphosphonates used for the treatment of bone disorders inhibit squalene synthase and cholesterol biosynthesis", Journal of Lipid Research, vol. 33, 1993, pp. 1657–1663.

*Primary Examiner*—Johann Richter
*Assistant Examiner*—Michael G. Ambrose
*Attorney, Agent, or Firm*—Burton Rodney

[57] ABSTRACT

α-Phosphonosulfonate compounds are provided which inhibit the enzyme squalene synthetase and thereby inhibit cholesterol biosynthesis. These compounds have the formula

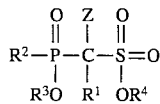

wherein $R^2$ is $OR^5$ or $R^{5a}$; $R^3$ and $R^5$ are independently H, alkyl, arylalkyl, aryl or cycloalkyl; $R^{5a}$ is H, alkyl, arylalkyl or aryl; $R^4$ is H, alkyl, aryl, arylalkyl, or cycloalkyl;, Z is H, halogen, lower alkyl or lower alkenyl; and $R^1$ is a lipophilic group which contains at least 7 carbons and is alkyl, alkenyl, alkynyl, mixed alkenyl-alkynyl, aryl, arylalkyl, cycloalkyl, cycloalkylalkyl, heteroaryl, heteroarylalkyl, cycloheteroalkyl, cycloheteroalkylalkyl; as further defined above; including pharmaceutically acceptable salts and or prodrug esters of the phosphonic (phosphinic) and/or sulfonic acids.

11 Claims, No Drawings

α-PHOSPHONOSULFONATE SQUALENE SYNTHETASE INHIBITORS AND METHOD

REFERENCE TO OTHER APPLICATIONS

This is a division of application Ser. No. 266,843, filed Jul. 5, 1994, now U.S. Pat. No. 5,470,845 which is a division of application Ser. No. 109,762, filed Aug. 20, 1993, now abandoned, which is a continuation-in-part of application Ser. No. 967,904, filed Oct. 28, 1992, now abandoned.

FIELD OF THE INVENTION

The present invention relates to new α-phosphonosulfonate compounds which are useful in inhibiting cholesterol biosynthesis by inhibiting de novo squalene production, to hypocholesterolemic and antiatherosclerotic compositions containing such compounds and to a method of using such compounds for inhibiting cholesterol biosynthesis and atherosclerosis.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413–441, J. Wiley and Sons, 1981, and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase along with HMG-CoA reductase have been shown to be down-regulated by receptor mediated LDL uptake (Faust, J. R.; Goldstein, J. L.; Brown, M. S. *Proc. Nat. Acad. Sci. U.S.A.* 1979, 76, 5018–5022), lending credence to the proposal that, inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

U.S. Pat. No. 3,657,282 (Merck) (Division U.S. Pat. No. 3,822,296) discloses antibiotics of the structure

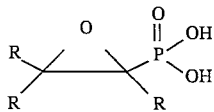

wherein R=$SO_3H$, $SO_2R^*$, H, hydrocarbyl other than alkyl (eg. alkenyl, alkynyl, phenyl and naphthyl), substituted hydrocarbyl, $CO_2H$, $CO_2R^*$, $SO_3NR_2$, heterocycle*, amino*, OH, OR, SH, SR, CHO, halogen $NO_2$, CN, $PO_3H_2$, $AsO_3H_2$, acyl, —$CHR^1R^3$ where $R^1$=H, Me; $R^3$=R as above, preferably at least one R not =H, R preferably contains 1–10 carbons. *=optionally substituted.

Starting materials employed to prepare the above antibiotics include

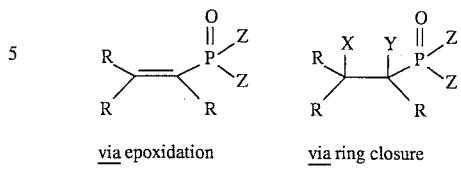

via epoxidation     via ring closure wherein R can be $SO_3H$, and X and Y are hydroxy or functional equivalent precursor to epoxide: eg. OH, halo, azide, $RCO_2$—, $RSO_2O$—, $R_2S^+$—, $R_3N^+$—, ArO—, $R_2PO_2$—, $RSO_2NR^1$—. One of X and Y must be an oxygen radical.

EP 89/0-344-980 (Smith Kline) discloses α-antagonists of the structure

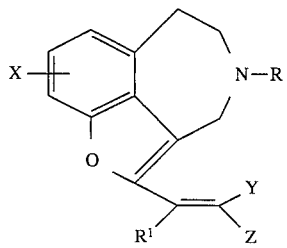

wherein Y or Z may be —$SO_2R$, —$P(R)O(OR)$, —$PR_2O$, —$PO(OR)_2$, and amides.

WO 88/00061 (Amersham) discloses Technetium-99 complexes for bone scanning having the structure

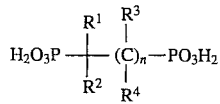

wherein $R^1$ and $R^3$=H, $SO_3H$ or alkyl substituted with $SO_3H$ and optionally one or more heteroatoms; $R^4$ can also be $SO_3H$ or OH, $NH_2$, NHMe, $NMe_2$, lower alkyl substituted with a polar group;

$R^2$=same as $R^4$ except not $SO_3H$ and n=0, 1.

U.S. Pat. No. 4,032,521 (Merck) discloses inter-mediates, in cephalosporin synthesis, of the structures

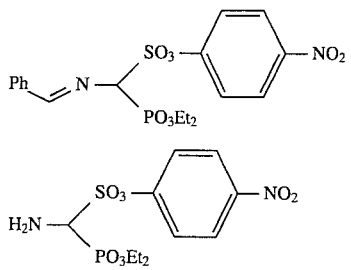

WO 90/07513 (Gas Research Institute) discloses electrolytes for fuel cells of the structure

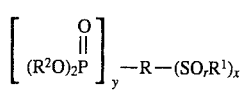

wherein

R=organic radicals with 1 or more F atoms;

$R^1$=H, alkali metal, Zn, Cd;

$R^2$=H, lower alkyl;

r=2, 3; and x, y=1, 2, 3.

U.S. Pat. No. 4,254,215 (Ciba Geigy AG) discloses a process for photographic developers wherein one component of a developer solution is:

HS—D—(W)$_n$ wherein n=1 to 4.

D=optionally substituted, saturated or unsaturated aliphatic radical (<40 carbons), can be interrupted by heteroatoms such as O, SO$_2$, NH, NR.

W=PO$_3$R$_2$, SO$_3$R, SO$_2$R, —NY—SO$_3$R, —SO$_2$NR$_2$, —SSO$_3$R, CO$_2$R, OH, NR$_3^+$, NR$_2$, CONR$_2$.

DE 89/3739691-A (Hoechst) (Derwent #89-173507/24) discloses herbicides and plant growth regulators of the structure wherein

Y=CH, N; X=O, S; Z=CH, N;

$R^1$, $R^2$=C1–C6 alkyl or alkoxy;

$R^3$=H, C1–C6 alkyl or alkoxy, C2–C6 alkenyl, alkynyl, alkenyloxy, alkynyloxy; all optionally substituted with one or more halogens; and $R^4$=H, C1–C4 alkyl or physiologically acceptable cation. New intermediates are disclosed of the structures Burton, D. J., J. Am. Chem. Soc. 1989, 111, 1773–1776 discloses electrolytes and chelators of the structures (HO)$_2$P(O)CF$_2$SO$_3$Na  (HO)$_2$P(O)CF$_2$SO$_3$H Su, D.; Cen. W.; Kirchmeier, R. L.; Shreeve, J. M., Can. J. Chem. 1989, 67, 1795–1799, disclose electrolytes and chelators of the structures (C$_2$H$_5$O)$_2$P(O)CFBrSO$_3$Na   (C$_2$H$_5$O)$_2$P(O)CFHSO$_3$Na (HO$_2$P(O)CFHSO$_3$Na   (HO)$_2$P(O)CFHSO$_3$H (C$_2$H$_5$O)$_2$P(O)CF(SO$_3$Na)(SO$_2$Na)

(C$_2$H$_5$O)$_2$P(O)CF(SO$_3$Na)$_2$

Farrington, G. K.; Kumar, A.; Wedler, F. C., J. Med. Chem. 1985, 28, 1668–1673 discloses compound 10 as an inhibitor of aspartate transcarbamylase. Compound 24 is a synthetic intermediate.

Musicki, B.; Widlanski, T. S. Tetrahedron Lett.1991, 32, 1267–1270 discloses compound 4 as a synthetic intermediate.

Carretero, J. C.; Demillequand, M.; Ghosez, L., Tetrahedron 1987, 43, 5125–5134 discloses (EtO)$_2$P(O)—CH$_2$SO$_3$X 1a X = Et
1b X = i-Pr
2a X = Li
2b X = n-Bu$_4$N for use in the synthesis of vinyl phosphonates via a Horner-Emmons reaction.

Callahan, L.; Ng, K.; Geller, D. H.; Agarwal, K.; Schwartz, N. B., Analytical Biochemistry 1989, 177, 67–71 discloses an analog of ADP (adenosine diphosphate) of the structure

DESCRIPTION OF THE INVENTION

In accordance with the present invention, there is provided α-phosphonosulfonate compounds which inhibit cholesterol biosynthesis, and thus are useful as hypocholesterolemic and antiatherosclerotic agents and have the following structure I.

I.  $R^2$—P(=O)(OR$^3$)—C(R$^1$)(Z)—S(=O)(=O)—OR$^4$ wherein $R^2$ is OR$^5$ or R$^{5a}$, $R^3$ and $R^5$ are the same or different and are H, alkyl, arylalkyl, aryl, cycloalkyl, a metal ion or other pharmaceutically acceptable cations as defined below, or a prodrug ester;

$R^{5a}$ is H, alkyl, arylalkyl or aryl;

$R^4$ is H, alkyl, cycloalkyl, aryl, arylalkyl, metal ion or other pharmaceutically acceptable cations as defined below, or a prodrug ester;

Z is H, halogen, lower alkyl or lower alkenyl;

$R^1$ a lipophilic group containing at least 7 carbons and is alkyl containing 7 to 25 carbons in the chain; alkenyl containing from 7 to 25 carbon atoms in the chain and from 1 to 6 double bonds; alkynyl containing 1 to 6 triple bonds; mixed alkenyl-alkynyl containing 1 to 5 double bonds and 1 to 5 triple bonds; and where in the above groups alkenyl and/or alkynyl may be substituted or unsubstituted; cycloalkyl; cycloheteroalkyl linked through a carbon on the ring or a heteroatom; aryl; heteroaryl; heteroarylalkyl; cycloalkylalkyl; cycloheteroalkylalkyl; or a group of the structure

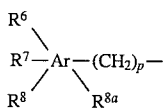

wherein Ar is aryl (such as phenyl or naphthyl), heteroaryl (5 or 6 membered) and may include one to three additional rings fused to Ar (such as aryl, cycloalkyl, heteroaryl or cycloheteroalkyl) and wherein $(CH_2)_p$ contains from 1 to 15 carbons, preferably 2 to 12 carbons, in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, preferably from 3 to 25 carbons, alkoxy containing 1 to 40 carbons, preferably from 3 to 25 carbons, alkenyl containing 2 to 40 carbons, preferably from 3 to 25 carbons, alkenyloxy containing 2 to 40 carbons, preferably from 3 to 25 carbons, alkynyl containing 2 to 40 carbons, preferably from 3 to 25 carbons, alkynyloxy containing 2 to 40 carbons, preferably from 3 to 25 carbons, cycloheteroalkyl, cycloheteroalkylalkyl, heteroaryl, cycloalkyl, cycloalkylalkyl, Ar-alkyl, (such as arylalkyl), ArO (such as aryloxy), Ar-amino (such as arylamino), hydroxy, halogen, nitro, Ar (such as aryl), amino, substituted amino wherein the amino includes 1 or 2 substituents (which are alkyl, alkenyl, aryl or any of the Ar groups mentioned above), thiol, alkylthio, Ar-thio (such as arylthio), alkylsulfinyl, Ar-sulfinyl (such as arylsulfinyl), alkylsulfonyl, Ar-sulfonyl (such as arylsulfonyl), carboxy, cyano, alkoxycarbonyl, aminocarbonyl, alkylcarbonyloxy, Ar-carbonyloxy (such as arylcarbonyloxy), Ar-carbonylamino (such as arylcarbonylamino) or alkylcarbonylamino, as well as any of the Ar groups as defined above, and preferably wherein the total number of carbons in the substituted $Ar-(CH_2)_p-$ group exceeds 10 carbons; including pharmaceutically acceptable salts thereof such as alkali metal salts such as lithium, sodium or potassium, alkaline earth metal salts such as calcium or magnesium, as well as zinc or aluminum and other FDA approved cations such as ammonium, choline, diethanolamine, ethylenediamine, and salts of naturally occuring amino acids such as arginine, lysine, alanine and the like.

The $(CH_2)_p$ group may contain 1, 2, 3 or more alkyl, alkoxy, alkenyl, alkynyl, hydroxy and/or halogen substituents as well as any of the substituents defined for $R^6$.

Thus, the compounds of the invention include the following sub-genuses:

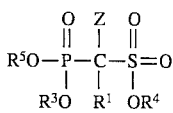

IA

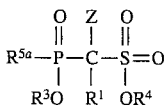

IB

The term "prodrug esters" as employed herein includes prodrug esters which are known in the art for both phosphorus and carboxylic acids. Examples include the following groups: (1-alkanoyloxy)alkyl such as,

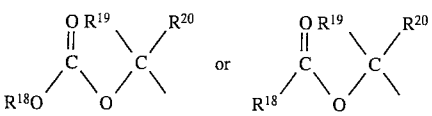

wherein $R^{18}$, $R^{19}$ and $R^{20}$ are H, alkyl, aryl or arylalkyl; however $R^{18}O$ cannot be HO. Examples of such prodrug esters include $CH_3CO_2CH_2-$,

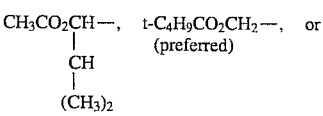

Other examples of suitable prodrug esters include

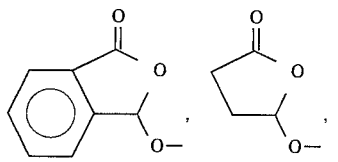

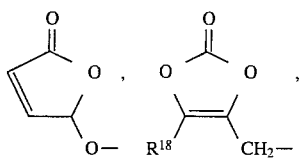

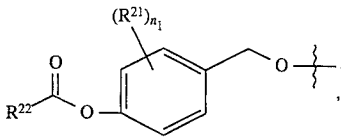

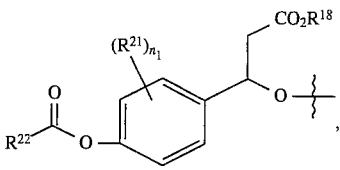

wherein $R^{18}$ can be H, alkyl (such as methyl or t-butyl), arylalkyl (such as benzyl) or aryl (such as phenyl); $R^{21}$ is H, alkyl, halogen or alkoxy, $R^{22}$ is alkyl, aryl, arylalkyl or alkoxyl, and $n_1$ is 0, 1 or 2; or $R^3$ and $R^5$ can be linked together as in

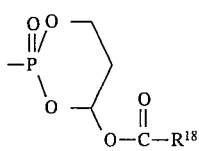

or

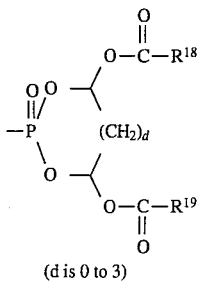

(d is 0 to 3)

Unless otherwise indicated, the term "lower alkyl" or "alkyl" as employed herein alone or as part of another group includes both straight and branched chain hydrocarbons, containing 1 to 40 carbons, preferably 1 to 20 carbons, in the normal chain, more preferably 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as F, Br, Cl or I or $CF_3$, alkoxy, aryl, arylalkyl, alkenyl, cycloalkyl, amino, hydroxy, alkylamido, alkanoylamino, arylcarbonylamino, nitro, cyano, thiol and/or alkylthio, as well as any of the other substituents as defined for $R^6$.

Unless otherwise indicated, the term "cycloalkyl" as employed herein alone or as part of another group includes saturated or partially unsaturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, cyclohexenyl, any of which groups may be substituted with 1 to 4 substituents such as halogen, alkyl, alkoxy, hydroxy, aryl, arylalkyl, cycloalkyl, alkylamido, alkanoylamino, arylcarbonylamino, amino, nitro, cyano, thiol and/or alkylthio, as well as any of the other substituents as defined for $R^6$.

Unless otherwise indicated, the term "aryl" as employed herein refers to monocyclic or bicyclic aromatic groups containing from 6 to 10 carbons in the ring portion, such as phenyl, naphthyl, or phenyl or naphthyl substituted with 1 to 4 substituents such as alkyl, halogen (Cl, Br or F), alkoxy, hydroxy, amino, alkanoylamino, arylcarbonylamino, aryl, arylalkyl, cycloalkyl, alkylamido, nitro, cyano, thiol and/or alkylthio, as well as any of the other substituents as defined for $R^6$.

The term "aralkyl", "aryl-alkyl" or "aryl-lower alkyl" as used herein alone or as part of another group refers to alkyl groups as discussed above having an aryl substituent, such as benzyl or phenethyl, or naphthylpropyl.

The term "lower alkoxy", "alkoxy", "aryloxy" or "aralkoxy" as employed herein alone or as part of another group includes any of the above alkyl, aralkyl or aryl groups linked to an oxygen atom.

The term "lower alkylthio", "alkylthio", "arylthio" or "aralkylthio" as employed herein, alone or as part of another group includes any of the above alkyl, alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 40 carbons, preferably 3 to 30 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkylamido, arylcarbonylamino, nitro, cyano, thiol and/or alkylthio, as well as any of the other substituents as defined for $R^6$.

Unless otherwise indicated, the term "lower alkynyl" or "alkynyl" as used herein by itself or as part of another group refers to straight or branched chain radicals of 2 to 40 carbons, preferably 2 to 20 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkylamido, arylcarbonylamino, nitro, cyano, thiol, and/or alkylthio, as well as any of the other substituents as defined for $R^6$.

Examples of suitable $(CH_2)_p$ groups include

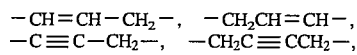

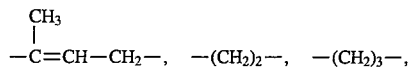

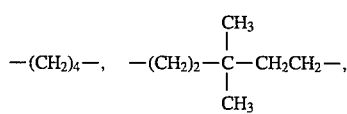

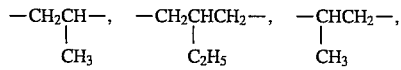

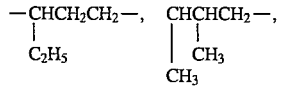

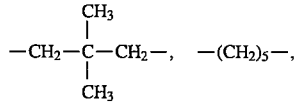

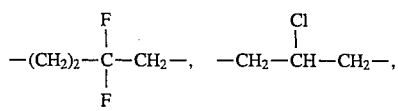

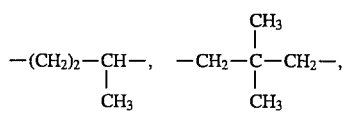

-continued

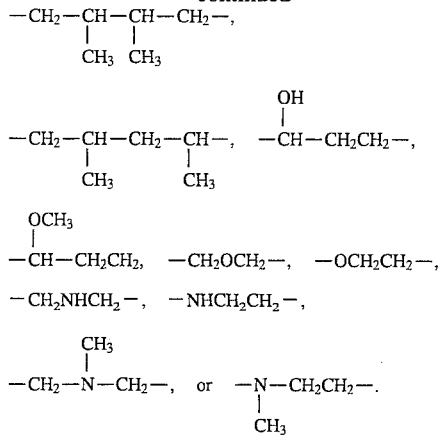

The term "halogen" or "halo" as used herein refers to chlorine, bromine, fluorine, and iodine as well as $CF_3$, with chlorine or fluorine being preferred.

The term "amino" as used herein refers to unsubstituted amino as well as monosubstituted amino or disubstituted amino wherein the substituents may be alkyl and/or aryl.

The term "metal ion" refers to alkali metal ions such as sodium, potassium or lithium and alkaline earth metal ions such as magnesium and calcium, as well as zinc and aluminum.

The term "cycloheteroalkyl" as used herein as an $R^1$ substituent refers to a 5-, 6- or 7-membered saturated ring which includes 1 to 2 hetero atoms such as nitrogen, oxygen and/or sulfur, linked to the carbon "C" of

through a carbon atom or a heteroatom, where possible, optionally via the linker $(CH_2)_p$ (which is defined above), such as

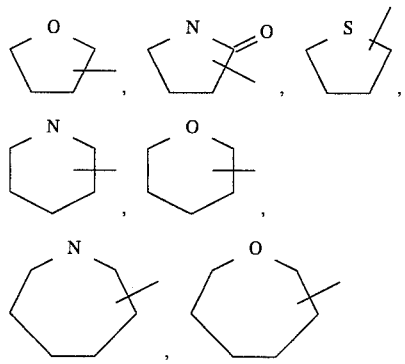

and the like. The above groups may include 1 to 3 substituents such as any of the $R^6$ groups as defined above. In addition, any of the above rings can be fused to a cycloalkyl, aryl, heteroaryl or cycloheteroalkyl ring.

The term "heteroaryl" as an $R^1$ substituent refers to a 5- or 6- membered aromatic ring which includes 1, 2, 3 or 4 hetero atoms such as nitrogen, oxygen or sulfur, which is linked to the carbon "C" of

through a carbon atom or a heteroatom, where possible, optionally via the linker $(CH_2)_p$ (which is defined above), such as

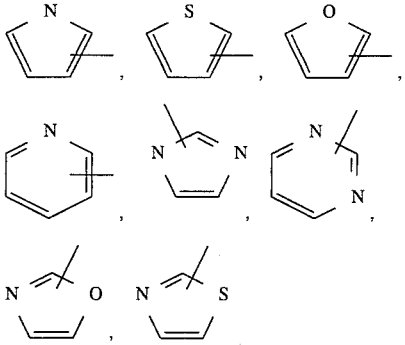

and the like. The above groups may include 1 to 3 substituents such as any of the $R^6$ groups as defined above. In addition, any of the above rings can be fused to a cycloalkyl, aryl, heteroaryl or cycloheteroalkyl ring.

The term cycloheteroalkylalkyl" as defined by $R^1$ refers to cycloheteroalkyl groups as defined above linked through a C atom or heteroatom to the "C" of

group through a $(CH_2)_p$ chain wherein p is preferably 1 to 8.

The term "heteroarylalkyl" as defined by $R^1$ refers to a heteroaryl group as defined above linked through a C atom or heteroatom to the

through a —$(CH_2)_p$— chain as defined above, where p is preferably 1 to 8.

Preferred are compounds of formula I and IA wherein $R^2$ is $OR^5$ and $R^5$ is a metal ion such as Na or K, or H or a pharmaceutically acceptable salt or more preferably a prodrug ester;

$R^3$ is H, a metal ion such as Na or K;

$R^4$ is a metal ion such as Na or K;

$R^1$ is alkenyl such as

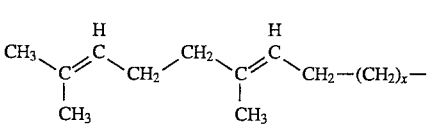

wherein $(CH_2)_x$ is defined as $(CH_2)_p$ above and x is preferably 2 to 8,

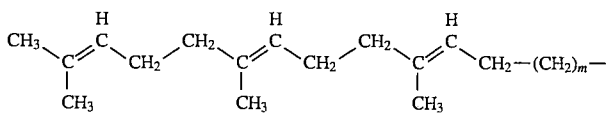

m is 1 to 5;

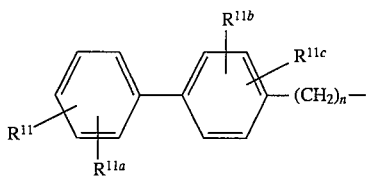

n=1 to 15;
$R^{11}$, $R^{11a}$, $R^{11b}$, and $R^{11c}$ are independently selected from H, alkyl such as propyl, alkoxy, such as methoxy or propyloxy, alkenyl such as

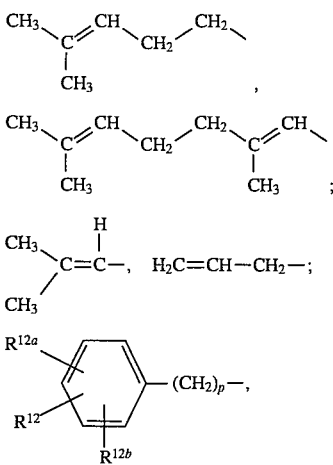

wherein $R^{12}$, $R^{12a}$ and $R^{12b}$ are independently selected from H, aryl (such as phenyl or naphthyl), alkylphenyl (such as p-propylphenyl, p-pentylphenyl), alkyl containing 1 to 20 carbons (such as p-heptyl), halo, alkoxy (such as methoxy or propyloxy), alkenyl (such as

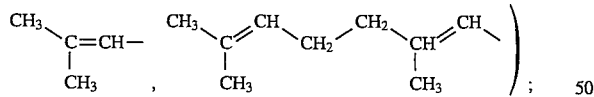

arylalkyloxy (such as phenethyloxy), alkenyloxy (such as

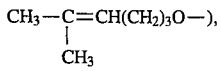

aryloxy (such as phenoxy), phenylalkyl (such as benzyl, phenylpropyl), alkylphenoxy (such as orthobutylphenoxy), alkenylphenyl (such as

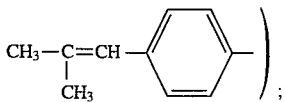

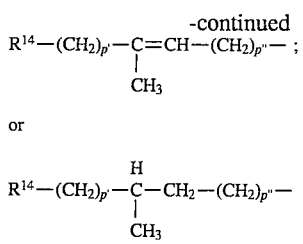

wherein $R^{14}$ is aryl, heteroaryl, aryloxy, heteroaryloxy, cycloalkyl, heterocycloalkyl, and $(CH_2)_{p'}$ and $(CH_2)_{p''}$ are as defined above for $-(CH_2)_p-$. Preferred p' and p" are independently 1 to 4;

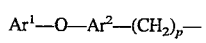

wherein $Ar^1$ and $Ar^2$ are independently selected from any of the Ar groups defined hereinbefore, and $(CH_2)_p$ is as defined hereinbefore.

The compounds of the invention may be prepared according to the following reaction sequences.

Schemes I, IA and II
General Schemes for the Preparation of α-Phosphonosulfonates
Scheme I

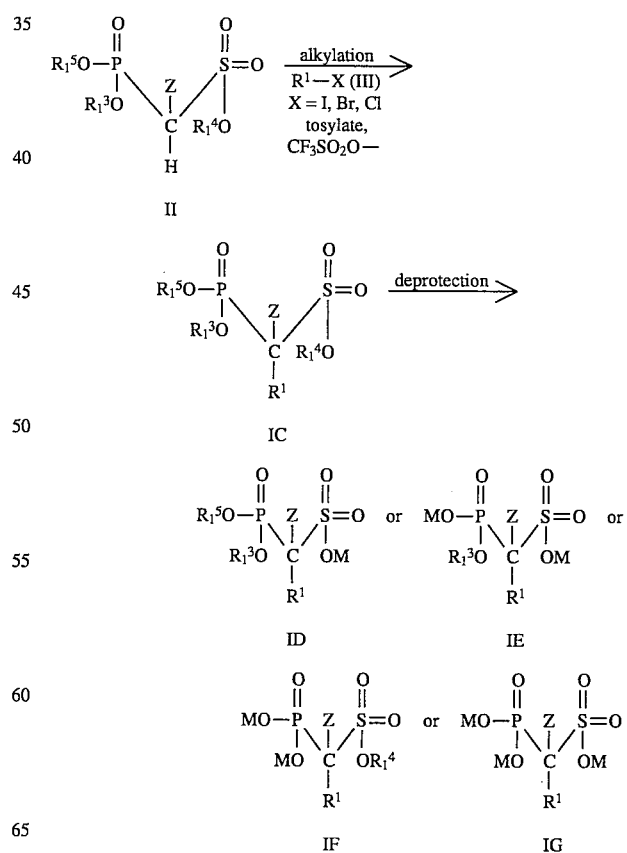

-continued
Schemes I, IA and II
General Schemes for the Preparation of α-Phosphonosulfonates
Scheme I ($R_1^3$, $R_1^4$, $R_1^5$ are independently alkyl, aryl, arylalkyl or cycloalkyl)
m = H, metal ion, or other pharmaceutically acceptable cation.

Scheme IA
Preparation of Starting Phosphonosulfonate II

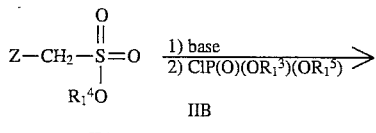
IIA

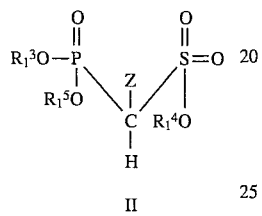
II

Procedure employed is similar to that described by Carretero, J. C.; Demillequand, M.; Ghosez, L., Tetrahedron, Vol. 43, 1987, pp 5125–5134.

Scheme II

Alternatively, Z can be added after $R^1$ (where Z = lower alkyl or halogen).

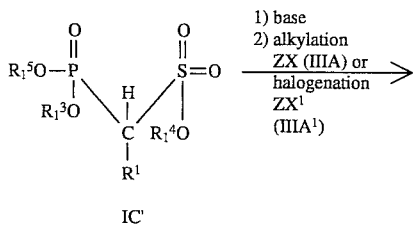
IC'

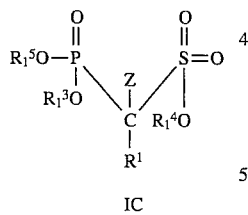
IC

Scheme III
Alkylation Reaction of Electrophiles III with Phosphonosulfonates II to Yield Triesters IC

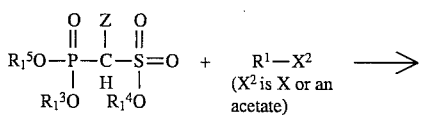

-continued
Scheme III
Alkylation Reaction of Electrophiles III with Phosphonosulfonates II to Yield Triesters IC

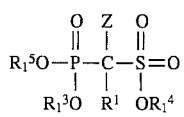
IC

Part A. II + $R^1X$ $\xrightarrow[\text{DMF}]{\text{NaH}}$ IC

Part B. II + $R^6-CH=CH-CH_2OCCH_3$ (with O double bond on C) $\xrightarrow[\text{THF}]{\text{Pd}^\circ, \text{Base}}$ (allylic acetate-Type 1)

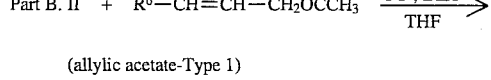
IC' or

Part C. II + 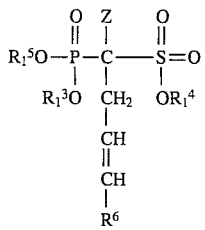 $\xrightarrow[\text{THF}]{\text{Pd}^\circ, \text{base}}$ IC'

(allylic acetate - Type 2)

Part D. IC' $\xrightarrow{\text{Hydrogenation}}$ 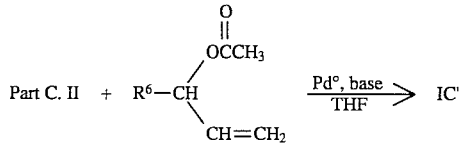
IC²

(where $R^1$ is $R^6-CH=CH-CH_2-$)

Scheme IV
Preparation of (Dialkoxyphosphinyl)-methanesulfonic Monoacid Salts A. 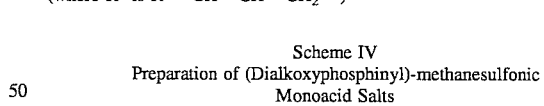 + R'I $\xrightarrow[\text{DMF}]{\text{Base}}$

II       IIIA

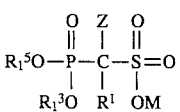
ID ($R_1^4$ = ethyl or other 1°alkyl)   M = K, Na

-continued
Scheme IV
Preparation of (Dialkoxyphosphinyl)-methanesulfonic Monoacid Salts B. 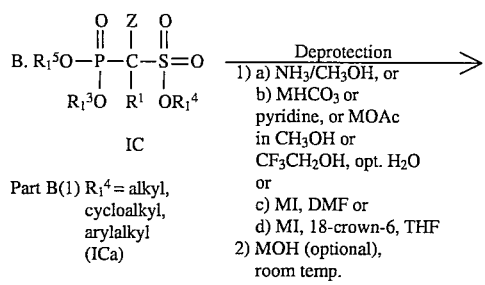

Part B(1) $R_1^4$ = alkyl, cycloalkyl, arylalkyl (ICa)

Deprotection
1) a) $NH_3/CH_3OH$, or
   b) $MHCO_3$ or pyridine, or MOAc in $CH_3OH$ or $CF_3CH_2OH$, opt. $H_2O$ or
   c) MI, DMF or
   d) MI, 18-crown-6, THF
2) MOH (optional), room temp.

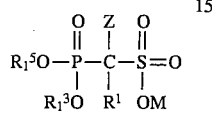

ID

Part B(2) $R_1^4$ = aryl (ICb)

MOH, R.T. to 80° C.

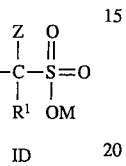

ID

Scheme V
Preparation of (Hydroxyalkoxyphosphinyl)methanesulfonic Diacid Salts IE Monoacid salt ID  →(Deprotection, KOH or NaOH, heat)→  Diacid salt IE

Scheme VI
Preparation of (Dihydroxyphosphinyl)-methanesulfonic Acid Monoesters IF IC →(Deprotection 1) Bromotrimethylsilane (TMSBr) optional proton scavenger 2) MOH, room temp.)→ Monoester, acid or salt IF $R_1^5$, $R_1^3$ = alkyl, cycloalkyl, arylalkyl

Scheme VII
Preparation of (Dihydroxyphosphinyl)-methanesulfonic Acids IG IC →Deprotection→ 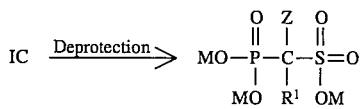

IG

1) Trimethylsilyliodide (TMSI) or TMSI and a proton scavenger
2) MOH

Part A. IC ————→ IG $R^4$ ≠ aryl

-continued
Scheme VII
Preparation of (Dihydroxyphosphinyl)-methanesulfonic Acids IG Part B. IC
1) Conversion to ID as described in Part B(1) or B(2) Scheme IV
2) TMSBr or TMSBr and a proton scavenger
3) MOH
→ IG Part C. IC
1) TMSBr or TMSBr and a proton scavenger
2) KI, 18-crown-6, THF
3) MOH
→ IG $R_1^4$ ≠ aryl

Schemes VIII, IX, IXA and X
General Schemes for the Preparation of α-(Alkyl-or Aryl-hydroxy-phosphinyl)sulfonates
Scheme VIII

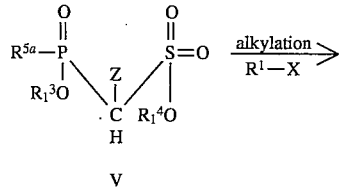  →(alkylation, $R^1$—X)→

V

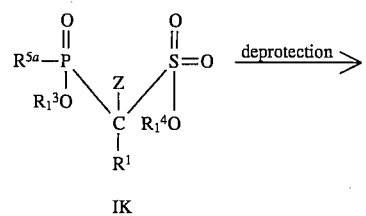  →deprotection→

IK

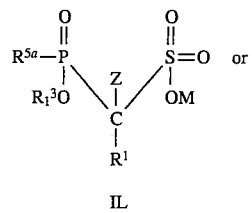 or

IL

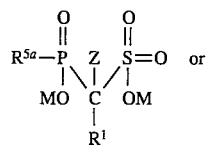 or

IM

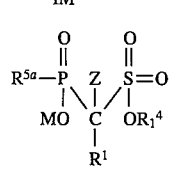

IN

-continued
Schemes VIII, IX, IXA and X
General Schemes for the Preparation of α-(Alkyl-or Aryl-hydroxy-phosphinyl)sulfonates

Scheme VIII $R_1^3$, $R_1^4$ = alkyl, aryl, arylalkyl, cycloalkyl

Scheme IX

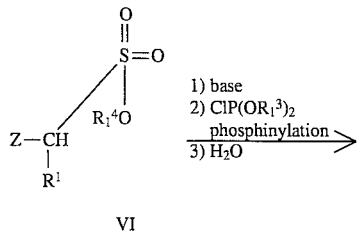

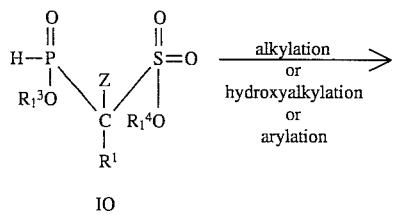

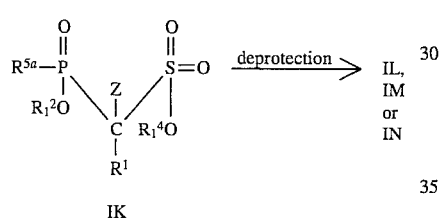

IK

Scheme X

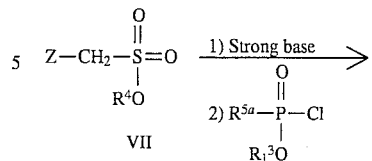

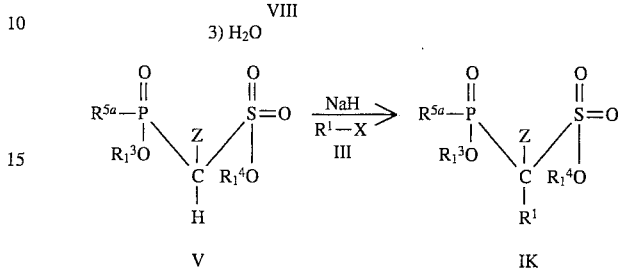

Scheme XI
Preparation of (Hydroxyphosphinyl)-methanesulfonic Acids

The diesters IL or IM are deprotected by treatment with aqueous alkali as shown below to yield the product IM.

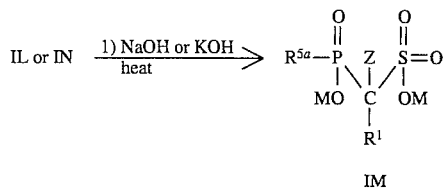

IM

Scheme IXA

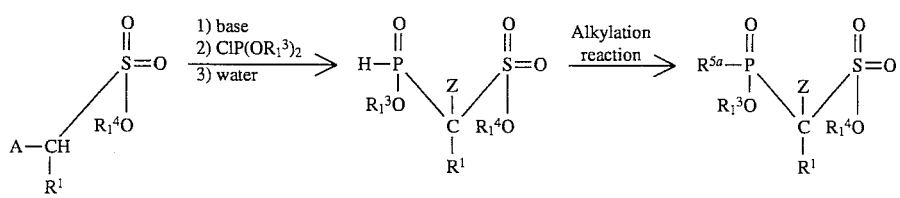

| Alkylation Reaction Methodology | | | product IK |
|---|---|---|---|
| A. | | A. 1) ≧1 eq. of base<br>2) $R^{5a}$-Hal (Hal = I or Br)<br>VIB | $R^{5a}$ ≠ Aryl |
| B. | | B. 1) Chlortrimethylsilane (TMSCl)<br>Et$_3$N<br>2) $R^{5a}$-Hal<br>VIB | $R^{5a}$ ≠ Aryl |
| C. | or | C. 1) base<br>2) aldehyde<br>1) TMSCl, (C$_2$H$_5$)$_3$N<br>2) aldehyde | $R^{5a}$ = $R^7$CHOH<br>$R^7$ = aryl, alkyl or H |
| D. | | D. 1) base<br>2) aryl halide, Pd[P(C$_6$H$_5$)$_3$]$_4$ or Ni[P(C$_6$H$_5$)$_3$]$_4$ | $R^{5a}$ = aryl |

Scheme XIA
Preparation of (Hydroxyphosphinyl)-methanesulfonic Acids.

Part A.

$$R^{5a}-\underset{\underset{R_1^3O}{|}}{\overset{\overset{O}{\|}}{P}}-\underset{\underset{R^1}{|}}{\overset{\overset{Z}{|}}{C}}-\overset{\overset{O}{\|}}{\underset{\underset{O}{\|}}{S}}-OR_1^4 \xrightarrow[20-150°C.]{\begin{array}{c}MOH, H_2O\\ \text{optional}\\ \text{organic}\\ \text{cosolvent}\\ \text{e.g. } C_2H_5OH\end{array}} R^{5a}-\underset{\underset{MO}{|}}{\overset{\overset{O}{\|}}{P}}-\underset{\underset{R^1}{|}}{\overset{\overset{Z}{|}}{C}}-\overset{\overset{O}{\|}}{\underset{\underset{O}{\|}}{S}}-OM$$

IK  IM

Part B.

IK $\xrightarrow[\text{2) MOH, H}_2O]{\begin{array}{c}\text{1) TMSBr,}\\ \text{optional}\\ \text{proton}\\ \text{scavenger}\end{array}}$ $$R^{5a}-\underset{\underset{MO}{|}}{\overset{\overset{O}{\|}}{P}}-\underset{\underset{R^1}{|}}{\overset{\overset{Z}{|}}{C}}-\overset{\overset{O}{\|}}{\underset{\underset{O}{\|}}{S}}-OR_1^4 \xrightarrow[\text{IV B(1)}]{\text{Dealkylation as per Scheme}} IM$$

IN ($R_1^4$ = alky, arylalkyl, cycloalky)

Part C.

IK $\xrightarrow[\text{IV B(1)}]{\begin{array}{c}\text{Dealkylation}\\ \text{as per Scheme}\end{array}}$ $$R^{5a}-\underset{\underset{R_1^3O}{|}}{\overset{\overset{O}{\|}}{P}}-\underset{\underset{R^1}{|}}{\overset{\overset{Z}{|}}{C}}-\overset{\overset{O}{\|}}{\underset{\underset{O}{\|}}{S}}-OM \xrightarrow{\begin{array}{c}\text{Method (1)}\\ \text{1) TMSBr, optional}\\ \text{proton scavenger}\\ \text{2) MOH (opt.) or H}_2O\\ \hline \text{Method (2)}\\ \text{MOH, H}_2O\\ \text{optional organic}\\ \text{cosolvent}\\ 10-1550°C.\end{array}} IM$$

IL ($R_1^4$ = alkyl, arylalkyl, cycloalkyl)

Part D.

IK $\xrightarrow[\text{Part C}]{\begin{array}{c}\text{As in Scheme}\\ \text{VII}\end{array}}$ IM ($R_1^4$ = alkyl, aryl, arylalkyl)

Scheme XII
Preparation of α-Hydroxyphosphinyl methanesulfonic Acids (phosphorous acids)

A. IO $\xrightarrow[\text{pref. = KI, acetone}]{\text{Dealkylation}}$ $$H-\underset{\underset{R_1^3O}{|}}{\overset{\overset{O}{\|}}{P}}-\underset{\underset{R^1}{|}}{\overset{\overset{Z}{|}}{C}}-\overset{\overset{O}{\|}}{\underset{\underset{O}{\|}}{S}}-OM$$

IP

IP $\xrightarrow[\text{optional cosolvent}]{\begin{array}{c}\text{Hydrolysis}\\ \text{MOH, H}_2O\end{array}}$ $$H-\underset{\underset{MO}{|}}{\overset{\overset{O}{\|}}{P}}-\underset{\underset{R^1}{|}}{\overset{\overset{Z}{|}}{C}}-\overset{\overset{O}{\|}}{\underset{\underset{O}{\|}}{S}}-OM$$

IQ

-continued
Scheme XII
Preparation of α-Hydroxyphosphinyl methanesulfonic Acids (phosphorous acids)

B. IP $\xrightarrow[\text{(R}^7\text{ is H, alkyl, aryl, arylalkyl)}]{\begin{array}{c}R^7CHO\\ \text{organic base}\end{array}}$ $$R^7-\underset{\underset{H}{|}}{\overset{\overset{HO}{|}}{C}}-\underset{\underset{R_1^3O}{|}}{\overset{\overset{O}{\|}}{P}}-\underset{\underset{R^1}{|}}{\overset{\overset{Z}{|}}{C}}-\overset{\overset{O}{\|}}{\underset{\underset{OM}{|}}{S}}=O$$

IL'

Scheme XIII
Alternative Route to IC or IK $$H-\underset{\underset{R^1}{|}}{\overset{\overset{Z}{\|}}{C}}-\overset{\overset{O}{\|}}{\underset{\underset{OR_1^4}{|}}{S}}=O \xrightarrow{\begin{array}{c}\text{1) base (as in Scheme IA)}\\ \text{2) Cl}-P(OR_1^3)(R^2)\\ (R^2 = OR_1^5 \text{ or } R^{5a})\\ \text{3) Oxidant}\\ \text{(e.g. MCPBA,}\\ t\text{-C}_4H_9OOH,\\ H_2O_2 \text{ or}\\ I_2/H_2O)\end{array}} \begin{array}{c}IC\\ (R^2 = OR_1^5)\\ \text{or}\\ (R^2 = R^{5a})\end{array}$$

IIA

Scheme XIV
Preparation of Prodrugs

Part A

IF $\xrightarrow[(X^1 = NO_3, ClO_4, CF_3SO_3)]{\begin{array}{c}AgX^1\\ (R_1^4 \neq aryl)\end{array}}$ $$\underset{\underset{AgO}{|}}{\overset{\overset{AgO}{|}}{P}}\underset{\underset{R^1}{|}}{\overset{\overset{O}{\|}}{-}}\underset{\underset{R^1}{|}}{\overset{\overset{Z}{|}}{C}}-\overset{\overset{O}{\|}}{\underset{\underset{OR_1^4}{|}}{S}}=O \xrightarrow[\text{(Hal = Cl, Br, I)}]{\begin{array}{c}R^x\quad O\\ |\quad\|\\ Hal-C-O-C-R^y\\ |\\ H\\ XI\end{array}}$$

IR $$(R^y-\underset{\underset{O}{\|}}{\overset{}{C}}-O-\underset{\underset{R^x}{|}}{\overset{}{C}}-O)_2-\underset{\underset{R^1}{|}}{\overset{\overset{O}{\|}}{P}}-\underset{\underset{OR_1^4}{|}}{\overset{\overset{Z}{|}}{C}}-S=O \xrightarrow[\text{R}_1^4 \neq aryl]{\begin{array}{c}\text{Dealkylation}\\ \text{(as per Scheme}\\ \text{IV B(1) (except}\\ CH_3OH, NH_3)\end{array}}$$

IS $$(R^y-\underset{\underset{O}{\|}}{\overset{}{C}}-O-\underset{\underset{R^x}{|}}{\overset{\overset{H}{|}}{C}}-O)_2-\underset{\underset{R^1}{|}}{\overset{\overset{O}{\|}}{P}}-\underset{\underset{OM}{|}}{\overset{\overset{Z}{|}}{C}}-S=O$$

IT ($R^y$ = aryl, aralkyl, alkyl or alkoxy)
($r^x$ = aryl, aralkyl, alkyl or H)

Scheme XIV
Preparation of Prodrugs
Part B

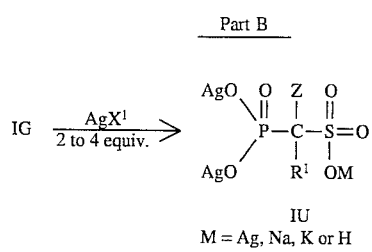

IU
M = Ag, Na, K or H

IT ←XI—— IU

Scheme XV
Preparation of Individual Enantiomers of Formula I Compounds
Part A

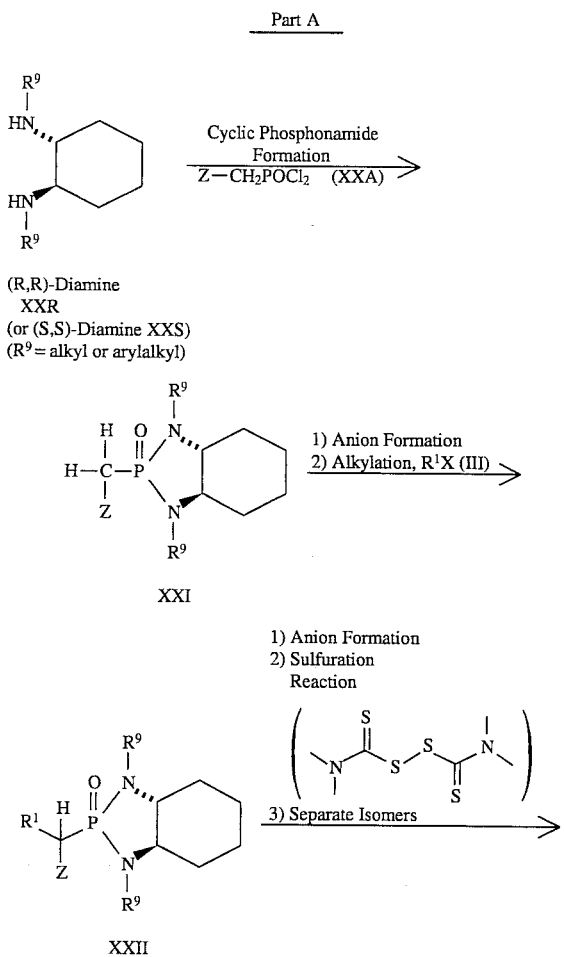

XXIIIS (Major when Z = H)
+
XXIIIR (Minor when Z = H)

When (S,S)-Diamine XXS is used as starting material, α-(R) is Major Isomer where (Z = H) and α-(S) is Minor Isomer (Z = H)

Scheme XV
Preparation of Individual Enantiomers of Formula I Compounds

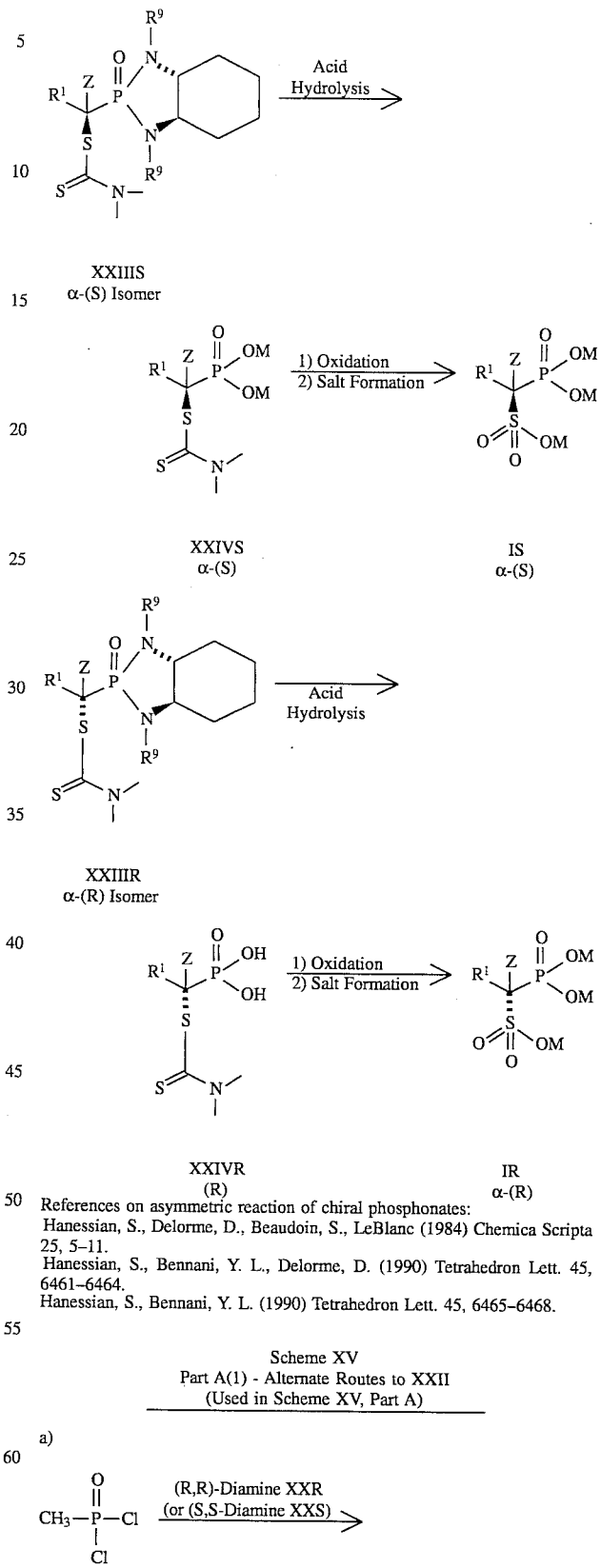

References on asymmetric reaction of chiral phosphonates:
Hanessian, S., Delorme, D., Beaudoin, S., LeBlanc (1984) Chemica Scripta 25, 5–11.
Hanessian, S., Bennani, Y. L., Delorme, D. (1990) Tetrahedron Lett. 45, 6461–6464.
Hanessian, S., Bennani, Y. L. (1990) Tetrahedron Lett. 45, 6465–6468.

Scheme XV
Part A(1) - Alternate Routes to XXII
(Used in Scheme XV, Part A)

-continued
Scheme XV
Part A(1) - Alternate Routes to XXII
(Used in Scheme XV, Part A)

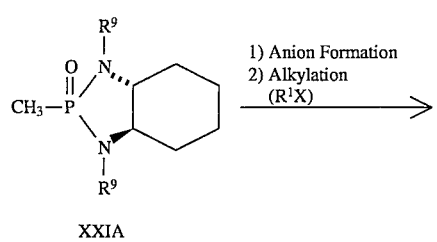

XXIA

1) Anion Formation
2) Alkylation
(R¹X)
→

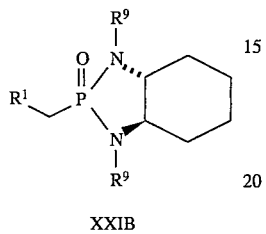

XXIB

↑ Diamine XXR (or XXS)

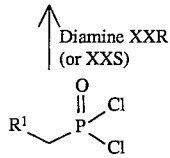

b)

XXIA  1) Anion Formation
2) Alkylation or Halogenation
→

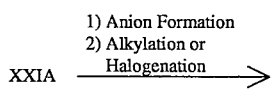

XXIC

1) Anion Formation
2) R¹X
→

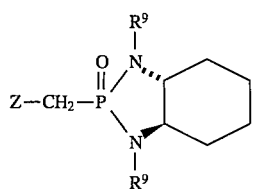

XXII c)

XXIB  1) Anion Formation
2) Alkylation or Halogenation
→ XXII

Scheme XV
Part B

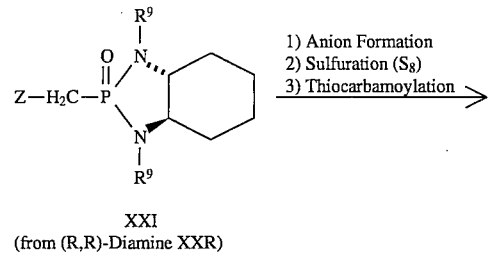

XXI
(from (R,R)-Diamine XXR)

1) Anion Formation
2) Sulfuration (S₈)
3) Thiocarbamoylation
→

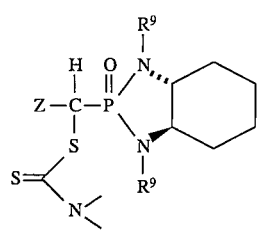

XXV 1) anion formation
2) alkylation
R¹Hal
↓

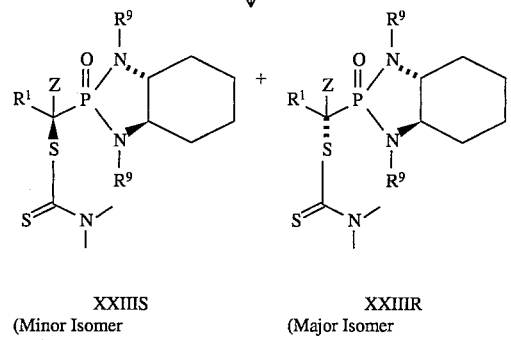

XXIIIS
(Minor Isomer
α-(S) when Z = H)

XXIIIR
(Major Isomer
α-(R) when Z = H)

When (S,S-Diamine XXS is the starting material, the α-(S) isomer XXIIIS is obtained as the major product when Z=H.

↓                    ↓
Continue as in Scheme XV Part A
↓                    ↓
IS                   IR

Scheme XV

Part C

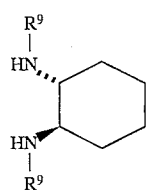

XXR (R,R)-Diamine
(or (S,S)-Diamine (XXS))

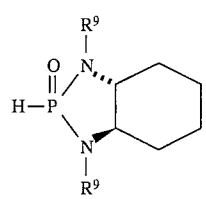

XXVII

1) Condensation Reaction
R¹CHO (XXVIII)
Silylating Agent
2) Separate Isomers
⟶ XXIXS + XXIXR

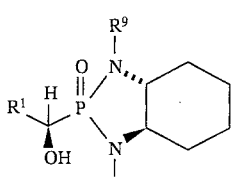

XXIXR      XXIXS

↓ Fluoride Source ↓

-continued
Scheme XV

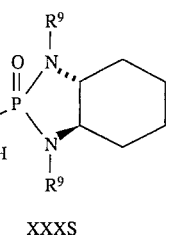

XXXR      XXXS

Alternatively, isomers can be separated at the alcohol stage, that is, XXXR and XXXS.

↓ Mitsunobu Displacement* ↓

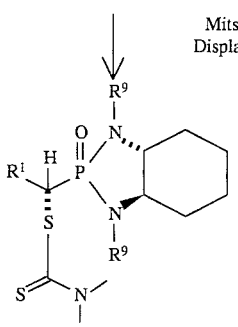 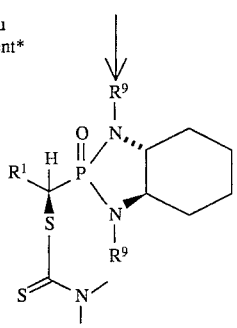

XXIIIR'      XXIIIS'
α-(R)      α-(S)

↓ ↓

Continue as in Scheme XV Part A

↓ ↓

IR      IS

*P. Rollin, Tetrahedron Lett. 1986, 27, 4169–4170

Part C (1)

XXVII
1) Condensation Reaction
R¹CHO (XXVIII)
Various Bases including Fluoride
2) Separate Isomers
⟶ XXXR + XXXS

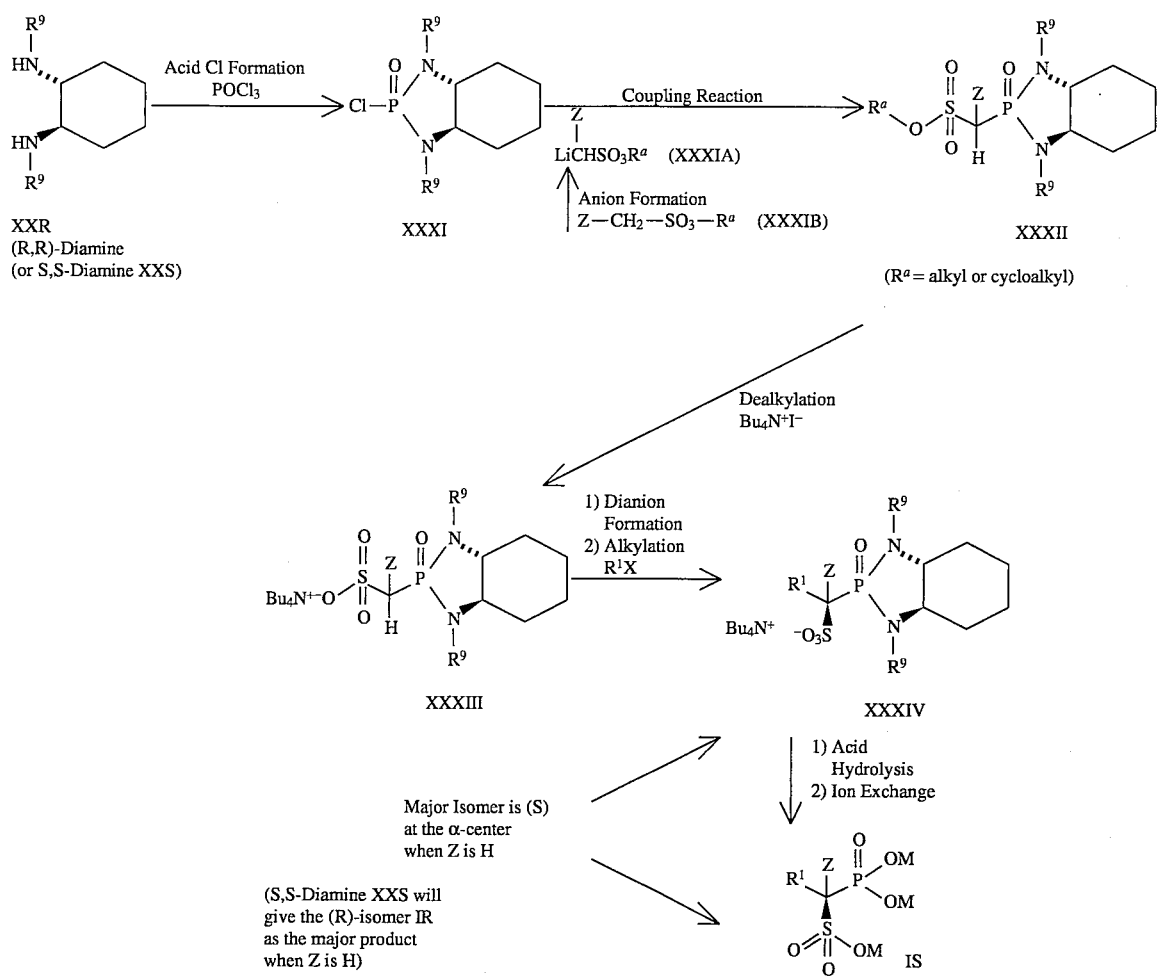
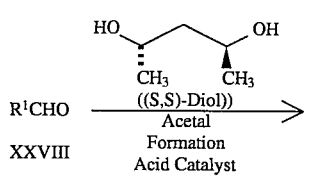
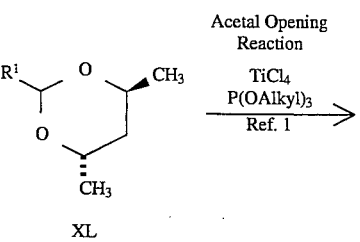
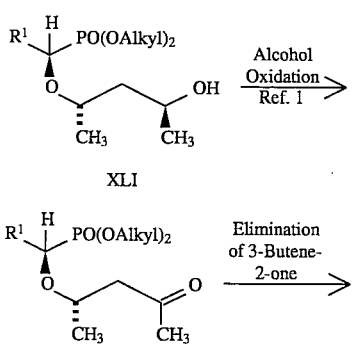

Scheme XVII
Preparation of Individual Enantiomer

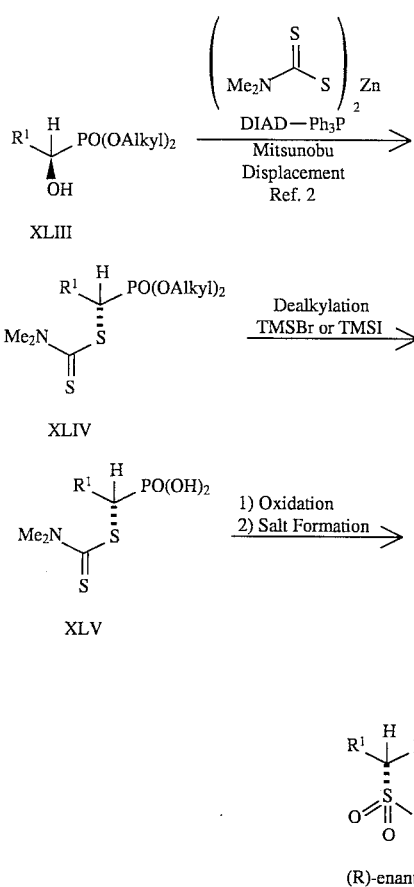

Use (R,R)-diol to obtain (S)-enantiomer (IS)

References:

(1) Yokomatsu T.; Shibuya, S., Tetrahedron Asymmetry 1992, 3, 377–378
(2) P. Rollin, Tetrahedron Lett. 1986, 27, 4186–4170

Scheme XIX
Preparation of Prodrugs of Desired Enantiomer

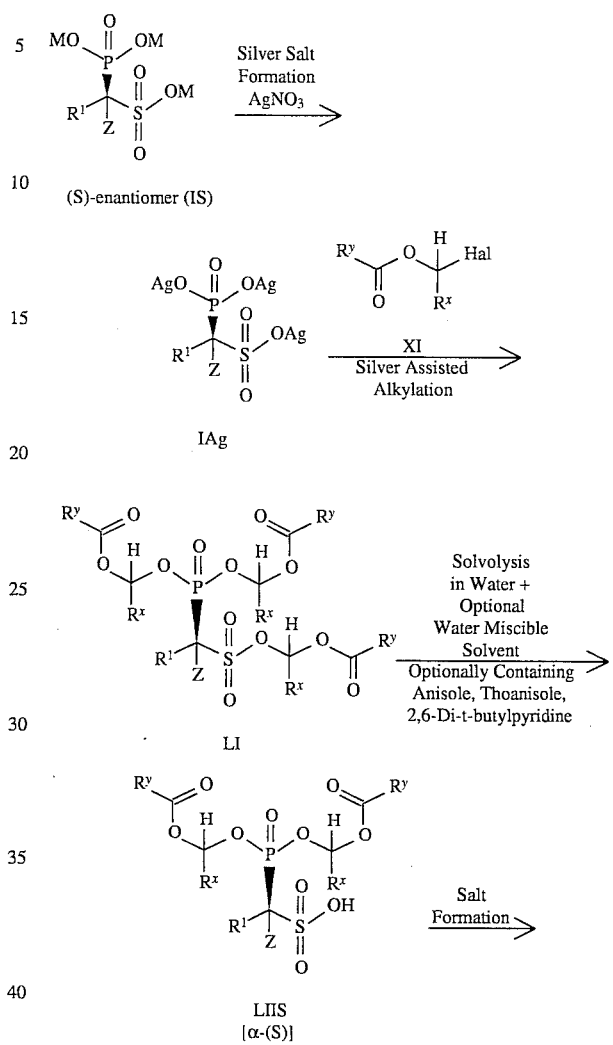

Scheme XVIII
Purification of Desired Enantiomer

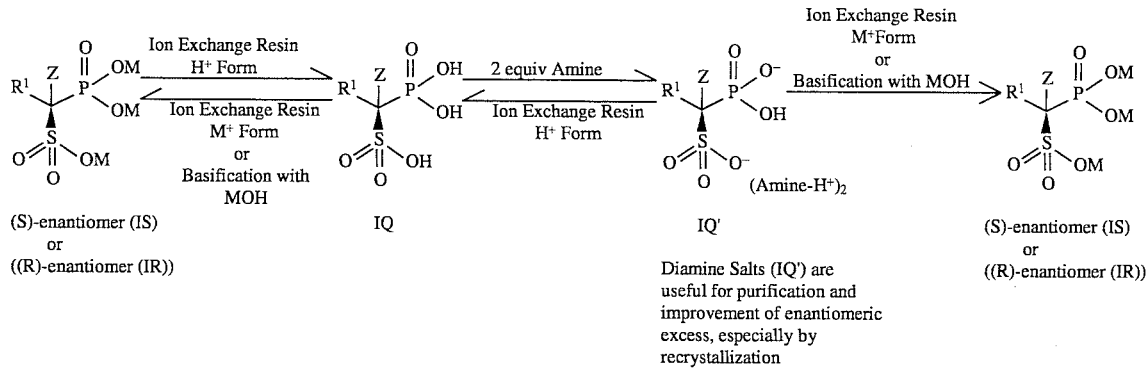

Diamine Salts (IQ') are useful for purification and improvement of enantiomeric excess, especially by recrystallization

-continued
Scheme XIX
Preparation of Prodrugs of Desired Enantiomer

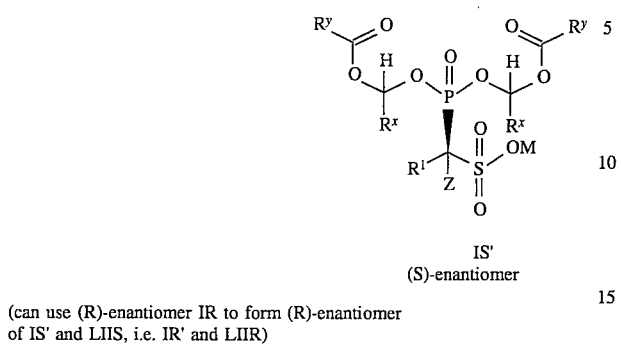

IS'
(S)-enantiomer (can use (R)-enantiomer IR to form (R)-enantiomer
of IS' and LIIS, i.e. IR' and LIIR)

Referring to "General Reaction" Scheme I, compounds of the invention IC may be prepared by alkylating the phosphonosulfonate II by reacting II with compound III in the presence of an appropriate base and an inert organic solvent under an inert atmosphere to form IC, followed by deprotection to the various acid forms ID, IE, IF and IG.

In carrying out the above reaction, the phosphonosulfonate II is employed in a molar ratio to compound III of within the range of from about 5:1 to about 0.8:1, and preferably from about 3:1 to about 1.2:1. The reaction is carried out under an inert atmosphere, such as argon, initially preferably at a reduced temperature of within the range of from about −78° to about 80° C., and more preferably from about 0° to about 50° C., although the reaction may be completed at room temperature.

Examples of inert organic solvents suitable for use herein include, but are not limited to dimethylformamide (DMF), tetrahydrofuran (THF), dimethylsulfoxide (DMSO), hexamethylphosphoramide (HMPA) or diethyl ether ($Et_2O$), or mixtures thereof.

Examples of bases suitable for use in carrying out the above reaction include, but are not limited to, alkali metal hydrides, such as sodium hydride (which is preferred), potassium hydride, lithium-, sodium- or potassium bis(trimethylsilyl)amide, lithium diisopropylamide or butyllithium.

Referring to Scheme IA, starting compounds of formula IIC wherein $R_1^2$, $R_1^3$, and $R_1^4$ of II as defined in Scheme I may be prepared by reacting starting sulfonate IIA with a strong base such as any of those used in Scheme I, in the presence of or followed by chlorophosphate IIB, and an inert organic solvent such as used in Scheme I, to form IIC.

In carrying out the reaction of Scheme IA, chlorophosphate IIB will be employed in a molar ratio to sulfonate IIA of within the range of from about 3:1 to about 1:2, and preferably from about 2.0:1 to about 1:1. The reaction is carried out at a temperature of within the range of from about −100° to about 30° C., and preferably from about −90° to about 0° C.

Referring to Scheme II, compounds of the invention IC may be prepared by alkylating the phosphonosulfonate IC' with an alkylhalide, ZX (IIIA) (Z is alkyl and X is as defined in Scheme I), or with a halogenating agent $ZX^1$ (where Z is halogen except F and $X^1$ is succinimido, Cl, Br or I, or OH; when Z is F, $ZX^1$ is $XeF_2$),

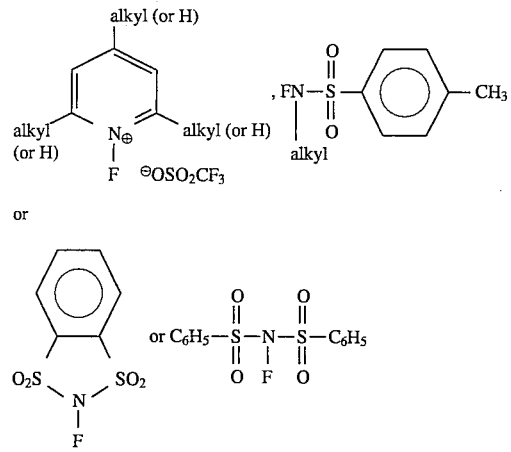

The above reactions are carried out in the presence of appropriate inert organic solvent as described above, under an inert atmosphere, to form IC.

In carrying out the above reaction, the phosphonosulfonate IC' is employed in a molar ratio to compound IIIA or IIIA' of within the range of from about 2:1 to about 0.2:1, and preferably from about 1.5:1 to about 0.7:1. The reaction is carried out under an inert atmosphere, such as argon, initially preferably at a reduced temperature of within the range of from about −78° C. to about 80° C., and more preferably from about 0° C. to about 50° C., although the reaction may be completed at room temperature. Bases and solvents appropriate for this reaction are as described for Scheme I.

Referring to Scheme III Part A, compounds of the invention IC may be prepared by alkylating the phosphonosulfonate II with compound III in the presence of an appropriate base and an inert organic solvent (as described hereinbefore with respect to Scheme I) preferably dimethylformamide (DMF), under an inert atmosphere to form IC.

In carrying out the above reaction, the phosphonosulfonate II is employed in a molar ratio to compound III of within the range of from about 5:1 to about 0.8:1, and preferably from about 3:1 to about 1.5:1. The reaction is carried out under an inert atmosphere, such as argon, initially, preferably at a reduced temperature of within the range of from about −78° to about 80° C., and more preferably from about 0° to about 50° C., although the reaction may be completed at room temperature.

Referring to Schemes III Part B and III Part C, compounds of the invention IC' may be prepared through the palladium catalyzed base promoted coupling of allylic acetates (Types 1 or 2) with the phosphonosulfonate II to provide the coupled product of the invention IC'. Either allylic isomer serves as a substrate in the reaction.

In carrying out the above reactions, the phosphonosulfonate II is employed in a molar ratio to allylic acetate of within the range of from about 5:1 to about 0.8:1, and preferably from about 3:1 to about 1.5:1. The reaction is carried out under an inert atmosphere, such as argon, initially preferably at a reduced temperature of within the range of from about −78° to about 110° C., and more preferably from about 0° to about 80° C., although the reaction may be completed at room temperature.

The above reactions are carried out in the presence of a suitable inert organic solvent as described hereinbefore with respect to Scheme I, preferably employing tetrahydrofuran (THF) or dimethylformamide (DMF). Suitable bases are sodium hydride and sodium bis(trimethylsilyl)amide, and preferably bis(trimethylsilyl)acetamide (BSA) in the presence of palladium (O) catalyst such as $Pd[(C_6H_5)_3]_4$.

The base or BSA is employed in a molar ratio to allylic acetate within the range of from about 4:1 to about 1:1, while the Pd(O) is employed in a molar ratio to allylic acetate of within the range of from about 0.005:1 to about 0.5:1.

Referring to Scheme IV, Part A, the coupling reaction is carried out with (dialkoxyphosphinyl)methane sulfonate ethyl ester II to yield the sulfonate salt ID directly from the reaction. The product emerges by means of a concomitant iodide promoted dealkylation of the sulfonate ester.

The Scheme IV Part A, reaction is carried out in a manner similar to Scheme I.

The sulfonate salt ID may also be formed as shown in Scheme IV, Part B(1) and (2). Part B(1) depicts the dealkylation of the sulfonate ester ICa to yield ID, using various reagents as shown in the reaction sequence set out hereinbefore, while B(2) shows the cleavage of an aryl methanesulfonate ester ICb by aqueous alkali containing from about 5 to about 20% by weight base) and heating at a temperature within the range of from about 40° to about 100° C., to give ID.

Referring to Scheme V, the diacid salt IE is prepared by the further hydrolysis of monoacid ID employing aqueous alkali (containing from about 5° to about 20% by weight base) optionally in the presence of a cosolvent, such as dimethoxyethane, dioxane or THF, and heating at a temperature within the range of from about 40° to about 100° C.

Referring to Scheme VI, the (dihydroxyphosphinyl) methanesulfonic acid monoester IF is prepared by the cleavage of the phosphorous ester IC (wherein $R_1^2$ and $R_1^3$ are each lower alkyl, arylalkyl, cycloalkyl and $R_1^4$ is lower alkyl, arylalkyl, cycloalkyl or aryl) with bromotrimethylsilane (TMSBr), optionally in the presence of a proton scavenger such as 2,4,6-collidine, hexamethyl disilazane, alkyl, trimethylsilane, bis(trimethylsilyl)trifluoroacetamide, pyridine or triethylamine, followed by aqueous alkali (as described above except that elevated temperatures are not necessary) or water wherein the TMSBr is employed in a molar ratio to IC of within the range of from about 2:1 to about 15:1, preferably from about 2: to about 5:1.

Scheme VII Parts A, B and C sets out the chemical processes employed for the deprotection of phosphonosulfonate triester IC to phosphonosulfonic acid IG.

In Scheme VII, Part A shows the direct deprotection of the ester IC through the agency of trimethylsilyl iodide (TMSI) (employs a molar ratio of TMSI:IC of within the range of from about 3:1 to about 20:1, preferably from about 3.5:1 to about 5:1) optionally in the presence of a proton scavenger as defined above, and followed by aqueous alkali (as described above) or water at a temperature of within the range of from about 0° to about 50° C.

In Scheme VII Part B, phosphonosulfonic triacid IG is formed via a two step process where in the first step, the sulfonate ester is removed as described in Part B, Scheme IV and in the second step treatment with bromotrimethylsilane optionally in the presence of a proton scavenger as defined above, yields the silyl esters which are then hydrolyzed via aqueous alkali (as described hereinbefore) or water.

In Scheme VII Part C, the phosphonate esters are removed (from IC) first with bromotrimethylsilane (TMSBr) (employing a molar ratio of TMSBr:IC of within the range of from about 2:1 to about 20:1, preferably about 2.5:1 to about 5:1) optionally in the presence of a proton scavenger as defined above, to provide the intermediate bis(silyl)esters. Subsequent cleavage of the sulfonate ester with potassium iodide (18-crown-6, THF) and hydrolysis (MOH and $H_2O$) yields the phosphonosulfonic triacid IG.

Schemes VIII, IX, IXA and X relate to the preparation of α-(alkyl- or aryl-hydroxyphosphinyl)sulfonates.

Schemes VIII and IX depict the general chemical process for the formation of diesters IK, and their deprotection to form IL and IO, respectively.

Scheme IXA depicts the P-H route to diester IK. Starting sulfonate VI is treated with a strong base followed by dialkyl chlorophosphite (employing a molar ratio of dialkyl chlorophosphite:VI of within the range of from 1:1 to about 10:1), followed by hydrolysis with water under acidic conditions, to form alkoxyphosphinyl sulfonate IO which serves as an intermediate for the synthesis of substituted (alkyl- or aryl-alkoxyphosphinyl)methylsulfonate diesters via alkylation of IO. The alkylation methods are shown in Parts A, B, C and D.

In Scheme IXA Part A, diester IK where $R^{5a} \neq$ aryl is formed by selective alkylation of IO by treating IO with base such as NaH, KH, LDA, butyllithium, Li-, Na- or K-bis(trimethylsilyl)amide and a halide VIB of the structure VIB 

wherein Hal is I or Br, as described with respect to Scheme I.

In Scheme IXA Part B, diester IN where $R^5 \neq$ aryl is formed by treatment of IO with chlorotrimethylsilane (TMSCl) and organic base such as triethylamine ($Et_3N$) in the presence of alkylating agent VIB. In carrying out this alkylation, the silane compound is employed in a molar ratio to IO of within the range of from about 1:1 to about 5:1, preferably from about 1:1 to about 3:1 while VIB is employed in a molar ratio to IO of within the range of from about 0.8:1 to about 10:1.

In Scheme IXA Part C, IK where $R^{5a}$ is $R^7CHOH$ (and $R^7$ is H, aryl or alkyl) is prepared by treating IO with base followed by aldehyde $R^7CHO$, carried out by employing a molar ratio of $R^7CHO$ to IO of from about 1:1 to about 10:1. Alternatively, IO can be treated with $(CH_3)_3SiCl$ and an organic base (such as triethylamine) followed by an aldehyde, followed subsequently with a standard desilylation reaction (such as tetrabutylammonium fluoride in THF) to provide IK with $R^5=R^7CHOH$.

In Scheme IXA, Part D IO is reacted with an aryl halide in the presence of a base such as triethylamine and $Pd[P(C_6H_5)_3]_4$, $Ni[P(C_6H_5)_3]_4$ or other nickel and palladium catalysts, to yield IK when $R^{5a}$ is aryl.

Scheme X depicts the preparation of (hydroxyphospinyl)methanesulfonic acid diester IN by alkylation of diester V by treatment of V with base, such as NaH, and alkylating agent III as described hereinbefore in Scheme I. The intermediate V may be prepared via a coupling reaction of the alkylsulfonate VII with phosphonic acid chloride VIII employing a molar ratio of VII:VIII of within the range of from about 0.5:1 to about 10:1, preferably from about 1.5:1 to about 3:1, similar to that described in Scheme IA, for the conversion of IIA to IIC.

Schemes XI and XIA depict various routes (A, B and C) for the deprotection of diesters IK to yield IM.

Scheme XII Part A depicts the preparation of salts IQ by dealkylating IO using techniques as described hereinbefore, preferably with KI and acetone, to form monoester IP and then subjecting IP to hydrolysis to form salt IQ.

In Scheme XII Part B, the ester IP is treated with aldehyde ($R^7CHO$) in the presence of organic base such as triethylamine, diisopropylethylamine or 1,8-diazabicyclo[5.4.0]undec-7-ene, to form IK where $R^{5a}$ is $R^7CHOH$. In this reaction, the aldehyde is employed in a molar ratio to IP of within the range of from about 1:1 to about 10:1, preferably from about 1:1 to about 5:1.

Scheme XIII depicts an alternate route to IC where IIA is treated with base (as per Scheme IA) and chlorophosphite (as described hereinbefore) and an oxidant such as m-chloroperbenzoic acid (MCPBA), t-C₄H₉COOH, hydrogen peroxide or I₂/H₂O to form IC.

Scheme XIV (Parts A and B) depict the preparation of prodrug esters.

Referring to Scheme XV, the individual isomers or enantiomers of the formula I compounds of the invention may be prepared, in accordance with the present invention, by treating the (R,R)-diamine XXR (or (S,S)-diamine XXS) where $R^a$ is alkyl or aralkyl, with an alkyl phosphonic dihalide XXA, such as methylphosphonic dichloride, in the presence of a tertiary amine base and an aprotic solvent such as benzene, toluene, dichloromethane or diethyl ether, to form the alkylphosphondiamide XXI which is metalated with a base such as n-butyllithium, sec-butyllithium, t-butyllithium or lithium diisopropylamide, to form the lithium anion of XXI which is then alkylated by treatment the halide $R^1X$ (IIIa) such as the iodide

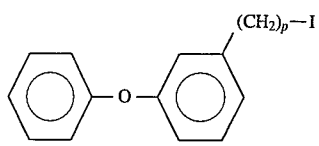

in the presence of an inert organic solvent such as tetrahydrofuran (THF), diethyl ether or dimethoxyethane or mixtures thereof, at a temperature within the range of from about −90° to about 25° C., preferably from about −80° to about 0° C., to form XXII. Compound XXII is reacted with a base as above to form the lithium anion of XXII which is sulfurated with tetramethylthiuram disulfide or the corresponding tetraethyl derivative at a temperature within the range of from about −100° to about 0° C., preferably from about −90° to about −60° C., to form a mixture of isomers XXIIIR and XXIIIS (which are novel compounds in accordance with the present invention).

Where the sulfuration is carried out at below about 0° C., preferably at about −60° C. to about −100° C., and the starting diamine is the (R,R)-diamine XXR and Z is H, a mixture of major XXIIIS (α-(S)) and minor XXIIIR (α-(R)) thiocarbamate isomers (about 3:1 mixture at −90° C.) is obtained.

It should be noted that in the above and following discussions and schemes α-(R) and α-(S) refer to the enantiomeric configuration at the chiral carbon center adjacent to the phosphorus and sulfur moieties.

It will be appreciated that where the (S,S)-diamine XXS is employed in place of (R,R)-diamine XXR and Z is H, the major isomer obtained will be the α-(R)-isomer XXIIIR.

The thiocarbamate isomers XXIIIS and XXIIIR can be separated by chromatography on silica gel, crystallization or HPLC. The individual and separate diastereomers (XXIIIS and XXIIIR) are then separately subjected to acid hydrolysis (such as treatment with aqueous acid such as HCl), to form compound XXIVR or XXIVS (which are novel compounds in accordance with the present invention) which are separately subjected to oxidation (such as reaction with H₂O₂ in the presence of formic acid, acetic acid or mixtures of formic and acetic acids) and salt formation by base treatment or ion exchange chromatography, to form the individual enantiomers IS and IR of the invention.

In carrying out the reactions of Scheme XV, the starting (R,R)-diamine with $R^9$=methyl is prepared by a two-step reductive methylation of the L-(+)- tartaric acid salt (available from racmeic 1,2-trans-cyclohexanediamine, Gasbol, F. et al (1972) Acta. Chem. Scand. 26, 3605 and Onuma, K. et al, (1980) Bull. Chem. Soc. Jap. 53, 2012) as follows:

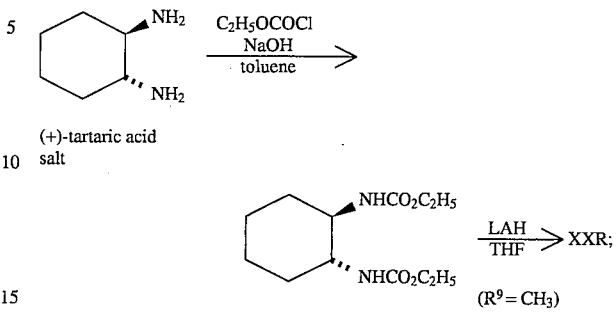

Other examples of XXR and XXS where $R^9$ is alkyl or aralkyl are prepared as reported in the prior art as follows: Alexakis, A. et al, *J. Org. Chem.*, 1992, 57, 1224–1237; Denmark, S. et al, *J. Org. Chem.*, 1991, 56, 5063–5079; Hanessian, S. et al, *Tetrahedron*, 1992, 33, 7659–7662; and Koeller, K. J. et al, *Tetrahedron Lett.*, 1991, 32, 6297–6300.

The (R,R)-diamine XXR (or XXS) is employed in a molar ratio to the alkylphosphonic dichloride XXA of within the range of from about 0.5:1 to about 3:1, preferably from about 0.9:1 to about 1.5:1. The amine base, such as triethylamine, pyridine, diisopropylethylamine will be employed in a molar ratio to the alkylphosphonic dichloride XXIA of within the range of from about 1:1 to about 5:1, preferably from 1.5:1 to about 3:1.

The metalation (anion formation) of XXI is carried out at a temperature within the range of from about −90° to about 0° C., preferably from about −80° to about −60° C., employing a molar ratio of base compound to alkylphosphondiamide XXI of within the range of from about 0.8:1 to about 2:1, preferably from about 0.9:1 to about 1.3:1. The alkylating agent R¹X (III) where X is preferably iodide, but may be Cl or Br as well, will be employed in a molar ratio to alkylphosphondiamide XXI of within the range of from about 1:1 to about 4:1, preferably from about 1:1 to about 2:1.

As seen in Scheme XVI Part A(1), compound XXII may be prepared by a variety of routes which will be apparent to those skilled in the art.

The metalation of XXII is carried out at a temperature within the range of from about −100° C. to about 0° C., preferably from about −60° C. to about −80° C. employing a molar ratio of base to XXII of within the range of from about 2:1 to about 0.8:1, preferably from about 1.4:1 to about 0.9:1.

The lithium anion of XXII is then sulfurated employing a molar ratio of tetramethylthiuram disulfide: lithium anion of XXII of within the range of from about 3:1 to about 1:1, preferably from about 2:1 to about 1:1.

The acid hydrolysis of the individual isomer XXIIIS and XXIIIR to the corresponding thiocarbamate XXIVS and XXIVR, respectively, is carried out by employing aqueous strong acid, such as aqueous HCl, formic acid or sulfuric acid, optionally in the presence of acetonitrile, dioxane or other inert organic solvent. The thiocarbamates XXIVS and XXIVR may be oxidized by conventional techniques, for example, by reaction with hydrogen peroxide in the presence of acetic acid or formic acid, or mixtures thereof or peracids such as peracetic in acetic acid or metachloroperbenzoic acids in dichloromethane or diethyl ether, or using Oxone in alcoholic solvents, to the sulfonic acid which is treated with alkali metal hydroxide, such as KOH, NaOH, or LiOH or an ion exchange resin to form the triacid salt, IS or IR.

Referring to Scheme XV Part B, in accordance with the present invention, in an alternate synthesis of the Part A method, alkylphosphondiamide XXI (or (S,S)-isomer) is metalated by reaction with a base as described above, such as n-butyllithium, sec-butyllithium, t-butyllithium or lithium diisopropylamide in the presence of an inert organic solvent such as hexane, tetrahydrofuran or diethylether to form the lithium anion of XXI which is sulfurated by treatment with sulfur and subjected to thiocarbamoylation with a dialkyl thiocarbamoyl halide to form XXV (a novel compound in accordance with the present invention). Compound XXV is then metalated by treatment with a base as described above, alkylated by treatment with R$^1$Hal and the resulting mixture of isomers XXIIIS and XXIIIR are separated as described hereinbefore. Isomers XXIIIS and XXIIIR may then be subjected to acid hydrolysis and oxidation and salt formation as described with respect to XXIIIS and XXIIIR in Part A, to form IR and IS.

In carrying out the Scheme XV Part B method, the base, preferably n-butyllithium, is reacted with alkylphosphondiamine XXI under an inert atmosphere such as argon or nitrogen at a temperature within the range of from about −100° to about 0° C., preferably from about −60° to about −80° C., employing a molar ratio of alkyllithium:XXI of within the range of from about 0.8:1 to about 2:1, preferably from about 1.2:1 to about 1:1.

The sulfuration reaction of lithiated XXI (with sulfur) is carried out at a temperature within the range of from about −90° to about 0° C., preferably from about −80° to about −40° C., employing a molar ratio of sulfur:lithiated XXI of within the range of from about 4:1 to about 1:1, preferably from about 2:1 to about 1:1.

Thiocarbamoylaton of the sulfurated XXI with the dialkylthiocarbamoyl halide, preferably, dimethyl- or diethyl-thiocarbamoyl chloride is carried out at a temperature within the range of from about −60° to about 25° C., preferably from about −30° to about 0° C., employing a molar ratio of dialkylthiocarbomoyl halide:sulfurated XXI of within the range of from about 4:1 to about 1:1, preferably from about 2:1 to about 1:1. The thiocarbamoylation reaction is optionally carried out in the presence of a weak organic base, such as triethylamine or pyridine.

The thiocarbamoylated compound XXV is metalated with a base, as described above, preferably n-butyllithium, at a temperature within the range of from about −90° to about −60° C., preferably from about −80° to about −70° C., under an inert atmosphere such as argon or nitrogen, employing a molar ratio of alkyllithium: thiocarbamoylated compound XXV of within the range of from about 2:1 to about 0.8:1, preferably from about 1.4:1 to about 0.9:1.

Alkylation of the lithiated XXV is carried out at a temperature within the range of from about −90° to about 0° C., preferably from about −80° to about −40° C., employing a molar ratio of R$^1$Hal:lithiated XXV of within the range of from about 4:1 to about 0.8:1, preferably from about 1.5:1 to about 0.9:1. The alkylation is preferably carried out in the presence of a weak base such as hexamethylphosphoramide (HMPA), or tetramethylethylene diamine.

Still another alternative method for preparing the desired enantiomers of formula I compounds, in accordance with the present invention, is shown in Scheme XV Part C wherein starting (R,R)-diamine XXR (or the corresponding (S,S-)-diamine XXS) is made to undergo a phosphorous diamide formation by treating a solution of XXR and weak organic base such as triethylamine or pyridine, in an inert organic solvent such as THF, dichloromethane or toluene, with phosphorus trichloride under an inert atmosphere such as argon or nitrogen, and then treating the resulting filtrate (chilled), under an inert atmosphere, such as argon, with water, and a tertiary amine base, to form the phosphorous diamide XXVII. The diamide XXVII may then be subjected to a condensation reaction with the aldehyde XXVIII

R$^1$CHO and a silylating agent such as, for example, bis(trimethylsilyl) acetamide, bis(trimethylsilyl) trifluoroacetamide or hexamethyl disilazane in the presence of an inert organic solvent, such as methylene chloride, toluene or THF, under an inert atmosphere, such as argon or nitrogen, to form a mixture of protected isomers XXIXR (α-(R)isomer) and XXIXS (α-(S)isomer).

The isomers XXIXR and XXIXS are separated by chromatography or other conventional means such as crystallization and each of the α-(R) isomer XXIXR and α-(S) isomer XXIXS in solution in an inert organic solvent such as THF, diethyl ether, acetonitrile or dichloromethane, is separately treated with a fluoride source such as tetrabutylammonium fluoride, aqueous hydrofluoric acid or lithium tetrafluoroborate, to form the compounds XXXR and XXXS.

Each of the isomers XXXR and XXXS can then be separately made to undergo a Mitsunobu displacement (Rollin, P., Tetrahedron Lett. 1986, 27, 4169–4170) wherein each of XXXR and XXXS is separately treated with dimethyl (or diethyl) dithiocarbamic acid, zinc salt, and triphenylphosphine, tributylphosphine, triethylphosphite and diethyl diazodicarboxylate (DEAD) or diisopropyl azodicarboxylate (DIAD), in the presence of an inert organic solvent such as THF, toluene, or dichloromethane, under an inert atmosphere such as argon or nitrogen, to form the separate isomers XXIIIS' and XXIIIR' which may be converted to the IS and IR isomers, respectively, as described in Scheme XV Part A. Alternatively, the isomer separation can be carried out at the stage of XXXR and XXXS.

If desired, the phosphorous diamide XXVII may be converted directly into the alcohols XXXR and XXXS by subjecting XXVII to a condensation reaction with aldehyde XXVIII in the presence of a base such as 1,8-diazabicyclo [5.4.0]undec-7-ene (DBU), triethylamine, basic alumina or a fluoride source such as described above or potassium or cesium fluoride, to form a mixture of XXXR and XXXS.

In carrying out the Scheme XV Part C method, the diamine XXR (or XXS) is reacted with phosphorus trichloride at a temperature of within the range of from about 50° C. to about −80° C., preferably from about 0° C. to about −80° C., employing a molar ratio of trichloride:XXR of within the range of from about 3:1 to about 0.8:1, preferably from about 1.5:1 to about 1:1.

The condensation reaction of the phosphorus diamide XXVII with the aldehyde XXVIII is carried out employing a molar ratio of diamide XXVII:aldehyde XXVIII of within the range of from about 2:1 to about 0.8:1, preferably from about 1.5:1 to about 1:1, and a molar ratio of silyl protecting compound:XXVII of within the range of from about 3:1 to about 1:1, preferably from about 1.5:1 to about 1:1.

Reaction of the individual isomers XXIXS and XXIXR with the fluoride source is carried out employing a molar ratio of fluoride source to XXIXS or XXIXR of within the range of from about 4:1 to about 1:1, preferably from about 2:1 to about 1.1:1.

Where the phosphorus diamide XXVII is converted directly to the isomers XXXR and XXXS (see Scheme XV Part C(1)), the condensation reaction of XXVII with the aldehyde XXVIII and base or fluoride source as described above will be carried out essentially under similar conditions previously described for formation of XXIXS and XXIXR, and XXXS and XXXR.

The Mitsunobu displacement of XXXR and XXXS is carried out employing a molar ratio of dimethyldithiocarbamic acid or diethyl derivative, zinc salt or equivalent: XXXS or XXXR of within the range of from about 2:1 to about 0.5:1, preferably from about 1.5:1 to about 0.6:1, and a molar ratio of triphenylphosphine or equivalent:XXXR or XXXS of within the range of from about 4:1 to about 1:1, preferably from about 2:1 to about 1:1.

A preferred method for forming the desired enantiomers of formula I is shown in Scheme XVI wherein a solution of the (R,R)-diamine XXR (or the corresponding (S,S)-diamine XXS where the α-(R) product is desired) in an aprotic solvent such as toluene, benzene, dichloromethane or THF, and weak organic base such as triethylamine, pyridine or diisopropylethylamine is created with phosphorus oxychloride to form the acid chloride XXXI which in solution with an inert organic solvent such as THF, diethylether or dimethoxyethane is subjected to a coupling reaction with

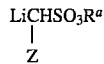     (XXXIA)

(prepared by reaction of an alkylmethanesulfonate XXXIB with alkyllithium) to form the sulfonate XXXII (which is a novel intermediate in accordance with the present invention). Sulfonate XXXII is dealkylated by treatment with a dealkylating agent such as tetrabutylammonium iodide, in the presence of an inert organic solvent such as THF, diethylether or acetone, to form sulfonate XXXIII (which is a novel intermediate in accordance with the present invention) which is made to undergo dianion formation by reaction with a metalating agent such as n-butyllithium, sec-butyllithium, t-butyllithium or lithium diisopropylamide, under an inert atmosphere such as argon or nitrogen, in the presence of an inert organic solvent such as hexane, THF or diethyl ether, and is then treated with alkylating agent $R^1Hal$ in an inert organic solvent such as THF, diethyl ether or hexane to form XXXIV (which is a novel intermediate in accordance with the present invention) optionally in the presence of hexamethyl phosphoramide (HMPA) or tetramethyl ethylenediamine (TMEDA). XXXIV may be subjected to acid hydrolysis and ion exchange to form the individual enantiomer IS, when Z is H.

As indicated, where the starting diamine XX is the (S,S)-enantiomer XXS, the final product will be the IR (R)-enantiomer, when Z is H.

In carrying out the Scheme XVI method, the phosphorus oxychloride will be employed in a molar ratio to the diamine XXR of within the range of from about 1.5:1 to about 0.8:1, preferably from about 1.1:1 to about 0.9:1. The reaction will be carried out at a temperature within the range of from about −20° to about 40° C., preferably from about 0° to about 25° C.

In forming

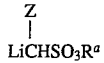     (XXXIA)

(where alkyl is preferably ethyl or cyclohexyl) the alkylmethanesulfonate XXXIB is reacted with the alkyllithium or other strong base an a temperature within the range of from about −90° to about 0° C., employing a molar ratio of alkyllithium:sulfonate XXXIB of within the range of from about 1.2:1 to about 0.8:1, preferably from about 1.1:1 to about 0.9:1.

The

compound XXXIA will be reacted with the acid chloride XXXI at a temperature within the range of from about −90° to about 0° C., preferably from about −80° to about −30° C., employing a molar ratio of Li compound XXXIA to XXXI of within the range of from about 4:1 to about 1:1, preferably from about 2.5:1 to about 1.5:1.

The dealkylation of sulfonate XXXII is carried out employing a molar ratio of iodide:XXXII of within the range of from about 1.5:1 to about 0.9:1, preferably about 1:1.

In the dianion formation, sulfonate XXXIII is treated with the base at a temperature within the range of from about −100° to about 0° C., preferably from about −90° to about −60° C., employing a molar ratio of base:XXXIII of within the range of from about 2:1 to about 0.8:1, preferably from about 1.5:1 to about 1:1.

The lithiated XXXIII compound is alkylated with $R^1Hal$ at a temperature within the range of from about −100° to about 0° C., preferably from about −90° to about −60° C., employing a molar ratio of $R^1Hal$:lithiated halide of within the range of from about 2:1 to about 1:1, preferably from about 1.5:1 to about 1.1:1.

The alkylated sulfonate XXXIV is made to undergo acid hydrolysis by treating XXXIV with strong aqueous acid, such as HCl, sulfuric or formic acids, and then with base such as KOH, NaOH or LiOH to form the major isomer IS where (S) is at the α-center when Z is H. As indicated, where the starting (S,S)-diamine XXS is employed, the major isomer obtained is IR where (R) is at the α-center when Z is H.

An alternative preferred method for forming the desired enantiomers of the invention is shown in Scheme XVII. The starting aldehyde XXVIII (can be prepared by reaction of the alcohol $R^1CH_2OH$ with methylsulfoxide, and oxalyl chloride in the presence of weak organic base such as triethylamine, that is the Swern oxidation or other standard alcohol oxidations), is treated with (2S,4S)-(+)-pentanediol (or the corresponding (2R,4R)-isomer) and p-toluenesulfonic acid in the presence of an inert solvent such as benzene, toluene or dichloroethane, to form the chiral acetal XL. Chiral acetal XL is subjected to an acetal opening reaction wherein acetal XL is reacted with a trialkylphosphite, such as triethylphosphite, in the presence of titanium (IV) chloride, and an inert organic solvent such as methylene chloride, toluene or benzene, under an inert atmosphere such as argon or nitrogen, to form the alcohol XLI which is oxidized via the Swern oxidation, pyridinium chlorochromate (PCC) or Jones reagent under standard conditions, to form XLII. The 3-butene-2-one portion of XLII is eliminated by treating XLII with p-toluenesulfonic acid or methanesulfonic acid in the presence of dioxane, or acetonitrile and water to form the diester XLIII which is subjected to a Mitsunobu displacement under the same conditions as described for the conversion of XXXS/R to XXIIIS'/R'. See P. Rollin, supra, to form XLIV. Compound XLIV is dealkylated by reaction with a dealkylating agent such as bromotrimethylsilane or iodotrimethylsilane in the presence of an inert organic solvent such as methylene chloride, benzene or toluene, under an inert atmosphere such as argon or nitrogen, to form the diacid XLV which is oxidized by treatment with hydrogen peroxide in formic acid, acetic acid or mixtures thereof or other oxidants as described for Scheme XV, and then treated with alkali metal hydroxide such as KOH, NaOH or LiOH, or ion exchange resin as described hereinbefore to form the (R)-enantiomer IR.

It will be appreciated that in carrying out the above method, where the aldehyde XXVIII is reacted with the (R,R)-diol, the final product obtained will be the α-(S)-enantiomer IS.

In carrying out the method of Scheme XVII, the (2S,4S)-(+)-pentanediol will be reacted with the starting aldehyde XXVIII at a temperature within the range of from about 25° to about 100° C., preferably from about 60° to about 90° C., employing a molar ratio of diol:XXVII of within the range of from about 4:1 to about 0.8:1, preferably from about 2:1 to about 1:1. The resulting chiral acetal XL is reacted with the trialkylphosphite and titanium(IV)chloride or equivalent at a temperature within the range of from about −90° to about −20° C., preferably from about −80° to about −40° C., employing a molar ratio of phosphite:XL of within the range of from about 5:1 to about 1:1, preferably from about 3:1 to about 2:1, and a molar ratio of phosphite:titanium tetrachloride of within the range of from about 3:1 to about 1:1, preferably from about 1.2:1 to about 1.6:1, to form alcohol XLI.

The oxidation of alcohol XLI is carried out at a temperature within the range of from about −80° to about 0° C., and the elimination reaction involving XLII is carried out at a temperature within the range of from about 30° to about 150° C., preferably from about 80° to about 120° C., employing a molar ratio of p-toluenesulfonic acid or equivalent:XLII of within the range of from about 0.5:1 to about 0.005:1, preferably from about 0.1:1 to about 0.05:1.

The Mitsunobu displacement reaction is as described previously for Scheme XV Part C.

Dealkylation of XLIV is carried out employing a molar ratio of dealkylating agent:XLIV of within the range of from about 10:1 to about 2:1, preferably from about 6:1 to about 4:1.

Scheme XVIII sets out a purification procedure wherein the desired individual enantiomers (salt thereof) is subjected to ion exchange ($H^+$ form) such as by treatment with AG 50-X8 ion exchange resin, to form the free triacid IQ which is treated with an amine such as adamantanamine or (S)-(−)-α-methylbenzylamine (under an inert atmosphere such as argon where the latter amine is employed), in a molar ratio of amine:IQ within the range of from about 2.2:1 to about 1.9:1, preferably about 2:1, to form the corresponding bisamine salt IQ' which is separated out by recrystallization. The so-formed diamine salt IQ' may be treated with ion exchange resin ($M^+$ form) such as Ag50-X8 ($K^+$ form) or basified with MOH (where M is K, Li or Na) to form the purified enantiomer. Amine salts IQ' of chiral amines and racemic triacid I may be used to resolve the racemate into α-(R) and (α)-S isomers by recrystallization.

If desired, the diamine salt IQ' may be treated with ion exchange resin ($H^+$ form) to form the triacid IQ which may be treated with ion exchange resin ($M^+$ form) or basified with MOH to form the purified enantiomers, IS or IR.

Scheme XIX set out a reaction sequence for preparing prodrugs of the desired enantiomer. As seen, the starting enantiomer IS (or IR) is treated with a silver salt such as silver nitrate to form the silver salt IAg which is alkylated by treatment of IAg (optionally in the presence of 4A molecular sieves, anisole, thioanisole, 2,6-di-t-butylpyridine and mixtures thereof) with alkylating agent XI to form triester LI.

The triester LI is subjected to solvolysis in water, or optionally a water-miscible solvent such as ethanol, methanol, 2,2,2-trifluoroethanol, acetonitrile or mixtures of water and the organic solvent, at 0° C. to 60° C., to form the diester LII which is made to undergo salt formation by treatment of LII with an alkali metal phosphate buffer, such as potassium phosphate buffer, or ion exchange, to form the salt IS'.

The various acid and salt forms of the invention ID, IE, IF, IG, IL, IM, IN, IO, IP, IQ, IR, IS, IR', IS', LIIR, LIIS, IT and IU can be interconverted by standard means, including ion exchange chromatography. It should be understood that all acids can be isolated either as salts (M=pharmaceutically acceptable cations such as $Li^+$, $Na^+$, $K^+$, $NH_4^+$), or free acids (M=H).

Examples of starting alkylating agents that is $R^1X$ or $R^1Hal$ suitable for use herein include the following which are either known in the literature or are simple derivatives of known compounds prepared by employing conventional procedures.

It will be appreciated that the $R^1X$ compounds listed in the following table represent all possible stereoisomers.

$R^1Hal$ where Hal is Cl, Br or I, or Otosyl or $OSO_2CF_3$ is as follows in A. through F.

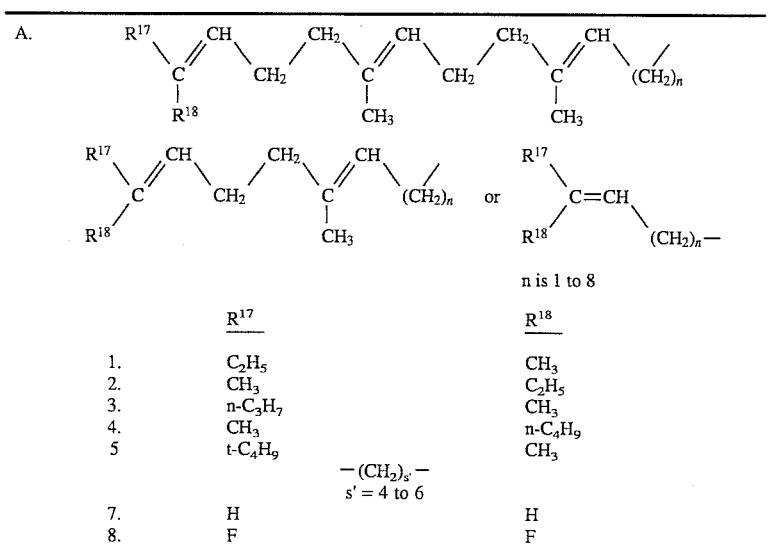

-continued
| | | | |
|---|---|---|---|
| | 9. | Cl | Cl |
| | 10. | CH$_2$F | CH$_3$ |
| | 11. | —CH=CH$_2$ | H |
| | 12. | CF$_3$(CH$_2$)$_t$ | H |
| | | t = 0 to 8 | |
B. 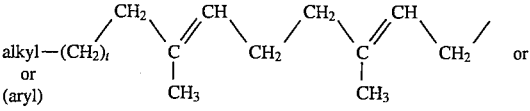 or
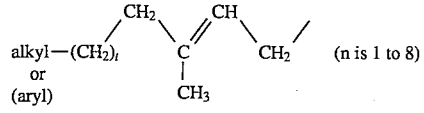 (n is 1 to 8)
1. alkyl(CH$_2$)$_t$—
CH$_3$(CH$_2$)$_t$ where t is 0 to 8
2. 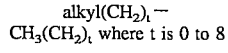 where t is 0 to 8
3. 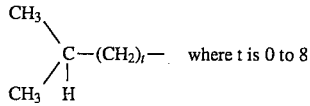 where t is 0 to 8
4. 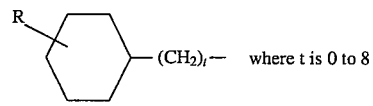 where t is 0 to 8
5. 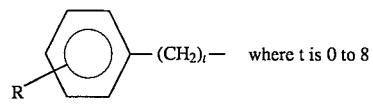
6. 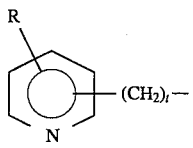
7. 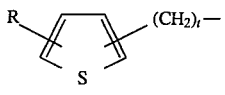
8. 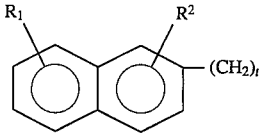
9. CF$_3$(CH$_2$)$_t$—
10. 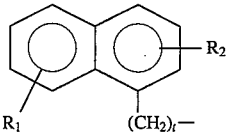
11. 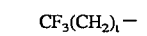

-continued

12.

[structure: benzene ring with R₃ substituent and —N(H)—(CH₂)ₜ—]

13.

[structure: benzene ring with R₃ substituent and —S—(CH₂)ₜ—]

15.

[structure: pyridine ring (N) with R₃ substituent and —O—(CH₂)ₜ—]

15.

[structure: cycloalkyl ring (CH₂)ₓ with —(CH₂)ₜ—]

Examples 5 to 10, t = 0 to 8
$R_1$, $R_2$ and $R_3$ may be the same or different and can be any of the radicals included in $R^6$.
Examples 11 to 15
t = 1 to 8
x = 3 to 8

C.

$$CH_3-C(CH_3)=C-CH_2+CH_2-C(CH_3)=C-CH_2\overline{)_t}+CH_2)_n-$$

t = 0, 1, 2, 3    n = 0 to 8

$$H-C(CH_3)(CH_3)-CH_2-CH_2+CH_2-CH(CH_3)-CH_2-CH_2\overline{)_t}+CH_2)_n-$$

t = 0, 1, 2, 3    n = 0 to 8

D.

[structure with CH₃, CH, CH₂, R²¹, R²², R²³ groups and (CH₂)ₙ]

n = 1 to 8 or

[structure with CH₃, CH, CH₂, R²¹, R²² groups and (CH₂)ₙ]

n = 1 to 8

| | $R^{21}$ | $R^{22}$ | $R^{22}$ |
|---|---|---|---|
| 1. | $C_2H_5$ | $C_2H_5$ | $CH_3$ |
| 2. | $CH_3$ | $CH_3$ | $C_2H_5$ |
| 3. | $CH_3$ | $C_2H_5$ | $C_2H_5$ |
| 4. | $C_2H_5$ | $C_2H_5$ | $C_2H_5$ |
| 5. | $CH_3$ | $C_2H_5$ | $CH_3$ |
| 6. | $CH_3$ | H | $CH_3$ |
| 7. | $CH_3$ | $CH_3$ | H |
| 8. | H | H | H |
| 9. | $CF_3$ | $CH_3$ | $CH_3$ |
| 10. | $CH_3$ | $CF_3$ | $CH_3$ |
| 11. | $CH_3$ | $CH_3$ | $CF_3$ |
| 12. | $CF_3$ | $CF_3$ | $CH_3$ |
| 13. | $CF_3$ | $CF_3$ | $CF_3$ |

E. 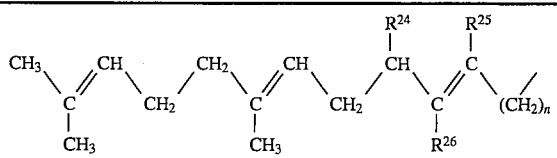
or    n = 1 to 8
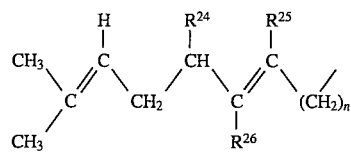
| | $R^{24}$ | $R^{25}$ | $R^{26}$ |
|---|---|---|---|
| 1. | H | I | H |
| 2. | H | H | I |
| 3. | H | $CH_3$ | $CH_3$ |
| 4. | $CH_3S$ | $CH_3$ | H |
| 5. | F | $CH_3$ | H |
| 6. | $CH_3$ | $CH_3$ | H |
| 7. | H | $CH_3$ | $CH_3$ |
| 8. | H | $CH_3$ | Cl |
| 9. | H | $CF_3$ | H |
| 10. | H | Cl | H |
| 11. | H | $CH_3$ | $(CH_3)_3Si$ |
| 12. | H | $CH_3$ | F |
| 13. | H | $CF_3$ | $CH_3$ |
| 14. | H | $CH_3$ | $CF_3$ |
F. Other examples of $R^1$ include the following
1. 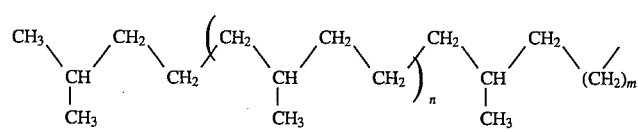
(n is 0, 1)
2. 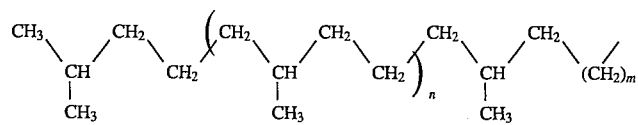
(n is 0, 1)
3. 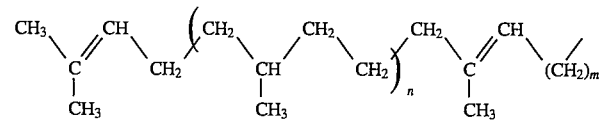
(n is 0, 1)
4. 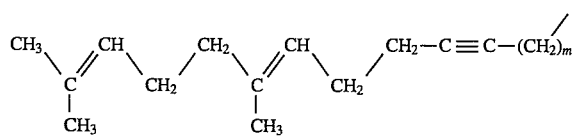
5. 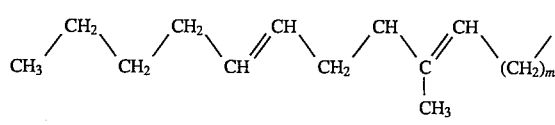
6. 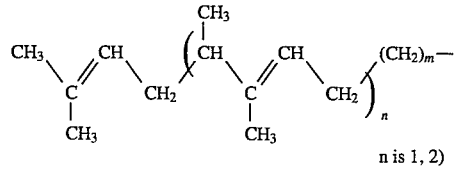
n is 1, 2)

7. 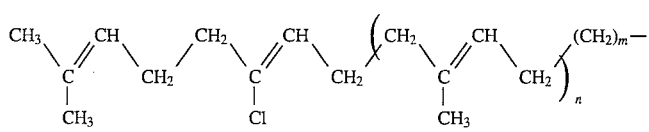
(n is 0, 1)
In Examples 1 to 5, m is 1 to 8.
In Examples 6 and 7, m is 0 to 8.
8. 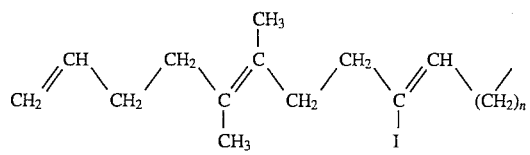
9. 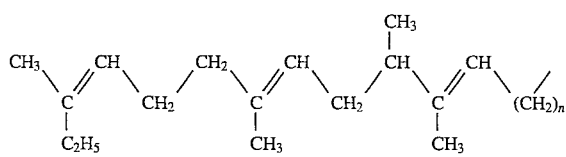
10. 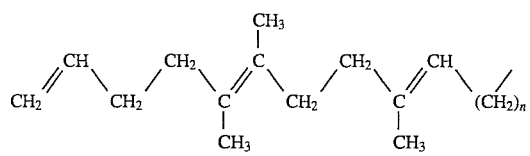
11. 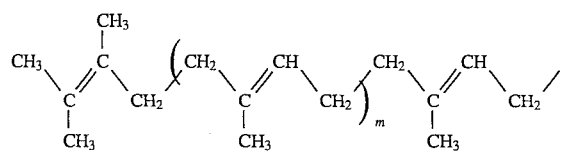
(m is 1, 2)
12. 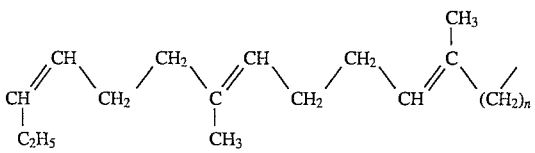
13. 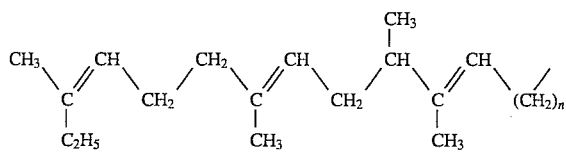
In Examples 8 to 13, n is 1 to 8.
14. 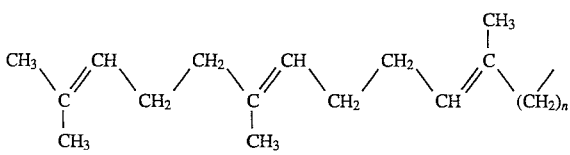
(n is 1 to 8)
15. 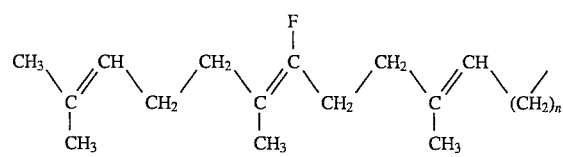
(n is 1 to 8)

-continued
16. 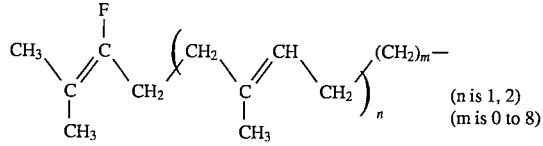
(n is 1, 2)
(m is 0 to 8)
17. 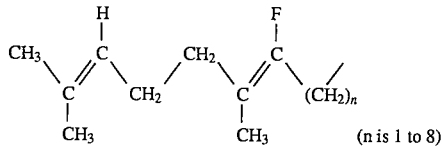
(n is 1 to 8)
18. 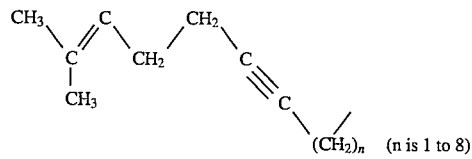
(n is 1 to 8)
19. 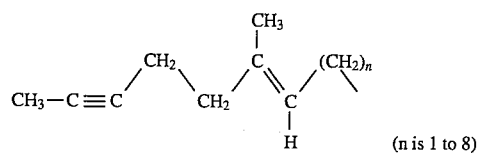
(n is 1 to 8)
20. $CH_3-C{\equiv}C-(CH_2)_n-$  (n = 4–12)
21. 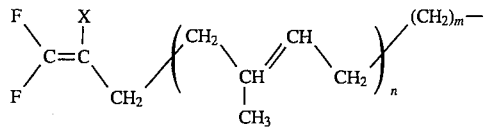
X = H, F, $CH_3$
n is 1 or 2
m is 0 to 8
22. $CH_3-C{\equiv}C-(CH_2)_n-C{\equiv}C-(CH_2)_m-$  (n = 0–10) (m is 0 to 8)
23. 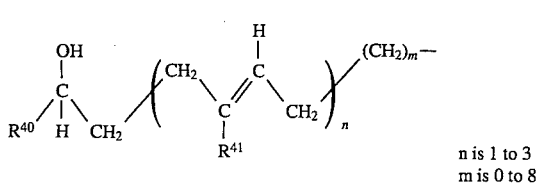
n is 1 to 3
m is 0 to 8
$R^{40}$ = H, alkyl, cycloalkyl, or aryl such as
methyl, ethyl, isopropyl, pentyl, phenyl
and cyclopentyl
$R^{41}$ = alkyl such as methyl, ethyl or halo
such as Cl or F
24. 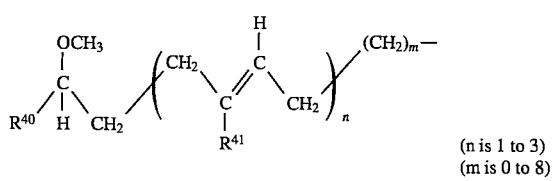
(n is 1 to 3)
(m is 0 to 8)
25. 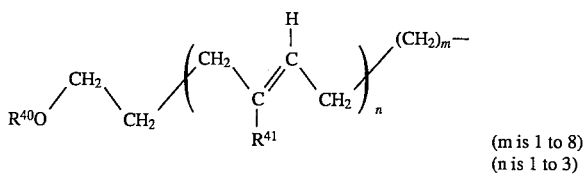
(m is 1 to 8)
(n is 1 to 3)

-continued

26. 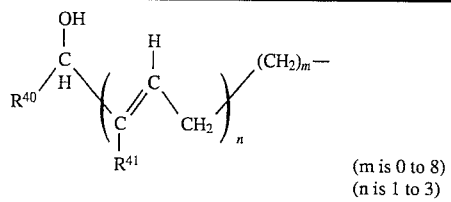

(m is 0 to 8)
(n is 1 to 3)

27. 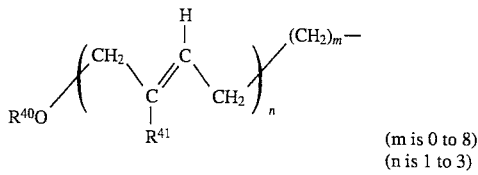

(m is 0 to 8)
(n is 1 to 3)

28. 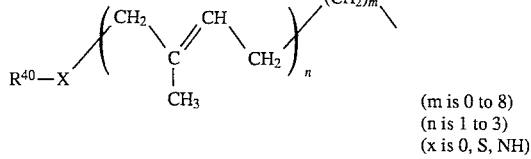

(m is 0 to 8)
(n is 1 to 3)
(x is O, S, NH)

29. 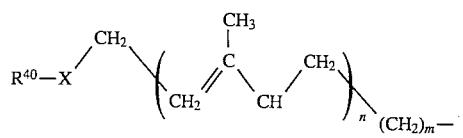

x is O, S, NH, $CH_2$)
(m is 0 to 8)
(n is 1 to 3)

Additional compounds within the scope of the invention are set out below.

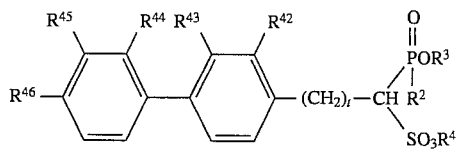

| | $R^{42}$ | $R^{43}$ | $R^{44}$ | $R^{45}$ | $R^{46}$ | t |
|---|---|---|---|---|---|---|
| 30) | H | H | H | H | n-$C_3H_7$ | 3 |
| 31) | H | H | H | H | n-$C_4H_9$ | 3 |
| 32) | H | H | H | H | $(CH_3)_2$—C=CH— | 4 |
| 33) | H | H | H | H | $(CH_3)_2$—C=CH—$CH_2$— | 2 |
| 34) | $CH_3$ | H | $CH_3$ | H | ▷—$CH_2$— | 3 |
| 35) | H | H | $CH_3$ | H | $(CH_3)_2$—CH—$CH_2$—O— | 3 |
| 36) | H | $CH_3$ | $CH_3$ | H | n-$C_3H_7$ | 3 |
| 37) | $CH_3O$ | H | H | H | n-$C_4H_9$ | 3 |
| 38) | H | H | H | H | $(CH_3)_2$—C=CH— | 3 |
| 39) | H | H | H | H | $(CH_3)_2$—C=CH—$CH_2$— | 4 |
| 40) | $CH_3$ | H | H | H | ▷—$CH_2$— | 5 |
| 41) | F | H | $CH_3$ | H | n-$C_3H_7$ | 3 |
| 42) | $CH_3$ | H | F | H | n-$C_4H_9$ | 3 |
| 43) | H | $CH_3$ | H | $CH_3$ | $(CH_3)_2$—C=CH— | 3 |
| 44) | H | H | H | $CF_3$ | $(CH_3)_2$—C=CH—$CH_2$— | 3 |
| 45) | H | H | H | F | ▷—$CH_2$— | 3 |
| 46) | H | Cl | Cl | H | $CH_2$=CH—$CH_2$— | 3 |

| | | | | | | |
|---|---|---|---|---|---|---|
| 47) CH₃ | H | H | H | C₄H₉ | | 3 |
| 48) H | H | OH | H | C₃H₇ | | 3 |
| 49) H | H | OCH₃ | H | C₃H₇ | | 4 |
| 50) H | H | CH₃ | H | C₃H₇ | | 3 |
| 51) H | OH | H | H | C₃H₇ | | 3 |
| 52) H | OCH₃ | H | H | C₃H₇ | | 4 |
| 53) H | CH₃ | H | H | C₃H₇ | | 3 |

$R^2$ = H, OMetal, alkyl, aryl
$R^3$ = H, metal ion or alkyl
$R^4$ = H, metal ion or alkyl 54) 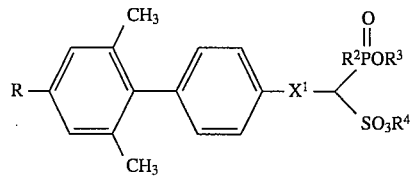

55) 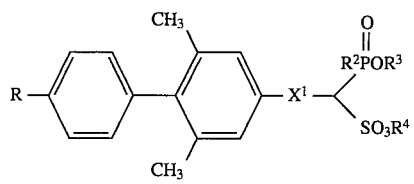

56) 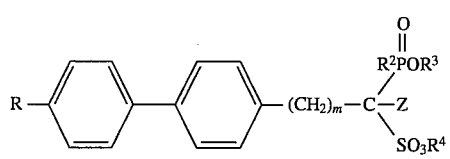

Re 54) to 56)
R is n-C₃H₇, n-C₄H₉, (CH₃)₂—C═CH—, CH₃—CH═CH—CH₂—,
(CH₃)₂—CH═CH—CH₂—, CH₂═CH—CH₂O—, (CH₃)₂—CH—O—, (CH₃)₂CHCH₂O—,

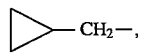

CH₂═CH—CH₂—, CH₂═CH—CH₂CH₂—, phenyl, pyridyl

57) 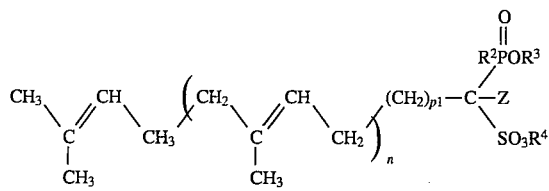

Z = Cl, F, alkyl such as methyl, ethyl,
propyl or allyl
n = 0, 1, 2
$p^1$ = 0–8
m = 2–8
In compounds 49) to 52)
$R^3$ = H, metal ion or alkyl
$R^4$ = H, metal ion, alkyl or aryl
$R^2$ = H, Ometal, alkyl, aryl 58) 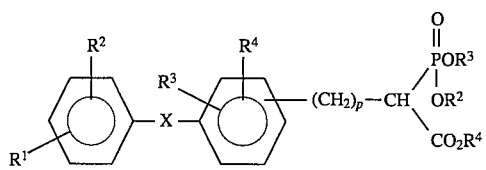

X is O, S NH, SO, SO₂, CR⁵R⁶, C═O
$R^1$, $R^2$, $R^3$, $R^4$, $R^5$ and $R^6$ are independently H,
halogen, C₁–C₅alkyl, C₁–C₅alkenyl, C₁–C₅alkoxy,
aryl, arylalkyl, aryloxy; for $R^5$ and $R^6$, halogen
can be fluorine only.

-continued
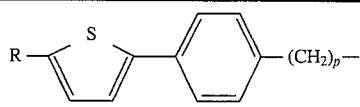
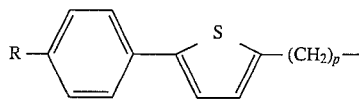
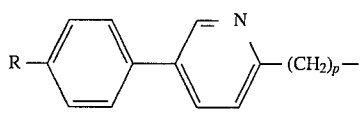
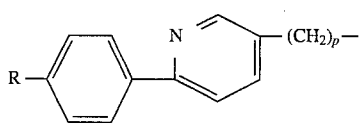
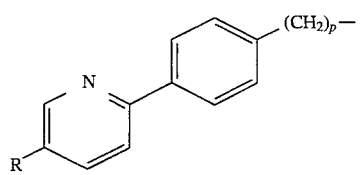
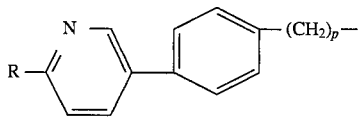
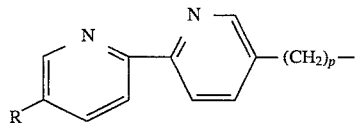
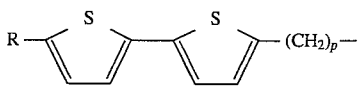
R is as defined for 54) to 56).
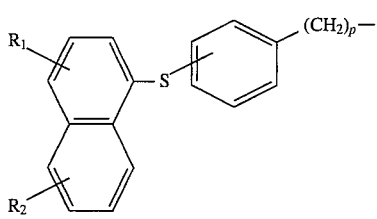
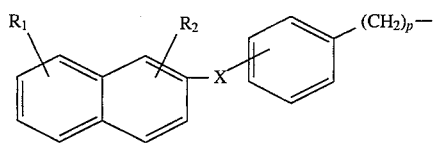
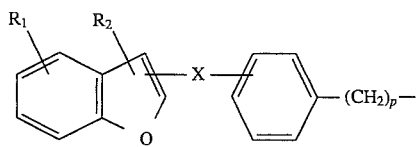

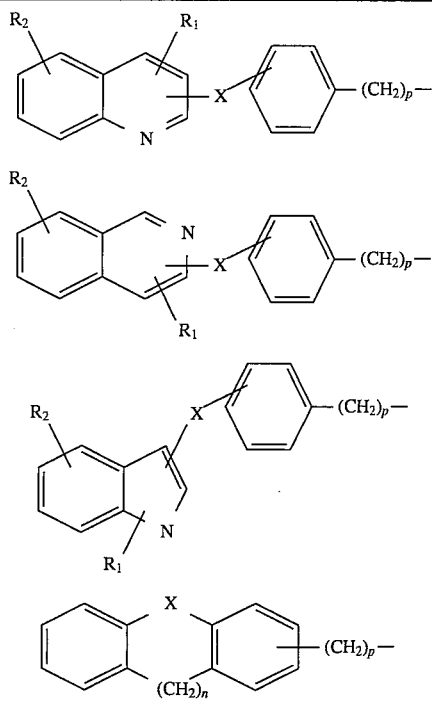

X = bond, O, NH, S, CH₂, CR⁵R⁶
p = 1 to 8
n = 0 to 4; R¹, R², R⁵ and R⁶ are independently halogen, alkyl, alkenyl, alkoxy, aryl, H, aryloxy; for R⁵ and R⁶ halogen can be fluorine only.

Preferred are enantiomers of compounds of formula I in the (S) configuration of the above preferred compounds, that is

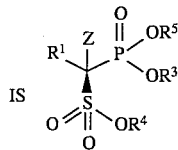

wherein Z is H, $R^1$ is preferably $Ar^1$—O—$Ar^2$—$(CH_2)_p$—, $R^3$, $R^5$ and $R^4$ are an alkali metal such as K or Na.

More preferred are prodrug (P.D.) esters of the (S)-enantiomer (IS), that is

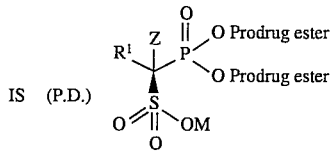

Most preferred are compounds of formula IS where $R^1$ is $Ar^1$—O—$Ar^2$—$(CH_2)_p$—

$R^4$ is an alkali metal such as K or Na

Z is H and Prodrug ester is bis(pivaloyloxymethyl) ester.

In addition, in accordance with the present invention new intermediates are provided which are prepared as described above, and have the following formulae:

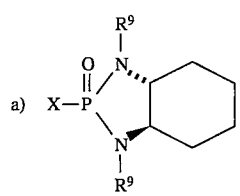   (XXIIIS or XXIIIR, XXIIIS' or XXIIIR')

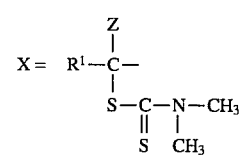   (XXV)

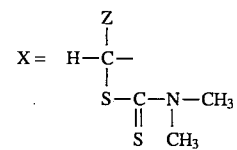   (XXXII)

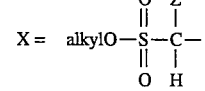

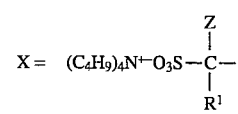   (XXXIV)

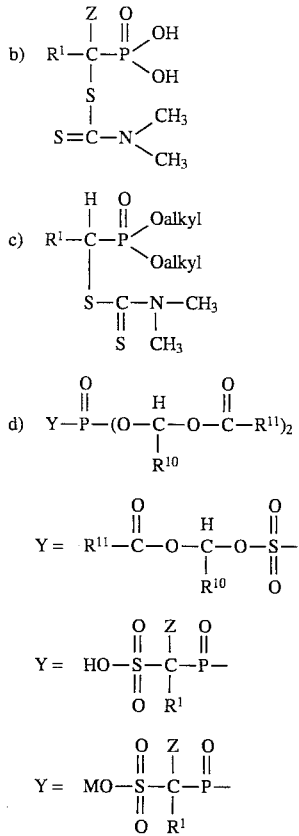

The compounds of Formula I of the invention inhibit cholesterol biosynthesis by inhibition of de novo squalene production. These compounds inhibit the squalene synthetase enzyme and, in addition, some of the compounds of Formula I of the invention inhibit other enzymes in the pathway from isopentenyl diphosphate to squalene, that is, farnesyl diphosphate synthetase and isopentenyl diphosphate-dimethylallyl diphosphate isomerase.

The compounds of the invention are useful in treating hyperlipoproteinemia, hyperlipidemia, hypercholesterolemia, hypertriglyceridemia, combined hypercholesterolemia and hypertriglyceridemia, and/or in preventing development of and/or treating atherosclerosis. Thus, the compounds of the invention may be used to treat diseases such as chylomicronemia syndrome, Type I hyperlipoproteinemia, familial combined hyperlipoproteinemia, familial hypertriglyceridemia, mixed hyperlipoproteinemia, familial hypercholesterolemia and Type III hyperlipoproteinemia and/or atherosclerosis.

In addition, the compounds of the invention may increase plasma high density lipoprotein cholesterol levels.

The compounds of the invention may also be useful in inhibiting formation of gallstones, treating hepatitis D (by virtue of protein prenyltransferase inhibition, Glenn et al, Science, Vol. 256, pp. 1331–1333, May 29, 1992), treating tumors, lowering blood pressure, lowering blood sugar, treating diabetes mellitus, treating inflammation, as a diuretic, as an inotropic agent, as an anti-arthritic (antirheumatic) agent, in treating other diseases of calcium and phosphate metabolism including treatment of bone resorption, Paget's disease, osteoporosis, calcification of joints, implants and metastasis, as antitartar and anticalculus agents in toothpastes and mouthwashes, treating various stones and calculi, treating sickle cell anemia, treating hypoxia and ischemic tissue, and as an anti-ameobal agent, as well as for use in complexes with technetium-99m and radioiodinated derivatives for use as diagnostics.

U.S. application Ser. No. 774,957, filed Oct. 11, 1991, discloses that post-translational modification of CAAX box containing proteins may be inhibited by administering a protein-prenyl transferase inhibitor which inhibits the transfer of the prenyl group [such as farnesyl (in the case of ras oncogene products), geranyl or geranylgeranyl] to the cysteine of the CAAX box by the protein-prenyl transferase enzyme. The protein-prenyl transferase inhibitor will block the protein-prenyl transferase enzyme from catalyzing the transfer of the prenyl group (for example, farnesyl, geranyl or geranyl-geranyl) from the prenyl pyrophosphate to the cys residue of the CAAX box, such as the ras p21 cys, or to the CAAX box cysteine of other CAAX box containing proteins. In the case of ras p21 oncogene products, inasmuch as the cys is not farnesylated, in the presence of the protein prenyl transferase inhibitor, it cannot effect interaction of the ras protein with the membrane so that neoplastic transformation of the cell will be prevented. In this manner protein-prenyl transferase inhibitors prevent neoplastic transformation of the cell, thereby acting as an anti-cancer agent for the treatment of and/or prevention of ras-related tumors.

Examples of CAAX box containing proteins which have been demonstrated or are believed to undergo prenylation include, but are not limited to, ras, nuclear lamins, α or γ subunits of heterotrimeric G-proteins, γ-subunits of retinal transducin, G25K and K-rev p21, and protein families including rho, rap, rac, ral, and rab.

The present invention includes a method for blocking or preventing the prenylation of CAAX box containing proteins such as rasoncogene products, and thereby inhibit disease promoting effects of the CAAX box containing protein or more specifically prevent and/or treat ras-related tumors, by administering to a patient in need of treatment a therapeutic amount of a compound of Formula I of the invention which serves as a protein-prenyl transferase inhibitor.

The Formula I protein-prenyl transferase inhibitors, unlike HMG CoA reductase inhibitors, will interfere with prenylation of the ras oncogene products and inhibit their transforming activity, yet may or may non interfere with the synthesis of FPP, a precursor in the synthesis of ubiquinones, dolichols and Haem A.

The compounds of the invention may also be employed in combination with an antihyperlipoproteinemic agent, hypocholesterolemic agent, and/or hypotriglyceridemic agent, and/or antiatherosclerotic agent such as one or more HMG CoA reductase inhibitors, for example, pravastatin, lovastatin, simvastatin, velostatin, fluvastatin, rivastatin, compactin, SDZ-63, 370 (Sandoz), CI-981 (W-L), HR-780, L-645, 164, CL-274,471, dalvastatin, α-, β-, and γ-tocotrienol, (3R, 5S, 6E)-9,9-bis(4-fluorophenyl)-3,5-dihydroxy-8-(1-methyl-1H-tetrazol-5-yl)-6,8-nonadienoic acid, L-arginine salt, (S)-4-[[2-[4-(4-fluorophenyl)-5-methyl-2-(1-methylethyl)-6-phenyl-3-pyridinyl]ethenyl]hydroxyphosphinyl]-3-hydroxybutanoic acid, disodium salt, BB-476, (British Biotechnology), dihydrocompactin, [4R-[4α,6β(E)]]-6-[2-[5-(4-fluorophenyl)-3-(1-methylethyl)-1(2-pyridinyl)-1H-pyrazol-4-yl]ethenyl]tetrahydro-4-hydroxy-2H-pyran-2-one, and/or 1H-pyrrole-1-heptanoic acid, 2-(4-fluorophenyl)-β,δ-dihydroxy-5-(1-methylethyl)-3-phenyl-4-[(phenylamino)carbonyl]calcium salt [R-(R*,R*)]; one or more fibric acid derivatives such as clofibrate, bezafibrate, Lopid(gemfibrozil) one or more other cholesterol biosynthesis inhibitors, such as NB-598, N-(1-oxododecyl)-4α,10-dimethyl-8-aza-trans-decal-3β-ol, 2,4-undecadienoic acid, 11-[3-(hydroxymethyl)-4-oxo-2-oxetanyl]-3,5,7-trimethyl-, [2R-[2α(2E,4E,7R*),3β]]; one or more bile acid sequestrants, for example, cholestyramine, colestipol, polidexide (DEAESephadex); one or more antioxidants, for example probucol and Vitamin E; and/or one or more other lipid lowering and/or antiatherosclerotic agents, for example nicotinic acid or derivatives thereof, neomycin, p-aminosalicylic acid, probucol, hydroxypropylmethylcellulose, LS-2904, ethanol, 2-[[1-methyl- 2-[3-(trifluoromethyl)phenyl]ethyl]amino]benzoate (ester).

The above compounds to be employed in combination with the squalene synthetase inhibitor of the invention will be used in amounts as indicated in the Physicians' Desk Reference (PDR).

The compounds of the invention may also be employed with sodium lauryl sulfate of other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

A further aspect of the present invention is a pharmaceutical composition consisting of at least one of the compounds of the invention, such as Formula I, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc., by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectable preparation is produced by asceptically placing 250 mg of sterile active ingredient into a vial, asceptically freeze-drying and sealing. For use, the contents of the vial are mixed with 2 mL of physiological saline, to produce an injectible preparation.

The following Examples represent preferred embodiments of the present invention.
Introduction to Experimental
All temperatures are reported in degrees Centigrade.
$^1$H and $^{13}$C chemical shifts are reported as δ-values with respect to Me$_4$Si (δ=0). $^{31}$P spectra were obtained using 85% H$_3$PO$_4$ as an external reference (δ=0). Coupling constants J are reported in Hz. For mass spectra (mass spec or MS) the value utilized for the parent M is that of the salt form which was prepared and tested.

All reactions were carried out under an atmosphere of dry argon or nitrogen. The following reagents and solvents were distilled prior to use from the indicated drying agents, where applicable: CH$_2$Cl$_2$, 2,4,6-collidine, and diisopropylamine (CaH$_2$); THF and diethyl ether (K, benzophenone); N,N-diethyltrimethylsilylamine and oxalyl chloride. Benzene was passed through neutral alumina (activity I) and stored over 4A-molecular sieves. Lithium bromide was dried at 100° C. over P$_2$O$_5$.(E,E)-Farnesol was purchased from Aldrich Chemical Company.

TLC was performed on E. Merck Silica Gel 60 F-254 plates (0.25 mm) or E. Merck Cellulose F plates (0.1 mm). Flash chromatography was carried out using E. Merck Kieselgel 60 (230–400 mesh).

Reverse-phase chromatographic purification of salts or mixed ester salts was carried on CHP20P gel or SP207SS gel, highly porous, polystyrenedivinyl benzene copolymers available from Mitsubishi Chemical Industries. The indicated general procedure was followed: An FMI Model RP-SY pump was utilized for solvent delivery. A column of CHP20P or SP207SS (2.5 cm diameter, 12–22 cm height) ws slurry packed and washed with water (500–1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300–500 mL of the organic solvent, or an aqueous-, organic mixture, just beneath the surface of a reservoir containing 300–500 mL of pure water. To start the gradient, the stopcock of the separatory funnel was opened, so that as the solvent was withdrawn by the pump from the reservoir, it was replaced with the solvent from the separatory funnel. HPLC-grade solvents were employed. Fractions were collected (10–15 mL each) at a flow rate of 5–10 mL per minute. Those fractions than contained pure product as judged by TLC or HPLC were pooled, the organic solvents were evaporated and the aqueous residue was lyophilized to dryness.

EXAMPLE 1

(E,E)-(6,10,14-Trimethyl-2-phosphono-5,9,13-pentadecatriene- 1-sulfonic acid, trisodium salt
A. Bishomofarnesol
(1) (E,E)-3,7,11,-Trimethyl-2,6,10-dodecatrieyl bromide (farnesyl bromide)

A solution of 1.00 g (4.5 mmol) of (E,E)-farnesol (Aldrich, further purified by flash chromatography) in 10 mL of distilled ether at 0° C. under argon in the dark was treated dropwise with a solution of 195 µL (2.05 mmol, 0.45 eq.) of PBr$_3$ in 2 mL of diethyl ether (ether). The resultant mixture was stirred at 0° C. for one hour, then quenched with water and separated. The organic phase was washed with 5 mL of H$_2$O, 5 ml of saturated NaHCO$_3$, and 5 mL of brine, dried over Na$_2$SO$_4$ and evaporated to give 1.26 g (98%) of crude bromide as a clear oil.

TLC Silica (2:8 ethyl acetate:hexane) Rf=O.69.
$^1$H NMR (CDCl$_3$, 270 MHz): δ5.52 (t, 1H, J=8.5 Hz), 5.08 (m, 2H), 4.01 (d, 2H, J=8.5 Hz), 2.20–1.90 (m, 8H), 1.73 (s, 3H), 1.68 (s, 3H), 1.60 (s, 6H) ppm.

(2) (E,E)-5,9,13-Trimethyl-4,8,12-tetradecatrienoic acid, 1.1-dimethylethyl ester To a solution of 9.60 mL (68.5 mmol, 1.5 eq.) of diisopropylamine in 100 mL of tetrahydrofuran (THF) at −78° C. under argon was added 28.2 mL (45.0 mmol, 1.0 eq.) of 1.6M n-butyllithium in hexanes over 20 minutes. After warming to 0° C. for 15 minutes, the solution was recooled to −78° C. and 6.05 mL (45 mmol, 1.0 eq.) of t-butyl acetate was added over 20 minutes. After an additional 15 minutes, 16.0 mL (92 mmol, 2.05 eq.) of hexamethylphosphoramide (HMPA) was added, followed by a solution of 12.53 g (45.0 mmol) of Part A (1) farnesyl bromide in 100 mL of THF over 20 minutes. The reaction was stirred at −78° C. for 2.5 hours, quenched with saturated NH$_4$Cl and allowed to warm to room temperature. After diluting with 400 mL of ethyl acetate, the mixture was washed with four 100 mL portions of water, and 200 mL of brine, dried over MgSO$_4$ and evaporated to provide 12.96 g of crude product as a yellow oil. Purification by flash chromatography on 1 kg of silica gel, eluted with 1:9 ethyl acetate:petroleum ether afforded 9.39 g (65%) of title compound as a pale yellow oil.

TLC Silica gel (2:98 ethyl acetate:hexane) R$_f$=0.16.

IR(neat) 2977, 2925, 2857, 1733, 1452, 1368, 1258, 1149 cm$^{-1}$.

$^1$H NMR(CDCl$_3$, 270 MHz): δ5.10 (m, 3H), 2.25 (m, 4H), 2.10–1.90 (m, 8H), 1.68 (s, 3H), 1.62 (s, 3H), 1.59 (s, 6H), 1.44 (s, 9H) ppm.

Mass spec. (CI-CH$_4$/N$_2$O) (+ ions) m/e 165 (M+H-C$_4$H$_8$), 247, 183, 137, 68, 67. (– ions) m/e 319 (M-H), 279, 251, 100.

(3) Bishomofarnesol

To a stirred solution of 5.00 g (15.6 mmol) of Part (2) compound in 45 mL of dry diethyl ether at 0° C. under argon was added 592 mg (15.6 mmol, 1 mol-eq.) of lithium aluminum hydride, and the resulting suspension was stirred at room temperature for 20 hours. After cooling to 0° C., the reaction was quenched by treating with 5 mL of H$_2$O, 5 mL of 15% NaOH, and 15 mL of H$_2$O and stirring the suspension for ½ hour. After adding Na$_2$SO$_4$, the slurry was filtered through Celite, washing well with diethyl ether and evaporated to obtain 3.62 g of crude product. Purification by flash chromatography on 300 g of silica gel, eluted with 1:9 ethyl acetate:petroleum ether provided 3.516 g (90%) of bishomofarnesol as a colorless liquid.

TLC Silica gel (2:8 ethyl acetate (EtOAc):hexane) R$_f$=0.19.

IR(neat) 3330, 2964, 2926, 2873, 2958, 1448, 1384, 1107, 1059, 401 cm$^{-1}$.

$^1$H NMR(CDCl$_3$, 270 MHz): δ5.10 (m, 3H), 3.63 (t, 2H, J=6.5 Hz), 2.20–1.90 (m, 10H), 1.68 (s, 3H), 1.62 (s, 3H), 1.60 (s+m, 8H) ppm.

Mass Spec (CI-CH$_4$/N$_2$O, + ions) m/e 251 (M+H), 249 (M+H-H$_2$), 137, 123, 109, 69.

A$^1$. Bishomofarnesol (alternative preparation)

(1) (E,E)-(3,7,11-Trimethyl-2,6,10-undecadienyl)propanedicarboxylic acid, diethyl ester To a suspension of 1.62 g (40.5 mmol, 3 eq.) of a 60% suspension of sodium hydride in mineral oil (washed three times with pentane) in 150 mL of tetrahydrofuran at room temperature under argon was slowly added 6.15 mL (40.5 mmol, 3 eq.) of diethyl malonate. The resulting solution was stirred for 0.5 hours, then treated with a solution of 3.83 g (13.5 mmol) of farnesyl bromide in 10 mL of tetrahydrofuran. After stirring for 6 hours, the reaction was quenched with saturated NH$_4$Cl and diluted with 300 mL of diethyl ether. The organic layer was washed with two 100 mL portions of water and 100 mL of brine, dried over MgSO$_4$ and evaporated and the bulk of the diethyl malonate removed by spinning under high vacuum to afford 4.29 g (87%) of crude title product.

TLC Silica gel (ethyl acetate:hexane 1:9) R$_f$=0.37.

(TLC shows slight amount of diethyl malonate and a second by-product.)

(2) (E,E)-5,9,13-Trimethyl-4,8,12-tetradecatrienoic acid, ethyl ester

A mixture of 4.103 g (11.2 mmol) of Part A$^1$ (1) diester, 200 μL (11.2 mmol, 1 eq.) of water and 950 mg (22.4 mmol. 2 eq.) of lithium chloride in 20 mL of dimethyl sulfoxide was heated at reflux (~190° C.) for four hours. After cooling, the reaction mixture was diluted with 180 mL of a 1:1 mixture of diethyl ether:petroleum ether and washed with five 50 mL portions of water and 50 mL of brine, dried over MgSO$_4$ and evaporated to yield 3.623 g of crude product as a yellow-orange oil. Kugelrohr distillation at 180° C. (meter setting) and 0.025 mm allowed the collection of 2.100 g of a pale yellow oil, which was, however, still contaminated (by TLC). The distillation, therefore, is unnecessary and should not be performed. Flash chromatography on 180 g of silica gel, eluted with 3:97 ethyl acetate:petroleum ether provided 1.844 g (56%) of desired title product as a pale yellow oil.

TLC Silica gel (ethyl acetate:hexane 5:95) R$_f$=0.27.

$^1$H-NMR (CDCl$_3$, 270 MHz): δ5.08 (m, 3H), 4.12 (q, 2H, J=6.7 Hz), 2.31 (m, 4H), 2.10–1.90 (m, 8H), 1.67 (s, 3H), 1.62 (s, 3H), 1.59 (s, 6H), 1.25 (t, 3H, J=6.7 Hz), ppm.

(3) Bishomofarnesol

A solution of 7.05 g (24 mmol) of Part A$^1$ (2) monoester in 65 mL of dry diethyl ether at 0° C. under argon was treated in portions with 915 mg (24 mmol) of lithium aluminum hydride and stirred at room temperature for three hours. After cooling to 0° C., the reaction was quenched with 7 mL of water, 7 mL of 15% NaOH; then stirred for 15 minutes. Additional 21 mL of water was added, and the reaction was stirred 0.5 hours, then dried with Na$_2$SO$_4$. The mixture was filtered through Celite, washing well with diethyl ether, and evaporated to give 5.665 g of a colorless oil. Purification by flash chromatography on silic gel eluted with 15:85 ethyl acetate:petroleum ether provided 5.23 g (87%) of title compound as a colorless oil.

TLC Silica gel (2:8 ethyl acetate:hexanes) R$_f$=0.21.

IR(neat) 3330, 2964, 2926, 2873, 2858, 1448, 1384, 1107, 1059, 401 cm$^{-1}$.

$^1$H-NMR (CDCl$_3$, 270 MHz): δ5.10 (m, 3H), 3.63 (t, 2H, J=6.5 Hz), 2.20–1.90 (m, 10H), 1.68 (s, 3H), 1.62 (s, 3H), 1.60 (s+m, 8H), ppm.

Mass Spec (CI-CH$_4$/N$_2$O, + ions) m/e 251 (M+H), 249 (M+H-H$_2$), 137, 123, 109, 69.

B.   (E,E)-5,9,13-Trimethyl-4,8,12-tetradecatrien-1-ol, methanesulfonate ester

To a stirred solution of 2.02 g (8.07 mmol) of bishomofarnesol (prepared as described in Example 1, Part A) in 20 mL of dichloromethane at 0° C. was added 2.2 mL (16.1 mmol) of triethylamine followed by 0.69 mL (8.90 mmol) of methanesulfonyl chloride, dropwise over 15 mintues. After stirring for 1.5 hours at 0° C., the reaction was diluted with dichloromethane, washed with 20 mL each of 10% HCl, saturated NaHCO$_3$ and brine, dried (MgSO$_4$) and evaporated to give 2.71 g (100%) of the crude title mesylate as a colorless oil.

TLC Silica gel (CH$_2$Cl$_2$) R$_f$=0.46.

$^1$H NMR (CDCl$_3$, 270 MHz): δ5.09 (t, 3H, J=6.5 Hz), 4.21 (t, 2H, J=7.0 Hz), 2.99 (s, 3H), 2.20–1.90 (m, 10H), 1.78 (quint, 2H, J=7.0 Hz), 1.65 (s, 3H), 1.61 (s, 3H), 1.60 (s, 6H), C. (E,E)-14-Iodo-2,6,10-trimethyl-2,6,10-tetradecatriene The crude Example 1, Part B mesylate prepared from 441.1 mg (1.76 mmol) of the corresponding alcohol according to the procedure of Example 1, Part B, was dissolved in 5 mL of acetone and treated with 530 mg (3.52 mmol) of sodium iodide. The reaction was allowed to stir for 16 hours at room temperature followed by 5 hours at reflux. The suspension was diluted with hexane and stirred with dilute aqueous sodium bisulfite to discharge to yellow color. The organic layer was washed with water and brine, dried (MgSO$_4$), and evaporated to provide 577 mg of crude product. Flash chromatography on 35 g of silica gel eluted with hexane gave 550.9 mg (87%) of title iodide as a colorless liquid.

TLC Silica gel (hexane) $R_f$=0.31.

$^1$H NMR (CDCl$_3$, 270 MHz): δ5.09 (m, 3H), 3.16 (t, 2H, J=7.0 Hz), 2.20–1.90 (m, 10H), 1.85 (quint., 2H, J=6.5 Hz), 1.67 (s, 3H), 1.63 (s, 3H), 1.59 (s, 6H) ppm.

Mass Spec (CI-CH$_4$/N$_2$O, + ions) m/e 361, 359 (M+H), 137.

D. (Diethoxyphosphinyl)methanesulfonic acid, ethyl ester

A solution of ethyl methanesulfonate (4.27 mL, 40.3 mmol) in 100 mL of dry THF was treated at −78° C. with 19.3 mL (44.4 mmol) of n-BuLi in hexane. After 15 min. diethyl chlorophosphate (3.30 ml, 22.2 mmol) was added. The solution was kept at −78° C. for 0.5 h and allowed to stay at −50° C. for 1 h. Saturated ammonium chloride (75 mL) was added to the solution and the mixture warmed to room temperature. The mixture was concentrated (THF removed), diluted with water and extracted with methylene chloride (3×70 mL). The combined organic fractions were dried (MgSO$_4$), concentrated and purified by distillation to yield 3.86 g (70%) of title compound.

b.p. 120°–130° C., 1 mm Hg.

$^1$H NMR (270 MHz, CDCl$_3$) δ4.40 (q, 2H, J=7.0 Hz) 4.20 (m, 4H) 3.80 (d, 2H, J=17.2 Hz) 1.40 (t, 3H, J=7.1 Hz) 1.25 (t, 6H, J=7.0 Hz).

Ref. Carretero, J. C.; Demillequ, M.; Ghosez, L. Tetrahedron Vol. 43, 1987, pp 5125.

E. (E,E)-1-(Diethoxyphosphinyl)-6,10,14-trimethyl-5,9,13-pentadecatriene-1-sulfonic acid, sodium salt To a suspension of 192 mg (8.00 mmol) of NaH in 6 mL of dry DMF at 0° C. under argon was added 2.16 g (8.33 mmol) of Part D sulfonate over 15 min. to give a yellow solution. The reaction was allowed to warm to room temperature and stir for 0.5 h when 1.00 g (2.77 mmol) of Part C iodide was added in one portion. The reaction mixture was stirred for 18 h when it was quenched with 10 mL of saturated NaCl solution and diluted with 50 mL of ethyl acetate. The layers were separated, the organics dried (Na$_2$SO$_4$) and evaporated to provide a crude glass. The glass was dissolved with 2.0 mL of 1M NaOH solution and purified by MPLC on a column of CHP20P gel (2.5 cm diam. ×15 cm height) eluting with water (150 mL), followed by a gradient created by the gradual addition of 400 mL of acetonitrile to a reservoir of 250 mL of water. Approximately 8 mL fractions were collected. The aqueous solution was concentrated and lyophilized to provide 0.78 g (57%) of title compound as a glass.

TLC Silica gel (8:1:1 propanol/conc. NH$_3$/water) $R_f$=0.75.

IR (film) 3476 2921, 1664, 1444, 1383, 1241, 1029, 968, 815 cm$^{-1}$.

$^1$H NMR (CDCl$_3$, 270 MHz): δ5.10 (m, 3H) 4.10 (m, 4H) 3.40 (dt, 1H, J=19.5, 6.0 Hz) 2.10–1.80 (m, 12H) 1.65 (s, 3H) 1.60 (m, 2H) 1.55 (s, 9H) 1.30 (t, 6H, J=6.0 Hz) ppm.

Mass Spec (FAB, + ions) m/e 510 (M+Na).

F. (E,E)-6,10,14-Trimethyl-1-phosphono-5,9,13-pentadecatriene-1-sulfonic acid, trisodium salt To a stirred solution of 0.75 g (1.50 mmol) of Part E salt in 8 mL of dichloromethane at room temperature was added 0.54 g (4.50 mmol) of 2,4,6-collidine followed by 0.82 g (5.35 mmol) of bromotrimethylsilane. The reaction was allowed to stir at room temperature for 14 h when the solvent was evaporated and the semisolid residue pumped (≈1 mm pressure) for 0.5 h. The residue was dissolved by adding 6.6 mL (6.60 mmol), of 1M NaOH solution then diluting with 15 mL of water. The solution was freeze dried to provide an off white solid. The solid was purified by MPLC on a column of CHP20P gel (2.5 cm diam. ×15 cm height) eluting with water (150 mL) followed by a gradient created by the gradual addition of 400 mL of acetonitrile to a reservoir of 250 mL of water. Approximately 10 mL fractions were collected. The acetonitrile was removed under reduced pressure and the aqueous solution was lyophilized to provide 0.34 g (46.5%) of the title compound as a white lyophilate.

TLC Silica gel (5:4:1 n-propanol/conc. ammonia/water) $R_f$=0.75.

IR (KBr) 3438, 2966, 2926, 2859, 1636, 1449, 1206, 1137, 1110, 976 cm$^{-1}$.

$^1$H NMR (D$_2$O, 400 MHz): δ5.15 (t, 1H, J=7.0 Hz) 5.06 (q, 2H, J=7.0 Hz) 2.77 (ddd, 1H, J=18.2, 7.0, 4.7 Hz) 2.10–1.80 (m, 12H) 1.54 (s, 3H) 1.49 (s, 3H) 1.47 (s, 6H) 1.50 (m, 2H) ppm.

Mass Spec (FAB, + ions) m/e 475 (M+H), 453 (MNa+2H).

Anal. Calc'd for C$_{18}$H$_{30}$O$_6$Na$_3$PS+1.70 H$_2$O: C, 42.80; H, 6.67; P, 6.13: S, 6.35 Found: C, 42.80; H, 7.01; P, 6.24; S, 6.56.

EXAMPLE 1A (E,E)-6,10,14-Trimethyl-1-phosphono-5,9,13-pentadecatriene- 1-sulfonic acid, trisodium salt A. Methanesulfonic acid, cyclohexyl ester To a stirred solution of 25.0 g (0.25 mol) of cyclohexanol (purchased from the Aldrich Chemical Company and used without purification) and 27.3 g (0.27 mol) of triethylamine in 500 mL of ether at −15° C. was added 28.6 g (0.25 mol) of methanesulfonyl chloride in 50 mL of ether dropwise over 35 min. The reaction was warmed to 0° C. and stirred for 1 h when the mixture was diluted water and washed with aqueous solutions of 1N HCl and brine. The organics were dried (MgSO$_4$) and concentrated under reduced pressure to provide 43.0 g, 96% yield of title mesylate as a colorless oil. The mesylate was used without further purification.

B. (Diethoxyphosphinyl)methanesulfonic acid, cyclohexyl ester

To a rapidly stirred, nitrogen-purged solution of 24.4 g (137 mmol) of Part A mesylate in 600 mL of THF under nitrogen at −78° C. was added 55 mL (137.5 mmol, 2.5M in hexanes) of n-butyl-lithium over 35 min. The temperature was not allowed to rise above −70° C. After an additional 10 min, 11.8 g (68.5 mmol) of freshly distilled diethyl chlorophosphate was added to the resulting slightly turbid solution at a rate to keep the temperature below −70° C. The reaction mixture was stirred for 45 min and then a solution of 8.30 g (138 mmol) of glacial acetic acid in 25 mL of THF was added over 5 minutes. The reaction mass was warmed to room temperature and evaporated at 30° C. at reduced pressure. The residue was partitioned between 250 mL of dichloromethane and 75 mL of water and extracted twice with dichloromethane. The extracts were combined, dried over MgSO$_4$ and evaporated. The crude product was purified by flash chromatography (8×50 cm column, 2 L of dichloromethane, then 4 L of 11:89 ether/dichloromethane, then 2 L of 1:4 ether/dichloromethane) to give title compound as a colorless oil, 11.4 g, 53%.

TLC Silica gel, (11:89 ether/dichloromethane) $R_f$=0.20.

$^1$H NMR (CDCl$_3$, 400 MHz) δ4.83 (m, 1H) 4.26 (m, 4H) 3.72 (d, 2H, J=7.1 Hz) 2.01 (m, 2H) 1.80–1.30 (m, 8H) 1.39 (t, 6H, J=7.3 Hz) ppm.

NOTE 1. The reaction is run under a rapid nitrogen stream in an attempt to rigorously exclude oxygen from the system.

NOTE 2. Efficient and rapid mechanical stirring is essential to prevent formation of the impurities sometimes seen in this reaction.

NOTE 3. In an independent experiment, a 15.5 g sample of crude material was chromatographed on 850 g of silica gel eluted with 20:80 isopropanol/hexane, collecting 50 mL fractions. Fractions 61–85 were combined to provide 13.8 g (73%) yield of pure triester.

C. (E,E)-1-(Diethoxyphosphinyl)-6,10,14-trimethyl-5,9,13-pentadecatriene-1-sulfonic acid, cyclohexyl ester To a suspension of 0.57 g (23.7 mmol, 1.9 eq.) of NaH in 50 mL of dry DMF at −20° C. under argon was added 9.00 g (28.7 mmol, 2.3 eq.) of Part B sulfonate over 15 min. to give a yellow solution. The reaction was allowed to warm to room temperature and stir for 0.5 h when 4.48 g (12.46 mmol, 1 eq.) of Example 1 Part C iodide was added in one portion. The reaction mixture was stirred for 12 h when it was quenched with 100 mL of saturated NaCl solution and diluted with 250 mL of ether. The layers were separated, the organics dried ($Na_2SO_4$) and evaporated to provide a crude oil. Flash chromatography was performed on 500 g of silica gel eluting with 3:7 ethyl acetate/hexane to provide 5.20 g (76%) of title compound in the form of a pale yellow oil.

TLC Silica gel (1:1 ethyl acetate/hexanes) $R_f$=0.60.

IR (film) 2934, 2861, 1449, 1352, 1260, 1173, 1053, 1024, 930 $cm^{-1}$.

$^1$H NMR ($CDCl_3$, 270 MHz) $\delta$5.05 (m, 3H) 4.75 (m, 1H) 4.15 (m, 4H) 3.40 (dt, 1H, J=19.3, 6.4 Hz) 2.10–1.80 (m, 14H) 1.65–1.25 (m, 6H) 1.60 (s, 3H) 1.53 (s, 9H) 1.30 (t, 6H, J=7.3 Hz) ppm.

Mass Spec. (CI, + ions) m/e 564 ($M+NH_4$), 547 (M+H), 482 ($M+NH_4-C_6H_{10}$), 465 ($M+H-C_6H_{10}$).

D. (E,E)-6,10,14-Trimethyl-1-phosphono-5,9,13-pentadecatriene-1-sulfonic acid, trisodium salt To a solution of 1.00 g (1.82 mmol) of Part C compound and 20 mL of methanol in a sealable tube at 0° C. was added $NH_3$ (g) until the solution was saturated. The tube was sealed and placed in an oil bath at 75° C. for 16 h, at which point the tube was opened and the volatiles removed under reduced pressure. The remainder was dissolved in dry toluene and evaporated two times (2×7.0 mL) leaving an amber oil. The oil was dissolved in 10 mL of dry methylene chloride and treated with 2.40 mL (9.0 mmol) of bis(trimethylsilyl)trifluoroacetamide (BSTFA) for 0.5 h, followed by 0.79 mL (6.0 mmol) of bromotrimethylsilane. The reaction mixture was stirred for 18 h when the solvent was evaporated and the residue pumped (≈0.5 mm pressure) for 0.5 h. The remainder was dissolved by adding 50 mL (10 mmol) of 0.2M NaOH solution and stirring vigorously for ten min. The soapy solution was freeze dried to provide a white solid. The solid was purified by MPLC on a column of CHP20P gel (0.30 L) eluting with water (0.5 L) followed by isocratic elution with 15% acetonitrile in water. Approximately 25 mL fractions were collected. Pure fractions were pooled and the aqueous solution lyophilized to provide 0.80 g (91%) of title salt as a white lyophilate. The lyophilate was diluted with 0.6 mL of water and the mixture mashed to a gummy white solid. The solid was repeatedly washed and mashed with acetone (3×4 mL) until a granular solid resulted. The granular solid was dried under vacuum for 10 h and collected to yield 0.75 g (85%) of title salt as a fine white powder.

TLC Silica gel (6:3:1 n-propanol/conc. ammonia/water) $R_f$=0.35.

IR (KBr) 3434, 2924, 2857, 1667, 1449, 1209, 1136, 1109, 976 $cm^{-1}$.

$^1$H NMR ($D_2O$, 400 MHz) $\delta$5.35 (t, 1H, J=7.0 Hz) 5.23 (q, 2H, J=7.0 Hz) 2.93 (ddd, 1H, J=18.2, 7.0, 4.7 Hz) 2.20–1.80 (m, 12H) 1.74 (s, 3H) 1.65 (s, 3H) 1.60 (s, 6H) 1.63 (m, 2H) ppm.

Mass Spec (FAB, + ions) m/e 497 (M+Na), 475 (M+H).

Anal. Calc'd for $C_{18}H_{30}O_6Na_3PS+0.81 H_2O$: C, 44.20; H, 6.52; P, 6.33; S, 6.55 Found: C, 43.83; H, 6.93; P, 6.02; S, 6.69.

EXAMPLE 1B (E,E)-6,10,14-Trimethyl-1-phosphono-5,9,13-pentadecatriene- 1-sulfonic acid, tripotassium salt To a solution of 11.11 g (20.3 mmol) of Example 1A, Part C compound and 120 mL of methanol in a sealable tube at 0° C. was added $NH_3$ (g) until the solution was saturated. The tube was sealed and placed in an oil bath at 65° C. for 24 h, at which point the tube was opened and the volatiles removed under reduced pressure. The remainder was dissolved in a 1:1 mixture of dry toluene/hexamethyl disilazane (HMDS) and evaporated two times (2×60 mL), leaving an amber oil. The oil was dissolved in 70 mL of dry methylene chloride and treated with 21.4 mL (101.6 mmol) of HMDS for 0.5 h at RT. The mixture was then treated with 16.0 mL (121.9 mmol) of bromotrimethylsilane. The reaction was allowed to stir at RT for 45 h when the solvent was evaporated and the residue pumped (≈0.5 mm pressure, 35° C.) for 0.5 h. The remainder was dissolved by adding 120 mL (120 mmol) of 1M KOH solution and stirring vigorously for ten min. The soapy solution was freeze dried to provide a white solid. The solid was purified by MPLC on a column of CHP20P gel (1 L) eluting with water (2 L) followed by a stepwise gradient created by the addition of: 1:9 acetonitrile/water (1.5 L), 1.5:8.5 acetonitrile/water (1.5 L), 2:8 acetonitrile/water (1 L) and finally 2.5:7.5 acetonitrile/water (1 L). Approximately 50 mL fractions were collected. Fractions 52 to 83 were pooled, the acetonitrile was removed under reduced pressure and the aqueous solution lyophilized to provide 8.11 g (78%) of title compound as a white lyophilate which was 98.5% pure by HPLC. The lyophilate was dissolved with 16 mL of water, and 40 mg (0.5 mol %) of Trolox was added. The product was precipitated with 16 mL acetone, and the precipitate was repeatedly washed (2×8 mL) and mashed with acetone until a solid resulted. The solid was dried under vacuum for 24 h and collected to yield 7.58 g (72%) of title compound as a fine white powder.

TLC Silica gel (6:3:1 n-propanol/conc. ammonia/water) $R_f$=0.35.

IR (KBr) 3435, 2924, 2857, 1632, 1449, 1204, 1140, 1109, 974 $cm^{-1}$.

$^1$H NMR ($D_2O$, 400 MHz) $\delta$5.15 (t, 1H, J=7.0 Hz) 5.06 (q, 2H, J=7.0 Hz) 2.77 (ddd, 1H, J=18.2, 7.0, 4.7 Hz) 2.10–1.80 (m, 12H) 1.54 (s, 3H) 1.50 (m, 2H) 1.49 (s, 3H) 1.47 (s, 6H) ppm.

Mass Spec (FAB, + ions) m/e 561 (M+K), 523 (M+H), 485 (M−K+2H).

Anal. Calc'd for $C_{18}H_{30}O_6K_3PS+0.59 H_2O$: C, 40.53; H, 5.89; P, 5.81; S, 6.13 Found: C, 40.50; H, 6.20; P, 5.67; S, 5.91.

EXAMPLE 2

(E)-6,10-Dimethyl-1-phosphono-5,9-undecadiene-1-sulfonic acid, trisodium salt

A. (E)-8-Chloro-2,6-dimethyl-2,6-octadiene

To a stirred solution of 30.0 g (0.194 mol) of (E)-3,7-dimethyl-2,6-octadien-1-ol and 28.27 mL (0.213 mol) of 2,4,6-collidine under argon at room temperature was added dropwise 8.23 g (0.194 mol) of lithium chloride in 100 mL of DMF. The mixture was cooled to 0° C. and treated with 16.56 mL (0.213 mol) of methanesulfonyl chloride dropwise over 10 minutes. The reaction was stirred at 0° C. for 1.5 hours (solid present), then was poured into 500 mL of ice/water. The aqueous solution was washed three times with 200 mL portions of hexane, the organic layers were combined and washed with 5% $KHSO_4$, water, $NaHCO_3$, brine, dried (MgSO$_4$) and evaporated to provide 29.95 g of a pale yellow oil. Rapid flash chromatography was performed on 400 g of silica gel, eluting with 3:9 EtOAc/hexane. Pure product fractions were combined and evaporated to provide 25.20 g (75%) of title compound as a pale yellow oil.

TLC Silica gel (8:1 hexane/EtOAc) R$_f$=0.68.

$^1$H-NMR (CDCl$_3$, 270 MHz): δ5.44 (m, 1H), 5.08 (m, 1H), 4.09 (d, 2H, J=8.2 Hz), 2.08 (m, 4H), 1.73 (s, 3H), 1.68 (s, 3H), 1.60 (s, 3H) ppm.

B. (E)-(3,7-Dimethyl-2,6-octadienyl)propanedioic acid, diethyl ester

To a stirred solution of 14.68 g (0.611 mol) of NaH (100%) in 400 mL of THF at 0° C. under argon was added dropwise 92.76 mL (0.611 mol) of diethyl malonate in 100 mL of THF over 0.5 hours. This solution was stirred for 0.5 hours at 0° C., at which time 35.20 g (0.204 mol) of Part A chloride in 50 mL of THF was added dropwise over 15 minutes. The reaction gradually warmed to room temperature, stirred for 18 hours then was quenched with 250 mL of saturated NH$_4$Cl and diluted with 250 mL of ether. The organic layer was washed with water, brine, dried (MgSO$_4$) and evaporated to remove solvent and provide 100 g of an oil. The excess diethyl malonate was removed by distillation at 75° C. (1.5 mm) to provide 65 g of title compound also containing some dialkylated product and diethyl malonate.

TLC Silica gel (1:1 Hexane/Ethyl acetate) R$_f$=0.37.

IR (CCl$_4$) 2982, 2926, 2854, 1751, 1734, 1446, 1369, 1332, 1269, 1236, 1209, 1149, 1111, 1095, 1035, 860 cm$^{-1}$.

$^1$H NMR (CDCl$_3$, 270 MHz): δ5.07 (q, 2H, J=7.1 Hz), 4.18 (q, 2H, J=7.0 Hz), 3.33 (t, 1H, J=7.6 Hz), 2.60 (t, 2H, J=7.3 Hz), 2.04–1.98 (m, 4H), 1.68 (s, 3H), 1.64 (s, 3H), 1.59 (s, 3H), 1.26 (t, 6H, J=7.0 Hz) ppm.

MS (CI—NH$_3$, + ions) m/e 314 (M+NH$_4$), 297 (M+H).

C. (E)-5,9-Dimethyl-4,8-decadienoic acid, ethyl ester

To a solution of 65 g of the crude Part B diester described above, 5.40 mL (0.30 mol) of water and 25.0 g (0.60 mol) of lithium chloride in 250 mL of DMSO was heated to 190° C. and stirred for 9 hours. The reaction was treated with a 1:1 solution of hexane/ether and then washed with water and brine. The organic layer was dried (MgSO$_4$) and evaporated to provide 34.6 g of title compound in the form of a yellow oil. No further purification was performed; the sample was carried on to the next step.

TLC Silica gel (95:5 Hexane/Ethyl acetate) R$_f$=0.30.

$^1$H NMR (CDCl$_3$, 270 MHz): δ5.00 (m, 2H), 4.04 (q, 2H, J=7.0 Hz), 2.23 (m, 4H), 1.99–1.87 (m, 4H), 1.59 (s, 3H), 1.54 (s, 3H), 1.51 (s, 3H), 1.17 3H, J=7.0 Hz) ppm.

MS (CI—NH$_3$, + ions) m/e 242 (M+NH$_4$), 225 (M+H).

D. (E)-5,9-Dimethyl-4,8-decadien-1-ol

To a stirred solution of 5.84 g (0.154 mol) of lithium aluminum hydride in 700 mL of ether at 0° C. under argon was added dropwise 34.50 g of crude Part C ester over 20 minutes. The mixture was stirred for 1.5 hours at which time it was quenched by the following: 5.8 mL (0.324 mol) of water, 5.8 mL of 15% NaOH in water and then 17.5 mL (0.973 mol) of water. The granular mixture was stirred and dried (MgSO$_4$) for 0.5 hours at which time the mixture was filtered through a celite cake and washed with ether followed by dichloromethane. The filtrate was evaporated to provide 28.16 g of an oil that was distilled using a short-path apparatus (bp 95°–96° C., 0.3 mm) to provide 20.5 g (55% overall from Part A chloride) of title alcohol as a colorless oil.

TLC Silica gel (Dichloromethane) R$_f$=0.11.

IR (CCl$_4$) 3620, 3340, 2966, 2924, 2877, 2856, 2729, 1670, 1446, 1377, 1350, 1278, 1199, 1155, 1107, 1057, 985, 829, 814, 792 cm$^{-1}$.

$^1$H NMR (CDCl$_3$, 270 MHz): δ5.10 (m, 2H), 3.62 (t, 2H, J=6.5 Hz), 2.11–1.94 (m, 7H), 1.67–1.58 (m, 2H), 1.67 (s, 3H), 1.61 (s, 6H) ppm.

MS (CI—NH$_3$, + ions) m/e 200 (M+NH$_4$), 183 (M+H).

E. (E)-5,9-Dimethyl-4,8-decadien-1-ol, methanesulfonate ester

To a stirred solution of 12.0 g (65.93 mmol) of Part D alcohol in 200 mL of dichloromethane at 0° C. under argon was added 11.95 mL (85.71 mmol) of triethylamine and 6.12 mL (79.12 mmol) of methanesulfonyl chloride. The reaction was stirred for 1 hour then was diluted with ether and washed with 5% KHSO$_4$, saturated NaHCO$_3$ and brine. The organic layer was dried (MgSO$_4$) and evaporated to provide 16.91 g (98%) of title compound as a pale yellow oil.

TLC Silica gel (Dichloromethane) R$_f$=0.53.

IR (CCl$_4$) 2963, 2927, 2922, 2882, 2875, 2856, 1455, 1450, 1381, 1363, 1347, 1178, 1007, 969, 957, 929, 793, 785, 758 cm$^{-1}$.

$^1$H NMR (CDCl$_3$, 270 MHz): δ5.09 (m, 2H), 4.21 (t, 2H, J=6.5 Hz), 2.98 (s, 3H), 2.13–1.99 (m, 6H), 1.79 (quint., 2H, J=6.7 Hz), 1.68 (s,3H), 1.61 (s, 3H), 1.60 (s, 3H)ppm.

MS (CI—NH$_3$, + ions ) m/e 278 (M+NH$_4$).

F. (E)-5,9-Dimethyl-4,8-decadien-1-yl iodide

To a stirred solution of 16.91 g (65.04 mmol) of Part E methanesulfonate in 500 mL of acetone at room temperature under argon was added 39.00 g (260.16 mmol) of sodium iodide. The reaction mixture was refluxed for 3.5 hours, then diluted with 400 mL of a 1:1 mixture of water/hexane. The organic layer was washed with saturated sodium sulfite, dried (MgSO$_4$) and evaporated to provide 17.57 g of a pale yellow oil. The oil residue was filtered through 400 g of silica gel eluting with hexane. The pure product fractions were combined and evaporated to provide 16.86 g (89%) of title iodide as a colorless oil.

TLC Silica gel (Hexane) R$_f$=0.37.

IR (CCl$_4$) 2962, 2924, 2852, 1444, 1375, 1342, 1261, 1226, 1201, 1163, 1107, 983, 873, 835, 819, 761, 742 cm$^{-1}$.

$^1$H NMR (CDCl$_3$, 270 MHz): δ5.07 (t, 2H, J=7.0 Hz), 3.18 (t, 2H, J=7.0 Hz), 2.14–1.96 (m, 6H), 1.86 (quint., 2H, J=7.0 Hz), 1.68 (s, 3H), 1.63 (s, 3H), 1.60 (s, 3H)ppm.

G. (E)-1-(Diethyoxyphosphinyl)-5,9-undecadiene-1-sulfonic acid, sodium salt

To a suspension of 153 mg (6.40 mmol) of NaH in 10 mL of dry DMF at 0° C. under argon was added 1.66 g (6.40 mmol) of Example 1 Part D sulfonate over 15 min. to give a yellow solution. The reaction was allowed to warm to room temperature and stir for 0.5 h when 0.75 g (2.56 mmol) of Part F iodide was added in one portion. The reaction mixture was stirred for 18 h when it was quenched with 15 mL of saturated aq NH$_4$Cl solution and diluted with 100 ml of ethyl acetate. The fractions were separated and the organic layer washed with brine, dried (Na$_2$SO$_4$) and evaporated to provide a crude glass. The glass was diluted with 2.5 ml (2.5 mmol) of 1M NaOH solution and purified by MPLC on a column of CHP20P gel (2.5 cm diam. ×15 cm height) eluting with water (150 mL) followed by a gradient created by the gradual addition of 400 mL of acetonitrile to a reservoir of 250 mL of water. Approximately 10 mL fractions were collected. The acetonitrile was removed under reduced pressure and the aqueous solution was lyophilized to provide 0.63 g (59%) of title salt as a white lyophilate.

TLC Silica gel (8:1:1 propanol/conc. NH$_3$/water) R$_f$=0.65.

IR (film) 3468, 2972, 2926, 1664, 1444, 1376, 1241, 1036, 968, 812 cm$^{-1}$.

$^1$H NMR (CD$_3$OD, 270 MHz) δ5.10 (t, 1H, J=6.9 Hz) 5.05 (t, 1H, J=6.0 Hz) 4.10 (m, 4H) 3.15 (dt, 1H, J=20.0, 6.5

Hz) 2.10–1.80 (m, 8H) 1.67 (m, 2H) 1.60 (s, 3H) 1.55 (s, 3H) 1.53 (s, 3H) 1.25 (t, 6H, J=7.1 Hz) ppm.

H. (E) -6,10-Dimethyl-1-phosphono-5,9-undecadiene-1-sulfonic acid, trisodium salt To a stirred solution of 0.63 g (1.50 mmol) of Part G salt in 8 mL of dichloromethane at RT was added 0.36 g (3.00 mmol) of 2,4,6-collidine followed by 1.14 g (7.50 mmol) of bromotrimethylsilane. The reaction was allowed to stir at RT for 14 h when the solvent was evaporated and the semisolid residue pumped (≈1 mm pressure) for 0.5 h. The residue was dissolved by adding 7.0 mL of 1M NaOH solution (7.0 mmol), then diluting with 15 mL of water. The solution was freeze dried to provide off white solids. The solids were purified by MPLC on a column of CHP20P gel (2.5 cm diam. ×15 cm height) eluting with water (150 mL) followed by a gradient created by the gradual addition of 400 mL of acetonitrile to a reservoir of 250 mL of Water. Approximately 10 mL fractions were collected. The acetonitrile was removed under reduced pressure and the aqueous solution was lyophilized to provide 0.40 g (65%) of title compound as a white lyophilate.

TLC Silica gel (5:4:1 n-propanol/conc. ammonia/water) $R_f$=0.45.

IR (KBr) 3425, 2964, 2926, 2858, 1641, 1450, 1203, 1099, 1053, 974 cm$^{-1}$.

$^1$H NMR (D$_2$O, 400 MHz): δ5.15 (t, 1H, J=7.0 Hz) 5.06 (t, 1H, J=7.0 Hz) 2.77 (ddd, 1H, J=18.7, 6.7, 4.4 Hz) 2.10–1.80 (m, 8H) 1.55 (s, 3H) 1.50 (m, 2H) 1.49 (s, 3H) 1.48 (s, 3H) ppm.

Mass Spec (FAB, + ions) m/e 429 (M+Na), 407 (M+H), 385 (M–Na+2H).

Anal. Calc'd for $C_{13}H_{22}O_6Na_3PS$+1.58 H$_2$O: C, 35.92; H, 5.83; P, 7.13; S, 7.38 Found: C, 35.92; H, 5.99; P, 7.24; S, 7.28.

EXAMPLE 3

α-Phosphono-[1,1'-Biphenyl]-4-butanesulfonic acid, trisodium salt

A. [1,1'-Biphenyl]-4-propanoic acid, 1,1-dimethylehtyl ester

To a stirred solution of 2.07 mL (14.80 mmol) of diisopropylamine in 15 mL of THF was added 6.2 mL (9.87 mmol) of 1.6M butyllithium in hexanes to give a pale yellow solution. The solution was warmed to 0° C. for 15 min and then cooled to –78° C. when 1.33 mL (9.87 mmol) of t-butyl acetate was added neat over 10 min. After 15 min, 3.5 mL (20.2 mmol) of HMPA was added and then 2.0 g (9.87 mmol) of 4-chloromethyl [1,1'-biphenyl] (Aldrich) was added in 20 mL of THF over 10 min. After 2 h at –78° C., the reaction was diluted with ether and quenched with saturated NH$_4$Cl. The organic layer was washed with water and brine, dried (MgSO$_4$) and evaporated to provide 3.8 g of a clear oil. The crude product was filtered through a pad of silica gel eluting with 500 mL each of pentane, CH$_2$Cl$_2$ and EtOAc. The latter two filtrates were combined and evaporated to provide 1.97 g of an oil. Further purification by flash chromatography on 200 g of silica gel packed in 3:1 pentane/CH$_2$Cl$_2$ and eluted with 2:1 pentane/CH$_2$Cl$_2$ gave 1.27 g (45%) of title ester as a clear, colorless oil.

IR (CCl$_4$) 2980, 2932, 1732, 1487, 1368, 1148, 698 cm$^{-1}$.

$^1$H NMR (CDCl$_3$, 270 MHz): δ7.50, 7.56 (two din, 2H each J=7 Hz) 7.42 (tm, 2H, J=7 Hz) 7.20–7.40 (m, 3H, H$_3$, H$_9$) 2.94 (t, 2H, J=7.6 Hz) 2.58 (t, 2H, J=7.6 Hz) 1.43 (s, 9H) ppm.

MS (CI—NH$_3$, + ions) m/z 300 (M+NH$_4$), 283 (M+H).

Anal. Calc'd for $C_{19}H_{22}O_2$: C, 80.81; H, 7.85 Found: C, 81.10; H, 7.88.

B. 4-(3-Hydroxypropyl) [1,1'-biphenyl]

To a suspension of 250 mg (6.58 mmol) of LAH in 15 mL of ether at 0° C. under argon was added 1.24 g (4.39 mmol) of Part A ester in 20 mL of ether over 10 min. After 0.5 h at 0° C., the reaction was carefully quenched by the sequential addition of 0.26 mL of water, 0.26 mL of 15% NaOH, and 0.79 mL of water. The mixture was stirred for 0.5 h, Na$_2$SO$_4$ was added and after an additional 1 h of stirring, the solids were removed by filtration through a pad of Celite. The solids were washed with ether, the filtrate was evaporated and the residue was purified by flash chromatography on 90 g of silica gel eluted with CH$_2$Cl$_2$ to provide 857 mg (92%) of title alcohol as a white solid, mp 72°–74° C.

IR (CCl$_4$) 3639, 3550 (br) 3029, 2939, 2875, 1602, 1487, 1041, 698 cm$^{-1}$.

$^1$H NMR (CDCl$_3$, 270 MHz): δ7.50, 7.55 (two dm, 2H each, J=7 Hz) 7.40 (tm, 2H, J=7 Hz) 7.29 (tm, 1H, J=7 Hz) 7.24 (d, 2H, J=7.6 Hz) 3.68 (t, 2H, J=6.3 Hz) 2.72 (t, 2H, J=7.6 Hz) 1.90 (tt, 2H, J=6.3, 7.6 Hz) 1.83 (br s, 1H, OH) ppm.

MS (CI—NH$_3$, + ions) m/z 230 (M+NH$_4$), 212 (M+H).

Anal. Calc'd for $C_{15}H_{16}O$: C, 84.87; H, 7.60 Found: C, 84.95; H, 7.67.

C. 4-(3-Iodopropyl) [1.1'-biphenyl]

To a stirred solution of 857 mg (4.04 mmol) of Part B alcohol, 1.16 g (4.44 mmol) of triphenylphosphine and 577 mg (8.48 mmol) of imidazole in 30 mL of dry THF under argon at room temperature was added 1.13 g (4.44 mmol) of iodine in 25 mL of THF dropwise over 40 min. After 1 h, the reaction was diluted with ether and washed with water, saturated Na$_2$S$_2$O$_3$ and brine, dried (MgSO$_4$) and evaporated to provide an oily, white solid. Flash chromatography on 65 g of silica gel eluted with CH$_2$Cl$_2$ provided 806 mg (62%) of title iodide as a white solid, mp 42°–43° C.

$^1$H NMR (CDCl$_3$, 270 MHz): δ7.50, 7.55 (two dm, 2H each, J=7 Hz) 7.41 (tm, 2H, J=7 Hz) 7.31 (tm, 1H, J=7 Hz) 7.25 (d, 2H, J=7.6 Hz) 3.18 (t, 2H, J=7 Hz) 2.75 (t, 2H, J=7 Hz) 2.14 (quint, 2H, J=7 Hz) ppm.

MS (CI—NH$_3$, + ions) m/z 340 (M+NH$_4$), 322 (M+H).

Anal. Calc'd for $C_{15}H_{15}I$: C, 55.92; H, 4.69; I, 39.39 Found: C, 56.04; H, 4.70; I, 39.37.

D. (E,E)-1-(Diethoxyphosphinyl)-[1,1,'-biphenyl]-4-butanesulfonic acid, sodium salt To a suspension of 223 mg (9.30 mmol) of NaH in 7 mL of dry DMF at 0° C. under argon was added 2.41 g (9.30 mmol) of Example 1 Part D sulfonate over 15 min. to give a yellow solution. The reaction was allowed to warm to room temperature and stir for 0.5 h when 1.00 g (3.10 mmol) of Part C iodide was added in 3 mL of DMF over 2 min. The reaction mixture was stirred for 18 h when it was quenched with 10 mL of saturated aq NaCl solution and diluted with 100 ml of ethyl acetate. The fractions were separated and the organic layer washed with brine, dried (Na$_2$SO$_4$) and evaporated to provide a crude glass. The glass was diluted with 2.5 ml of 1M NaOH solution and purified by MPLC on a column of CHP20P gel (2.5 cm diam. ×15 cm height) eluting with water (150 mL) followed by a gradient created by the gradual addition of 400 mL of acetonitrile to a reservoir of 250 mL of water. Approximately 10 mL fractions were collected. The acetonitrile was removed under reduced pressure and the aqueous solution was lyophilized to provide 1.10 g (79%) of title salt as a viscous glass.

TLC Silica gel (7:2:1 propanol/conc. NH$_3$/water) $R_f$=0.55.

IR (film) 3466, 2984, 2932, 1614, 1485, 1444, 1392, 1368, 1240, 1069, 1035, 970, 794 cm$^{-1}$.

$^1$H NMR (CDCl$_3$, 270 MHz) δ7.40–7.10 (m 9H) 4.10 (m, 4H) 3.15 (m, 1H) 2.65 (m, 2H) 2.30 (m, 1H) 2.00 (m, 3H) 1.25 (t, 6H, J=7.1 Hz)ppm.

Mass Spec (FAB, + ions) m/e 471 (M+Na), 449 (M+H).

E. α-Phosphono-[1,1'-biphenyl]-4-butanesulfonic acid, trisodium salt

To a stirred solution of 1.10 g (2.45 mmol) of Part D salt in 8 mL of dichloromethane at RT was added 1.49 g (9.80 mmol) of bromotrimethylsilane. The reaction was allowed to stir at RT for 14 h when the solvent was evaporated and the semisolid residue pumped (≈1 mm pressure) for 0.5 h. The residue was dissolved by adding 10 mL of 1M NaOH solution (10 mmol). The solution was purified by MPLC on a column of CHP20P gel (2.5 cm diam. ×15 cm height) eluting with water (150 mL) followed by a gradient created by the gradual addition of 400 mL of acetonitrile to a reservoir of 250 mL of water. Approximately 10 mL fractions were collected. Pure fractions were combined and the acetonitrile was removed under reduced pressure. The aqueous solution was lyophilized to provide 0.27 g (25%) of title salt as a white lyophilate.

TLC Silica gel (5:4:1 n-propanol/conc. ammonia/water) $R_f$=0.45.

IR (KBr) 3433, 3029, 2931, 1636, 1487, 1450, 1202, 1094, 1053, 973 $cm^{-1}$.

$^1$H NMR ($D_2O$, 270 MHz) δ7.70, 7.55, 7.45 (3m, 9H) 2.97 (ddd, 1H, J=15.8, 6.5, 4.7 Hz) 2.75 (m, 2H) 2.00 (m, 4H)

Mass Spec (FAB, + ions) m/e 459 (M+Na), 437 (M+H), 415 (M−Na+2H).

Anal. Calc'd for $C_{16}H_{16}O_6Na_3PS+2.00$ $H_2O$; C, 40.69; H, 4.27; P, 6.56; S, 6.79 Found: C, 40.90; H, 4.39; P, 6.43; S, 6.89.

EXAMPLE 4

(E)-4-(4-Heptylphenyl)-1-phosphono-3-butene-1-sulfonic acid, tripotassium salt

A. 4-Heptylbenzaldehyde

To a stirred solution of 6.60 g (30 mmol) of 4-heptylbenzoic acid (obtained from Aldrich Chemical Company (#23,064-2) and used without purification) in 50 mL of dichloromethane at room temperature under nitrogen was added 4.0 mL (45 mmol, 1.5 equivalents) of oxalyl chloride and then 0.1 mL (1.3 mmol) of DMF. The resulting vigorously bubbling solution was stirred for 1 h and then evaporated. The semi-solid residue was dissolved in 40 mL of benzene under argon and 350 mg (0.31 mmol) of tetrakis(triphenylphosphine)palladium was added. To this stirring solution at room temperature was added 11.1 mL (34 mmol) of tributyltin hydride over 20 min. The solution turns yellow and warms autogenously to 40° C. After 1 h, the reaction was treated with 100 mL of 10% aqueous potassium fluoride and stirred vigorously for 30 min. The reaction mass was filtered, the filtrate diluted with ether, washed with water, and the organic layer separated, dried ($MgSO_4$) and evaporated onto 10 g of silica gel. Purification by flash chromatography (5×20 cm column, 3:7 dichloromethane/hexanes as elutent) gave 5.95 g, 97% yield, of title compound as a colorless oil.

B. α-Ethenyl-4-heptylbenzenemethanol, acetate ester

To a stirred slurry of 42.0 mL (42.0 mmol, 1M in THF) of vinyl magnesium bromide in 40 mL of THF at −40° C. under argon was added a solution of 5.85 g (28.6 mmol) of Part A compound in 10 mL of THF over 20 min. The resulting pale yellow solution was warmed to room temperature, stirred for 2 h and then quenched with saturated ammonium chloride solution. The reaction mixture was extracted twice with ether. The extracts were combined, dried ($MgSO_4$) and evaporated. The resulting yellow oil was dissolved in 50 mL of dichloromethane at room temperature under nitrogen and 5.6 mL (40 mmol) of triethylamine and 3.8 mL (40 mmol) of acetic anhydride were added, followed by 100 mg (0.4 mmol) of 4-dimethylaminopyridine (DMAP). After 30 minutes, the reaction mixture was diluted with ether, washed twice with 10% citric acid, once with brine and once with saturated sodium bicarbonate. The organic phase was dried, ($MgSO_4$) and evaporated onto 10 g of silica gel. Purification by flash chromatography (5×25 cm column, 35:65 dichloromethane/hexanes as elutent) gave 7.12 g, 91%, of title compound.

C. (E) -1-(Diethoxyphosphinyl)-4-(4-heptylphenyl)-3-butenesulfonic acid, 1-methylethyl ester To a stirred solution of 2.75 g (10.0 mmol) of Part B compound, 6.7 mL (27 mmol, 2.2 equiv.) of bis(trimethylsilyl)acetamide, 3.45 g (12.6 mmol, 1.26 equiv.) of Example 1A, Part B sulfonate and 270 mg (1 mmol) of triphenylphosphine in 30 mL of THF under argon was added 600 mg (0.54 mmol) of tetrakis(triphenylphosphine)-palladium. The resulting mixture was heated to reflux for 1 hour. The reaction was cooled, evaporated, diluted with ether and washed once with 10% citric acid and thrice with water. The organic phase was dried ($MgSO_4$) and evaporated. Purification by flash chromatography on silica gel (5×20 cm column) eluted with 1:19 ether/dichloromethane gave title compound as a colorless oil, 3.10 g, 67% yield.

D. (E)-4-(4-Heptylphenyl)-1-phosphono-3-butene-1-sulfonic acid, tripotassium salt To a stirred solution of 458 mg (1.0 mmol) of Part C compound, in 5 mL of dichloromethane under argon at room temperature was added 420 mL (2.0 mmol) of bis(trimethylsilyl)trifluoroacetamide and then 530 mL (4.0 mmol) of bromotrimethylsilane. After 16 h, the resulting clear solution was evaporated at 25° C. and the residue dissolved in 5 mL of THF. To this stirred solution was added 200 mg (1.2 mmol) of dried, finely ground potassium iodide and 5 mg (0.02 mmol) of 18-crown-6. The resulting slurry was heated to reflux for 24 h, evaporated and then stirred for 1 h with 6 mL (3 mmol) of 0.5M potassium hydroxide solution. The solution was lyophilized and then purified by MPLC (2.5× 20 cm column of Mitsubishi Kasei Sepadbeads HP-20 resin): 11.5 mL fractions, 7 mL/min flow rate, eluted with 200 mL of water and then a gradient prepared from 400 mL of water and 450 mL of 2:1 acetonitrile/water). Fractions 23–25 were collected and lyophilized to give title salt as a white solid, 485 mg, 89% yield.

IR (KBr pellet) 3414, 2924, 2853, 1653, 1198, 1154, 1092, 972 $cm^{-1}$.

$^1$H NMR ($D_2O$, 400 MHz) δ23 (d, 2H, J=7.1 Hz) 7.06 (d, 2H, J=7.1 Hz) 6.35 (m, 2H) 2.91 (dm, 1H, J=14.5 Hz) 2.79 (t, 1H, J=13.6 Hz) 2.64 (m, 1H) 2.79 (t, 1H, J=13.6 Hz) 2.43 (t, 2H, J=6.6 Hz) 1.42 (m, 2H) 1.12 (m, 8H) 0.68 (t, 3H, J=6.0 Hz) ppm.

Anal. Calc'd for $C_{17}H_{24}K_3O_6PS.2.25$ $H_2O$: C, 37.45; H, 5.27; P, 5.68; S, 5.88 Found: C, 37.09; H, 5.43; P, 6.08; S, 6.12.

MS (FAB, + ions) m/e 543 (M+K), 505 (M+H), 423 (M−2K−3H).

EXAMPLE 5

α-Heptyl-α-phosphonobenzenebutanesulfonic acid, tripotassium salt

A. α-(Diethoxyphosphinyl)-4-heptylbenzenebutanesulfonic acid, 1-methylethyl ester To an argon-purged solution of 675 mg (1.38 mmol) of Example 4 Part C compound and 100 mg of 10% palladiumon-carbon in 20 mL of ethyl acetate in a 500 mL one-neck round bottom flask was attached a hydrogen-filled rubber bladder of approximately 1 L capacity. The reaction mixture was vigorously stirred for 16 h, purged with nitrogen, filtered through Celite and the filtrate evaporated. The oily residue was redissolved in dichlormethane, filtered through a 0.75 m filter and re-evaporated to give title compound as a colorless oil, 640 mg, 94% yield. The product was used without further purification.

B. 4-Heptyl-α-phosphonobenzenebutanesulfonic acid, tripotassium salt

To a stirred solution of 620 mg (1.26 mmol) of Part A compound in 5 mL of dichloromethane under argon at room temperature was added 660 mL (5 mmol) of bromotrimethylsilane. After 24 h, the resulting clear solution was evaporated at 25° C. and the residue dissolved in 5 mL of THF. To this stirred solution was added 225 mg (1.4 mmol) of dried, finely ground potassium iodide and 3 mg (0.01 mmol) of 18-crown-6. The resulting slurry was heated to reflux for 24 h, evaporated and then stirred for 1 h with 4 mL (4 mmol) of 1.0M potassium hydroxide solution. The solution was lyophilized and then purified by MPLC (2.5×20 cm column of Mitsubishi Kasei Sepadbeads HP-20 resin): 11.5 mL fractions, 7 mL/min flow rate, eluted with 200 mL of water and then a gradient prepared from 400 mL of water and 450 mL of 2:1 acetonitrile/water). Fractions 36–41 were collected and lyophilized to give title compound as a white solid, 550 mg, 84% yield.

IR (KBr pellet) 3434, 2926, 2855, 1649, 1460, 1200, 1084, 1049, 966 cm$^{-1}$.

$^1$H NMR (D$_2$O, 270 MHz) δ7.08 (d, 2H, J=7.6 Hz) 7.02 (d, 2H, J=7.6 Hz) 2.81 (dm, 1H, J=17 Hz) 2.47 (m, 2H) 2.41 (t, 2H, J=7.9 Hz) 1.78 (m, 4H) 1.41 (m, 2H) 0.69 (t, 3H, J=6.4 Hz) ppm.

Anal. Calc'd for C$_{17}$H$_{26}$K$_3$O$_6$PS.0.75 H$_2$O: C, 39.25: H, 5.33; P, 5.95; S, 6.16 Found: C, 39.45; H, 5.72; P, 5.71; S, 5.83.

MS (FAB, + ions) m/e 545 (M+K), 507 (M+H), 469 (M–K+2H).

EXAMPLE 6

(E) -4-(4'-Propyl[1,1'-biphenyl]-4-yl)-1-phosphono-3-butene-1-sulfonic acid, tripotassium salt A. (E)-(4'-Propyl[1,1'-biphenyl]-4-yl)- 2-propen-1-ol. acetate ester A(1). (E)-(4'-Propyl[1,1'-biphenyl]-4-yl)- 2-propenoic acid, n-butyl ester A stirred solution of 4.13 g (15 mmol) of 4-bromo-4'-n-propylbiphenyl, 106 mg (0.35 mmol) of tri-p-tolylphosphine, 2.7 mL (19 mmol) of n-butyl acrylate, 7.4 mL (30.8 mmol) of tributylamine and 10 mg (0.1 mmol) of hydroquinone was purged with a stream of nitrogen gas for 20 min at room temperature. To this mixture was added 4 mg (0.018 mmol) of palladium acetate. The reaction was heated to 150° C. for 18 h under argon and then cooled to room temperature. The resulting slurry was diluted with ether, extracted twice with 50 mL of 1M hydrochloric acid, once with brine and once with saturated sodium bicarbonate solution. The organic phase was dried (MgSO$_4$) and evaporated. The Crude product (4.5 g) was purified by flash chromatography on silica gel (5×25 cm column) eluted with 1 L of hexanes and then 1:1 dichloromethane/hexanes to give 4.08 g (81%) of title ester as a colorless oil.

A(2). (E)-(4'-propyl[1,1'-biphenyl]-4-yl)-2-propen-1-ol, acetate ester

To a stirred solution of 3.22 g (10.0 mmol) of Part A(1) ester in 50 mL of dichloromethane at 0° C. under nitrogen was added a solution of 22 mL (22 mmol, 1M in hexanes) of diisobutylaluminum hydride over 5 min. The resulting pale yellow solution was stirred for 2 h and then quenched with 2 mL of methanol. The solution was then treated with 150 mL of 1M potassium sodium tartrate. A gel formed which dissolved within 5 min. The reaction mixture was extracted twice with ether. The extracts were combined, dried (Na$_2$SO$_4$) and evaporated. The resulting oil (2.6 g) was dissolved in 25 mL of THF, cooled to 0° C. under nitrogen and 4.6 mL (25 mmol) of diisopropylethylamine and 2.4 mL (25 mmol) of acetic anhydride was added. After 1 h, the reaction mixture was diluted with ether, washed twice with 1M hydrochloric acid once with brine and once with saturated sodium bicarbonate. The organic phase was dried (MgSO$_4$) and evaporated onto 10 g of silica gel. Purification by flash chromatography on silica gel (5×20 cm column) eluted with 9:11 dichloromethane:hexane to give title compound as a colorless oil, 2.21 g, 88% from Part A(1) ester.

B. (E)-1-(Diethoxyphosphinyl)-4-(4'-propyl[1,1'-biphenyl]-4-yl)-3-butene-1-sulfonic acid, cyclohexyl ester To a stirred solution of 1.91 g (6.50 mmol) of Part A compound, 2.5 mL (10 mmol, 1.5 equiv.) of bis(tri-methylsilyl)acetamide, 3.00 g (9.5 mmol, 1.46 equiv.) of Example 1A, Part B sulfonate and 180 mg (0.7 mmol) of triphenylphosphine in 10 mL of THF under argon was added 400 mg (0.35 mmol) of tetrakis (tri-phenylphosphino) palladium. The resulting mixture was heated to reflux for 1 hour. The reaction was cooled, evaporated, diluted with ether and washed once with 10% citric acid and thrice with water. The organic phase was dried (MgSO$_4$) and evaporated. Purification by flash chromatography on silica gel (5×20 cm column) eluted with 3:97 ether/dichloromethane gave title compound as a colorless oil, 2.32 g, 65% yield.

C. (E)-4-(4'-Propyl[1,1'-biphenyl]-4-yl)-1-phosphono-3-butene-1-sulfonic acid, tripotassium salt To a stirred solution of 578 mg (1.05 mmol) of Part B compound in 5 mL of dichloromethane under argon at room temperature was added 560 mL (2.1 mmol) of bis(trimethylsilyl)trifluoroacetamide and then 560 mL (4.2 mmol) of bromotrimethylsilane. After 72 h, the resulting clear solution was evaporated at 25° C. and the residue dissolved in 5 mL of THF. To this stirred solution was added 180 mg (1.1 mmol) of dried, finely ground potassium iodide and 3 mg (0.01 mmol) of 18-crown-6. The resulting slurry was heated to reflux for 20 h, evaporated and then stirred for 1 h with 8 mL (4 mmol) of 0.5M potassium hydroxide solution. The solution was lyophilized and then purified by MPLC (2.5× 20 cm column of Mitsubishi Kasei Sepadbeads SP-207SS resin): 11.5 mL fractions, 7 mL/min flow rate, eluted with 200 mL of water and then a gradient prepared from 400 mL of water and 450 mL of 2:1 acetonitrile/water). Fractions 20–34 were collected and lyophilized to give title salt as a white solid, 505 mg, 85% yield.

IR (KBr pellet) 3422, 2959, 2930, 2870, 1653, 1497, 1202, 1080, 968 cm$^{-1}$.

$^1$H NMR (D$_2$O, 400 MHz) δ7.45 (d, 2H, J=8.6 Hz) 7.43 (d, 2H, J=8.6 Hz) 7.39 (d, 2H, J=8.1 Hz) 7.15 (d, 2H, J=8.1 Hz) 6.44 (m, 2H) 2.98 (dm, 1H, J=13.2 Hz) 2.87 (tm, 1H, J=13.6 Hz) 2.68 (m, 1H) 2.44 (t, 2H, J=6.0 Hz) 1.46 (dq, 2H, J=6.0 Hz) 0.73 (t, 3H, J=6.0 Hz) ppm.

Anal. Calc'd for C$_{19}$H$_{20}$K$_3$O$_6$PS.2.2 H$_2$O: C, 40.45; H, 4.36; P, 5.49; S, 5.68 Found: C, 40.11; H, 4.70; P, 5.18; S, 5.95.

MS (FAB, + ions) m/e 563 (M+K), 525 (M+H), 487 (M–K+2H).

EXAMPLE 7

α-Phosphono-4'-Propyl[1,1'-biphenyl]-4-butanesulfonic acid, triponassium salt

A. α-(Diethoxyphosphinyl)-4'-propyl[1,1'-biphenyl]-4-butanesulfonic acid, cyclohexyl ester To a nitrogen-purged solution of 1.30 mg (2.37 mmol) of Example 6 Part B compound in 50 mL of ethyl acetate in a 500 mL one-neck round bottom flask was attached a hydrogen-filled rubber bladder of approximately 1 L capacity. The reaction mixture was vigorously stirred for 16 h, purged with nitrogen, filtered through Celite and the filtrate evaporated. The oily residue was redissolved in dichlormethane, filtered through a 0.75 μ (micron) filter and re-evaporated to give title compound as a colorless oil, 1.28 g, 98% yield. The product was used without further purification.

B. α-Phosphono-4'-propyl[1,1'-biphenyl]-4-butanesulfonic acid, tripotassium salt To a stirred solution of 1.14 g (2.06 mmol) of Part A compound in 10 mL of dichloromethane under argon at room temperature was added 1.10 mL (8.3 mmol) of bromotrimethylsilane. After 24 h, the resulting clear solution was evaporated at 25° C. and the residue dissolved in 10 mL of THF. To this stirred solution was added 340 mg (2.1 mmol) of dried, finely ground potassium iodide and 5 mg (0.02 mmol) of 18-crown-6. The resulting slurry was heated to reflux for 24 h, evaporated and then stirred for 1 h with 8 mL (8 mmol) of 1.0M potassium hydroxide solution. The solution was lyophilized and then purified by MPLC (2.5× 20 cm column of Mitsubishi Kasei Sepadbeads SP207SS resin): 11.5 mL fractions, 7 mL/min flow rate, eluted with 200 mL of water and then a gradient prepared from 400 mL of water and 450 mL of 1:1 acetonitrile/water). Fractions 27–31 were collected and lyophilized to give title compound as a white solid, 450 mg, 39% yield.

IR (KBr pellet) 3432, 2957, 2930, 2870, 1636, 1499, 1198, 1080, 1049, 966 cm$^{-1}$.

$^1$H NMR (D$_2$O, 400 MHz) δ7.47 (d, 2H, J=7.5 Hz) 7.46 (d, 2H, J=7.3 Hz) 7.28 (d, 2H, J=7.5 Hz) 7.21 (d, 2H, J=7.3 Hz) 2.86 (dm, 1H, J=18.4 Hz) 2.58 (m, 2H) 2.49 (t, 2H, J=7.2 Hz) 1.85 (m, 4H) 1.50 (m, 2H) 0.78 (t, 3H, J=6.0 Hz) ppm.

Anal. Calc'd for C$_{19}$H$_{22}$K$_3$O$_6$PS.1.9 H$_2$O: C, 40.68; H, 4.64; P, 5.52; S, 5.72 Found: C, 40.69; H, 5.00; P, 5.46; S, 6.00.

MS (ion spray, + ions) m/e 495 (M−3K+4H+2CH$_3$CN), 492 (M−2K+3H+CH$_3$CN), 489 (M−K+2H), 454 (M−3K+4H+CH$_3$CN), 451 (M−2K+3H), 413 (M−3K+4H).

EXAMPLE 8

4-(2-Phenylethoxy)-α-phosphonobenzenebutanesulfonic acid, dipotassium salt

A. 4-(2-Phenylethoxy)benzenepropanoic acid, 2-phenylethyl ester

To a stirred solution of 5.00 g (30.1 mmol) of 4-hydroxybenzenepropanoic acid, 8.0 mL of 2-phenylethanol (67 mmol) and 16.3 g (61 mmol) of triphenyl-phosphine in 50 mL of THF at −10° C. under argon was added a solution 12.0 mL (61 mmol) of diisopropyl diazodicarboxylate in 50 mL of THF over the course of 4 hours. The resulting light yellow solution was allowed to warm to room temperature, stirred 16 h and then evaporated. The oily residue was triturated in 500 mL of hot hexane until a precipitate formed. The solids were filtered off and treated with an additional 100 mL of hot hexane. The filtrates were combined and concentrated. Purification of the residue by flash chromatography (5×20 cm column, 3:2 dichloromethane/hexanes as elutent) gave 6.51 g, 58% yield, of title compound as a colorless oil.

B. 1-(3-Iodopropyl)-4-(2-phenylethoxy)benzene

To a stirred solution of 6.20 g (16.6 mmol) of Part A compound in 50 mL of THF at room temperature under argon was added a 1M solution of lithium aluminum hydride (9.0 mL, 2.2 equivalents) in THF. After 2 h, the reaction was quenched with 1M sodium potassium tartrate solution and extracted twice with ether. The organic extracts were dried (MgSO$_4$) and evaporated.

The residue was stirred in 25 mL of dichloromethane at 0° C. under argon with 2.8 mL (20 mmol) of triethyl amine. To this solution was added, over 20 min, 1.3 mL (17 mmol) of methanesulfonyl chloride. After an additional 20 min, the reaction mixture was diluted with dichloromethane and washed twice with 10% citric acid. The organic extracts were dried (MgSO$_4$) and evaporated.

The resulting yellow oil was stirred at reflux under argon in a solution of 25 mL of acetone containing 3 g (20 mmol) of sodium iodide. After 16 h, the reaction mixture was cooled and diluted with an iced solution of 5% aqueous sodium bisulfite. After two extractions with hexane, the extracts were dried (MgSO$_4$) and evaporated. Purification on silica gel (5×20 cm column, 1:7 dichloromethane/hexanes as elutent) gave 4.13 g, 68%, of Part B compound from Part A compound.

C. α-(Diethoxyphosphinyl)-4-(2-phenylethoxy) benzenebutanesulfonic acid, cyclohexyl ester To a stirred slurry of 120 mg (3.0 mmol, 60% mineral oil dispersion) of sodium hydride in 3 mL of DMF under argon at −20° C. was added a solution of 1.12 g (3.56 mmol, 1.3 equiv.) of Example 1A, Part B sulfonate in 1 mL of DMF. After addition was complete, the reaction was warmed to room temperature and stirred for 30 min. To the resulting solution was added a solution of 1.00 g (2.73 mmol) of Part B compound in 1 mL of DMF. The reaction was stirred for 16 h, diluted with ether and washed once with 10% citric acid and thrice with water. The organic phase was dried (MgSO$_4$) and evaporated. Purification by chromatography on silica gel (5×20 cm column) eluted with 1:19 ether/dichloromethane gave title compound as a colorless oil, 935 mg, 62% yield.

D. 4-(2-Phenylethoxy)-α-phosphonobenzenebutanesulfonic acid, dipotassium salt

To a stirred solution of 648 mg (1.2 mmol) of Part C compound in 5 mL of dichloromethane under argon at room temperature was added 620 mL (3.0 mmol) of bis(trimethylsilyl)trifluoroacetamide and then 620 mL (6.9 mmol) of bromotrimethylsilane. After 16 h, the resulting clear solution was evaporated at 25° C. and the residue dissolved in 6 mL of THF. To this stirred solution was added 250 mg (1.5 mmol) of dried, finely ground potassium iodide and 3 mg (0.01 mmol) of 18-crown-6. The resulting slurry was heated to reflux for 24 h, evaporated and then stirred for 1 h with 8 mL (4 mmol) of 0.5M potassium hydroxide solution. The solution was lyophilized and then purified by MPLC (2.5× 20 cm column of Mitsubishi Kasei Sepadbeads HP-20 resin): 11.5 mL fractions, 7 mL/min flow rate, eluted with 200 mL of water and then a gradient prepared from 400 mL of water and 450 mL of 2:1 acetonitrile/water). Fractions 25–32 were collected and lyophilized to give title salt as a white solid, 385 mg, 57% yield.

IR (KBr pellet) 3434, 3088, 2936, 2868, 1636, 1512, 1198, 1076, 966 cm$^{-1}$.

$^1$H NMR (D$_2$O, 400 MHz) δ7.21 (m, 5H) 7.09 (d, 2H, J=8.6 Hz) 6.76 (d, 2H, J=8.6 Hz) 4.15 (t, 2H, J=6.4 Hz) 2.91 (t, 2H, J=6.4 Hz) 2.77 (dm, 1H, J=18.0 Hz) 2.44 (m, 2H) 1.67 (m, 2H) ppm.

Anal. Calc'd for C$_{18}$H$_{21}$K$_2$O$_7$PS.3.75 H$_2$O: C, 38.73; H, 5.15; P, 5.55; S, 5.74 Found: C, 38.73; H, 5.10; P, 5.24; S, 5.51.

MS (FAB, + ions) m/e 567 (M+2K−H), 529 (M+K).

EXAMPLE 9

6-(Hexyloxy)-α-phosphono-2-naphthalenebutanesulfonic acid, dipotassium salt

A. 2-Bromo-6-(hexyloxy)naphthalene

To a stirred solution of 4.46 g (20.0 mmol) of 6-bromo-2-naphthalenol (obtained from Aldrich Chemical Company (#B7,340-6) and used without purification), in 20 mL of DMF at room temperature under argon was added 480 mg (20 mmol) of 95% sodium hydride over the course of 15 min. The resulting light yellow solution was stirred 30 min and 3.5 mL (22 mmol) of 1-bromohexane was added. The reaction was heated to 50° C. and stirred for 60 min. The reaction was quenched with ice water, the resultings solids filtered, washed with water and dried in vacuo at 60° C. Purification of the residue by chromatography on silica gel (5×20 cm column, hexanes as elutant) gave 5.00 g, 81% yield, of title compound as a colorless oil.

B. α-Ethenyl-6-(hexyloxy)-2-naphthalenemethanol

To a stirred solution of 2.23 g (7.25 mmol) of Part A compound in 25 mL of THF under argon at −78° C. was added a solution of 8.5 mL (14.5 mmol) of 1.7M t-butyllithium in pentane over 10 min. After 15 min, a yellow slurry had formed. This was warmed to 0° C. and the resulting organic solution was stirred for 30 min. To this reaction mixture was added 550 mL (9.5 mmol, 1.3 equivalents) of freshly distilled acrolein at a rate to keep the temperature below 5° C. After an additional 30 min, the reaction was quenched with saturated ammonium chloride solution, extracted twice with ether, dried ($MgSO_4$) and evaporated. Recrystallization from hexanes gave title compound as a white solid, mp 47°–48° C., 1.83 g, 89%.

C. α-Ethenyl-6-(hexyloxy)-2-naphthalenemethanol, acetate ester

To a solution of 1.43 g (5.0 mmol) of Part B compound and 1.1 mL (8 mmol) of triethylamine in 15 mL of $CH_2Cl_2$ at room temperature under argon was added 0.7 mL (6.6 mmol) of acetic anhydride and 20 mg (0.16 mmol) of 4-dimethylaminopyridine. After 10 min, the reaction mixture was evaporated, diluted with ether, washed once with 10% citric acid, once with water, once with saturated sodium bicarbonate solution, dried ($MgSO_4$) and evaporated to give title compound as a colorless oil, 1.54 g, 94%. The compound was used without further purification for the subsequent reaction.

D. (E)-1-(Diethoxyphosphinyl)-4-[6-(hexyloxy)-2-naphthalenyl]-3-butenesulfonic acid, cyclohexyl ester To a stirred solution of 1.47 g (4.5 mmol) of Part C compound, 1.55 mL (6.6 mmol, 1.5 equiv.) of bis(trimethylsilyl)acetamide, 1.85 g (5.85 mmol, 1.3 equiv.) of Example 1A, Part B sulfonate and 125 mg (0.5 mmol) of triphenylphosine in 10 mL of THF under argon was added 270 mg (0.24 mmol) of tetrakis(triphenylphosphine)palladium. The resulting mixture was heated to reflux for 1 hour. The reaction was cooled, evaporated, diluted with ether and washed once with 10% citric acid and thrice with water. The organic phase was dried ($MgSO_4$) and evaporated. Purification by flash chromatography on silica gel (5×20 cm column) eluted with 1:24 ether/dichloromethane gave title compound as a colorless oil, 1.06 g, 41% yield.

E. α-(Diethoxyphosphinyl)-6-(hexyloxy)-2-naphthalenebutanesulfonic acid, cyclohexyl ester To an argon-purged solution of 965 mg (1.66 mmol) of Part D compound and 100 mg of 10% palladium-on-carbon in 15 mL of ethyl acetate in a 500 mL one-neck round bottom flask was attached a hydrogen-filled rubber bladder of approximately 1 L capacity. The reaction mixture was vigorously stirred for 16 h, purged with nitrogen, filtered through Celite and the filtrate evaporated. The oily residue was redissolved in dichlormethane, filtered through a 0.75 μ (micron) filter and re-evaporated to give title compound as a colorless oil, 950 mg, 98% yield. The product was used without further purification.

F. 6-(Hexyloxy)-α-phosphono-2-naphthalenebutanesulfonic acid, dipotassium salt

To a stirred solution of 885 mg (1.52 mmol) of Part E compound in 10 mL of dichloromethane under argon at room temperature was added 800 μL, (8.9 mmol) of bromotrimethylsilane. After 18 h, the resulting clear solution was evaporated at 25° C. and the residue dissolved in 15 mL of THF. To this stirred solution was added 320 mg (1.9 mmol) of dried, finely ground potassium iodide and 3 mg (0.01 mmol) of 18-crown-6. The resulting slurry was heated to reflux for 24 h, evaporated and then stirred for 1 h with 9 mL (4.5 mmol) of 0.5M potassium hydroxide solution. The solution was lyophilized and then purified by MPLC (2.5× 20 cm column of Mitsubishi Kasei Sepadbeads CHP-20P resin): 11.5 mL fractions, 7 mL/min flow rate, eluted with 200 mL of water and then a gradient prepared from 400 mL of water and 450 mL of 1:1 acetonitrile/water). Fractions 44–52 were collected and lyophilized to give title compound a white solid, 475 mg, 53% yield.

IR (KBr pellet) 3434, 3057, 2932, 2861, 1653, 605, 1181, 1076, 966 $cm^{-1}$.

$^1$H NMR ($D_2O$, 400 MHz) δ7.60 (d, 1H, J=9 Hz) 7.56 (s, 1H) 7.52 (d, 1H, J=8.3 Hz) 7.32 (d, 1H, J=8.3 Hz) 7.00 (s, 1H) 6.94 (d, 1H, J=9.0 Hz) 3.78 (t, 2H, J=6.4 Hz) 2.83 (dm, 1H, J=18.0 Hz) 2.65 (m, 2H) 1.89 (m, 4H) 1.48 (m, 2H) 1.16 (m, 2H) 1.07 (m, 4H) 0.67 (t, 2H, J=5.5 Hz) ppm.

Anal. Calc'd for $C_{20}H_{27}K_2O_7PS.3.81 H_2O$: C, 40.76; H, 5.92; P, 5.26; S, 5.44 Found: C, 40.76; H, 5.81; P, 5.35; S, 5.35.

MS (FAB, + ions) m/e 559 (M+K), 521 (M+H).

EXAMPLE 10

4-[(5-Methyl-4-hexenyl)oxy]-α-phosphonobenzenebutanesulfonic acid, tripotassium salt A. 5-Methyl-4-hexenoic acid, 1,1-dimethylethyl ester To a stirred solution of 20.0 mL (142 mmol) of diisopropylamine in 160 mL of THF under argon at −10° C. was added a solution of 56 mL (140 mmol) of 2.5M n-butyllithium in hexane at a rate to keep the temperature below 0° C. The resulting light yellow solution was stirred 15 min and to this reaction mixture was added 20 mL (115 mmol) of HMPA. After an additional 10 min, the reaction was cooled to −75° C. and 18.8 mL (140 mmol) of 1,1-dimethylethanol, acetate ester was added at a rate to keep the temperature below −60° C. The resulting colorless solution was stirred for 30 min and 20 g (134 mmol) of 4-bromo-2-methyl-2-butene was added over 10 min. The reaction was stirred at −75° C. for 6 h and then warmed to room temperature. After 16, h, the reaction Was quenched with saturated ammonium chloride solution, extracted twice with ether, dried ($MgSO_4$) and evaporated. Purification by distillation (b.p. 64°–67° C. @6 mmHg) gave title compound as a colorless oil, 20.1 g, 82% yield.

B. 5-Methyl-4-hexen-1-ol

To a stirred slurry of 1.71 g (45.1 mmol) of lithium aluminum hydride in 50 mL of ether under nitrogen at 0° C. was added a solution of 15.5 g (84 mmol) of Part A compound in 20 mL of ether over 20 min. The reaction was warmed to room temperature and stirred. After 24 h, the reaction was quenched with 1M sodium potassium tartrate solution, extracted twice with 50 mL portions of ether, dried (MgSO$_4$) and filtered. The extract was distilled at atmospheric pressure through a 10 cm Vigreau column until the head temperature reached 80° C. The residue was purified by vacuum distillation (b.p. 76°–77° C. @14 mmHg) to give title compound as a colorless oil, 9.06 g, 94% yield.

C. 4-[(5-Methyl-4-hexenyl)oxy]benzenepropanoic acid, ethyl ester

To a stirred solution of 1.14 g (10.0 mmol) of Part B compound, 1.94 g (10.0 mmol) of ethyl 4-hydroxyphenyl-3-propanoate and 2.62 g (10.0 mmol) of triphenylphosphine in 20 mL of THF at −10° C. under nitrogen was added a solution 2.0 mL (10 mmol) of diisopropyl diazodicarboxylate in 20 mL of THF over the course of 2 hours. The resulting light yellow solution was allowed to warm to room temperature, stirred 16 h and then evaporated. The oily residue was triturated in 500 mL of hot hexane until a precipitate formed. The solids were filtered off and treated with an additional 100 mL of hot hexane. The filtrates were combined and concentrated. Purification of the residue by flash chromatography (5×15 cm column, 1:1 dichloromethane/hexanes as elutent) gave 2.58 g, 89% yield, of title compound as a colorless oil.

D. 4-[(5-Methyl-4-hexenyl)oxy]benzenepropanol

To a stirred solution of 2.28 g (7.85 mmol) of Part C compound in 15 mL of THF at room temperature under nitrogen was added a 1M solution of lithium aluminum hydride (4.5 mL, 2.4 equivalents) in THF. After 20 min, the reaction was quenched with 1M sodium potassium tartrate solution and extracted twice with ether. The organic extracts were dried (MgSO$_4$) and evaporated twice from hexanes to give 1.88 g of title compound, 96% yield, as a colorless oil.

E. 1-(3-Iodopropyl)-4-[(5-methyl-4-hexenyl)oxy]benzene

To a stirred solution of 1.86 g (7.5 mmol) of Part D compound, 1.96 g (7.5 mmol) of triphenylphosphine and 1.13 g (16.5 mmol) of imidazole in 25 mL of THF at room temperature under nitrogen was added 1.91 g (7.5 mmol) of solid iodine, portionwise, over 30 min. After an additional 10 min, the reaction mixture was diluted with hexanes and washed once with saturated sodium bisulfite solution. The organic extracts were dried (MgSO$_4$) and evaporated. Purification by flash chromatography (5×12 cm column, 1:4 dichloromethane/hexanes as elutent) gave 2.26 g, 84%, of title compound.

F. α-(Diethoxyphosphinyl)-4-[(5-methyl-4-hexenyl) oxy] benzenebutanesulfonic acid, cyclohexyl ester To a stirred slurry of 120 mg (3.0 mmol, 60% mineral oil dispersion) of sodium hydride in 3 mL of DMF under argon at −10° C. was added a solution of 1.12 g (3.56 mmol, 1.3 equiv.) Example 1A, Part B sulfonate in 1 mL of DMF. After addition was complete, the reaction was warmed to room temperature and stirred for 30 min. To the resulting solution was added a solution of 1.00 g (2.79 mmol) of Part E compound in 1 mL of DMF. The reaction was stirred for 16 h, diluted with ether and washed once with 10% citric acid and thrice with water. The organic phase was dried (MgSO$_4$) and evaporated. Purification by flash chromatography on silica gel (5×20 cm column) eluted with 3:47 ether/dichloromethane gave title compound as a colorless oil, 685 mg, 45% yield.

G. 4-[(5-Methyl-4-hexenyl)oxy]-α-phosphonobenzenebutanesulfonic acid, tripotassium salt A solution of 680 mg (1.25 mmol) of Part F compound in 10 mL of methanol under argon at room temperature was saturated with ammonia gas. The flask containing the reaction mixture was sealed and heated to 75° C. After 16 h, the reaction was cooled to room temperature and evaporated under dry conditions. The residue was dissolved in 10 mL of dichloromethane and 1.7 mL (6.4 mmol) of bis(trimethylsilyl)trifluoroacetamide and then 670 μL (5.0 mmol) of bromotrimethylsilane was added. After 24 h, the resulting clear solution was evaporated at 25° C. and then stirred for 1 h with 8 mL (4 mmol) of 0.5M potassium hydroxide solution. The solution was lyophilized and then purified by MPLC (2.5×20 cm column of Mitsubishi Kasei Sepadbeads HP-20 resin): 11.5 mL fractions, 7 mL/min flow rate, eluted with 200 mL of water and then a gradient prepared from 400 mL of water and 450 mL of 3:1 acetonitrile/water). Fractions 25–31 were collected and lyophilized to give title salt as a white solid, 504 mg, 74% yield.

IR (KBr pellet) 3432, 2963, 2928, 2866, 1636, 512, 1242, 1202, 1080, 966 cm$^{-1}$.

$^1$H NMR (D$_2$O, 400 MHz) δ7.09 (d, 2H, J=8.5 Hz) 6.77 (d, 2H, J=8.5 Hz) 5.06 (t, 1H, J=6.7 Hz) 3.85 (t, 1H, J=6.4 Hz) 2.79 (ddd, 1H, J=4.3, 6.0, 18.0 Hz) 2.45 (m, 2H) 1.98 (m, 2H) 1.77 (m, 4H) 1.61 (m, 2H) 1.52 (s, 3H) 1.43 (s, 3H) ppm.

Anal. Calc'd for C$_{17}$H$_{24}$K$_3$O$_7$PS.1.33 H$_2$O: C, 37.49; H, 4.93; P, 5.69; S, 5.89 Found: C, 37.48; H, 5.28; P, 5.62; S, 5.64.

MS (FAB, + ions) m/e 559 (M+K), 521 (M+H), 483 (M−K+2H).

EXAMPLE 11

1-Phosphono-1-pentadecanesulfonic acid, tripotassium salt

A. (Diethoxyphosphinyl)methanesulfonic acid, 1-methylethyl ester

To a rapidly stirred solution of 8.28 g (60 mmol) of isopropyl methanesulfonate in 150 mL of THF at −73° C. (internal temp.) was added 25 mL (60 mmol) of 2.4M n-butyllithium dropwise over 20 min. The internal temperature was not allowed to rise above −69° C. throughout the course of the addition. After an additional 15 min., 5.17 g (30 mmol) of freshly distilled diethyl chlorophosphate was added at a rate to keep the solution temperature below −69° C. The reaction mixture was stirred for 0.3 h at −73° C. and for 0.5 h at −40° C. when it was quenched with 125 mL of saturated NH$_4$Cl solution. The reaction mass was warmed to room temperature and the THF removed under reduced pressure. The remainder was partitioned between methylene chloride and water (3×75 mL). The extracts were dried (Na$_2$SO$_4$), concentrated, and purified by flash chromatography (350 g silica gel) eluting with 1:1 methylene chloride/ether to provide 5.20 g (67%) of title compound as a colorless oil.

TLC Silica gel (1:1 methylene chloride/ether) R$_f$=0.37.

$^1$H NMR (CDCl$_3$, 270 MHz) δ5.05 (sept, 1H, J=6.0 Hz) 4.20 (quint, 4H, J=7.0 Hz) 3.75 (d, 2H, J=17.5 Hz) 1.50 (d, 6H, J=6.0 Hz) 1.40 (t, 6H, J=7.5 Hz) ppm.

B. 1-(Diethoxyphosphinyl)pentadecanesulfonic acid, 1-methylethyl ester

To a suspension of 0.10 g (4.38 mmol) of NaH in 7 mL of dry DMF at 0° C. under argon was added 1.20 g (4.38 mmol) of Part A compound over 5 min. to give a yellow solution. The reaction was allowed to warm to room temperature and stir for 0.5 h when 0.55 g (2.00 mmol) of tetradecanyl bromide was added in one portion. The reaction mixture was stirred for 24 h when it was quenched with 20 mL of saturated NaCl solution and diluted with 50 mL of ether. The layers were separated, the organics dried (Na$_2$SO$_4$) and evaporated to provide a crude oil. Flash chromatography was performed on 100 g of silica gel eluting with 3:7 ethyl acetate/hexane to provide 0.30 g (31%) of title compound in the form of a pale yellow oil.

TLC Silica gel (1:1 ethyl acetate/hexanes) $R_f$=0.50.

IR (film) 2924, 2853, 1466, 1358, 1260, 1177, 1053, 1024, 930 cm$^{-1}$.

$^1$H NMR (CDCl$_3$, 300 MHz) 5.05 (sept., 1H, J=6.0 Hz) 4.20 (m, 4H) 3.35 (dt, 1H, J=20.0, 6.4 Hz) 2.10 (m, 2H) 1.45 (m, 2H) 1.40 (d, 6H, J=6.5 Hz) 1.30 (t, 6H, J=7.3 Hz) 1.20 (m, 22H) 0.85 (t, 3H, J=6.5 Hz) ppm.

Mass Spec (CI, + ions) m/e 488 (M+NH$_4$), 471 (M+H), 347 (M+H–SO$_3$C$_3$H$_8$).

C. 1-Phosphono-1-pentadecanesulfonic acid, tripotassium salt

To a stirred solution of 0.25 g (0.53 mmol) of Part B compound in 5 mL of dichloromethane at 0° C. and in the dark was added 4.24 g (2.12 mmol) of iodotrimethylsilane. The reaction was allowed to stir for 16 h when the solvent was evaporated and the semisolid residue pumped ($\mp$1 mm pressure) for 0.5 h. The residue was dissolved by adding 3 mL of 1M (3.0 mmol) KOH solution and freeze dried to provide an off white solid. The solid was purified by MPLC on a column of CHP20P gel (2.5 cm diam.×15 cm height) eluting with water (100 mL) followed by a gradient created by the gradual addition of 400 mL of acetonitrile to a reservoir of 250 mL of water. Approximately 7 mL fractions were collected. The acetonitrile was removed under reduced pressure and the aqueous solution was lyophilized to provide 0.15 g (62%) of title salt as a white lyophilate.

TLC Silica gel (6:3:1 n-propanol/conc. ammonia/water) $R_f$=0.40.

IR (KBr) 3443, 2920, 2851, 1653, 1468, 1215, 1163, 1045, 966 cm$^{-1}$.

$^1$H NMR (D$_2$O, 300 MHz) $\delta$2.80 (dt, 1H, J=19.0, 6.0 Hz) 1.85 (m, 2H) 1.50 (m, 2H) 1.20 (m, 22H) 0.90 (t, 3H, J=6.0 Hz) ppm.

Mass Spec (FAB, + ions) m/e 525 (M+K), 487 (M+H).

Anal. Calc'd for C$_{15}$H$_{30}$O$_6$K$_3$PS+2.19 H$_2$O: C, 34.24; H, 6.59; P, 5.89; S, 6.09 Found: C, 34.03; H, 6.88; P, 5.57; S, 6.02.

EXAMPLE 12

(E)-10,14-Dimethyl-1-phosphono-9,13-pentadecadiene-1-sulfonic acid, dipotassium salt A. Dichloro[μ-[1-hexanolato(2-)-C$^6$:O$^1$]]dimagnesium To a stirred solution of 11.00 g (80.0 mmol) of 6-chloro-1-propanol (Aldrich) in 20 mL of THF at −20° C. was added 27.0 mL (81.0 mmol) of 3.0M methylmagnesium chloride in THF dropwise over 25 minutes. After 0.5 hours at −20° C., the reaction was allowed to warm to room temperature and 2.88 g (118.0 mmol) of magnesium turnings were added and the reaction was heated to reflux. The reaction was initiated by adding a few crystals of iodine at the start of reflux and after 1 hour of heating. After 2 hours at reflux the reaction was cooled to room temperature providing the Grignard solution. The molarity of the reaction mixture was determined by titration: 5.20 mL (2.60 mmol) of a 0.5M solution of 2-propanol in benzene was slowly added to a blood red solution of 2-2'-biquinoline (indicator) in benzene and 2.0 mL of the freshly prepared Grignard solution. The endpoint color was light green and the molarity was determined to be 1.3M.

B. (E)-9,13-Dimethyl-8,12-tetradecadiene-1-ol

A solution of 21.5 mL (28.0 mmol) of 1.3M Part A Grignard reagent in THF and 5.0 mL of HMPA at 0° C. was treated dropwise with 1.21 g (7.0 mmol) of geranyl chloride in 7 mL of THF over 7 minutes. After the addition the reaction was allowed to warm to room temperature and stir for 2 hours, at which point the reaction was diluted with ether and quenched with 50 mL (50.0 mmol) of 1M HCl solution. The organic layer was washed two times with NH$_4$Cl solution, dried over MgSO$_4$ and evaporated to provide a crude oil. Flash chromatography was performed on 125 g of silica gel packed, loaded and eluted with 1:4 ethyl acetate/hexanes to provide 1.10 (66%) of title alcohol as an amber oil.

TLC Silica gel (1:9 ethyl acetate:hexane) $R_f$=0.20.

IR (CCl$_4$ solution) 3636, 2928, 2854, 1450, 1377, 1055 cm$^{-1}$.

$^1$H NMR (CDCl$_3$, 270 MHz): $\delta$5.40 (q, 2H, J=7.0 Hz), 3.69 (t, 2H, J=7.0 Hz), 2.25–1.85 (m, 8H), 1.75 (s, 3H), 1.70 (s, 6H), 1.65 (m, 2H), 1.39 (s, 7H) ppm.

MS (CI, NH$_3$, + ions) 256 (M+NH$_4$).

C. (E) -9,13-Dimethyl-8,12-tetradecadien-1-yl iodide

To a stirred solution of 1.10 g (4.62 mmol) of Part B alcohol and 1.40 mL (10.00 mmol) of triethylamine in 10 mL of methylene chloride at 0° C. was added 0.37 mL (4.80 mmol) of methanesulfonyl chloride dropwise over 15 minutes. After 1 hour at 0° C. the reaction was diluted with ether and washed with aqueous solutions of NH$_4$Cl, NaHCO$_3$, and brine. The organic layer was dried (MgSO$_4$) and concentrated under reduced pressure to provide 1.42 g (~4.5 mmol) of the crude mesylate. The residual oil was dissolved in 25 mL of acetone and treated with 3.00 g (20.0 mmol) of NaI. The resulting suspension was heated to reflux for 4 hours and diluted with ether, washed with brine, dried over MgSO$_4$, and concentrated to provide a yellow oil. Flash chromatography was performed on 100 g of silica gel packed, loaded and eluted with hexanes to provide 1.10 g (68% overall yield) of title iodide in the form of a colorless oil.

TLC Silica gel (hexanes) $R_f$=0.45.

IR (CCl$_4$ solution) 2962, 2928, 2854, 1450, 1375, cm$^{-1}$.

$^1$H NMR (CDCl$_3$, 270 MHz): $\delta$5.41 (q, 2H, J=7.0 Hz), 3.47 (t, 2H, J=7.0 Hz), 2.40–2.20 (m, 6H), 2.11 (quint., 2H, J=7.0 Hz), 1.97 (s, 3H), 1.89 (s, 6H), 1.60 (m, 8H) ppm.

MS (CI, NH$_3$, + ions) 366 (M+NH$_4$), 348 (M).

D. (E)-α-(Diethyoxyphosphinyl)-10,14-dimethyl-9,13-pentadecadiene-1-sulfonic acid, cyclohexyl ester To a stirred suspension of 191 mg (4.77 mmol, 2 eq.) of sodium hydride (as a 60% mineral oil dispersion) in 2 mL of dry dimethylformamide (DMF) at 0° C. was added a solution of 1.50 g (4.77 mmol, 2 eq.) of Example 1A Part B sulfonate in 3 mL of DMF dropwise over 7 min. The solution was warmed to RT and stirred for 50 min. To the resulting clear yellow solution was added a solution of 831 mg (2.39 mmol, 1 eq.) of Part C iodide in 3 mL of dry DMF dropwise over 5 min. The reaction was stirred at RT for 16 h diluted with ether (100 mL) and washed with water (50 mL). The aqueous layer was extracted with ether (2×20 mL) and the combined organic layers were washed with brine, dried (MgSO$_4$), and concentrated to afford 1.77 g of a yellow oil. Flash chromatography was performed on 300 g of silica gel eluting with 30% ethyl acetate in hexanes. Fractions (40 mL each) containing clean product by TLC were pooled and concentrated to afford, after high vac (0.25 mmHg) removal of solvent remnants, 782 mg (61%) of title compound as a clear yellow oil.

TLC Silica gel (10% ether in CH$_2$Cl$_2$): $R_f$ 0.50.

E. (E)-10,14-Dimethyl-1-phosphono-9,13-pentadecadiene- 1-sulfonic acid, dipotassium salt To a solution of 515 mg (0.96 mol, 1 eq.) of Part D compound in 10 mL of methanol at 0° C. was bubbled ammonia until the solution was saturated. The reaction tube was then sealed and heated at 75° C. for 16 h. The reaction mixture was allowed to cool to RT and then concentrated.

The oily residue was dried by coevaporation with toluene (2×). High vac (0.25 mmHg) removal of solvent remnants afforded 480 mg of light yellow oil.

To a solution of the yellow oil in 4 mL of dry dichloromethane at RT was added 636 μL (4.81 mmol, 5 eq.) of 2,4,6-collidine all at once. To the resulting clear light yellow solution was added 890 μL (6.74 mmol, 7 eq.) of bromotrimethylsilane (TMSBr) dropwise over 3 min. As the TMSBr was added a white precipitate formed and upon completion of TMSBr addition, 1 mL of dichloromethane was added to the thick reaction mixture to facilitate stirring. After 17 h at RT the reaction was concentrated and the resulting semisolid was placed on high vac (0.25 mm Hg) for 1 h. The residue was dissolved by adding 4.8 mL (5 eq.) of 1M potassium hydroxide followed by 10 mL of water and lyophilized to afford an off-white lyophilate. The lyophilate was purified by MPLC on a column of CHP20P (2.5 cm×25 cm) eluting initially with 150 mL of water followed by a gradient formed by the gradual addition of 400 mL of 30% acetonitrile in water to a reservoir containing 400 mL of 10% acetonitrile in water. Fractions containing clean product by HPLC (Method 8) were pooled and concentrated. The semisolid residue was taken up in water, filtered, concentrated and finally triturated with acetone to afford, after high vac (0.025 mm Hg) removal of acetone remnants, 207 mg (43%) of title salt in the form of a white solid.

TLC silica gel (5:4:1 n-propanol:ammonium hydroxide:water): $R_f$ 0.39

IR (KBr) 3450(br), 2920, 2851, 1462, 1215, 1080, 1040 $cm^{-1}$.

$^1$H NMR ($D_2O$, 300 MHz) δ5.01 (t, 1H, J=7.6 Hz) 4.96 (t, 1H, J=7.0 Hz) 2.87 (dt, 1H, J=18.1, 5.4 Hz) 1.90 (m, 2H) 1.82 (m, 6H) 1.49 (s, 3H) 1.43 (m, 2H) 1.42 (s, 6H) 1.15 (bs, 8H) ppm.

$^{13}$C NMR ($D_2O$, 75.6 MHz) δ135.7 132.7 125.5 124.7 61.0 (d, $J_{CP}$=126 Hz) 39.4 29.6 29.4 29.2 (d, $J_{CP}$=7 Hz) 29.1 29.1 28.1 27.2 26.3 25.3 17.4 15.6 ppm.

MS (FAB, + ions) m/z 473 (M+H), 511 (M+K), 549 (M−H+K).

Anal. Calc'd for $C_{17}H_{31}O_6PSK_2 \cdot 1.4\ H_2O$: C, 41.01; H, 6.84; S, 6.44; P, 6.22 Found: 41.19; H, 6.52; S, 6.30; P. 5.95

EXAMPLE 13

(E,E)-6,10,14-Trimethyl-1-phosphono-5,9,13-pentadecatriene-1-sulfonic acid, phenyl ester, dipotassium salt A. Methanesulfonic acid, phenyl ester To a solution of 40.0 g (0.42 mol, 1 eq.) of phenol in 250 mL of dichloromethane at 0° C. was added 250 mL (1.8 mol, 4.2 eq.) of triethylamine. After 5 min, 49.3 mL (0.64 mol, 1.5 eq.) of methanesulfonyl chloride was added dropwise over 20 min. The resulting cloudy yellow solution was warmed to RT and stirred for 14 h. The reaction was partitioned between ether (250 mL) and water (100 mL) and the resulting organic layer was washed with cold 6N hydrochloric acid (2×200 mL). The combined aqueous layers were extracted with ether (2×50 mL) and the combined organic layers were washed with water (100 mL), saturated sodium bicarbonate (200 mL), brine (200 mL), dried ($MgSO_4$) and concentrated. Recrystallization of the orange solid from isopropanol afforded 44.94 g (61%) of the title compound as light yellow crystals; mp 58.0°–58.5° C.

TLC Silica gel (25% ethyl acetate in hexanes): $R_f$ 0.29.

B. (Diethoxyphosphinyl)methanesulfonic acid, phenyl ester

To a turbid solution of 174 mL (0.174 mol, 1 eq.) of potassium bis(trimethylsilyl)amide (20% by weight in tetrahydrofuran (THF) from Callory Chem.) at −88° C. (internal temperature) was added a solution of 30.0 g (0.174 mol, 1 eq.) of Part A compound in 75 mL of dry THF am a rate to keep the internal temperature below −85° C. (addition took 20 min). The reaction was stirred for 5 min at −85° C. then 15.2 mL (104 mmol, 0.6 eq.) of freshly distilled diethylchlorophosphate was added dropwise at a rate that kept the temperature below −72° C. (addition took 13 min). After stirring at −65° C. for 1 h, the reaction was quenched at −65° C. by the addition of a solution of 9.97 mL (0.174 mol, 1 eq.) of acetic acid in 25 mL of THF over 5 min. The resulting solution was warmed to RT and the majority of the solvent was removed in vacuo. The residue was partitioned between dichloromethane (300 mL) and water (100 mL). The aqueous layer was extracted with dichloromethane (2×20 mL) and the combined organic layers were dried ($MgSO_4$) and concentrated to afford 43.82 g of solid/liquid mixture. The product was isolated by flash chromatography on silica gel (1000 g) eluting with 7:3 ethyl acetate:hexanes. Fractions (40 mL each) containing clean product by TLC were pooled to afford 17.19 g (54%) of title compound as a white solid; m.p. 50.5°–51.5° C.

TLC Silica gel (10% ether in dichloromethane): $R_f$ 0.38.

C. (E,E)-1-(Diethyoxyphosphinyl)-6,10,14-trimethyl-5,9,13-pentadecatriene-1-sulfonic acid, phenyl ester To a suspension of 333 mg (8.32 mmol, 2 eq.) of sodium hydride (60% mineral oil dispersion) in 5 mL of dry dimethylformamide (DMF) at 0° C. was added a solution of 2.56 g (8.32 mmol, 2 eq.) of Part B compound in 5 mL of dry DMF. The hetero-geneous bubbling solution was warmed to RT and stirred for 30 min. To the resulting homogeneous yellow solution was added a solution of 1.50 g (4.16 mmol, 1 eq.) of Example 1 Part C iodide in 5 mL of dry DMF and the reaction was stirred for 41 h at RT. The reaction was diluted with ether (150 mL) and washed with water (50 mL). The aqueous layer was extracted with ether (2×15 mL) and the combined organic layers were washed with brine, dried ($MgSO_4$) and concentrated to afford 3.11 g of a yellow oil. The product was isolated via flash chromatography on silica gel (200 g) eluting with 35% ethyl acetate in hexanes. Fractions (40 mL each) containing clean product by TLC were pooled and concentrated to afford 1.39 g (62%) of title compound as a clear light yellow oil.

TLC Silica gel (10% ether in hexanes): $R_f$ 0.66.

D. (E,E)-6,10,14-Trimethyl-1-phosphono-5,9,13-pentadecatriene-1-sulfonic acid, phenyl ester, dipotassium salt To a solution of 500 mg (0.92 mmol, 1 eq.) of Part C compound in 4 mL of dichloromethane at RT was added 367 μL (2.8 mmol, 3 eq.) of 2,4,6-collidine followed by 488 μL (3.7 mmol, 4 eq.) of bromotrimethylsilane (TMSBr). After 28 h an additional 100 μL (0.76 mmol, 0.8 eq.) of TMSBr was added to consume intermediate monoester. After 18 h (46 h total), reaction mixture was concentrated and placed on high vac (0.25 mmHg) for 2 h. The resulting yellow oil was dissolved by adding 1.9 mL (1.9 mmol, 2.1 eq.) of 1M potassium hydroxide. The resulting cloudy solution (pH 8.42) was lyophilized and the light brown lyophilate was chromatographed on a column of CHP20 (2.5 cm×25 cm) eluting initially with 150 mL of water then with a gradient formed by the gradual addition of 400 mL of acetonitrile to a reservoir containing 400 mL of water. Fractions containing clean product by HPLC were pooled and concentrated. The residue was taken up in a minimal amount of water, filtered and lyophilized to afford 411 mg of title salt in the form of an off-white lyophilate.

TLC Silica gel (7:2:1 n-propanol:ammonium hydroxide:water): $R_f$ 0.38.

IR (KBr): 3410 (br), 2965, 2924, 1636, 1487, 1339, 1194, 1148, 1098 cm$^{-1}$.

$^1$H NMR (D$_2$O, 400 MHz) δ7.10 (m, 4H) 6.99 (t, 1H, J=7..1 Hz) 4.97 (t, 1H, J=6.4 Hz) 4.74 (m, 2H) 3.42 (dt, 1H, J=17.1, 5.6 Hz) 2.08 (m, 2H) 1.98 (m, 1H) 1.88 (m, 1H) 1.68–1.47 (m, 10H) 1.37 (s, 3H) 1.29 (s, 3H) 1.20 (s, 3H) 1.17 (s, 3H) ppm.

$^{13}$C NMR (D$_2$O, 75.6 MHz) δ148.8 135.7 134.4 130.4 130.0 127.0 124.4 124.3 124.3 122.4 62.3 (d, J$_{CP}$=107 Hz) 39.8 39.6 29.0 (d, J$_{CP}$=5 Hz) 28.1 27.5 26.8 26.7 25.3 17.3 15.9 15.7 ppm.

MS (FAB, + ions): m/z 523 (M–K+2H)$^+$, 561 (M+H)$^+$, 599 (M+K)$^+$.

Anal. Calc'd for C$_{24}$H$_{35}$O$_6$PSK$_2$.0.84 H$_2$O: C, 50.05: H, 6.42; P, 5.38; S, 5.72 Found: C. 50.05; H, 6.74; P, 5.11; S, 5.45

EXAMPLE 14

(E,E)-9,13,17-Trimethyl-1-phosphono-8,12,16-octadecatriene-1-sulfonic acid triponassium salt A. Dichloro[μ-[1-propanolato(2-)-C$^{3'}$:O$^1$]]dimagnesium A modification of the procedure of G. Cahiez et al was employed (Tetrahedron Letters, 1978, 3013–4): To a stirred solution of 1.89 g (20 mmol) of 3-chloropropanol in 20 mL of THF under argon at –20° C. was added 10 mL (20 mmol) of 2M phenylmagnesium chloride in THF over 15 minutes. After 10 minutes at 20° C., the reaction was allowed to warm to RT, 730 mg (30 mmol) of magnesium turnings were added and the reaction was heated to reflux. Two 40 μL portions of 1,2-dibromoethane were added, the first portion injected at the start of reflux, and the second after 1 hour. After refluxing for a total of 2 hours, the reaction was allowed to cool to RT and was diluted with 37 mL of THF for a theoretical concentration of 0.3M.

B. (E.E)-8,12,16-Trimethyl-7,11,15-heptadecatrien- 1-ol

Copper (I) iodide (18 mg, 0.097 mmol) was added to a solution of Example 1 Part C iodide (3.50 g, 9.72 mmol) in THF (50 mL) under argon, and the mixture was cooled to 0° C. The Part A Grignard solution (23.4 mL, 0.5M in THF, 11.7 mmol) was added dropwise over 10 min, and the resultant cloudy white reaction was stirred at 0° C. for 10 min. The ice bath was removed and the reaction was stirred at RT for 1 h. Isopropanol (1.5 mL) was added dropwise slowly to quench the reaction. followed by addition of 1M KHSO$_4$ (30 mL). The mixture was stirred for 5 min at RT, whereupon two layers separated. Diethyl ether (250 mL) was added, and the organic layer was washed with water (20 mL), saturated NH$_4$Cl (50 mL), and brine (50 mL), then dried over MgSO$_4$. Evaporation gave a yellow oil which was purified by flash chromatography on 100 g silica gel eluting with 15:85 EtOAc/hexanes to give title compound (2.62 g, 92%) as a colorless oil.

C. (E,E)-17-Iodo-2,6,10-trimethyl-2,6,10-heptadecatriene

A solution of iodine (861 mg, 3.39 mmol) in THF (4 mL) was added dropwise to a solution of Part B compound (900 mg, 3.08 mmol), triphenylphosphine (888 mg, 3.39 mmol), and imidazole (461 mg, 6.78 mmol) in THF (10 mL) under argon at RT. The reaction became slightly exothermic during addition. The resultant brown reaction mixture was stirred at RT for 5 min, diluted with hexane (70 mL) and washed with 10% aqueous sodium bisulfite and brine (10 mL each), then dried over MgSO$_4$. Silica gel (4 g) was added to the filtrate, and the solvent was evaporated to give a white solid. Purification by flash chromatography on 50 g silica gel eluting with hexane gave title compound (1.19 g, 96%) as a colorless oil.

D. (E,E)-1-(Diethoxyphosphinyl)-9,13,17-trimethyl-8,12,16-octadecatriene-1-sulfonic acid, cyclohexyl ester A solution of Example 1A, Part B sulfonate (958 mg, 3.05 mmol) in DMF (2 mL) was added dropwise over 5 min to a suspension of dry sodium hydride (67 mg, 2.79 mmol) in DMF at –15° C. under argon (note: H$_2$ evolution). The cooling bath was removed and the suspension was stirred at RT for 1 h, whereupon a clear yellow solution was obtained. A solution of Part C compound (1.02 g, 2.54 mmol) in DMF (3 mL) was added dropwise over 3 min, and the reaction was stirred at RT for 23 h. The reaction was quenched by addition of saturated NH$_4$Cl (2 mL), and the resultant mixture was partitioned between diethyl ether (100 mL) and water (20 mL). The organic layer was washed with water (10 mL) and brine (50 mL), then dried over MgSO$_4$. Evaporation gave an opaque oil which was purified by flash chromatography on 125 g silica gel eluting with 20:80 EtOAc/hexane followed by 30:70 EtOAc/hexane to give title compound (981 mg, 66%) as a colorless oil.

E. (E,E)-9,13,17-Trimethyl-1-phosphono-8,12,16-octadecatriene-1-sulfonic acid, tripotassium salt Ammonia was bubbled through a solution of Part D compound (876 mg, 1.49 mmol) in methanol (20 mL) at 0° C. for 15 min. The reaction mixture was then heated at 75 C. in a sealed tube for 20 h, cooled to RT, and concentrated in vacuo to give a yellow gum. The crude product was dissolved in CH$_2$Cl$_2$ (7 mL) under argon. Bis(trimethylsilyl)trifluoroacetamide (2.0 mL, 7.45 mmol) was added and the reaction was stirred at RT for 10 min. Bromotrimethylsilane (786 mL, 5.96 mmol) was added dropwise and the resultant cloudy yellow reaction mixture was stirred at RT for 22 h. Additional bromotrimethylsilane (197 mL, 1.49 mmol) was added to the clear yellow solution and the reaction was stirred for another 18 h at RT. The reaction was concentrated in vacuo then pumped at high vacuum for 1 h to give a yellow oil, which was dissolved in 1N KOH (7.5 mL, 7.5 mmol) and stirred at RT for 2 h. The resultant heterogeneous yellow mixture was lyophilized to give a tan solid, which was purified by chromatography on CHP20P gel (2.5×20 cm column) eluting with water followed by a gradient created by the gradual addition of acetonitrile to a reservoir of water. The product fractions were concentrated to approximately a 10 mL volume, then lyophilized. The white solid was dissolved in water (600 mL) and acetone (2 mL) was added. The white semi-solid which precipitated was washed with acetone (3×2 mL) then pumped at high vacuum to give title salt (517 mg, 62%) as a white solid.

TLC Silica gel (6:3:1 n-propanol/NH$_4$OH/H$_2$O): R$_f$=0.21

IR (KBr) 2924, 2855, 1624, 1449, 1383, 1213, 1148, 1092, 1044, 966, 714 cm$^{-1}$.

$^1$H NMR (D$_2$O, 300 MHz) δ5.04 (m, 3H) 2.76 (ddd, 1H, J=18.3, 5.9, 4.9 Hz) 1.84 (m, 12H) 1.50 (s, 3H) 1.44 (s, 3H) 1.42 (s, 6H) 1.40 (m, 2H) 1.17 (br s, 6H) ppm.

$^{13}$C NMR (D$_2$O, 75 MHz) δ135.15 131.56 125.27 124.53 124.44 61.69 (d,J=123 Hz) 39.54 39.46 29.85 29.72 29.60 29.26 28.71 27.86 26.49 25.29 17.32 15.66 ppm.

MS (FAB, + ions) m/z 527 (M+2H–K), 565 (M+H), 603 (M+K).

Anal. Calc'd for C$_{21}$H$_{36}$K$_3$O$_6$PS. 1.0 equiv H$_2$O: C, 43.27; H, 6.57; P, 5.31; S, 5.50. Found: C, 42.93; H, 6.93; P, 5.03; S, 5.87.

EXAMPLE 15

(E,E)-1-(Ethoxyhydroxyphosphinyl)-6,10,14-trimethyl- 5,9,13-pentadecatriene-1-sulfonic acid, dipotassium salt To a solution of 0.44 g (0.80 mmol) of Example 1A Part C compound and 10 mL of methanol in a sealable tube at 0°

C. was added NH$_3$ (g) until the solution was saturated. The tube was sealed and placed in an oil bath at 70° C. for 24 h, at which point the tube was opened and the volatiles removed under reduced pressure. The remainder was dissolved in dry ethanol and evaporated two times (2×10 mL) leaving an amber oil. The oil was dissolved in 4.0 mL of a 1:1 ethanol/water solution and treated with 0.45 g (8.00 mmol) of potassium hydroxide. The mixture was heated to 80° C. for 72 h when the solvent was evaporated and the residue pumped (≈0.5 mm pressure) for 0.5 h. The remainder was purified by MPLC on a column of CHP20P gel (2.5 cm diam.×20 cm height) eluting with water (150 mL) followed by a gradient created by the gradual addition of 400 mL of acetonitrile to a reservoir of 350 mL of water. Approximately 7 mL fractions were collected. Pure fractions were combined and the acetonitrile was removed under reduced pressure. The aqueous solution was lyophilized to provide 0.30 g (74%) of title salt as a white lyophilate.

TLC Silica gel (6:3:1 n-propanol/conc. ammonia/water) $R_f$=0.55.

IR (KBr) 3459, 3052, 2969, 2926, 2859, 1636, 1445, 1383, 1221, 1105, 1190, 1055, 1038, 945 cm$^{-1}$.

$^1$H NMR (D$_2$O, 400 MHz) δ5.19 (t, 1H, J=7.0 Hz) 5.11 (q, 2H, J=6.5 Hz) 3.90 (m, 2H) 3.00 (dt, 1H, J=18.4, 6.0 Hz) 2.10–1.80 (m, 12H), 1.61 (s, 3H) 1.56 (s, 3H) 1.54 (s, 6H) 1.55 (m, 2H) 1.17 (t, 3H, J=7.2 Hz) ppm.

Mass Spec (FAB, + ions) m/e 551 (M+K), 513 (M+H).

Anal. Calc'd for C$_{20}$H$_{35}$O$_6$K$_2$PS: C, 46.85; H, 6.88; P, 6.04; S, 6.25 Found: C, 46.76; H, 6.89; P, 5.67; S, 6.60.

EXAMPLE 16

(E)-8,12-Dimethyl-1-phosphono-7,11-tridecadiene-1-sulfonic acid, dipotassium salt A. (E)-7,11-Dimethyl-6,10-dodecadienoic acid, 1,1-dimethylethyl ester To a stirred solution of 1.10 mL (7.71 mmol) of freshly distilled diisopropylamine in 7.0 mL of THF under argon at −78° C. was added 3.20 mL (5.14 mmol) of 1.6M n-butyllithium in hexanes to give a pale yellow solution. The solution was allowed to warm to 0° C. for 15 minutes then cooled again to 78° C., at which time 693 μL (5.14 mmol) of t-butyl-acetate (t-BuOAc) was added neat. After an additional 15 minutes at −78° C., 1.79 mL (10.28 mmol) of HMPA was added followed by the addition of 1.50 g (5.14 mmol) of Example 2, Part F iodide in 5 mL of THF dropwise over 5 minutes. The reaction was stirred at −78° C. for 2 hours at which time it was warmed to room temperature, diluted with 50 mL of ether and quenched with saturated NH$_4$Cl. The organic layer was washed with water, brine, dried, (MgSO$_4$) and evaporated to provide 1.39 g of a pale yellow oil. Flash chromatography was performed on 100 g of silica gel eluting with hexane (1 L) and 9:1 hexane/EtOAc (1 L). Product fractions were combined and evaporated to provide 1.15 g (92%) of title compound as a pale yellow oil.

TLC Silica gel (9:1 hexane/ethyl acetate) $R_f$=0.70.

IR (CCl$_4$) 2976, 2928, 2857, 1732, 1454, 1368, 1155 cm$^{-1}$.

$^1$H NMR (270 MHz, CDCl$_3$): δ5.20 (t, 1H, J=6.9 Hz), 5.18 (t, 1H, J=6.9 Hz), 2.30 (t, 2H, J=7.3 Hz), 2.14 (m, 2H), 2.08 (m, 4H), 1.77 (s, 3H), 1.69 (m+s, 8H), 1.53 (s, 9H), 1.47 (m, 2H) ppm.

MS (CI–NH$_3$, + ions) m/e 298 (M+NH$_4$), 281 (M+H).

B. (E)-7,11-Dimethyl-6,10-dodecadien-1-ol

To a stirred solution of 234 mg (6.16 mmol) of lithium aluminum hydride in 10 mL of ether at 0° C. under argon was added dropwise over 10 minutes 1.15 g (4.10 mmol) of Part A ester. The reaction was stirred for 1 hour at which time it was quenched by the following: 234 μL of water, 234 μL of 15% NaOH in water and 700 μL of water. The granular mixture was stirred and dried (Na$_2$SO$_4$) for 0.5 hours at which time the mixture was filtered through a celite cake and the cake was washed with ether followed by dichloromethane. The filtrate was evaporated to provide 834 mg of a colorless oil. Flash chromatography was performed on 100 g of silica gel eluting with 1:1 hexane/EtOAc (1 L). Pure product fractions were combined and evaporated to provide 824 mg (96%) of title alcohol as a colorless oil.

TLC Silica gel (9:1 hexane/ethyl acetate) $R_f$=0.15.

IR (CCl$_4$) 3300, 2928, 2856, 1450, 1377, 1151, 1107, 1055 cm$^{-1}$.

$^1$H NMR (270 MHz, CDCl$_3$): δ5.13 (t, 1H, J=7.0 Hz), 5.10 (t, 1H, J=7.0 Hz), 3.63 (t, 2H, J=6.5 Hz), 2.10 (m, 2H), 2.01 (m, 4H), 1.68 (s, 3H), 1.60 (s, 6H), 1.56 (m, 2H), 1.36 (m, 4H) ppm.

MS (CI–NH$_3$) m/e 228 (M+NH$_4$).

C. (E)-12-Iodo-2,6-dimethyl-2,6-dodecadiene

To a stirred solution of 820 mg (3.90 mmol) of Part B alcohol in 8 mL of THF under argon at room temperature was added 3.07 g (11.71 mmol) of triphenylphosphine, 797 mg (11.71 mmol) of imidazole and 1.98 g (7.81 mmol) of iodine. After 1 hour, the brown solution was diluted with ether and washed with saturated sodium sulfite, brine, dried (MgSO$_4$) and evaporated. Flash chromatography was performed on 100 g of silica gel eluting with hexane. Pure product fractions were combined and evaporated to provide 913 mg (73%) of title iodide as a colorless oil.

TLC Silica gel (Hexane) $R_f$=0.46.

IR (CCl$_4$) 2922, 2853, 1449, 1383 cm$^{-1}$.

$^1$H NMR (270 MHz, CDCl$_3$): δ5.22 (t, 1H, J=6.5 Hz), 5.19 (t, 1H, J=6.5 Hz), 3.29 (t, 2H, J=7.0 Hz), 2.14 (m, 2H), 2.09 (m, 4H), 1.93 (quint, 2H, J=7.0 Hz), 1.78 (s, 3H), 1.70 (s, 6H), 1.45 (m, 4H) ppm.

MS (CI–NH$_3$, + ions) m/e 338 (M+NH$_4$), 320 (M).

D. (E)-1-(Diethoxyphosphinyl)-8,12-dimethyl- 7,11-tridecadiene-1-sulfonic acid, cyclohexyl ester To a stirred suspension of 187 mg (4.68 mmol, 1.5 eq.) of sodium hydride (as a 60% mineral oil dispersion) in 1.5 mL of dry dimethylformamide (DMF) at 0° C. was added a solution of 1.47 g (4.68 mmol, 1.5 eq.) of Example 1A Part B compound in 2 mL of DMF dropwise over 5 min. The solution was warmed to RT and stirred for 30 min. To the resulting clear yellow solution was added a solution of 1.00 g (3.12 mmol, 1 eq.) of Part C iodide in 3 mL of dry DMF dropwise over 5 min. The reaction was stirred at RT for 70 h, diluted with ether (100 mL) and washed with water (50 mL). The aqueous layer was extracted with ether (2×15 mL) and the combined organic layers were washed with brine, dried (MgSO$_4$), and concentrated to afford 1.14 g of a yellow oil. Flash chromatography was performed on 250 g of silica gel eluting with 30% ethyl acetate in hexanes. Fractions (40 mL each) containing clean product by TLC were pooled and concentrated to afford, after high vac (0.25 mmHg) removal of solvent remnants, 410 mg (26%) of title compound as a clear yellow oil.

TLC Silica gel (10% ether in CH$_2$Cl$_2$): $R_f$ 0.49.

E. (E)-8,12-Dimethyl-1-phosphono-7,11-tridecadiene-1-sulfonic acid, dipotassium salt To a solution of 400 mg (0.79 mol, 1 eq.) of Part D compound in 8 mL of methanol in a sealable tube at 0° C. was bubbled ammonia until the solution was saturated. The reaction tube was then sealed and heated at 75° C. for 17 h. The reaction mixture was allowed to cool to RT and then concentrated. The oily residue was dried by coevaporation with toluene (2×). High vac (0.25 mmHg) removal of solvent remnants a light yellow oil.

To a solution of the yellow oil in 5 mL of dry dichloromethane at RT was added 522 μL (3.95 mmol, 5 eq.) of 2,4,6-collidine. To the resulting clear light yellow solution was added 729 μL (5.53 mmol, 7 eq.) of bromotrimethylsilane (TMSBr) dropwise over 4 min. As the TMSBr was added a white precipitate formed and the reaction became exothermic. An ice bath was used to cool reaction mixture until addition of TMSBr was complete. After 16 h at RT the reaction was concentrated and the resulting semisolid was placed on high vac (0.25 mm Hg) for 2 h. The residue was dissolved by adding 4.95 mL (6.3 eq.) of 1M potassium hydroxide followed by 5 mL of water and lyophilized to afford an off-white lyophilate. The lyophilate was purified by MPLC on a column of CHP20P (2.5 cm×25 cm) eluting initially with 150 mL of water followed by a gradient formed by the gradual addition of 400 mL of 50% acetonitrile in water to a reservoir containing 400 mL of 10% acetonitrile, in water. Fractions containing clean product by HPLC were pooled and concentrated. The semisolid residue was taken up in water, filtered, concentrated and finally triturated with acetone to afford, after high vac (0.025 mm Hg) removal of acetone remnants, 305 mg (77%) of title salt as a white solid.

TLC silica gel (5:4:1 n-propanol:ammonium hydroxide:water): $R_f$ 0.39

IR (KBr): 3450(br), 2924, 2855, 1653, 1447, 1209, 1148, 1044 $cm^{-1}$.

$^1$H NMR ($D_2O$, 300 MHz) δ5.10 (t, 1H, J=6.9 Hz) 5.03 (t, 1H, J=6.5 Hz) 2.73 (ddd, 1H, J=17.9, 6.5, 4.6 Hz) 1.95 (m, 2H) 1.86 (m, 4H) 1.75 (m, 2H) 1.52 (s, 3H) 1.46 (s, 6H) 1.41 (m, 2H) 1.18 (m, 4H) ppm.

$^{13}$C NMR ($D_2O$, 75.6 MHz) δ136.4 133.7 125.6 124.7 61.8 (d, $J_{CP}$=121 Hz) 39.0 29.5 (d, $J_{CP}$=7 Hz) 29.2 29.0 28.7 27.5 26.0 25.0 17.2 15.5 ppm.

MS (FAB, + ions): m/z 445 (M+H), 483 (M+K), 521 (M−H+2K).

Anal. Calc'd for $C_{15}H_{27}O_6PSK_2 \cdot 3.2\ H_2O$: C, 35.87; H, 6.70; S, 6.38; P, 6.17 Found: C, 35.91; H, 6.30; S, 6.11; P, 6.10

EXAMPLE 17

α-Phosphono[1,1'-biphenyl]-4-heptanesulfonic acid, tripotassium salt

A. 4-(6-Iodohexyl) [1.1'-biphenyl]

A(1). 6-([1,1'-Biphenyl]-4-yl)-6-hexyl-1-ol

To suspension of 0.361 g (2.04 mmol, 0.02 eq) of palladium chloride and 1.07 g (4.08 mmol, 0.04 eq) of triphenylphosphine in 300 mL of diethylamine at room temperature was added 26.1 g (112 mmol, 1.1 eq) of 4-bromobiphenyl (from Aldrich) followed by 0.766 g (4.08 mmol, 0.04 eq) of copper (I) iodide (99.999% pure, from Aldrich). After 5 min, 10.0 g (102 mmol, 1.0 eq) of 5-hexyn-1-ol (from Aldrich) was added neat. After 43 h, the reaction was concentrated and the residue was partitioned between water (250 mL) and $CH_2Cl_2$ (250 mL). The aqueous solution was extracted with $CH_2Cl_2$ and the combined organic solutions were concentrated. To remove the catalyst the residue was filtered through silica gel (40 g) eluting initially with $CH_2Cl_2$ then with $CH_2Cl_2$ containing 2% EtOAc. Concentration afforded 31.9 g of a brownish orange solid which was chromatographed on silica gel (400 g) eluting with 2% EtOAc in $CH_2Cl_2$ (4 L), then 4% EtOAc in $CH_2Cl_2$ (2 L). The isolated solid was then recrystallized from chloroform/hexanes to afford 16.2 g (64%) of the title compound as a white solid; m.p. 64.0°–64.5° C.

TLC Silica gel (25% EtOAc in hexanes): $R_f$ 0.14.

A(2). [1.1'-Biphenyl]-4-hexanol

To a solution of 9.0 g (36 mmol, 1 eq) of Part A(1) alcohol in 100 mL of THF was added 300 mg (0.36 mmol, 0.01 eq) of 10% palladium on activated carbon. The resulting heterogeneous mixture was placed under an $H_2$ atmosphere at RT. After 67 h, the reaction was filtered through Celite and the filter cake was washed with $Et_2O$ and $CH_2Cl_2$. Concentration afforded 9.07 g (99%) of the title compound as a fluffy white solid; m.p. 77.0°–77.5° C.

TLC Silica gel (25% EtOAc in hexanes): $R_f$ 0.19.

A(3). 4-(6-Iodohexyl) [1.1'-biphenyl]

To a solution of 7.00 g (28 mmol, 1.0 eq) of Part A(2) biphenylhexanol in 30 mL of dry THF were added 8.66 g (33 mmol, 1.2 eq) of triphenylphosphine and 4.50 g (66 mmol, 2.4 eq) of imidazole. To the resulting homogeneous solution was added dropwise a solution of 8.38 g (33 mmol, 2.4 eq) of iodine in 40 mL of dry THF over 25 min. After 45 min, the reaction was diluted with $Et_2O$ and washed with 10% aqueous sodium bisulfite, brine and dried ($MgSO_4$). The solution was filtered and the volume was reduced approximately by 50%. Silica gel (35 g) was added and the remainder of the solvent was removed. The product adsorbed onto silica gel was loaded onto a pre-equilibrated column (hexanes) of silica gel (20 g) and eluted with hexanes. Fractions containing clean product were pooled and concentrated to afford 9.40 g (94%) of the title compound as a clear, colorless oil.

TLC Silica gel (25% EtOAc in hexanes): $R_f$ 0.69.

B. α-(Diethoxyphosphinyl) [1,1'-biphenyl]-4-heptanesulfonic acid, phenyl ester

To a stirred suspension of 329 mg (8.23 mmol, 2 eq.) of sodium hydride (as a 60% mineral oil dispersion) in 3 mL of dry dimethylformamide (DMF) at 0° C. was added a solution of 2.54 g (8.23 mmol, 2 eq.) of Example 13 Part B compound in 6 mL of DMF dropwise over 10 min. The solution was warmed to RT and stirred for 30 min. To the resulting clear yellow solution was added a solution of 1.50 g (4.12 mmol, 1 eq.) of Part A iodide in 6 mL of dry DMF dropwise over 5 min. The reaction was stirred at RT for 43 h, diluted with ether (200 mL) and washed with water (100 mL). The aqueous layer was extracted with ether (2×25 mL) and the combined organic layers were washed with brine, dried ($MgSO_4$), and concentrated to afford 3.36 g of a yellow oil. Flash chromatography was performed on 400 g of silica gel eluting with 40% ethyl acetate in hexanes. Fractions (40 mL each) containing clean product by TLC were pooled and concentrated to afford, after high vac (0.25 mmHg) removal of solvent remnants, 1.06 g of a clear yellow oil, as well as 742 mg of the desired product contaminated with dialkylated material. The contaminated material was rechromatographed on 200 g of silica gel and the clean product was combined with the previously isolated product to afford 1.375 g (61%) of title compound as a clear light yellow oil.

TLC Silica gel (10% ether in $CH_2Cl_2$): $R_f$ 0.57.

C. α-Phosphono[1,1'-biphenyl]-4-heptanesulfonic acid, tripotassium salt

To a solution of 600 mg (1.1 mmol, 1 eq.) of Part B compound in 5 mL of dioxane at RT was added 1.1 mL (1.1 mmol, 1 eq.) of 1M potassium hydroxide. The initially turbid solution became homogeneous within 2 h. After 19 h, starting material was still evident by TLC as well as a lower Rf spot (presumably due to over hydrolysis). An additional 1.1 mL (1.1 mmol, 1 eq.) of KOH was added and reaction was stirred for 16 h (35 h total) at RT. The reaction mixture was concentrated and the residual yellow oil was co-evaporated with toluene (4∴) to remove water and placed on high vac (0.25 mmHg) for 2 h to afford a yellow solid.

To a heterogeneous solution of the yellow solid in 5 mL of dry dichloromethane at RT was added 1.45 mL (11.0 mmol, 10 eq.) of bromotrimethylsilane (TMSBr) dropwise over 3 min. As the TMSBr was added the solution began to clear and upon completion of TMSBr addition the reaction was nearly homogeneous. After 17 h, an additional 750 μL (5.7 mmol, 5.1 eq.) of TMSBr was added to complete consumption of the intermediate monoester. After 22 h (39 h total ) at RT, the reaction was concentrated and the resulting oil was placed on high vac (0.25 mm Hg) for 13 h. The residue was dissolved by adding 4.4 mL (4.4 mmol, 4 eq.) of 1M potassium hydroxide followed by 20 mL of water and sonicating at 40° C. for 10 min. The crude product was purified by MPLC on a column of CHP20P (2.5 cm ×25 cm) eluting initially with 150 mL of water followed by a gradient formed by the gradual addition of 400 mL of acetonitrile in water to a reservoir containing 400 mL of water. Fractions containing clean product were pooled and concentrated. The semisolid residue was taken up in water, filtered and lyophilized to afford 243 mg (39%) of a white lyophilate.

TLC silica gel (5:4:1 n-propanol: ammonium hydroxide:water): $R_f$ 0.38.

IR (KBr): 3403(br), 2928, 2857, 1651, 1202, 1163, 1072 cm$^{-1}$.

$^1$H NMR (D$_2$O, 300 MHz): δ7.52 (d, 2 H, J=7.8 Hz) 7.45 (d, 2H, J=8.0 Hz) 7.35 (t, 2H, J=7.5 Hz) 7.24 (t, 1H, J=8.0 Hz) 7.22 (d, 2H, J=8.0 Hz) 2.73 (ddd, 1H, J=17.8, 6.6, 4.4 Hz) 2.51 (t, 2H, J=7.5 Hz) 1.74 (m, 2H) 1.48 (m, 2H) 1.39 (m, 2H) 1.20 (bs, 4H) ppm.

$^{13}$C NMR (D$_2$O, 75.6 MHz): δ143.4 140.6 137.9 129.4 129.3 127.6 127.0 126.9 61.8 (d, $J_{CP}$=121 Hz) 34.7 30.9 29.5 (d, $J_{CP}$=6 Hz) 29.1 28.7 28.5 ppm.

MS (FAB): m/z 489 (M−K+2H)$^+$, 527 (M+H)$^+$.

Anal. Calcd for C$_{19}$H$_{22}$O$_6$PSK$_3$.2.31 H$_2$O: C, 40.15; H, 4.72; S, 5.64; P, 5.45 Found: C, 40.15; H, 4.89; S, 5.60; P, 5.47

EXAMPLE 18

(E)-4-(4'-Pentyl[1,1'-biphenyl]-4-yl)-1-phosphono-3-butene-1-sulfonic acid, tripotassium salt A. α-Ethenyl-4'-pentyl[1,1'-biphenyl]-4-methanol, acetate ester To a stirred solution of 3.03 g (10.0 mmol) of 4-bromo-4'-pentyl[1,1'-biphenyl] in 20 mL of THF under argon at −78° C. was added a solution of 12.5 mL (21.2 mmol) of 1.7M t-butyllithium in pentane over 1 h. A dark-colored slurry had formed. This was warmed to 0° C. and the resulting organic solution was stirred for 25 min. To this reaction mixture was added 0.8 mL (12 mmol, 1.2 equivalents) of freshly distilled acrolein an a rate to keep the temperature below 5° C. After an additional 30 min, the reaction was quenched with saturated ammonium chloride solution, extracted twice with ether, dried (MgSO$_4$) and evaporated. The resulting yellow solid was dissolved in 50 mL of dichloromethane and stirred under argon. To this solution was added 2.5 mL (18 mmol) of triethylamine, 1.5 mL (15 mmol) of acetic anhydride and 20 mg (0.16 mmol) of 4-N,N-dimethylaminopyridine at room temperature. After 14 h, the reaction mixture was evaporated, redissolved in ether, washed once with 10% citric acid, once with water and once with saturated sodium bicarbonate solution. The extract was dried (MgSO$_4$) and evaporated. Purification by flash chromatography on silica gel (5×25 cm column, 2:3 dichloromethane/hexanes as elutent) gave title compound as a colorless oil, 2.20 g, 68% yield.

B. (E)-1-(Diethoxyphosphinyl)-4-(4'-pentyl[1,1'-biphenyl- 4-yl)-3-butene-1-sulfonic acid, 1-methylethyl ester To a stirred solution of 1.50 g (4.65 mmol) of Part B compound, 2.7 mL (10.7 mmol, 2.3 equiv.) of bis(trimethylsilyl)acetamide, 2.5 g (9.3 mmol, 2.0 equiv.) of Example 11, Part A sulfonate and 125 mg (0.5 mmol) of triphenylphosphine in 10 mL of THF under argon was added 270 mg (0.24 mmol) of tetrakis(triphenylphosphine)palladium. The resulting mixture was heated to 45° C. for 2 hour. The reaction was cooled, evaporated, diluted with ether and washed once with 10% citric acid and thrice with water. The organic phase was dried (MgSO$_4$) and evaporated. Purification by flash chromatography on silica gel (5×20 cm column) eluted with 4:96 ether/dichlo-romethane gave title compound as a colorless oil, 1.65 g, 66% yield.

C. (E)-4-(4'-Pentyl[1,1'-biphenyl]-4-yl)-1-phosohono-1-butene-1-sulfonic acid.

A solution of 670 mg (1.24 mmol) of Part B compound in 10 mL of methanol under argon at room temperature was saturated with ammonia gas. The flask containing the reaction mixture was sealed and heated to 75° C. After 16 h, the reaction was cooled to room temperature and evaporated under dry conditions. The residue was dissolved in 10 mL of dichloromethane and 560 μL (6.4 mmol) of bis(trimethylsilyl)trifluoroacetamide and then 670 μL (5.0 mmol) of bromotrimethylsilane was added. After 24 h, the resulting clear solution was evaporated at 25° C. and then stirred for 1 h with 8 mL (4 mmol) of 0.5M potassium hydroxide solution. The solution was lyophilized and then purified by MPLC (2.5×20 cm column of Mitsubishi Kasei Sepadbeads HP-20 resin): 11.5 mL fractions, 7 mL/min flow rate, eluted with 200 mL of water and then a gradient prepared from 400 mL of water and 450 mL of 3:1 acetonitrile/water). Fractions 42–50 were collected and lyophilized to give title salt as a white solid, 505 mg, 85% yield.

IR (KBr pellet) 3430, 2928, 2855, 1636, 1497, 1202, 1078, 968 cm$^{-1}$.

$^1$H NMR (D$_2$O, 400 MHz) δ7.28 (m, 4H) 7.21 (d, 2H, J=7.1 Hz) 6.88 (d, 2H, J=7.3 Hz) 6.40 (m, 2H) 2.94 (dm, 1H, J=17.1 Hz) 2.82 (m, 1H) 2.67 (m, 1H) 2.25 (t, 2H, J=5.5 Hz) 1.27 (dq, 2H, J=6.0 Hz) 0.98 (m, 4H) 0.58 (t, 3H, J=6.8 Hz,) ppm.

Anal. Calc'd for C$_{21}$H$_{24}$K$_3$O$_6$PS.2.2 H$_2$O: C, 42.58; H, 4.83; P, 5.23; S, 5.41 Found: C, 42.18; H, 5.19; P, 5.63; S, 5.42.

MS (FAB, + ions) m/e 591 (M+K), 553 (M+H), 515 (M−K+2H).

EXAMPLE 19

α-Phosphono-4'-Pentyl[1,1]-biphenyl]-4-butanesulfonic acid, tripotassium salt

A. α-(Diethoxyphosphinyl)-4'-propyl[1,1'-biphenyl]-4-butanesulfonic acid, 1-methylethyl ester To an argon-purged solution of 550 mg (1.02 mmol) of Example 18 Part B compound and 100 mg of 10% palladium-on-carbon in 25 mL of ethyl acetate in a 200 mL one-neck round bottom flask was attached a hydrogen-filled rubber bladder of approximately 1 L capacity. The reaction mixture was vigorously stirred for 16 h, purged with nitrogen, filtered through Celite and the filtrate evaporated. The oily residue was triturated in hexanes and re-evaporated to give title compound as a colorless oil, 545 mg, 99% yield. The product was used without further purification.

B. α-Phosphono-4'-pentyl[1,1'-biphenyl]-4-butanesulfonic acid, tripotassium salt To a stirred solution of 520 mg (1.00 mmol) of Part A compound in 5 mL of dichloromethane under argon at room temperature was added 400 μL (4.5 mmol) of bromotrimethylsilane. After 18 h, the resulting clear solution was evaporated at 25° C. and the residue dissolved in 10 mL of THF. To this stirred solution was added 330 mg (2 mmol) of dried, finely ground potassium iodide and 3 mg (0.01 mmol) of 18-crown-6. The resulting slurry was heated to reflux for 24 h, evaporated and then stirred for 1 h with 6 mL (4.5 mmol) of 0.5M potassium hydroxide solution. The solution was lyophilized and then purified by MPLC (2.5×20 cm column of Mitsubishi Kasei Sepadbeads CHP-20P resin): 11.5 mL fractions, 7 mL/min flow rate, eluted with 200 mL of water and then a gradient prepared from 400 mL of water and 450 mL of acetonitrile). Fractions 26–31 were collected and lyophilized to give title salt as a white solid, 400 mg, 69% yield.

IR (KBr pellet) 3424, 3088, 2928, 2859, 1663, 1499, 1202, 1082, 1049, 966 $cm^{-1}$.

$^1$H NMR ($D_2O$, 400 MHz) 7.34 (d, 1H, J=7.7 Hz) 7.31 (d, 1H, J=7.8 Hz) 7.18 (d, 1H, J=7.8 Hz) 7.02 (d, 1H, J=7.7 Hz) 2.80 (dt, 1H, J=17.8, 5.1 Hz) 2.35 (t, 1H, J=7.0 Hz) 1.81 (m, 4H) 1.36 (m, 2H) 1.06 (m, 4H) 0.63 (t, 2H, J=6.8 Hz) ppm.

Anal. Calc'd for $C_{21}H_{26}K_3O_6PS \cdot 1.42\ H_2O$: C, 43.46; H, 5.01; P, 5.34; S, 5.52 Found: C, 43.46; H, 4.93; P, 5.37; S, 5.25.

MS (FAB, + ions) m/e 593 (M+K), 555 (M+H), 517 (M–K+2H).

EXAMPLE 20

4-(2-Naphthalenyl)-α-phosphonobenzenebutanesulfonic acid, tripotassium salt

A. 2-(4-Bromophenyl)naphthalene

To a stirred solution of 4.14 g (20.0 mmol) of 2-bromonaphthalene in 50 mL of THF at –78° C. under nitrogen was added a solution of 23.5 mL (40.0 mmol, 1.7M in pentane) of t-butyllithium over 10 minutes. The resulting slurry was stirred for 30 minutes and then warmed to 0° C. for 15 minutes. To this deep indigo solution was added a solution of 3.50 g (25.6 mmol) of thrice-fused zinc chloride in 25 mL of THF. The resulting light yellow solution was warmed to room temperature and stirred for 1 hour. After cooling to –78° C., a solution of 5.66 g (20.0 mmol) 1-bromo-4-iodobenzene and 300 mg (0.26 mmol) of tetrakis(triphenylphosphine)palladium in 20 mL of THF was added over the course of 15 minutes. After an additional 20 min, the cooling bath was removed, the reaction stirred at room temperature for 16 hours and then quenched with 50 mL of 2M hydrochloric acid. The mixture was extracted thrice with ether, the extracts combined, washed once with saturated sodium bicarbonate solution and once with 10% sodium thiosulfate. The organic extract was dried ($MgSO_4$) and evaporated. The crude product was purified by flash chromatography on silica gel (5×25 cm column, hexanes as elutent) to give 4.05 g (72%) of title compound as a white solid, mp 121°–123° C.

B. α-Ethenyl-4-(2-naphthalenyl)benzenemethanol, acetate ester

To a stirred solution of 2.59 g (9.13 mmol) of Part A compound in 20 mL of THF at –78° C. under nitrogen was added a solution of 10.8 mL (18.4 mmol, 1.7M in pentane) of t-butyllithium over 20 minutes. The resulting magenta slurry was warmed to 0° C. and stirred for 1 h. To the resulting solution was added 0.8 mL (14 mmol) of freshly distilled acrolein over 5 min. The resulting light yellow solution was stirred for 1 hour and then quenched with saturated ammonium chloride. The mixture was extracted twice with ether, dried ($MgSO_4$) and evaporated to give a white solid.

The solid was dissolved in 50 mL of dichloromethane, stirred under nitrogen at room temperature and treated with 2.0 mL (14.4 mmol) of triethylamine, 1.23 mL (13 mmol) of acetic anhydride and 50 mg (0.4 mmol) of DMAP. After 16 h, the reaction mixture was evaporated, redissolved in ether and washed once with 10% citric acid solution, once with brine and once with saturated sodium bicarbonate solution. The organic phase was dried ($MgSO_4$) and evaporated. The crude product was purified by flash chromatography on silica gel (5×20 cm column, 1:1 dichloromethane/hexanes as elutent) to give 1.83 g (66% from Part A compound) of title compound as a white solid, mp 61°–63° C.

C. (E)-1-(Diethoxyphosphinyl)-4-[4-(2-napthalenyl) phenyl]-3-butene-1-sulfonic acid, 1-methylethyl ester To a stirred solution of 1.55 g (5.13 mmol) of Part B compound, 2.75 mL (12.9 mmol, 2.5 equivalents) of bis(trimethylsilyl)acetamide, 2.81 g (10.2 mmol, 2.0 equivalents) of Example 11, Part A sulfonate and 125 mg (0.48 mmol) of triphenylphosphine in 10 mL of THF under nitrogen was added 270 mg (0.24 mmol) of tetrakis(triphenylphosphine)palladium. The resulting mixture was heated to 45° C. for 2 h. The reaction was cooled and evaporated and pumped at room temperature @0.2 Torr for 24 hours. The residue was diluted with dichloromethane and evaporated onto 5 g of silica gel. Purification by flash chromatography on silica gel (5×20 cm column) eluted with 1:16 ether/dichloromethane gave title compound as a yellow oil, 950 mg, 36% yield.

D. α-(Diethoxyphosphinyl)-4-(2-naphthalenyl)benzenebutanesulfonic acid, 1-methylethyl ester To a nitrogen-purged solution of 950 mg (1.85 mmol) of Part C compound and 350 mg of 10% Pd/C in 25 mL of ethyl acetate in a 200 mL one-neck round bottom flask was attached a hydrogen-filled rubber bladder of approximately 1 L capacity. The reaction mixture was vigorously stirred for 16 h, purged with nitrogen, filtered through Celite and the filtrate evaporated. The oily residue was redissolved in dichlormethane, filtered through a 0.75 m filter and re-evaporated to give title compound as a colorless oil, 960 mg, 100% yield. The product was used without further purification.

E. 4-(2-Naphthalenyl)-α-phosphonobenzenebutanesulfonic acid, tripotassium salt

To a stirred solution of 950 mg (1.81 mmol) of Part D compound in 10 mL of dichloromethane under nitrogen at room temperature was added 1.4 mL (10.5 mmol) of bromotrimethylsilane. After 24 h, the resulting clear solution was evaporated at 25° C. and the residue dissolved in 10 mL of THF. To this stirred solution was added 0.5 g (3 mmol) of dried, finely ground potassium iodide and 6 mg (0.02 mmol) of 18-crown-6. The resulting slurry was heated to reflux for 20 h, evaporated and then stirred for 1 h with 12 mL (6 mmol) of 0.5M potassium hydroxide solution. The solution was lyophilized and then purified by MPLC (2.5×20 cm column of CHP20P resin): 11.5 mL fractions, 7 mL/min flow rate, eluted with 200 mL of water and then a gradient prepared from 400 mL of water and 450 mL of 2:1 acetonitrile/water). Fractions 66–72 were collected and lyophilized to give title salt as a white solid, 560 mg, 55% yield.

IR (KBr pellet) 3418, 3055, 2934, 2864, 1661, 1503, 1339, 1196, 1078, 966 $cm^{-1}$.

$^1$H NMR ($D_2O$, 400 MHz) δ7.68 (s, 1H) 7.57 (m, 3H) 7.37 (dd, 1H, J=1.3, 8.6 Hz) 7.31 (d, 1H, J=8.1 Hz) 7.27 (m, 2H) 7.14 (d, 1H, J=8.1 Hz) 2.82 (ddd, 1H, J=2.1, 6.4, 17.5 Hz) 2.56 (m, 2H) 1.74 (m, 4H) ppm.

MS (FAB, + ions) m/e 573 (M+K), 535 (M+H), 497 (M–K+2H).

Anal. Calc'd for $C_{20}H_{18}K_3PSO_6 \cdot 3H_2O$: C, 43.04; H, 3.72; P, 5.55; S, 5.74 Found: C, 43.04; H, 3.86; P, 5.79; S, 6.09.

EXAMPLE 21

4-Phenoxy-α-phosphonobenzenebutanesulfonic acid, tripotassium salt

A. α-Ethenyl-4-phenoxybenzenemethanol tert-Butyllithium (24.5 mL, 1.7M in pentane, 42.2 mmol) was added dropwise over 30 min to a solution of 4-bromodiphenyl ether (5.00 g, 20.1 mmol) in THF (50 mL) at −78° C. under argon. The cooling bath was removed and the bright yellow reaction mixture was warmed to 0° C. over 20 min. The reaction was stirred at 0° C. for 30 min, at which time a tan-colored solution developed. Freshly distilled acrolein (1.6 mL, 24 mmol) was added dropwise over 5 min. The colorless reaction mixture was stirred at 0° C. for 15 min, then quenched by addition of saturated $NH_4Cl$ (10 mL). The mixture was diluted with diethyl ether (200 mL) and the organic layer was washed with water (20 mL) and brine (50 mL), then dried over $MgSO_4$. Evaporation gave a crude oil which was purified by flash chromatography on silica gel (400 g) eluted with a step gradient of 10:90 EtOAc/hexane to 15:85 EtOAc/hexane to 20:80 EtOAc/hexane to provide title compound (3.31 g, 73%) as a colorless oil.

B. α-Ethenyl-4-phenoxybenzenemethanol, acetate ester

Acetic anhydride (1.7 mL, 18 mmol) and 4-dimethylaminopyridine (18 mg, 0.15 mmol) were added to a solution of Part A alcohol (3.30 g, 14.6 mmol) and triethylamine (4.1 mL, 29.2 mmol) in $CH_2Cl_2$ (50 mL), and the reaction was stirred at RT under argon for 1.5 h. The reaction mixture was diluted with $CH_2Cl_2$ (50 mL) and washed with water (10 mL) and brine (20 mL), then dried over $MgSO_4$. Evaporation gave a yellow oil which was purified by flash chromatography on silica gel (100 g) eluted with 10:90 EtOAc/hexane to give title compound (3.83 g, 98%) as a pale yellow oil.

C. (E)-1-(Diethoxyphosphinyl)-4-(4-phenoxyphenyl)-3-butene-1-sulfonic acid, 1-methylethyl ester Tetrakis(triphenylphosphine)palladium (200 mg, 0.17 mmol) was added to a mixture of Part B compound (1.50 g, 5.60 mmol), Example 11, Part A compound (3.07 g, 11.2 mmol), bis(trimethylsilyl)acetamide (2.76 mL, 11.2 mmol), and triphenylphosphine (73 mg, 0.28 mmol) in THF (20 mL). The, reaction was heated at reflux for 45 min, cooled to RT, and concentrated in vacuo to give a gold-colored oil. The crude product was purified by flash chromatography on silica gel (150 g) eluted with a gradient of 40:60 EtOAc/hexane to 50:50 EtOAc/hexane to afford title compound (914 mg, 34%) as a colorless oil.

D. α-(Diethoxyphosphinyl)-4-phenoxybenzenebutanesulfonic acid, 1-methylethyl ester A mixture of Part C compound (900 mg, 1.87 mmol) and 10% palladium on carbon (50 mg) in EtOAc (6 mL) was stirred at RT under an atmosphere of $H_2$ (balloon) overnight (18 h), then was filtered through a pad of Celite with the aid of EtOAc. Evaporation gave title compound (855 mg, 94%) as a colorless oil.

E. 4-Phenoxy-α-phosphonobenzenebutanesulfonic acid, tripotassium salt

Ammonia gas was bubbled through a solution of Part D compound (780 mg, 1.61 mmol) in methanol (15 mL) for 15 min at RT. During the saturation, the solution turned yellow and became slightly exothermic. The reaction mixture was heated at 75° C. in a sealed tube overnight (17 h), then was cooled to RT. The reaction was concentrated in vacuo, and the residue was azeotroped with toluene (2×10 mL) to give a thick yellow syrup.

The crude product was dissolved in $CH_2Cl_2$ (5 mL) under argon and bromotrimethylsilane (1.5 mL, 11.3 mmol) was added dropwise. The cloudy yellow reaction was stirred at RT overnight, concentrated in vacuo, and pumped at high vacuum for 3 h.

The crude residue was dissolved in 1N KOH (8.1 mL, 8.1 mmol) and stirred at RT for 30 min. The reaction was heterogeneous. Additional 1N KOH (1.6 mL, 1.6 mmol) was added along with water (5 mL). The still heterogeneous reaction mixture was lyophilized to give a beige solid, which was purified by chromatography on CHP20P gel (2.5×20 cm column) eluted with water followed by a gradient created by the gradual addition of acetonitrile to a reservoir of water. The product fractions were concentrated to approximately a 5 mL volume, then lyophilized to provide title salt (488 mg, 61%) as a white solid.

TLC (silica gel) (6:3:1 n-propanol/$NH_4OH/H_2O$): $R_f$=0.15

IR (KBr) 3042, 2936, 2864, 1663, 1589, 1507, 1489, 1240, 1198, 1076, 966 $cm^{-1}$.

$^1H$ NMR ($D_2O$, 400 MHz) δ7.27 (t, 2H, J=7.9 Hz) 7.19 (d, 2H, J=8.3 Hz) 7.04 (t, 1H, J=7.5 Hz) 6.91 (d, 2H, J=7.7 Hz) 6.87 (d, 2H, J=8.3 Hz) 2.79 (dm, 1H) 2.52 (m, 2H) 2.00–1.63 (m, 4H) ppm.

$^{13}C$ NMR ($D_2O$, 75 MHz) δ157.22 154.56 138.96 130.15 130.08 123.66 119.04 118.57 61.69 (d, J=120 Hz) 34.74 31.53 (d, J=7Hz) 28.61 (d, J=2 Hz) ppm.

MS (FAB, + ions) m/z 463 (M+2H−K), 501 (M+H), 539 (M+K).

Anal. Calc'd for $C_{16}H_{16}K_3O_7PS$. 1.0 equiv $H_2O$: C, 37.05; H, 3.50; P, 5.97; S, 6.18. Found: C, 36.77; H, 3.86; P, 6.42; S, 6.48.

EXAMPLE 22

1-Phosphono-7-(4-propylphenoxy)-1-heptanesulfonic acid, tripotassium salt

A. 1-[(6-Bromohexyl)oxy]-4-propylbenzene

A solution of diisopropylazodicarboxylate (2.12 g, 10.5 mmol) in THF (25 mL) was added via syringe pump over 1.5 h to a mixture of 4-propylphenol (purchased from Aldrich Chemical Co.) (1.36 g, 10.0 mmol), 6-bromo-1-hexanol (purchased from Aldrich Chemical Co.) (1.81 g, 10.0 mmol), and triphenylphosphine (2.75 g, 10.5 mmol) in THF (25 mL) at 0° C. under argon. The slightly yellow reaction was stirred at 0° C. for 30 min, whereupon additional triphenylphosphine (262 mg, 1.00 mmol) was added, followed by addition of diisopropyl-, azodicarboxylate (200 mL, 1.0 mmol) over 30 min. The reaction was allowed to warm to RT, at which time silica gel (15 g) was added. The mixture was concentrated in vacuo and the white powder obtained was purified by flash chromatography on silica gel (150 g) eluted with a step gradient of hexane to 2:98 EtOAc/hexane. The slightly impure product obtained was rechromatographed on silica gel (150 g) eluted with 1:99 EtOAc/hexane to give title compound (2.00 g, 67%) as a colorless oil.

B. 1-[(6-Iodohexyl)oxy]-4-propylbenzene

A mixture o f Part A compound (1.85 g, 6.19 mmol), sodium iodide (4.65 g, 31.0 mmol), and anhydrous sodium bicarbonate (520 mg, 6.19 mmol) in methyl ethyl ketone (15 mL) was brought to reflux and maintained at that temperature for 2 h, then allowed to cool to RT. The solvent was removed from the colorless reaction in vacuo and the residue was partitioned between diethyl ether (70 mL) and water (20 mL). The organic layer was washed with water (10 mL) and brine (10 mL), then dried over $MgSO_4$. Evaporation gave title compound (2.09 g, 98%) as a opaque oil.

C. 1-(Diethoxyphosphinyl)-7-(4-propylphenoxy)-1-heptanesulfonic acid, cyclohexyl ester A solution of Example 1A, Part B sulfonate (4.65 g, 14.8 mmol) in DMF (5 mL) was added dropwise over 5 min to a suspension of dry sodium hydride (283 mg, 11.8 mmol) in DMF (5 mL) at −15° C. under argon (note: $H_2$ evolution). The cooling bath was removed and the suspension was stirred at RT for 30 min, whereupon a clear yellow solution was obtained. A solution of Part B iodide (2.04 g, 5.90 mmol) in DMF (10 mL) was added dropwise over 5 min, and the reaction was stirred at RT overnight. The reaction was quenched by addition of saturated $NH_4Cl$ (10 mL), and the resultant mixture was partitioned between diethyl ether (50 mL) and water (50 mL). The aqueous layer was extracted with diethyl ether (50 mL). The organic extracts were combined and washed with water (20 mL) and brine (2×20× 20 mL), then dried over $MgSO_4$. Evaporation gave a yellow oil which was purified by flash chromatography on silica gel (200 g) eluted with 30:70 EtOAc/hexane to give title compound (2.12 g, 68%) as a colorless oil.

D. 1-Phosphono-7-(4-propylphenoxy)-1-heptanesulfonic acid, tripotassium salt

Ammonia gas was bubbled through a solution of Part C compound (810 mg, 1.52 mmol) in methanol (15 mL) for 10 min at RT. During the saturation, the solution turned yellow and became slightly exothermic. The reaction mixture was heated at 75° C. in a sealed tube overnight (20 h), then cooled to RT. The reaction was concentrated in vacuo, and the residue was azeotroped with toluene (2×10 mL) to give a white semi-solid.

The crude product prepared above was dissolved in $CH_2Cl_2$ (8 mL) under argon and bromotrimethylsilane (1.4 mL, 10.6 mmol) was added dropwise. The cloudy yellow reaction was stirred at RT overnight (19 h), concentrated in vacuo, and pumped at high vacuum for 3 h.

The crude residue prepared above was dissolved in 1N KOH (7.6 mL, 7.6 mmol) and stirred at RT for 15 min, diluted with water (5 mL), then lyophilized to give a white solid. Purification was performed by chromatography on CHP20P gel (2.5×20 cm column) eluted with water followed by a gradient created by the gradual addition of acetonitrile to a reservoir of water. The product fractions were concentrated to approximately a 5 mL volume, then lyophilized to provide title salt (406 mg, 53%) as a white solid.

TLC (silica gel) (6:3:1 n-propanol/$NH_4OH$/$H_2O$): $R_f$=0.21

IR (KBr) 2932, 2868, 1636, 1512, 1200, 1074, 966 $cm^{-1}$.

$^1H$ NMR ($D_2O$, 300 MHz) δ7.05 (d, 2H, J=8.4 Hz) 6.79 (d, 2H, J=8.4 Hz) 3.90 (t, 2H, J=6.6 Hz) 2.72 (ddd, 1H, J=4.5, 6.3, 17.8 Hz) 2.37 (t, 2H, J=7.5 Hz) 1.93–1.10 (m, 12H) 0.71 (t, 3H, J=7.3 Hz) ppm.

$^{13}C$ NMR ($D_2O$, 75 MHz) δ156.24 136.23 129.78 115.03 69.14 61.76 (d, J=120 Hz) 36.41 29.42 (d, J=7Hz) 28.92 28.63 28.54 25.24 24.31 13.07 ppm.

MS (FAB, + ions) m/z 509 (M+H), 547 (M+K).

Anal. Calc'd for $C_{16}H_{24}K_3O_7PS$. 1.6 equiv $H_2O$: C, 35.75; H, 5.10; P, 5.76; S, 5.97. Found: C, 35.79; H, 5.49; P, 5.54; S, 5.95.

EXAMPLE 23

α-Phosphono-4-(4-propylphenoxy)benzenebutanesulfonic acid, tripotassium salt

A. 4-(4-Propylphenoxy)benzaldehyde

Anhydrous potassium carbonate (14.9 g, 0.12 mol) was added to a mixture of 4-propylphenol (13.6 g, 0.10 mol) and 4-fluorobenzaldehyde (12.4 g, 0.10 mol) in N,N-dimethylacetamide (100 mL) under argon. The heterogeneous mixture was brought to reflux, maintained at that temperature for 5 h, then cooled to RT. Water (100 mL) and $CH_2Cl_2$ (100 mL) were added, resulting in a tri-phase system. The bottom layer was removed; the middle layer was dried over $MgSO_4$; and, the top layer was extracted with $CH_2Cl_2$ (100 mL) and dried over $MgSO_4$. The dried layers were combined and concentrated in vacuo at 50° C. to give an orange oil. The crude product was purified by distillation to give title compound (16.6 g, 69%) as a colorless oil. bp 138°–150° C. (0.2 mm Hg)

B. α-Ethenyl-4-(4-propylphenoxy)benzenemethanol acetate ester

A solution of Part A compound (2.00 g, 8.33 mmol) in THF (15 mL) was added dropwise over 10 min to a solution of vinylmagnesium bromide (9.2 mL, 1.0M in THF, 9.2 mmol) in THF (15 mL) at −40° C. under argon. The reaction was warmed to −20° C. over 30 min, whereupon the heterogeneous mixture went to clear yellow. Additional vinylmagnesium bromide (1.5 mL, 1.0M in THF, 1.5 mmol) was added dropwise. The reaction was stirred at −20° C. for 10 min, then quenched by addition of saturated $NH_4Cl$ (10 mL). The solvent was removed in vacuo, and the mixture was diluted with diethyl ether (50 mL). The organic layer was washed with water (10 mL), 1N HCl (10 mL), and brine (20 mL), then dried over $MgSO_4$. Evaporation gave the alcohol (2.6 g) as a yellow oil.

Acetic anhydride (0.94 mL, 10.0 mmol), triethylamine (2.3 mL, 16.7 mmol), and 4-dimethylaminopyridine (10 mg, 0.08 mmol) were added to a solution of the crude alcohol in $CH_2Cl_2$ (30 mL) under argon. The yellow reaction was stirred at RT for 2.5 h, diluted with $CH_2Cl_2$ (50 mL), and washed with water and brine (20 mL each), then dried over $MgSO_4$. Evaporation gave a heterogeneous yellow oil, which was purified by flash chromatography on silica gel (150 g) eluted with 3:97 EtOAc/hexane to give title compound (1.85 g, 72%) as a pale yellow oil.

C. (E)-1-(Diethoxyphosphinyl)-4-[4-(4-propylphenoxy)phenyl]- 3-butene-1-sulfonic acid, 1-methylethyl ester Tetrakis(triphenylphosphine)palladium (196 mg, 0.17 mmol) was added to a mixture of Part B compound (1.74 g, 5.61 mmol), Example 11, Part A compound (3.07 g, 11.2 mmol), bis(trimethylsilyl)acetamide (2.8 mL, 11 mmol), and triphenylphosphine (73 mg, 0.28 mmol) in THF (20 mL). The reaction was heated at 45° C. for 3 h, cooled to RT, and concentrated in vacuo to give a yellow oil. The crude product was purified by flash chromatography on silica gel (200 g) eluted with a step gradient of 30:70 EtOAc/hexane to 40:60 EtOAc/hexane to afford title compound (706 mg, 24%) as a colorless oil.

D. 1-(Diethoxyphosphinyl)-4-(4-propylphenoxy) benzenebutanesulfonic acid, 1-methylethyl ester A mixture of Part C compound (700 mg, 1.34 mmol) and 10% palladium on carbon (40 mg) in EtOAc (5 mL) was stirred at RT under an atmosphere of $H_2$ (balloon) overnight, then was filtered through a pad of Celite with the aid of $CH_2Cl_2$. Evaporation gave title compound (669 mg, 95%) as a colorless oil.

E. α-Phosphono-4-(4-propylphenoxy)benzenebutanesulfonic acid, tripotassium salt

Ammonia gas was bubbled through a solution of Part D compound (610 mg, 1.16 mmol) in methanol (10 mL) for 10 min at RT. During the saturation, the solution turned yellow and became slightly exothermic. The reaction mixture was heated at 75° C. in a sealed tube overnight (20 h), then cooled to RT. The reaction was concentrated in vacuo, and the residue was azeotroped with toluene (2×10 mL) to give a pale yellow oil.

The crude product prepared above was dissolved in CH$_2$Cl$_2$ (6 mL) under argon and bromotrimethylsilane (1.1 mL, 8.1 mmol) was added dropwise. The cloudy yellow reaction was stirred at RT overnight (19 h), concentrated in vacuo, and pumped at high vacuum for 3 h.

The crude residue prepared above was dissolved in 1N KOH (5.8 mL, 5.8 mmol) and stirred at RT for 15 min, diluted with water (5 mL), then lyophilized to give a white solid. Purification was performed by chromatography on CHP20P gel (2.5×20 cm column) eluted with water followed by a gradient created by the gradual addition of acetonitrile to a reservoir of water. The product fractions were concentrated to approximately a 5 mL volume, then lyophilized to provide title salt (445 mg, 71%) as a white solid.

TLC (silica gel) (6:3:1 n-propanol/NH$_4$OH/H$_2$O): R$_f$=0.18

IR (KBr) 2959, 2870, 1503, 1240, 1200, 1078, 966 cm$^{-1}$.

$^1$H NMR (D$_2$O, 400 MHz) δ7.16 (d, 2H, J=8.6 Hz) 7.10 (d, 2H, J=8.6 Hz) 6.83 (2d, 4H, J=6.4, 6.8 Hz) 2.79 (ddd, 1H, J=4.3, 6.2,. 16.9 Hz), 2.50 (m, 2H) 2.42 (t, 2H, J=7.5 Hz) 1.97–1.62 (m, 4H) 1.45 (sextet, 2H, J=7.5 Hz) 0.73 (t, 3H, J=7.5 Hz) ppm.

$^{13}$C NMR (D$_2$O, 75 MHz) δ154.93 138.64 130.01 118.70 118.63 61.54 (d, J=120 Hz) 36.56 34.73 31.51 (d, J=7 Hz) 28.52 24.27 13.06 ppm.

MS (FAB, + ions) m/z 543 (M+H), 581 (M+K).

Anal. Calc'd for C$_{19}$H$_{22}$K$_3$O$_7$PS. 2.0 equiv H$_2$O: C, 39.43; H, 4.53; P, 5.35: S, 5.54. Found: C, 39.63; H, 4.70; P, 5.18; S, 5.50.

EXAMPLE 24

(E,E)-1-(Diethoxyphosphinyl)-6,10,14-trimethyl-5,9,13-pentadecatriene-1-sulfonic acid, sodium salt To a solution of 0.50 g (0.91 mmol) of Example 1A Part C compound and 10 mL of methanol in a sealable tube at 0° C. was added NH$_3$ (g) until the solution was saturated. The tube was sealed and, placed in an oil bath at 70° C. for 24 h, at which point the tube was opened and the volatiles removed under reduced pressure. The remainder was dissolved with 1.20 mL (1.20 mmol) of 1N sodium hydroxide solution. The compound was purified by MPLC by loading the basic solution on a column of CHP20P gel (2.5 cm diam.×20 cm height) and eluting with water (150 mL) followed by a gradient created by the gradual addition of 400 mL of acetonitrile to a reservoir of 350 mL of water. Approximately 7 mL fractions were collected. Pure fractions (#30–34) were combined and the acetonitrile was removed under reduced pressure. The aqueous solution was lyophilized to provide 0.39 g (87%) of title salt as an amber oil.

TLC Silica gel (6:3:1 n-propanol/conc. ammonia/water) R$_f$=0.80.

IR (CHCl$_3$) 3459, 2969, 2926, 2859, 1647, 1445, 1236, 1165, 1098, 1069, 1034, 970 cm$^{-1}$.

$^1$H NMR (CD$_3$OD, 300 MHz) δ5.15 (m, 3H) 4.18 (quint., 4H, J=7.0 Hz) 3.22 (dt, 1H, J=18.4, 6.0 Hz) 2.10–1.80 (m, 12H) 1.70 (s, 3H) 1.65 (s, 3H) 1.60 (s, 6H) 1.60 (m, 2H) 1.30 (t, 3H, J=7.0 Hz) ppm.

Mass Spec (FAB, + ions) m/e 509 (M+Na).

Anal. Calc'd for C$_{22}$H$_{40}$O$_6$NaPS·0.73 H$_2$O: C, 53.91; H, 8.31; P, 6.32; S, 6.54 Found: C, 53.91; H, 8.23; P, 6.17; S, 6.33.

EXAMPLE 25

(E)-6-Methyl-10-phenyl-1-phosphono-5-decene-1-sulfonic acid, tripotassium salt

A. 5-Methyl-9-phenyl-non-4-en-1-ol

To a solution of 1.5 g (4.26 mmol) of the Example 35, Part B iodide in 10 mL of THF at 0° C. was added 12.9 mL (25.8 mmol) of benzylmagnesium chloride in THF (purchased from Aldrich Chemical) followed by 10 mg (catalyst) of copper (I) iodide. The reaction was stirred at 0° C. for 1 h, and at room temperature for 3 h. The reaction was diluted with ether and aqueous NH$_4$Cl solution. The organic fraction was washed with water and brine, dried (MgSO$_4$) and concentrated to provide 2.70 g of a crude oil. The oil was purified by flash chromatography (250 g of silica gel) eluting with 8:2 ethyl acetate/hexane to provide 1.10 g (99%) of title compound as a colorless oil.

TLC Silica gel (8:2 hexane/ethyl acetate) R$_f$=0.29.

B. (E)-(9-Iodo-5-methyl-5-nonenyl)benzene

A solution of 980 mg (4.22 mmol) of Part A alcohol in 10 mL of methylene chloride and 0.76 mL (5.49 mmol) of triethylamine at 0° C. was treated with 0.39 mL (5.07 mmol) of methanesulfonyl chloride dropwise over 0.2 h. The reaction mixture was stirred for 1.0 h when it was quenched with saturated aqueous KHSO$_4$ solution and diluted with ether. The layers were separated and the organic fraction was washed with solutions of NaHCO$_3$ and brine, dried (MgSO$_4$) and evaporated to provide the mesylate as a pale yellow oil.

The crude mesylate was diluted with 100 mL of acetone and treated with 3.65 g (24.39 mmol) of NaI at room temperature for 48 h. The mixture was diluted with 200 mL of a hexane/water mixture. The organic fraction was extracted with NaHSO$_3$, brine, dried (MgSO$_4$) and concentrated to provide a colorless oil. The oil was purified by flash chromatography (50 g of silica gel ) eluting with 8:2 ethyl acetate/hexane to provide 1.05 g (76%) of title compound as a colorless oil.

TLC Silica gel (8:2 hexane/ethyl acetate) R$_f$=0.64.

C. (E)-1-(Diethoxyphosphinyl)-6-methyl-10-phenyl-5-decene-1-sulfonic acid, cyclohexyl ester To a stirred solution of 0.93 g (2.95 mmol) of Example 1A Part B compound in 3 mL DMF at −20° C. was added 51 mg (2.13 mmol) of sodium hydride. After the hydrogen evolution diminished, the reaction was brought to RT and stirred for 10 minutes. When hydrogen evolution subsided Completely, 0.56 g (1.64 mmol) of Part B iodide was added and the reaction stirred 24 hours before storing at −80° C. for 30 hours. The reaction was quenched with 10 mL of saturated aqueous ammonium chloride solution, diluted with ether (150 mL) and water (75 mL). The aqueous layer was removed and the organics washed with saturated sodium chloride. The combined aqueous layers were back extracted with ether and the combined organic fractions dried (over sodium sulfate) and evaporated. The crude material was purified by flash chromatography on silica gel (60 g), packed, loaded, and eluted with 60:40 hexane/ethyl acetate. The pure fractions (#8–18) were combined and concentrated to yield 0.55 g (64%) of title compound as a clear oil.

TLC Silica gel (60:40 hexane/ethyl acetate) R$_f$=0.25.

MS (CI, + ions) m/e 529 (M+H), 546 (M+NH$_4$).

IR (KBr) 2934, 2858, 1452, 1454, 1260, 1194, 1053, 1024, 928 cm$^{-1}$.

$^1$H NMR (400 MHz, CDCl$_3$) δ7.18 (t, 2H, J=7.5 Hz) 7.08 (d, 3H, J=7.5 Hz) 5.03 (t, 1H, J=7.0 Hz) 4.76 (m, 1H) 4.14 (m, 4H) 3.35 (dt, 1H, J=19.7, 6.5 Hz) 2.53 (t, 2H, J=7.7 Hz) 2.05 (m, 2H) 1.95 (m, 5H) 1.77–1.17 (m, 16H) 1.50 (s, 3H) 1.28 (s, 6H, J=8.0 Hz) ppm.

D. (E)-6-Methyl-10-phenyl-1-phosphono-5-decene-1-sulfonic acid, tripotassium salt To a solution of 0.496 g (1.93 mmol) of Part C triester in 10 mL methanol in a sealable tube was added ammonia gas at 0° C. until saturated. The tube was then sealed and heated at 65° C. for 24 hours. The tube was opened and the solution evaporated to a glassy oil which was evaporated from toluene two times and dried under high vacuum, leaving an amber oil. The residue was dissolved in 3.5 mL methylene chloride and treated sequentially with 1.53 mL (11.55 mmol) of collidine and 1.78 mL (13.47 mmol) of bromotrimethylsilane bromide. The reaction mass was stirred at RT under argon for 24 hours, at which point an additional 0.254 mL (13.47 mmol) of collidine and 0.508 mL (3.86 mmol) of bromotrimethylsilane were added. After 45 hours at room temperature, the reaction was quenched with 6.95 mL (6.95 mmol) of 1N KOH and lyophilized. The remainder was purified by MPLC on a column of CHP-20P gel (2.5 cm diameter×21 cm height), eluting with water (100 mL), followed by a gradient formed by the gradual addition of 400 mL acetonitrile to a reservoir of 350 mL water. Approximately 10 mL fractions were collected. Pure fractions (#30–32) were combined, concentrated to 0.36 g, and passed through a column of 30 g (153 meg) AG 50W-XG ($K^+$ form) with water. The potassium salt eluted in fractions 1 to 4, which were lyophilized, providing a granular powder. The lyophilate was diluted in 150 μL water and triturated with 2 mL portions of acetone three times. The product was dried under high vacuum for three days, yielding 259 mg (26%) of title salt as a pale beige powder.

IR (KBr) 3424, 2932, 2857, 1653, 1200, 1080, 966 cm$^{-1}$.

MS (Ion Spray, + ions) 429 (M–2K+3H), 467 (M–K+2H), 505 (M+H).

$^1$H NMR (300 MHz, D$_2$O) δ7.25 (m, 5H) 5.25 (t, 1H, J=6.5 Hz) 2.85 (dt, 1H, J=19.0, 6.0 Hz) 2.60 (t, 2H, J=8.5 Hz) 2.00 (m, 6H) 1.53 (s, 3H) 1.53 (m, 4H) 1.40 (quint, 2H, J=6.4 Hz) ppm.

Anal. Calc'd. for $C_{17}H_{24}K_3PO_6S$-2.1 H$_2$O: C, 37.64; H, 5.24; P, 5.71; S, 5.91 Found: C, 37.64; H, 5.19; P, 5.34; S, 6.09

EXAMPLE 26

4-(3-Phenylpropyl)-α-phosphonobenzenebutanesulfonic acid, tripotassium salt

A. 4-(1-Hydroxy-3-phenyl-2-propynyl)benzoic acid, methyl ester

To a stirred solution of 4.40 mL (40.0 mmol) of phenylpropyne in 30 mL of THF under nitrogen at –75° C. was added a solution of 16 mL (40 mmol) of 2.5M n-butyllithium in hexane over 20 min. The resulting light yellow solution was warmed to 0° C. and stirred for 30 min. This solution was added via syringe to a slurry of 6.25 g (38.0 mmol) of methyl 4-formylbenzoate in 30 mL of THF at –30° C. over 20 min. The resulting light yellow solution was warmed to room temperature and stirred for 30 min. The reaction was quenched with saturated ammonium chloride solution, extracted twice with ether, dried (MgSO$_4$) and evaporated. Purification by flash chromato-graphy (5×15 cm column, 1:19 ether/dichloromethane as eluent) gave title compound as a white solid, mp 48°–50° C., 9.36 g, 88% yield.

B. 4-(3-Phenylpropyl)benzoic acid, methyl ester

A 500 mL Parr vessel was charged with 3.11 g (11.7 mmol) of Part A compound in 100 mL of methanol and purged with a rapid stream of nitrogen for 15 min. The solution was treated with 0.5 g of Pearlman's catalyst (20% Pd(OH)$_2$ on carbon, 31% H$_2$O). This mixture was agitated for 16 h at an initial hydrogen pressure of 42 psi. Total hydrogen uptake was 15 psi. The reaction was purged with nitrogen, filtered through Celite and evaporated. The oily residue was dissolved in dichloromethane, dried (MgSO$_4$) and filtered to give title compound as a colorless oil, 2.85 g, 97% yield. The material was used without further purification.

C. 4-(3-Phenylpropyl)benzaldehyde

To a stirred solution of 2.80 g (11.0 mmol) of Part B compound in 20 mL of methanol under nitrogen at room temperature was added 22 mL (22 mmol) of 1M NaOH solution. The milky solution was heated to 60° C. for 2 h. The resulting clear solution was cooled and 1M HCl solution was added to bring the reaction mixture to pH 2. The resulting solids were collected, washed with water and dried in vacuo at 60° C. to give 2.55 g (96%) of the carboxylic acid of the Part B compound.

This solid was dissolved in 25 mL of dichloromethane under nitrogen and 1.4 mL (15 mmol) of oxalyl chloride followed by 0.1 mL of DMF. The resulting vigorously bubbling solution was stirred for 1 h and then evaporated. The semi-solid residue was dissolved in 25 mL of benzene under nitrogen and 170 mg (0.15 mmol) of tetrakis(triphenylphosphine)palladium was added. To this stirring solution at room temperature was added 11.1 mL (34 mmol) of tributyltin hydride over 20 min. The solution turns yellow and warms autogenously to 40° C. After 1 h, the reaction was treated with 40 mL of 10% aqueous potassium fluoride and stirred vigorously for 30 min. The reaction mass was filtered, the filtrate diluted with ether, washed with water, and the organic layer separated, dried (MgSO$_4$) and evaporated onto 10 g of silica gel. Purification by flash chromatography (5×20 cm column, 45:55 dichloromethane/hexanes as eluent) gave 2.15 g, 87% yield (84% yield from Part B compound), of title compound as a colorless oil.

D. α-Ethenyl-4-(3-phenylpropyl)benzenemethanol, acetate ester

To a stirred slurry of 11.0 mL (11.0 mmol, 1M in THF) of vinyl magnesium bromide in 20 mL of THF at –40° C. under argon was added a solution of 1.95 g (8.7 mmol) of Part C compound in 10 mL of THF over 20 min. The resulting pale yellow solution was warmed to room temperature, stirred for 2 h and then quenched with saturated ammonium chloride solution. The reaction mixture was extracted twice with ether. The extracts were combined, dried (MgSO$_4$) and evaporated. The resulting yellow oil was dissolved in 20 mL of dichloromethane at room temperature under nitrogen and 2.2 mL (16 mmol) of triethylamine and 1.4 mL (15 mmol) of acetic anhydride were added, followed by 100 mg (0.4 mmol) of DMAP. After 30 minutes, the reaction mixture was diluted with ether, washed twice with 10% citric acid, once with brine and once with saturated sodium bicarbonate. The organic phase was dried (MgSO$_4$) and evaporated onto 10 g of silica gel. Purification by flash chromatography (5×25 cm column, 2:3 dichloromethane/hexanes as eluent) gave 7.12 g, 92%, of title compound as a colorless oil.

E. (E)-1-(Diethoxyphosphinyl)-4-[4-(3-phenylpropyl)phenyl]- 3-butene-1-sulfonic acid, 1-methylethyl ester To a stirred solution of 1.33 g (4.52 mmol) of Part D compound, 2.5 mL (10 mmol, 2.2 equiv.) of bis(trimethylsilyl)acetamide, 2.48 g (9.0 mmol, 2.0 equiv.) of Example 11 Part A sulfonate and 125 mg (0.5 mmol) of triphenylphosphine in 20 mL of THF under argon was added 270 mg (0.24 mmol) of tetrakis(triphenylphosphine)-palladium. The resulting mixture was heated to reflux for 30 min. The reaction was cooled, evaporated, diluted with ether and washed once with 10% citric acid and thrice with water. The organic phase was dried (MgSO$_4$) and evaporated. Purification by flash chromatography on silica gel (5×25 cm column) eluted with 2:23 ether/dichloro-methane gave title compound as a colorless oil, 1.10 g, 55% yield.

F. α-(Diethoxyphosphinyl)-4-(3-phenylpropyl)benzenebutanesulfonic acid, 1-methylethyl ester To an argon-purged solution of 890 mg (1.75 mmol) of Part E compound and 100 mg of 10% palladium-on-carbon in 20 mL of ethyl acetate in a 500 mL one-neck round bottom flask was attached a hydrogen-filled rubber bladder of approximately 1 L capacity. The reaction mixture was vigorously stirred for 16 h, purged with nitrogen, filtered through Celite and the filtrate evaporated. The oily residue was redissolved in dichlormethane, filtered through a 0.75μ filter and re-evaporated to give title compound as a colorless oil, 865 mg, 99% yield. The product was used without further purification.

G. 4-(3-Phenylpropyl)-α-phosphonobenzenebutanesulfonic acid, tripotassium salt

To a stirred solution of 860 mg (1.7 mmol) of Part F compound in 10 mL of dichloromethane under argon at room temperature was added 700 μL (5.3 mmol) of bromotrimethylsilane. After 24 h, the resulting clear solution was evaporated at 25° C. and the residue dissolved in 10 mL of THF. To this stirred solution was added 560 mg (3.4 mmol) of dried, finely ground potassium iodide and 3 mg (0.01 mmol) of 18-crown-6. The resulting slurry was heated to reflux for 24 h, evaporated and then stirred for 1 h with 6 mL (6 mmol) of 1.0M potassium hydroxide solution. The solution was lyophilized and then purified by MPLC (2.5×20 cm column of Mitsubishi Kasei Sepadbeads HP-20 resin): 1.5 mL fractions, 7 mL/min flow rate, eluted with 200 mL of water and then a gradient prepared from 400 mL of water and 450 mL of 2:1 acetonitrile/water). Fractions 38–48 were collected and lyophilized to give title salt as a white solid, 640 mg, 69% yield.

IR (KBr pellet) 3428, 3084, 2934, 2859, 1659, 514, 1196, 1107, 1084, 966 cm$^{-1}$.

$^1$H NMR (D$_2$O, 400 MHz) δ7.10 (m, 9H) 2.76 (dm, 1H, J=17.3 Hz) 2.45 (m, 6H) 1.74 (m, 6H) ppm.

Anal. Calc'd for C$_{20}$H$_{18}$K$_3$O$_6$PS.1.1 H$_2$O: C, 41.77; H, 4.46; P, 5.67; S, 5.87 Found: C, 41.77; H, 4.68; P, 5.46; S,6.08.

MS (FAB, + ions) m/e 565 (M+K), 527 (M+H), 489 (M–K+ 2H).

EXAMPLE 27

(E,E)-1-(Hydroxymethylphosphinyl)-6,10,14-trimethyl-5,9,13-pentadecatriene-1-sulfonic acid, dipotassium salt.

A. Chloromethylphosphinic acid, ethyl ester

To a solution of 15.0 g (98.6 mmol, 1 eq) of diethyl methylphosphonate in 20 mL of dry benzene at room temperature was added 20.5 g (98.6 mmol, 1 eq) of phosphorus pentachloride as a solid all at once. The reaction became very exothermic and began to reflux. Stirring was discontinued and the flask was cooled to 0° C. After 5 minutes, the ice bath was removed and the reaction mixture was warmed to room temperature and stirred for 2 hours, then heated at reflux for 1 hour. After cooling to room temperature, the reaction mixture was concentrated. High vacuum (0.1 mmHg) removal of phosphorus oxychloride (POCl$_3$, a volatile by-product of the reaction; Note 1) and any solvent remnants for 13 h afforded 3.42 g of a cloudy yellow liquid which was used without purification or characterization.

Note 1: The product is volatile and the lengthy high vacuum exposure resulted in loss of a significant amount of the desired chlorophosphonate.

B. (Ethoxymethylphosphinyl)methanesulfonic acid, cyclohexyl ester

To a solution of 8.55 g (48.0 mmol, 1 eq) of Example 1A Part A mesylate in 200 mL of dry THF at –75° C. was added 19.2 mn (48.0 mmol, 1 eq) of n-butyllithium (2.5M hexane solution) dropwise at a rate that kept the temperature below –72° C. (addition time 35 min). The resulting clear light yellow solution was stirred for 10 min at –74° C. A solution of 3.42 g of Part A chloride in 20 mL of dry THF was added dropwise at a rate that again kept the temperature below –72° C. (addition time 40 min). The resulting brown reaction mixture was stirred for 90 min at –74° C. and then quenched by addition of a solution of 2.75 mL (48.0 mmol, 1 eq) of glacial acetic acid in 10 mL of THF over 5 min. The solution was warmed to room temperature and concentrated. The viscous brown residue was taken up in dichloromethane (200 mL), washed with water (100 mL), brine (100 mL), dried (MgSO$_4$) and concentrated to afford after high vac removal of solvent remnants 9.26 g of a viscous brown oil. The desired product was isolated by flash chromatography on silica gel (1000 g) eluting initially with ethyl acetate (5 L) followed by 10% ethanol in ethyl acetate (2 L). Fractions (40 mL) containing the clean product were pooled and concentrated to afford 3.91 g of title compound as a viscous yellow oil (57% assuming starting phosphonyl chloride was pure).

TLC Silica gel (Ethyl acetate): R$_f$ 0.35.

C. (E,E)-1-(Ethoxymethylphosphinyl)-6,10,14-trimethyl-5,9,13-pentadecatriene-1-sulfonic acid, cyclohexyl ester To a suspension of 222 mg (5.6 mmol, 2 eq) of sodium hydride (as a 60% mineral oil dispersion) in 1 mL of dry dimethylformamide (DMF) at 0° C. was added dropwise a solution of 1.58 g (5.6 mmol, 2 eq) of Part B compound in 3 mL of dry DMF. The vigorously bubbling solution was stirred for 5 min at 0° C. followed by 30 min at room temperature. To the resulting homogeneous brown solution was added a solution of 1.0 g (2.8 mmol, 1 eq) of Example 1 Part C iodide in 3 mL of DMF. After 16 h at room temperature, the reaction was quenched by adding 25 mL of water. The heterogeneous solution was partitioned between ether (100 mL) and brine (25 mL). The aqueous layer was extracted with ether (4×20 mL) and the combined organic layers were dried (MgSO$_4$) and concentrated to afford after high vac (0.25 mmHg) removal of solvent remnants 1.49 g of crude product as a light brown oil. The desired product was isolated via flash chromatography on silica gel (250 g) eluting with 9% isopropanol in hexanes. Fractions (40 mL each) containing clean product were pooled and concentrated to afford 813 mg of title compound (56%) as a light yellow oil. TLC Silica gel (15% isopropanol in hexanes): R$_f$ 0.34.

D. (E,E)-1-(Hydroxymethylphosphinyl)-6,10,14-trimethyl-5,9,13-pentadecatriene-1-sulfonic acid, dipotassium salt Into a solution of 800 mg (1.55 mmol, 1 eq) of Part C compound in 10 mL of dry methanol (MeOH) at 0° C. was bubbled gaseous ammonia until the solution was saturated. The tube was sealed with a threaded teflon cap fitted with an O-ring and heated at 75° C. for 17 h. The volatiles were removed in vacuo and the oily residue was co-evaporated twice with toluene before placing on high vac (0.25 mmHg) for three hours. To the resulting clear yellow oil was added 8 mL of dry CH$_2$Cl$_2$ followed by 2.04 mL (15.5 mmol, 10 eq) of dry 2,4,6-collidine. To the resulting light yellow clear solution was added 2.04 (15.5 mmol, 10 eq) of bromotrimethylsilane (TMSBr) and the resulting white heterogeneous mixture was stirred at room temperature. After 16 h, the reaction mixture was concentrated and placed on high vac (0.25 mmHg) for 3 h. The resulting yellow white solid was dissolved by adding 7.3 mL (7.3 mmol, 4.7 eq) of 1M potassium hydroxide (pH 12.35), frozen and lyophilized. The light brown lyophilate was dissolved in water and chromatographed on a column of CHP20P (2.5 cm×25 cm) eluting initially with water (150 mL) followed a gradient formed by the gradual addition of acetonitrile (400 mL) to a reservoir containing water (400 mL). No fractions (10 mL each) containing clean product by were obtained. The fractions containing approximately 2% of an impurity (which eluted just before the desired product) were pooled, concentrated and rechromatographed using the same conditions. Fractions containing clean product by HPLC were concentrated and the reasidual waxy residue was triturated with acetone to afford 274 mg of title salt (37%) as a white solid.

TLC Silica gel (7:2:1 n-propanol:ammonium hydroxide:water): $R_f$ 0.47.

$^1$H NMR ($D_2O$, 300 MHz): δ5.09 (t, 1 H, J=6.8 Hz) 5.01 (t, 1H, J=6.9 Hz) 4.98 (t, 1H, J=6.8 Hz) 2.75 (dt, 1H, J=15.0, 5.6 Hz) 1.90 (m, 10H) 1.76 (m, 2H,) 1.51 (s, 3H) 1.47 (s, 3H) 1.44 (s, 6H$_5$) 1.43 (m, 2H) 1.21 (d, 3H, J=14.3 Hz) ppm.

$^{13}$C NMR ($D_2O$, 75.6 MHz): δ136.7 136.3 133.0 124.8 124.8 124.7 63.0 (d, $J_{CP}$=81 Hz) 39.4 39.3 29.6 (d, $J_{CP}$=5 Hz) 27.8 26.9 26.4 26.3 25.3 17.4 16.0 (d, $J_{CP}$=98 Hz) 15.7 ppm.

IR (KBr) 2922, 2857, 1213, 1188, 1088, 1034 cm$^{-1}$.

MS (FAB, + ions ) m/z 483 (M+H), 445 (M+2H–K), 407 (M+3H–2K).

Anal. Calcd. for $C_{19}H_{33}O_5PSK_2$: C, 47.28; H, 6.89; P, 6.42; S, 6.64 Found: C, 47.30; H, 6.92; P, 6.04; S, 6.94

EXAMPLE 28

(E,E)-1-(Hydroxyphosphinyl)-6,10,14-trimethyl-5,9,13-pentadecatriene-1-sulfonic acid, dipotassium salt A. (E,E)-6,10,14-Trimethyl-5,9,13-pentadecxatriene-1-sulfonic acid, ethyl ester n-Butyllithium (11.1 mL, 2.5M in hexanes, 27.8 mmol) was added dropwise over 15 min to a solution of ethyl methanesulfonate (5.17 g, 41.7 mmol) in THF (50 mL) at −78° C. under argon. The clear colorless reaction mixture was stirred at −78° C. for 20 min, whereupon a solution of Example 1 Part C iodide (5.00 g, 13.9 mmol) in THF (10 mL) was added dropwise over 10 min. The reaction was warmed to −60° C. (internal temperature) and stirred at that temperature for 1.5 h. The reaction was then warmed to −20° C. over 2 h, then quenched by addition of saturated NH$_4$Cl (20 mL). Diethyl ether (300 mL) was added, and the organic layer was washed with water (2×50 mL) and brine (10 mL), then dried over MgSO$_4$. Evaporation gave a yellow oil, which was purified by flash chromatography on silica gel (200 g) eluting with a step gradient of 5:95 to 8:92 EtOAc/hexane to provide title compound (3.61 g, 73%) as a colorless oil.

B. (E,E)-1-(Ethoxyphosphinyl)-6,10,14-trimethyl-5,9,13-pentadecatriene-1-sulfonic acid, ethyl ester n-Butyllithium (2.7 mL, 2.5M in hexanes, 6.7 mmol) was added dropwise to a solution of Part A compound (2.00 g, 5.62 mmol) in THF (15 mL) at −78° C. under argon. The yellow reaction was stirred at −78° C. for 30 min, whereupon diethyl chlorophosphite (2.4 mL, 16.9 mmol) was added rapidly in one portion. The colorless reaction was stirred at −78° C. for 1 h, then allowed to warm to RT over 2.5 h. The reaction was diluted with anhydrous diethyl ether (50 mL). Water (10 mL) was then added, and the resultant biphase mixture was stirred vigorously at RT for 1 h. The aqueous layer was removed, and the organic layer was washed with water (10 mL) and brine (15 mL), then dried over MgSO$_4$. Evaporation gave a colorless oil, which was purified by flash chromatography on CC7 buffered silica gel (250 g) eluting with a step gradient of 25:75 to 35:65 to 45:55 EtOAc/hexane to give title compound (2.07 g, 82%) as a colorless oil as a 1:1 mixture of diastereomers.

C. (E,E)-1-(Hydroxyphosphinyl)-6,10,14-trimethyl-5,9,13-pentadecatriene-1-sulfonic acid, dipotassium salt Potassium iodide (317 mg, 1.91 mmol) was added to a solution of Part B compound (816 mg, 1.82 mmol) in acetone (10 mL) under argon. As the mostly insoluble potassium iodide reacted, the product precipitated out of the reaction mixture. The white heterogeneous reaction was stirred at RT overnight, concentrated in vacuo, then pumped at high vacuum to give a white solid.

The crude sulfonate salt was dissolved in 1N KOH (3.6 mL, 3.6 mmol), then chromatographed on CHP-20P gel (2.5×20 cm column) eluting with water followed by a gradient created by the gradual addition of acetonitrile to a reservoir of water. The product fractions were concentrated in vacuo to give an opaque white gum. Acetone (2 mL) was added and the product was precipitated out as a solid. The solid was filtered, washed with acetone (2×5 mL), then pumped at high vacuum to give title salt (507 mg, 60%) as a white solid.

TLC (silica gel) (7:2:1 n-propanol/NH$_4$OH/H$_2$O): $R_f$=0.43

IR (KBr) 2928, 2857, 2288, 1202, 1094 cm$^{-1}$.

$^1$H NMR ($D_2O$, 400 MHz) δ7.02 (d, 1H, J=548 Hz) 5.12 (t, 1H, J=6.8 Hz) 5.06 (t, 1H, J=6.8 Hz) 5.04 (t, 1H, J=6.8 Hz) 2.85 (dt, 1H, J=6.4, 13.7 Hz) 2.03–1.85 (m, 10H) 1.78 (m, 2H) 1.54 (s, 3H) 1.49 (s, 3H) 1.47 (s, 6H) 1.44 (m, 2H) ppm.

$^{13}$C NMR ($D_2O$, 100 MHz) δ136.53 135.96 132.67 124.60 124.55 124.47 62.42 (d, J=81 Hz) 39.29 39.18 28.41 (d, J=6 Hz) 27.56 26.23 26.19 25.15 24.93 17.24 15.55 ppm.

MS (ES, + ions) m/z 393 (M+3H−2K), 410 [(M+2H−2K)+NH$_4$], 427 [(M+2H−2K)+NH$_3$+NH$_4$], 431 (M+2H−K), 448 [(M+2H−K)+NH$_3$], 469 (M+H).

Anal. Calc'd for $C_{18}H_{31}K_2O_5PS$: C, 46.13; H, 6.67; P, 6.61; S, 6.84. Found: C, 46.18; H, 6.68; P, 6.28; S, 7.17.

EXAMPLE 29

4-(Phenylmethyl)-α-phosphonobenzenebutanesulfonic acid, tripotassium salt

A. 1-Bromo-4-(phenylmethyl)benzene

To a stirred solution of 21 mL (42 mmol, 2.0M in THF) of benzylmagnesium chloride at room temperature under nitrogen was added a solution of 6.80 g (50.0 mmol) of thrice-fused zinc chloride, in 50 mL of THF. The resulting tan slurry was stirred for 1 hour. To this slurry was added 10.0 g (35.3 mmol) 1-bromo-4-iodobenzene and 450 mg (0.4 mmol) of tetrakis(tri-phenylphosphine)palladium in 30 mL of THF. The reaction was stirred at room temperature for 16 hours and then quenched with 50 mL of 2M hydrochloric acid. The mixture was extracted thrice with hexanes, the extracts combined, washed once with saturated sodium bicarbonate solution and once with 10% sodium thiosulfate. The organic extract was dried (MgSO$_4$) and evaporated. The crude product was purified by flash chromatography on silica gel (5×25 cm column, hexanes as elutent) to give 7.05 g (80%) of title compound as a colorless oil.

B. α-Ethenyl-4-(phenylmethyl)benzenemethanol acetate ester

To a stirred solution of 2.47 g (10.0 mmol) of Part A compound in 30 mL of THF at −60° C. under nitrogen was added a solution of 12 mL (20 mmol, 1.7M in pentane) of t-butyllithium over 20 minutes. The resulting deep red solution was warmed to 0° C. and stirred for 30 min. To the resulting solution was added 1.0 mL (18 mmol) of freshly distilled acrolein over 5 min. The resulting light yellow solution was stirred for 30 min, quenched with saturated ammonium chloride. The mixture was extracted twice with ether, dried (MgSO$_4$) and evaporated to give a colorless oil.

The solid was dissolved in 30 mL of dichloromethane, stirred under nitrogen at room temperature and treated with 2.2 mL (15.8 mmol) of triethylamine, 1.3 mL (14 mmol) of acetic anhydride and 50 mg (0.4 mmol) of DMAP. After 30 min, the reaction mixture was evaporated, redissolved in ether and washed once with 10% citric acid solution, once with brine and once with saturated sodium bicarbonate solution. The organic phase was dried (MgSO$_4$) and evaporated. The crude product was purified by flash chromatography on silica gel (5×15 cm column, 1:1 dichloromethane/hexanes as elutent) to give 2.51 g (94% from Part A compound) of title compound as a colorless oil.

C. (E)-1-(Diethoxyphosphinyl)-4-[4-(phenylmethyl) phenyl]-3-butene-1-sulfonic acid, cyclohexyl ester To a stirred solution of 1.45 g (5.44 mmol) of Part B compound, 2.5 mL (11.7 mmol, 2.15 equivalents) of bis(t-rimethylsilyl)acetamide, 3.14 g (10.0 mmol, 1.8 equivalents) of Example 1A Part B sulfonate and 270 mg (1.0 mmol) of triphenylphosphine in 15 mL of THF under nitrogen was added 600 mg (0.53 mmol) of tetrakis(triphenylphosphine)palladium. The resulting mixture was heated to reflux for 1 h. The reaction was cooled and evaporated and pumped at room temperature @0.2 Torr for 24 hours. The residue was diluted with dichloromethane and evaporated onto 5 g of silica gel. Purification by flash chromatography on silica gel (5×25 cm column) eluted with 1:13 ether/dichloromethane gave title compound as a yellow oil, 1.65 g, 58% yield.

D. α-(Diethoxyphosphinyl)-4-(phenylmethyl) benzenebutanesulfonic acid, cyclohexyl ester To a nitrogen-purged slurry of 1.15 g (2.2 mmol) of Part C compound and 120 mg of 10%Pd/C in 50 mL of ethyl acetate in a 200 mL one-neck round bottom flask was attached a hydrogen-filled rubber bladder of approximately 1 L capacity. The reaction mixture was vigorously stirred for 16 h, purged with nitrogen, filtered through Celite and the filtrate evaporated.. The oily residue was redissolved in dichloromethane, filtered through a 0.75µ filter and re-evaporated to give title compound as a colorless oil, 1.15 g, 99% yield. The product was used without further purification.

E. 4-(Phenylmethyl)-α-phosphonobenzenebutanesulfonic acid. tripotasisum salt

To a stirred solution of 1.15 g (2.20 mmol) of Part D compound in 10 mL of dichloromethane under nitrogen at room temperature was added 1.0 mL (7.5 mmol) of bromotrimethylsilane. After 24 h, the resulting clear solution was evaporated at 25° C. and the residue dissolved in 10 mL of THF. To this stirred solution was added 830 mg (5 mmol) of dried, finely ground potassium iodide and 6 mg (0.02 mmol) of 18-crown-6. The resulting slurry was heated to reflux for 20 h, evaporated and then stirred for 1 h with 7 mL (7 mmol) of 1M potassium hydroxide solution. The solution was lyophilized and then purified by MPLC (2.5×20 cm column of Mitsubishi Kasei Sepadbeads CHP20P resin): 11.5 mL fractions, 7 mL/min flow rate, eluted with water. Fractions 29–55 were collected and lyophilized to give title salt as a white solid, 840 mg, 76% yield.

IR (KBr pellet) 3426, 3063, 2934, 2864, 1636, 1198, 1074, 966 cm$^{-1}$.

$^1$H NMR (D$_2$O, 400 MHz) 7.16 (m, 5H) 7.08 (d, 2H, J=8.3, H$_3$) 7.05 (d, 2H, J=8.3, H$_2$) 3.78 (s, 2H) 2.72 (ddd, 1H, J=3.9, 6.4, 18 Hz) 2.45 (m, 2H) 1.75 (m, 4H) ppm.

MS (FAB, + ions) m/e 536 (M+K), 499 (M+H), 461 (M−K+2H).

Anal. Calc'd for C$_{17}$H$_{18}$K$_3$PSO$_6$.1H$_2$O: C, 39.33; H, 3.94; P, 5.97; S, 6.18 Found: C, 39.33; H, 4.06; P, 5.71; S, 5.89.

EXAMPLE 30

(E,E)-1-[Hydroxy(methoxymethyl)phosphinyl]-6,10,14-trimethyl-5,9,13-pentadecatriene-1-sulfonic acid, dipotassium salt A. (Methoxymethyl)phosphonic acid, diethyl ester To a sample of 17.90 mL (0.104 mol) of triethylphosphite at −78° C. under argon was added, dropwise 8.50 mL (0.104 mol) of bromomethyl methyl ether. The mixture slowly warmed to RT and stirred for 24 h, when it was fractionally distilled 100° C., 5 mm) to provide 16.22 g (98%) of title compound as a pale yellow oil.

TLC Silica Gel (Ethyl acetate) R$_f$=0.50.

B. Chloro(methoxymethyl)phosphinic acid, ethyl ester

To a solution of 5.0 g (27.6 mmol, 1 eq) of Part A compound in 5 mL of dry benzene at 0° C. was added 5.75 g (27:6 mmol, 1 eq) of phosphorus pentachloride as a solid in one portion. The resulting heterogeneous solution was stirred at 0° C. for 5 min, then warmed to room temperature and stirred for 5 min. The resulting homogeneous solution was heated at reflux for 1 h, cooled to room temperature and concentrated. The residue was co-evaporated twice with benzene followed by exposure to high vacuum (0.25 mmHg) for 1 h to afford 4.52 g (95%) of title compound as a yellow liquid which was used in the next step without purification.

C. [Ethoxy(methoxymethyl)phosphinyl]methanesulfonic acid, cyclohexyl ester

To a solution of 9.84 g (55.2 mmol, 2.1 eq) of Example 1A Part A mesylate compound in 200 mL of dry tetrahydrofuran (THF) at −75° C. (internal temperature) was added dropwise via syringe 22.1 mL (55.2 mmol, 2.1 eq) of a 2.5M n-butyllithium solution in hexanes at a rate that kept the temperature below −71° C. (over 40 min). The , resulting solution was stirred for 5 min at −75° C. A solution of 4.52 g (26.2 mmol, 1 eq) of freshly prepared Part B compound in 20 mL of THF was added dropwise at a rate to keep the temperature below −71° C. (over 30 min) and the resulting light brown solution was stirred at −75° C. for 1 h. The reaction was quenched by addition of a solution of 3.16 mL (55.2 mmol, 2.1 eq) of glacial acetic acid in 15 mL of THF over 5 min, then allowed to warm to room temperature. The solution was concentrated and the viscous residue was taken up in dichloromethane (250 mL), washed with water (100 mL), brine (100 mL), dried (MgSO$_4$) and concentrated to afford 12.4 g of a light brown oil. The desired product was isolated by flash chromatography on silica gel (250 g) eluting with ethyl acetate. The fractions containing product by TLC were combined and concentrated to afford a solid which was contaminated by an unknown impurity as evidenced by extraneous peaks in the $^1$H NMR spectrum. The solid was recrystallized from hexanes/chloroform to afford 5.04 g (61%) of the title compound as a white solid, m.p. 78.5°–79.5 C.

TLC Silica gel (ethyl acetate) R$_f$ 0.40.

D. (E,E)-1-[Ethoxy(methoxymethyl)phosphinyl]-6,10,14-trimethyl-5,9,13-pentadecatriene-1-sulfonic acid, cyclohexyl ester To a suspension of 222 mg (5.6 mmol, 2 eq) of sodium hydride (as a 60% dispersion in mineral oil) in 1 mL of dry dimethylformamide (DMF) at 0° C. was added a solution of 1.74 g (5.6 mmol, 2 eq) of Part C compound in 4 mL of DMF dropwise over 10 min. The bubbling heterogeneous mixture was allowed to warm to room temperature and stir for 30 min. To the resulting homogeneous solution was added a solution of 1.0 g (2.8 mmol, 1 eq) of Example 1 Part C iodide in 3 mL of DMF. After 20 h, the reaction was diluted with brine (25 mL). The resulting cloudy solution was extracted with ether (1×100 mL, 3×15 mL), dried ($MgSO_4$) and concentrated to afford 1.64 g of a yellow oil. The desired product was isolated by flash chromatography on silica gel (250 g) eluting with 40% ethyl acetate in hexanes. Fractions containing clean product by TLC were pooled and concentrated to afford 801 mg.(52%) of title compound as a viscous yellow oil.

TLC Silica gel (1:1 ethyl acetate:hexanes): $R_f$ 0.23.

E. (E,E)-1-[Hydroxy(methoxymethyl)phosphinyl)- 6,10,14-trimethyl-5,9,13-pentadecatriene- 1-sulfonic acid, dipotassium salt To a solution of 600 mg of Part D compound in 12 mL of dry methanol am 0° C. was introduced ammonia until the solution was saturated. The tube was sealed with a threaded teflon cap fitted with an O-ring and heated at 75° C. for 16 h. The volatiles were removed in vacuo and the oily residue was co-evaporated twice with toluene before placing on high vac (0.25 mmHg) for three hours. To the resulting clear yellow oil was added 7 mL of dry $CH_2Cl_2$ followed by 806 μL (6.1 mmol, 4.5 eq) of dry 2,4,6-collidine. To the resulting light yellow clear solution was added 1.25 mL (9.5 mmol, 7 eq) of bromotrimethylsilane (TMSBr) and the resulting white heterogeneous mixture was stirred at room temperature. After 21 h, the reaction mixture was concentrated and placed on high vac (0.25 mmHg) for 30 min. The resulting yellow white solid was dissolved by adding 7.0 mL (7.0 mmol, 5.2 eq) of 1M potassium hydroxide, and the resulting solution was frozen and lyophilized. The light brown lyophilate was dissolved in water and chromatographed on a column of CHP20P (2.5 cm×25 cm) eluting initially with water (150 mL) followed a gradient formed by the gradual addition of a 63% solution of acetonitrile in water (400 mL) to a reservoir containing water (400 mL). No fractions (10 mL each) containing clean product by HPLC were obtained. The fractions containing approximately 2% of an impurity (which eluted just before the desired product) were pooled, concentrated and rechromatographed using a step gradient. After eluting with water (150 mL) the column was eluted with 15% acetonitrile in water (300 mL) followed by 20% acetonitrile in water (500 mL). Fractions containing pure product by HPLC were concentrated and the residual waxy residue was triturated with acetone to afford 245 mg of title salt (35%) as a white solid.

TLC Silica gel (7:2:1 n-propanol:ammonium hydroxide:water): $R_f$ 0.42.

$^1$H NMR ($D_2O$, 300 MHz): δ5.06 (t, 1H, J=6.8 Hz) 4.98 (t, 1H, J=6.9 Hz) 4.96 (t, 1H, J=7.2 Hz) 3.56 (dd, 1H, J=12.9, 6.9 Hz) 3.40 (dd, 1H, J=12.9, 7.5 Hz) 3.23 (s, 3H) 2.92 (m, $C_{18}$) 1.83 (m, 12H) 1.49 (s, 3H) 1.46 (s, 3H) 1.43 (m, 2H) 1.41 (s, 6H)ppm.

$^{13}$C NMR ($D_2O$, 75.6 MHz): δ136.3 135.7 132.3 124.6 70.9 (d, $J_{CP}$=116 Hz) 60.8 (d, $J_{CP}$=12 Hz) 59.9 (d, $J_{CP}$=81 Hz) 39.5 39.4 29.5 (d, $J_{CP}$=5 Hz) 27.7 26.5 26.4 26.3 (d, $J_{CP}$=4 Hz) 25.3 17.4 15.7 ppm.

IR (KBr): 3437, 2926, 1449, 1200, 1076, 1030 cm$^{-1}$.

MS (FAB, + ions) m/z 551 (M+K), 513 (M+H).

Anal. Calc'd for $C_{20}H_{35}O_6PSK_2$.0.55 $H_2O$: C, 45.96; H, 6.96; P, 5.93; S, 6.13 Found: C, 45.96; H, 6.80; P, 5.54; S, 6.50

EXAMPLE 31

(E,E)-1-[Hydroxy(hydroxymethyl)phosphinyl]-6,10,14-trimethyl-5,9,13-pentadecatriene-1-sulfonic acid, dipotassium salt Potassium iodide (370 mg, 2.23 mmol) was added to a solution of Example 28 Part B compound (950 mg, 2.12 mmol) in acetone (10 mL) under argon. As the mostly insoluble potassium iodide reacted, the product precipitated out of the reaction mixture. The white heterogeneous reaction was stirred at RT overnight, concentrated in vacuo, then pumped at high vacuum to give a white solid.

A heterogeneous mixture of the sulfonate salt paraformaldehyde (254 mg, 8.48 mmol), and diisopropylethylamine (184 mL, 1.06 mmol) in absolute ethanol (7 mL) was heated at 60° C. under argon. After 15 min, the reaction went from milky white to clear and colorless. After 7 h at 60° C., the reaction was allowed to cool to RT. The reaction was concentrated in vacuo, then pumped at high vacuum to give a white semi-solid.

Aqueous KOH (6.4 mL, 1N, 6.4 mmol) was added to the mono-ester prepared above. The initially white foamy dispersion was stirred at RT under argon overnight, after which time the reaction was clear and colorless. The reaction mixture was chromatographed on CHP20P gel (2.5×20 cm column) eluting with water followed by a gradient created by the gradual addition of acetonitrile to a reservoir of water. The product fractions were concentrated in vacuo to give an opaque white gum. Acetone (5 mL) was added and the product was precipitated out as a solid. The solid was filtered, washed with acetone (3×5 mL), then pumped at high vacuum to give the title product (520 mg, 49%) as a white solid.

TLC (silica gel) (7:2:1 n-propanol/$NH_{40}H/H_2O$): $R_f$=0.36
IR (KBr) 3430, 2926, 1636, 1449, 1204, 1078, 1024 cm$^{-1}$.
$^1$H NMR ($D_2O$, 400 MHz) δ5.12 (t, 1H, J=6.6 Hz) 5.05 (t, 1H, J=6.8 Hz) 5.03 (t, 1H, J=7.7 Hz) 3.76 (dd, 1H, J=4.3, 14.4 Hz) 3.53 (dd, 1H, J=6.6, 14.4 Hz) 2.98 (ddd, 1H, J=4.7, 6.8, 13.3 Hz) 1.88 (m, 10H) 1.75 (m, 2H) 1.55–1.35 (m, 2H) 1.53 (s, 3H) 1.48 (s, 3H) 1.46 (s, 6H,) ppm.
$^{13}$C NMR ($D_2O$, 100 MHz) δ136.35 135.78 132.37 124.56 60.65 (d, J=109 Hz) 60.49 (d, J=78 Hz) 39.34 39.24 29.30 (d, J=6 Hz) 27.69 26.35 26.28 26.10 25.17 17.24 15.56 ppm.
Mass Spec (FAB, + ions) m/z 499 (M+H), 537 (M+K).
Anal. Calc'd for $C_{19}H_{33}K_2O_6PS$: C, 45.76; H, 6.67; P, 6.21; S, 6.43. Found: C, 45.41; H, 6.92; P, 6.47; 6.77.

EXAMPLE 32

(E,E)-7,11,15-Trimethyl-2-phosphono-6,10,14-hexadecatriene- 2-sulfonic acid, tripotassium salt A. (E,E)-7,11,15-Trimethyl-2-(diethoxyphosphinyl)-6,10,14-hexadecatriene-2-sulfonic acid, cyclohexyl ester To a suspension of 47 mg (1.2 mmol, 1.1 eq) of sodium hydride (as a 60% mineral oil dispersion) in 1 mL of dry DMF at 0° C. was added a solution of 580 mg (1.1 mmol, 1 eq) of Example 1A Part C compound in 2 mL of DMF over 1 min. The bubbling solution was allowed to warm to RT and stirred for 30 min. To the resulting yellow homogeneous solution of anion at RT was added 264 μL (4.2 mmol, 4 eq) of methyl iodide over 1 min. After 16 h, the turbid yellow reaction mixture was diluted with ether (100 mL) and washed with brine (50 mL). The aqueous layer was extracted with ether (2×15 mL) and the combined organic layers were dried (MgSO$_4$) and concentrated to afford 583 mg of a light yellow cloudy oil. $^1$H NMR of the crude oil indicated no unalkylated starting material was present. The desired product was isolated via flash chromatography on silica gel (75 g) eluting with 35% ethyl acetate in hexanes. Fractions containing the desired product by TLC were pooled and concentrated to afford 418 mg (68%) of title compound as a clear viscous oil.

TLC Silica gel (10% ether in CH$_2$Cl$_2$): R$_f$ 0.46.

B. (E,E)-7,11,15-Trimethyl-2-phosphono- 6,10,14-hexadecatriene-2-sulfonic acid, tripotassium salt To a solution of 408 mg of Part A compound in 8 mL of dry methanol at 0° C. was introduced ammonia until the solution was saturated. The tube was sealed with a threaded teflon cap fitted with an O-ring and heated at 75° C. for 17 h. The volatiles were removed in vacuo and the oily residue was co-evaporated twice with toluene before placing on high vac (0.25 mmHg) for three hours. To the resulting clear yellow oil was added 4 mL of dry CH$_2$Cl$_2$ followed by 769 μL (5.8 mmol, 8 eq) of dry 2,4,6-collidine. To the resulting light yellow clear solution was added 768 μL (5.8 mmol, 8 eq) of bromotrimethylsilane (TMSBr) and the resulting white heterogeneous mixture was stirred at room temperature. After 84 h, the reaction mixture was concentrated and placed on high vac (0.25 mmHg) overnight. The resulting yellow white solid was dissolved by adding 5.0 mL (5.0 mmol, 6.8 eq) of 1M potassium hydroxide (pH 12.45) and 5 mL of water and the resulting solution (pH 12.35) was frozen and lyophilized. The light brown lyophilate was dissolved in water and chromatographed on a column of CHP20P (2.5 cm×25 cm) eluting initially with water (150 mL) followed a gradient formed by the gradual addition of acetonitrile (400 mL) to a reservoir containing water (400 mL). Fractions (10 mL each) were collected and analyzed by HPLC (Method 8). One fraction contained material ≧98% pure. This fraction was concentrated, taken up in a minimum volume of water, filtered and precipitated using acetone. The resulting solid was dryed on high vac to afford 134 mg of an off-white solid which did not pass elemental analysis. The >95% material from the column above was rechromatographed on CHP20P under isocratic conditions with 20% acetonitrile in water. Fractions containing ≧98% material were combined with the >98% material obtained from the first column, dissolved in water and concentrated. The resulting glassy solid was triturated with acetone to afford, after high vacuum removal of the acetone remnants, 94 mg title salt in the form of an off-white solid (24%).

TLC Silica gel (5:4:1 n-propanol:ammonium hydroxide:water): R$_f$ 0.24.

$^1$H NMR (D$_2$O, 300 MHz): δ5.08 (m, 1H) 4.98 (m, 1H) 4.95 (m, 1H) 1.86 (m, 12H) 1.49 (s, 3H) 1.45 (s, 3H) 1.43 (m) 1.42 (s, 6H) 1.28 (d, J=13.6 Hz) ppm.

$^{13}$C NMR (D$_2$O, 75.6 MHz): δ136.2 135.8 132.3 125.1 124.7 62.3 (d, J$_{CP}$=126 Hz) 39.5 39.4 34.2 28.8 26.5 26.4 25.3 24.9 (d, J$_{CP}$=3 Hz) 18.2 17.4 15.8 15.7 ppm.

IR (KBr): 3434, 2928, 1452, 1202 cm$^{-1}$.

MS (FAB, + ions) m/z 499 (M+2H−K), 521 (M−K+Na+H), 537 (M+H).

Anal. Calc'd for C$_{19}$H$_{32}$O$_6$PSK$_3$.0.5 H$_2$O: C, 41.81; H, 6.09; P, 5.67 Found: C, 42.20; H, 6.41; P, 4.94.

EXAMPLE 33

4'-(2-Methyl-1-propenyl)-α-phosphono[1,1'-biphenyl]-4-butanesulfonic acid, tripotassium salt A. 1-Bromo-4-(2-methyl-1-propenyl)benzene To a stirred slurry of 17.29 g (40.0 mmol) of isopropyltriphenylphosphonium iodide and 500 mg (2 mmol) of 18-crown-6 in 100 mL of THF under nitrogen at 5° C. was added 4.50 g (40.0 mmol) of potassium t-butoxide over 5 min. the resulting deep red-orange slurry was stirred 10 min and then a solution of 6.50 g (35.0 mmol) 4-bromobenzaldehyde in 40 mL of THF was added at a rate to keep the temperature below +10° C. The resulting bright yellow slurry was stirred for 20 min and then poured into 300 mL of hexanes. The solids were filtered off and the filtrate evaporated. This residue was purified by flash chromatography (5×15 cm column) and eluted with hexanes to provide 5.66 g (77%) of title bromide as a colorless oil.

TLC Silica gel (hexanes) R$_f$=0.32.

$^1$H NMR (CDCl$_3$, 270 MHz) δ7.40 (d, 2H, J=8.4 Hz) 7.05 (d, 2H, J=8.4 Hz) 6.17 (s, 1H) 1.88 (s, 1H) 1.81 (s, 1H) ppm.

Anal. Calc'd for C$_{10}$H$_{11}$Br: C, 56.90; H, 5.25 Found: C, 56.83; H, 5.22.

MS (CI—NH$_3$, -ions) m/e 209 (M−H).

B. 4'-(2-Methyl-1-propenyl) [1,1-biphenyl]- 4-carboxylic acid, methyl ester

To a stirred solution of 52 mL (88.4 mmol, 1.7M in pentane) of t-butyllithium at −78° C. under argon was added a solution of 7.92 g (37.5 mmol) of Part A bromide in 15 mL of THF over 10 minutes. The resulting deep red slurry was stirred for 1 hour, warmed to −22° C. and a solution of 6.16 g (45.2 mmol) of thrice-fused zinc chloride in 40 mL of THF was added over 20 minutes. The light yellow, faintly turbid solution was stirred for 1 hour and then cannula ted into a stirred solution of 7.04 g (26.9 mmol) of methyl 4-iodobenzoate and 600 mg (0.52 mmol) of tetrakis(triphenylphosphine)palladium in 30 mL of THF at −22° C. under argon. After the addition was complete, the reaction was warmed to room temperature and stirred for 16 hours. The reaction mixture was diluted with ether, washed successively with 1M hydrochloric acid, saturated sodium bicarbonate and saturated sodium sulfite solution. The organic extract was dried (MgSO$_4$) and evaporated to give a dark brown solid. Recrystallization from methanol gave title ester as a light yellow solid, mp 66°–68° C., 6.13 g, 86% yield.

C. 4'-(2-Methyl-1-propenyl) [1,1'-biphenyl]-4-methanol

To a stirred solution of 3.00 g (11.3 mmol) of Part B ester in 10 mL of THF at room temperature under nitrogen was added 6.0 mL of lithium aluminum hydride solution (1.0M in THF, 6.0 mmol). After 1 hour, the reaction was quenched with 1 mL of brine and then sufficient 1M hydrochloric acid to bring the solution to pH 1. The resulting mixture was extracted twice with ether, the combined extracts washed with saturated sodium bicarbonate solution, dried (MgSO$_4$) and evaporated. Purification by flash chromatography on silica gel (5×10 cm column, 3:97 ether/dichloromethane as elutent) gave title alcohol as a colorless oil, 2.42 g, 90% yield.

D. 4-(Bromomethyl)-4'-(2-methyl-1-propenyl) [1,1'-biphenyl]

To a stirred solution of 2.82 g of triphenylphosphine (8.4 mmol) and 2.33 g (9.79 mmol) of Part C alcohol in 30 mL of dichloromethane under argon at −40° C. was added 1.92 g (11.7 mmol) of N-bromosuccinimide over 20 minutes. After 1 hour, the reaction mixture was evaporated onto 10 g of silica gel., Purification by flash chromatography on silica gel (5×20 cm column, 12% CH$_2$Cl$_2$ in hexanes as the elutent) gave title bromide as a colorless oil, 2.75 g, 93% yield.

E. 4'-(2-Methyl-1-propenyl) [1,1-biphenyl]-4-propanoic acid, 1,1-dimethylethyl ester To a stirred solution of 1.01 mL (7.2 mmol) of diisopropylamine in 15 mL of THF at −5° C. under argon was added 2.8 mL (7.0 mmol, 2.5M in hexane) of n-butyllithium at a rate to keep the temperature below 0° C. After stirring the resulting pale yellow solution for 15 minutes, 3.0 mL (17 mmol) of hexamethylphosphoramide was added. After an additional 15 minutes, the deep yellow solution was cooled to −78° C. and 0.98 mL (7.2 mmol) of t-butyl acetate was added over the course of 5 minutes. The solution was stirred for 30 minutes and then a solution of 1.75 g (5.8 mmol) of Part D bromide in 10 mL of THF was added over 5 minutes. The reaction mixture was stirred for 8 hours at −78° C., quenched with 10% citric acid solution and extracted twice with ether. The extracts were combined, washed twice with water, once with saturated sodium bicarbonate solution, dried (MgSO$_4$) and evaporated. Purification by flash chromatography on silica gel (5×20 cm column, 1:1 hexanes/dichloromethane as elutent) gave title ester as a white foamy solid, 1.85 g, 95% yield.

F. 4'-(2-Methyl-1-propenyl) [1,1'-biphenyl]- 4-propanol

To a stirred solution of 1.08 g (3.20 mmol) of Part E ester in 5 mL of THF at room temperature under nitrogen was added 2.0 mL of lithium aluminum hydride solution (1.0M in THF, 2.0 mmol). The reaction was heated to reflux for 1 hour, quenched with 1 mL of brine and then sufficient 1M hydrochloric acid to bring the solution to pH 1. The resulting mixture was extracted twice with ether, the combined extracts washed with saturated sodium bicarbonate solution, dried (MgSO$_4$) and evaporated. The oily residue was passed through a 2 cm high pad of silica gel, eluting with dichloromethane to give title alcohol as a white solid, 0.824 g, 97% yield.

G. 4-(3-Iodopropyl)-4'-(2-methyl-1-propenyl) [1.1'-biphenyl]

To a stirred solution of 813 mg (3.05 mmol) of Part F alcohol, 882 mg (3.36 mmol) of triphenylphosphine and 440 mg (6.4 mmol) of imidazole in 20 mL of THF was added a solution of 813 mg (3.2 mmol) of iodine in 10 mL of THF over 20 min. After 10 min, the light yellow reaction mixture was diluted with hexanes and washed once each with 10% sodium bisulfite solution, water and brine. The organic layer was dried (MgSO$_4$) and evaporated onto 5 g silica gel. Purification by flash chromatography on silica gel (5×5 cm column) eluted with dichloromethane gave title iodide, 1.11 g (97%) as a white solid, mp 58°–61° C.

H. 4'-(2-Methyl-1-propenyl)-α-phosphono[1,1'-biphenyl]-4-butanesulfonic acid, cyclohexyl ester To a stirred slurry of 85 mg (2.1 mmol, 60% mineral oil dispersion) of sodium hydride in 3 mL, of DMF under argon at −10° C. was added a solution of 670 mg (2.4 mmol, 1.3 equiv.) of Example 1A Part B compound in 1 mL of DMF. After addition was complete, the reaction was warmed to room temperature and stirred for 30 min. To the resulting solution was added a solution of 700 mg (1.86 mmol) of Part G compound in 1 mL of DMF. The reaction was stirred for 16 h, diluted with ether and washed once with 10% citric acid and thrice with water. The organic phase was dried (MgSO$_4$) and evaporated. Purification by flash chromatography on silica gel (5×20 cm column) eluted with 1:24 ether/dichloromethane gave title salt as a colorless oil, 610 mg, 62% yield.

I. 4'-(2-Methyl-1-propenyl)-α-phosphono[1,1'-biphenyl]-4-butanesulfonic acid, tripotassium salt A solution of 500 mg (0.89 mmol) of Part H ester in 15 mL of methanol under argon at room temperature was saturated with ammonia gas. The flask containing the reaction mixture was sealed and heated to 75° C. After 16 h, the reaction was cooled to room temperature and evaporated under dry conditions. The residue was dissolved in 10 mL of dichloromethane and 0.59 mL (4.5 mmol) of 2,4,6-collidine and then 940 mL (7.1 mmol) of bromotrimethylsilane was added. After 24 h, the resulting clear solution was evaporated at 25° C. and then stirred for 1 h with 8 mL (4 mmol) of 0.5M potassium hydroxide solution. The solution was lyophilized and then purified by MPLC (2.5×20 cm column of Mitsubishi Kasei Sepadbeads HP-20 resin): 11.5 mL fractions, 7 mL/min flow rate, eluted with water and then a gradient prepared from 400 mL of water and 450 mL of 2:1 acetonitrile/water). Fractions 39–48 were collected and lyophilized to give title salt as a white solid, 310 mg, 62% yield.

IR (KBr pellet) 3403, 2967, 2932, 1653, 1497, 1184, 1051, 966 cm$^{-1}$.

$^1$H NMR (D$_2$O, 400 MHz) δ7.45 (d, 2H, J=8.1 Hz) 7.44 (d, 2H, J=8.1 Hz) 7.25 (d, 2H, J=8.1 Hz) 7.19 (d, 2H, J=8.1 Hz) 6.17 (s, 1H) 2.78 (dt, 1H, J=5, 18 Hz) 2.54 (m, 2H) 1.77–1.91 (m, 4H) 1.74 (s, 3H) 1.69 (s, 3H) ppm.

Anal. Calc'd for C$_{20}$H$_{22}$K$_3$O$_6$PS.1.5 H$_2$O: C, 42.46; H, 4.45; P, 5.47; S, 5.67 Found: C, 42.35; H, 4.80; P, 5.20; S, 6.06.

Mass Spec (FAB, + ions) m/e 577 (M+K), 539 (M+H), 501 (M−K+2H).

EXAMPLE 34

4'-Butyl-α-phosphono[1,1'-biphenyl]-4-butanesulfonic acid, tripotassium salt

A. 4'-Butyl[1,1'-biphenyl]-4-propanoic acid, ethyl ester

To a stirred solution of 3.20 g (15.0 mmol) of 1-bromo-4-butylbenzene (Aldrich Chemical Company #33,576-2) at −78° C. under argon was added, dropwise over 30 min, 18.0 mL (30.6 mmol, 1.7M in pentane) of t-butyllithium solution. The resulting light yellow solution was warmed to 0° C. and stirred for 1 h. To this solution was added 3.4 g (25 mmol) of thrice-fused zinc chloride in 20 mL of THF. The resulting slurry was stirred for 30 min and then a solution of 2.0 g (6.5 mmol) of 4-iodobenzenepropanoic acid, ethyl ester (Example 43, Part B) and 0.4 g (0.35 mmol) of tetrakis(triphenylphosphine)-palladium(0) in 5 mL of THF was added. The reaction was stirred for 16 h, diluted with ether and washed once with 10% citric acid. The organic phase was dried (MgSO$_4$) and evaporated. Purification by flash chromatography on silica gel (5×20 cm column) eluted with 1:1 hexanes/dichloromethane gave title compound as a colorless oil, 1.79 g , 91% yield.

B. 4'-Butyl[1,1'-biphenyl]-4-propanol

To a stirred solution of 1.72 g (5.54 mmol) of Part A ester in 10 mL of THF at room temperature under argon was added, over the course of 2 min, a solution of 4 mL (4 mmol, 1M in THF) of lithium aluminum hydride. The resulting solution was stirred for 16 h. The reaction was quenched with 1M sodium potassium tartrate and extracted twice with ether. The ether extracts were dried over MgSO$_4$, filtered and evaporated. Recrystallization from hexanes provided title alcohol as a white solid, 1.19 g, 80% yield, mp 62°–64° C.

C. 4'-Butyl[1,1-biphenyl]-4-propyl iodide

To a stirred solution of 1.19 g (4.43 mmol) of Part B alcohol, 1.16 g (4.43 mmol) of triphenylphosphine, and 0.66 g (7.4 mmol) of imidazole in 15 mL of THF under argon at room temperature was added a solution of 1.12 g (4.7 mmol) of iodine in 5 mL of THF, dropwise over 20 min. After addition was complete, the reaction was diluted with hexanes and washed once with saturated sodium bisulfite solution. The organic phase was dried (MgSO$_4$) and evaporated. Purification by flash chromatography on silica gel (5×20 cm column) eluted with dichloromethane gave title iodide as a white waxy solid, 1.52 g, 91% yield.

D. 4'-Butyl-α-(diethoxyphosphinyl) [1,1'-biphenyl]-4-butanesulfonic acid, cyclohexyl ester To a stirred slurry of 190 mg (4.75 mmol, 60% mineral oil dispersion) of sodium hydride in 5 mL of DMF under argon at −10° C. was added a solution of 1.66 g (5.28 mmol) of Example 1A Part B sulfonate in 2 mL of DMF. After addition was complete, the reaction was warmed to room temperature and stirred for 30 min. To the resulting solution was added a solution of 1.00 g (2.64 mmol) of Part C iodide in 5 mL of DMF. The reaction was stirred for 16 h, diluted with ether and washed once with 10% citric acid and thrice with water. The organic phase was dried (MgSO$_4$) and evaporated. Purification by flash chromatography on silica gel (5×25 cm column) eluted with 3:47 ether/dichloromethane gave title compound as a colorless oil, 0.825 g, 55% yield.

E. 4'-Butyl-α-Phosphono[1,1'-biphenyl]-4-butanesulfonic acid, tripotassium salt

To a stirred solution of 0.82 g (1.55 mmol) of Part F ester in 5 mL of dichloromethane under argon at room temperature was added 0.62 mL (4.7 mmol) of bromotrimethylsilane. After 24 h, the resulting clear solution was evaporated at 25° C. and the residue dissolved in 10 mL of THF. To this stirred solution was added 0.8 g (5 mmol) of dried, finely ground potassium iodide and 5 mg (0.015 mmol) of 18-crown-6. The resulting slurry was heated to reflux for 24 h, evaporated and then stirred for 1 h with 5 mL (5 mmol) of 1.0M potassium hydroxide solution. The solution was lyophilized and then purified by MPLC (2.5×20 cm column of CHP-20P resin): 11.5 mL fractions, 6 mL/min flow rate, eluted with 250 mL of water, then a gradient of 450 mL of 3:1 acetonitrile/water into 450 mL of water). Fractions 32–40 were collected and lyophilized to give title salt as a white solid, 425 mg, 49% yield.

IR (KBr pellet) 3424, 3027, 2957, 2930, 2859, 1653, 1499, 1200, 1078, 966 cm$^{-1}$.

$^1$H NMR (D$_2$O, 400 MHz) δ7.47 (d, 2H, J=8.1 Hz) 7.46 (d, 2H, J=8.1 Hz) 7.27 (d, 2H, J=8.1 Hz) 7.21 (d, 2H, J=8.6 Hz) 2.79 (ddd, 1H, J=17.5, 5.6, 3.8 Hz) 2.55 (m, 4H) 1.92 (m, 4H) 1.46 (m, 2H) 1.19 (m, 4H) 0.75 (t, 3H, J=7.5 Hz) ppm.

Anal. Calc'd for C$_{20}$H$_{24}$K$_3$O$_6$PS.0.75 H$_2$O: C, 43.34; H, 4.64; P, 5.59; S, 5.78 Found: C, 43.01; H, 4.88; P, 5.16; S, 6.21.

Mass Spec (FAB, + ions) m/e 579 (M+K), 541 (M+H), 503 (M−K+2H), 465 (M−2K+3H).

EXAMPLE 35

(E)-6-Methyl-1-phosphono-9-(4-propylphenyl)-5-nonene-1-sulfonic acid, tripotassium salt A. Bromo(4-propylphenyl)magnesium A solution of 30.80 mL (0.20 mol) of 1-bromo-4-propylbenzene in 50 mL dry THF was added to 9.60 g (0.40 mol) of magnesium turnings in 200 mL THF at a rate to maintain low reflux. After the addition was complete, the reaction was heated to 55° C. for one hour. The THF solution was transferred via cannula to a sure-seal bottle and sealed for storage. Titration of 3.00 mL of the title Grignard reagent with 1N isopropanol in toluene against 2,2'-biquinoline as an indicator required volumes of 5.4 and 5.3 mL, indicating the concentration to be 1.74N.

B. 2,2-Dimethylpropanoic acid, (E)-8-iodo-5-methyl-4-octen-1-yl ester

The above iodide is prepared as described in Example 35 Part A.

C. (E)-5-Methyl-8-(4-propylphenyl)-4-octen-1-ol

A solution of 2.15 g (6.10 mmol) of Part B iodide in 10 mL THF at 0° C. was treated with 10 mg (1 mol %) of copper iodide and 21.00 mL (36.60 mmol) of the 1.74N solution of Part A Grignard reagent. The mixture was stirred for one hour at 0° C. and fifteen hours at RT, at which time an additional 7.00 mL (12.00 mmol) of Part A Grignard reagent were added. After twenty four hours, the reaction was chilled to 0° C. and quenched with 105 mL ammonium chloride and diluted with 200 mL ether and 1.00 mL ammonium hydroxide. The aqueous fraction was removed and the organics were washed with ammonium chloride solution (3×30 mL), water (2×30 mL), saturated sodium chloride (30 mL), dried (sodium sulfate), and concentrated. The resulting oil was purified by flash chromatography on silica gel packed, loaded, and eluted with 85:15 hexane/ethyl acetate. Pure fractions (#67–100) were combined and concentrated to yield 1.11 g (69%) of title alcohol as a clear oil.

TLC (7:3 hexane/ethyl acetate) R$_f$=0.18.

MS (CI, NH$_3$, + ions) m/e 261 (M+H), 278 (M+NH$_4$).

IR (neat) 3335, 2959, 2932, 2861, 1898, 1669, 1539, 1456, 1379, 1059, 802 cm$^{-1}$.

$^1$H NMR (CDCl$_3$, 400 MHz) δ7.11 (s, 4H) 5.19 (t, 1H, J=7.5 Hz) 3.66 (t, 2H, J=6.4 Hz) 2.58 (m, 4H) 2.12 (q, 2H, J=7.5 Hz) 2.05 (t, 2H, J=7.5 Hz) 1.76 (m, 2H) 1.64 (m, 4H) 1.63 (s, 3H) 0.97 (t, 3H, J=7.5 Hz) ppm.

D. (E)-1-(8-Iodo-4-methyl-4-octen-1-yl)-4-propylbenzene

A solution of 1.11 g (4.20 mmol) of Part C alcohol in 5 mL CH$_2$Cl$_2$ at 0° C. was treated sequentially with 10 mg (2.5 mol %) of 4-dimethylaminopyridine, 0.36 mL (5.50 mmol) of triethylamine, and 0.77 mL (4.70 mmol) of methanesulfonyl chloride. The reaction was allowed to stir at room temperature for 80 minutes before diluting with ether. The organic solution was washed with water (2×25 mL), saturated sodium chloride, dried (sodium sulfate), and evaporated to a clear oil. The oil was dissolved in 20 mL acetone and stirred with 1.92 g (12.80 mmol) of sodium iodide for fifteen hours. The reaction was driven to completion by heating at 50° C. for three more hours, then concentrated to a slurry, which was redissolved in hexane and water. The aqueous layer was removed, and the organic layer was washed with water, saturated sodium sulfite, saturated sodium chloride, dried (sodium sulfate), and evaporated. The resulting yellow oil was purified by flash chromatography on silica gel (100 g), packed, loaded, and eluted with hexane. Pure fractions were combined and concentrated to yield 1.04 g (67%) of title iodide as a clear oil.

TLC (85:15 hexane/ethyl acetate): R$_f$=0.70.

MS (CI, NH$_3$, + ions) m/e 270 (M+H).

IR (film) 2957, 2930, 2859, 1514, 1456, 1445, 1379, 1341, 1316, 1227, 1202, 1165, 1092, 1020, 839, 820, 802, 739 cm$^{-1}$.

$^1$H NMR (CDCl$_3$, 400 MHz) δ7.24 (s, 4H) 5.24 (t, 1H, J=7.5 Hz) 3.33 (t, 2H, J=7.0 Hz) 2.69 (q, 4H, J=6.0 Hz) 2.26 (q, 2H, J=7.2 Hz) 2.18 (t, 2H, J=7.5 Hz) 2.01 (quint, 2H, J=7.0 Hz) 1.86 (m, 2H) 1.78 (s, 3H) 1.77 (m, 2H) 1.09 (t, 3H, J=7.2 Hz) ppm.

E. (E)-1-(Diethoxyphosphinyl)-6-methyl-9-(4-propylphenyl)-5-nonenesulfonic acid, cyclohexyl ester To a solution of 1.53 g (4.87 mmol) of Example 1A Part B sulfonate in 4.00 mL DMF at −20° C. was added 84.5 mg (3.25 mmol) of sodium hydride. The reaction was stirred at −20° C. until hydrogen evolution diminished, and at RT until gas evolution subsided completely, when 1.0 g (2.71 mmol) of Part D iodide in 1.0 mL DMF was added. After stirring at RT for 23 hours, the reaction was quenched with 5 mL ammonium chloride and diluted with ether and water. The aqueous layer was removed and the organic layer was washed with saturated sodium chloride. The combined aqueous fractions were back extracted with ether, and the combined organic fractions were dried (sodium sulfate) and concentrated to an oil (1.84 g). The crude product was purified by flash chromatography on silica gel (140 g), packed, loaded, and eluted with 70:30 hexane/ethyl acetate. Pure fractions (#57–103) were combined and concentrated to yield 0.58 g (38%) of title compound as a clear oil.

TLC (7:3 hexane/ethyl acetate) $R_f$=0.18.1

MS (CI, $NH_3$, + ions) m/e 557 (M+H), 574 (M+$NH_4$).

IR (film) 2934, 2863, 1614, 1452, 1354, 1262, 1175, 1053, 1024, 972, 930, 866, 828, 802, 758 $cm^{-1}$.

$^1$H NMR ($CDCl_3$, 400 MHz) δ7.01 (s, 4H) 5.05 (t, 1H, J=6.6 Hz) 4.76 (m, 1H) 4.15 (m, 4H) 3.35 (dt, 1H, J=19.6 Hz, 6.2 Hz) 2.46 (m, 4H) 2.04 (m, 2H) 1.94 (m, 6H) 1.62 (m, 8H) 1.52 (s, 3H) 1.43 (m, 1H) 1.31 (m, 5H) 1.27 (t, 6H, J=6.8 Hz) 0.86 (t, 3H, J=7.3 Hz) ppm.

F. (E)-6-Methyl-1-phosphono-9-(4-propylphenyl)-5-nonene-1-sulfonic acid, tripotassium salt A solution of 0.57 g (1.02 mmol) of Part E compound in 10 mL methanol in a sealable tube was chilled to 0° C. and saturated with ammonia gas. The tube was then sealed and heated at 65° C. for twenty four hours. After cooling, the tube was opened and the methanol evaporated. The residue was dissolved in toluene and evaporated twice (2×10 mL), leaving a glassy oil. The oil was dissolved in 2.00 mL of methylene chloride and treated sequentially with 1.38 mL (5.20 mmol) of bistrimethylsilyl trifluoroacetamide and 0.83 mL (6.24 mmol) of trimethylsilyl bromide. The reaction stirred for 24 hours, at which point the organics were removed under vacuum, and the residue treated with 6.00 mL (6.00 mmol) of 1N KOH and lyophilized. The crude product was purified by MPLC on a column of CHP-20P gel (2.5 cm diam.×25 cm height) eluting with water (100 mL) followed by a gradient created by the gradual addition of 400 mL acetonitrile to a resevoir of 350 mL water. Approximately 7 mL fractions were collected. Pure fractions (#41–45) were combined and concentrated to yield 348 mg (64%) of a waxy solid, which was triturated with acetone (3×2.00 mL) and dried on high vacuum to yield 270 mg (50%) of title compound, as an off-white solid.

TLC (5:4:1 n-propanol/ammonium hydroxide/water) $R_f$=0.22.

MS (FAB, + ions) 533 (M+H), 457 (M+H–K).

IR (KBr) 3235, 2934, 2872, 1653, 1458, 1144, 1098, 1052, 964 $cm^{-1}$.

$^1$H NMR ($CDCl_3$, 400 MHz) δ7.07 (s, 4H) 5.16 (m, 1H) 2.76 (m, 1H) 2.42 (m, 4H) 1.79 (m, 6H) 1.53 (m, 2H) 1.48 (s, 3H) 1.43 (m, 2H), 0.74 (t, 2H, J=7.3 Hz) ppm.

Anal. Calc'd for $C_{19}H_{28}O_6PSK_3 \cdot H_2O$: C, 41.43; H, 5.49; S, 5.82; P, 5.62; Found C, 41.43; H, 5.72; S, 6.23; P, 5.29.

EXAMPLE 35A 2,2-Dimethylpropanoic acid, (E) -8-iodo-5-methyl-4-octen-1-yl-ester (1). 2,2-Dimethylpropanoic acid, (E) -5,9-dimethyl- 4,8-decadienyl ester To a solution of 10.00 g (54.94 mmol) of Example 2 Part D alcohol in 50 mL of dichloromethane at 0° C. was added 0.67 g (5.50 mmol) of 4-dimethylaminopyridine (DMAP) and 11.49 mL (82.41 mmol) of triethylamine followed by the addition of 8.12 mL (65.93 mmol) of trimethylacetyl chloride over 15 min. The reaction mixture was stirred for 1 h at 0° C. and 2.5 h at room temperature. The suspension was diluted with 200 mL of dichloromethane and 300 mL of water. The layers were separated and the organic fraction was washed with solutions of $KHSO_4$, $NaHCO_3$ and NaCl, dried ($MgSO_4$) and concentrated to provide title compound as a colorless liquid.

TLC Silica gel (8:2 hexanes/ethyl acetate) $R_f$=0.25.

(2). 2,2-Dimethylpropanoic acid, (E) -8-bromo-9-hydroxy-5,9-dimethyl-4-decenyl ester To a solution of 10.00 g (37.59 mmol) of Part (1) ester in 100 mL of a solution of 7:3 t-butanol/water at 0° C. was added 6.69 g (37.59 mml) of N-bromosuccinimide portionwise with the aid of a solid addition funnel over 0.5 h. The reaction mixture was stirred at 0° C. for 3 h, diluted with 300 mL of ether, washed with solutions of $K_2CO_3$ and NaCl, dried ($MgSO_4$) and concentrated. The residue obtained was purified by flash chromatography (800 g of silica gel) eluting with 9:1 hexanes/ethyl acetate to provide 11.30 g (63%) of title alcohol as a colorless oil.

TLC Silica gel (8:2 hexanes/ethyl acetate) $R_f$=0.42.

(3). 2,2-Dimethylpropanoic acid, (E)-8,9-epoxy- 5,9-dimethyl-4-decenyl ester

To a stirred solution of 11.00 g (30.30 g) of Part (2) alcohol in 100 mL of THF at −78° C. was added 21.68 mL (30.30 mmol) of a 1.4M potassium bis(trimethylsilyl)amide solution in THF over 15 min. The reaction mixture was stirred at −78° C. for 0.5 h and then warmed to room temperature over 2 h. The mixture was quenched with 200 mL of water and diluted with 150 mL of dichloromethane. The layers were separated and the organic fraction washed with water, dried ($MgSO_4$) and concentrated to provide 8.57 g (100%) of title epoxide as a pale yellow oil.

TLC Silica gel (9:1 hexanes/ethyl acetate) $R_f$=0.38.

(4). 2,2-Dimethylpropanoic acid, (E)-5-methyl-8-oxo-4-octenyl ester

To a stirred solution of 8.50 g (30.14 mmol) of Part (3) epoxide in 100 mL of THF at 0° C. was added 6.90 g (30.27 mmol) of periodic acid over 15 min. The reaction mixture was stirred at 0° C. for 1 h, when it was diluted with 200 mL of ether and 200 mL of water. The layers were separated and the organic fraction was washed with solutions of $NaHCO_3$ and brine, dried ($MgSO_4$), and concentrated. The residue (≈7.5 g) obtained was purified by flash chromatography (800 g of silica gel) eluting with 95:5 hexanes/ethyl acetate to provide 4.25 g (59%) of title aldehyde as an oil.

TLC Silica gel (9:1 hexanes/ethyl acetate) $R_f$=0.28.

(5). 2,2-Dimethylpropanoic acid, (E)-5-methyl-8-hydroxy-4-octenyl ester

To a stirred solution of 2.00 g (8.33 mmol) of Part (4) aldehyde in 20 mL of methanol at 0° C. was added 0.16 g (4.17 mmol) of $NaBH_4$. The reaction mixture was stirred for 0.5 h, when it was diluted with ether and quenched with $NH_4Cl$ solution. The layers were separated and the organic fraction was washed with solutions of $NaHCO_3$ and brine, dried ($MgSO_4$) and concentrated to provide 2.00 g (100%) of title alcohol as a colorless oil.

TLC Silica gel (9:1 hexanes/ethyl acetate) $R_f$=0.06.

(6). 2,2-Dimethylpropanoic acid, (E)-5-methyl-8-[(methylsulfonyl)oxy]-4-octenyl ester.

A solution of 2.00 g (8.26 mmol) of Part (5) alcohol in 20 mL of methylene chloride and 1.50 mL (10.74 mmol) of triethylamine at 0° C. was treated with 0.77 mL (9.91 mmol) of methanesulfonyl chloride dropwise over 0.2 h. The reaction mixture was stirred for 2.0 h when it was quenched with saturated aqueous $KHSO_4$ solution and diluted with ether. The layers were separated and the organic fraction was washed with solutions of $NaHCO_3$ and brine, dried ($Na_2SO_4$) and evaporated to provide title mesylate as a pale yellow oil.

(7). 2,2-Dimethylpropanoic acid, (E)-8-iodo-5-methyl-4-octenyl ester

The crude Part (6) mesylate (≈8.0 mmol) was diluted with 100 mL of acetone and treated with 5.86 g (39.06 mmol) of NaI at room temperature for 48 h. The mixture was diluted with 200 mL of hexane and extracted with NaHSO$_3$, brine, dried (MgSO$_4$) and concentrated to provide a colorless oil. The oil was purified by flash chromatography (80 g of silica gel) eluting with 8:2 ethyl acetate/hexane to provide 2.11 g (77%) of title iodide as a colorless oil.

TLC Silica gel (8:2 hexane/ethyl acetate) R$_f$=0.81.

EXAMPLE 36

(E)-6-Methyl-8-phenyl-1-phosphono-5-octene-1-sulfonic acid, tripotassium salt

A. 4-[(t-Butyldimethylsilyl)oxy]-1-butanol

To a solution of 300 mL of THF, 90 g (1 mol) of butanediol and 13.6 g (0.20 mol) of imidazole was added 30.1 g (0.20 mol) of t-butyldimethylsilyl chloride in 50 mL of THF. After 2 h the reaction mixture was diluted with 700 mL of water and 500 mL of diethyl ether. The layers were equilibrated and separated. The organic fraction was washed with water, dried (MgSO$_4$) and concentrated to leave 38.7 g (95%) of title alcohol as a colorless oil.

TLC Silica gel (3:7 ehtyl acetate/hexane) R$_f$=0.35.

IR (neat) 3450, 2940, 2880, 1465, 1385, 1250, 1100, 1055, 835, 770 cm$^{-1}$.

$^1$H NMR (CDCl$_3$, 300 MHz) δ3.59 (t, 2H, J=5.7 Hz) 3.56 (t, 2H, J=5.9 Hz) 3.40 (m, 1H, OH) 1.58 (m, 4H) 0.83 (s, 9H) 0.00 (s, 6H) ppm.

Mass Spec (CI—NH$_3$, + ions) m/e 205 (M+H).

B. 4-[(t-Butyldimethysilyl)oxy]butanol

To a solution of 100 mL of methylene chloride and 3.21 g (41.17 mmol) of methyl sulfoxide at −78° C. was added 6.67 g (37.74 mmol) of oxalyl chloride dropwise over 15 min. After gas evolution ceased (≈15 min.), 7.0 g (34.31 mmol) of Part A alcohol was added to the reaction mixture. The mixture was stirred at −78° C. for 0.5 h, when 13.8 g (137.2 mmol) of triethylamine was added rapidly over 4 min. The mixture was warmed to −20° C. over 0.5 h and quenched with 200 mL of ether and 200 mL of water. The layers were equilibrated and separated. The organic fraction was dried (Na$_2$SO$_4$) and concentrated to leave 5.85 g (85%) of title aldehyde as a colorless oil.

TLC Silica gel (1:9 ethyl acetate/hexane) R$_f$=0.45.

$^1$H NMR (CDCl$_3$, 300 MHz) δ9.75 (t, 1H, J=2.5 Hz) 3.60 (t, 2H, J=5.0 Hz) 2.45 (td, 2H, J=2.5, 5.5 Hz) 1.83 (quint., 2H, J=6.5 Hz) 0.90 (s, 9H) 0.03 (s, 6H) ppm.

C. (E)-2-Methyl-6-[(t-butyldimethylsilyl) oxy]-2-hexenoic acid, ethyl ester

To a solution of 8.62 g (36.25 mmol) of triethyl 2-phosphonopropionate in 50 mL of THF at 0° C. was added 0.84 g (35.0 mmol) of NaH in three equal portions over 15 min. After gas evolution ceased, 5.85 g (29 mmol) of Part B aldehyde was added in one portion. The mixture was warmed to RT over 30 min. and diluted with 100 NH$_4$Cl solution and 100 mL of ether. The layers were equilibrated and separated. The organic fraction was dried (Na$_2$SO$_4$) and concentrated. The remainder was purified by flash chromatography (300 g of silica gel ) with 5:95 ethyl acetate/hexanes to yield 5.50 g (66%) of title ester as an amber oil.

TLC Silica gel (1:9 ethyl acetate/hexanes) R$_f$=0.33.

$^1$H NMR (CDCl$_3$, 300 MHz) δ6.72 (t, 1H, J=7.0 Hz) 4.15 (q, 2H, J=7.2 Hz) 3.59 (t, 2H, J=6.1 Hz) 2.20 (q, 2H, J=7.8 Hz) 1.77 (s, 3H) 1.60 (quint., 2H, J=7.0 Hz) 1.23 (t, 3H, J=7.0 Hz) 0.90 (s, 9H) 0.05 (s, 6H) ppm.

D. (E)-2-Methyl-6-[(t-butyldimethylsilyl) oxy]-2-hexen-1-ol

To a solution of 25 mL of dichloromethane and 5.20 g (18.18 mmol) of Part C ester at −78° C. was added 40 mL (40 mmol) of a 1M solution of diisobutylaluminum hydride in cyclohexane over 20, min. After 1 h, the mixture was diluted with 100 mL (100 mmol) of an aqueous 1M solution of sodium potassium tartrate and 100 mL of ether. The mixture was stirred at RT for 2.5 h when the layers were separated, the organics dried (Na$_2$SO$_4$) and concentrated. The remainder was purified by flash chromatography (250 g silica gel ) with 15:85 ethyl acetate/hexanes to yield 3.0 g (67%) of title alcohol as a colorless oil.

TLC Silica gel (3:7 ethyl acetate/hexanes) R$_f$=0.45.

IR (film) 3347, 2953, 2859, 1472, 1406, 1256, 1098, 837 cm$^{-1}$.

$^1$H NMR (CDCl$_3$, 300 MHz) δ5.38 (t, 1H, J=7.2 Hz) 3.93 (d, 2H, J=4.2 Hz) 3.56 (t, 2H, J=6.4 Hz) 2.04 (q, 2H, J=7.4 Hz) 1.94 (t, 1H, J=4.0 Hz, OH) 1.61 (s, 3H) 1.53 (quint., 2H, J=6.6 Hz) 0.87 (s, 9H) 0.00 (s, 6H)ppm.

Mass Spec (CI—NH$_3$, + ions) m/e 262 (M+NH$_4$), 245 (M+H), 227 (M+H-H$_2$O).

E. (E)-1-Chloro-2-methyl-6-[(E-butyldimethylsilyl)oxy]-2-hexene

To a solution of 30 mL of dichloromethane, 3.00 g (13.30 mmol) of Part D alcohol and 2.83 g (28.00 mmol) of triethylamine at 0° C. was added 1.60 g (14.00 mmol) Of methanesulfonyl chloride in 5 mL of dichloromethane. After 2 h the reaction mixture was diluted with 70 mL of water and 125 mL of diethyl ether. The layers were equilibrated and separated. The organic fraction was washed with water, dried (Na$_2$SO$_4$) and concentrated to leave the crude mesylate. The residue was diluted with 10 mL of dimethylformamide and treated with 1.70 g (40.00 mmol) of LiCl. The reaction mixture was stirred at RT for 6 h, at which point it was diluted with 100 mL of ether and 100 mL of water. The layers were equilibrated and the organic fraction dried (Na$_2$SO$_4$) and concentrated. The residue was purified by flash chromatography (100 g of silica gel) with 2:98 ethyl acetate/hexane to yield 1.20 g (35%) of title chloride as an amber oil.

TLC Silica gel (1:9 ethyl acetate/hexane) R$_f$=0.80.

IR (film) 2930, 2859, 1472, 1389, 1256, 1103, 837 cm$^{-1}$.

$^1$H NMR (CDCl$_3$, 400 MHz) δ5.50 (t, 1H, J=7.0 Hz) 3.95 (s, 2H) 3.57 (t, 2H, J=6.5 Hz) 2.04 (q, 2H, J=7.5 Hz) 1.70 (s, 3H) 1.65 (quint., 2H, J=6.6 Hz) 0.87 (s, 9H) 0.00 (s, 6H) ppm.

Mass Spec (CI—NH$_3$, + ions) m/e 263, 265 (M+H), 227 (M+H-HCl).

F. (E)-3-Methyl-1-phenyl-7-[(t-butyldimethylsilyl) oxy]-3-heptene

A solution of 3 mL (6 mmol) of 2M benzylmagnesium chloride in THF and 2 mL of HMPA at 0° C. was treated dropwise with 1.0 g (3.80 mmol) of Part E chloride in 5 mL of THF over 5 min. The solution was allowed to warm to RT and stir for 2 h, at which point the reaction was diluted with ether and 3 mL (3 mmol) of 1N HCl solution. The organic layer was washed two times with NH$_4$Cl solution, dried (MgSO$_4$) and concentrated to an oil. The oil was purified by flash chromatography performed on 125 g of silica gel packed, loaded and eluted with 3:95 ethyl acetate/hexane to provide 1.10 g (91%) of title compound as a colorless oil.

TLC Silica gel (5:95 ethyl acetate/hexane) R$_f$=0.80.

IR (film) 3086, 3063, 3028, 2930, 2859, 1603, 1497, 1472, 1256, 1101, 1032, 1007, 964, 837 cm$^{-1}$.

$^1$H NMR (CDCl$_3$, 300 MHz) δ7.20, 7.10 (two m, 5H) 5.10 (t, 1H, J=7.0 Hz) 3.56 (t, 2H, J=6.4 Hz) 2.65 (t, 2H, J=7.5 Hz) 2.23 (t, 2H, J=7.4 Hz) 1.97 (q, 2H, J=6.8 Hz) 1.60 (s, 3H) 1.48 (quint., 2H, J=7.0 Hz) 0.87 (s, 9H) 0.00 (s, 6H) ppm.

Mass Spec (CI—NH$_3$, + ions) m/e 336 (M+NH$_4$), 319 (M+H).

G. (E)-5-Methyl-7-phenyl-4-hepten-1-ol

A solution of 2 mL of THF and 1.10 g (3.45 mmol) of Part F compound at 0° C. was treated dropwise with 0.30 mL (5.00 mmol) of acetic acid and 4.0 mL (4.00 mmol) of a 1M tetrabutylammonium fluoride solution in THF. The solution was allowed to warm to RT and stir for 48 h, at which point the reaction was diluted with 50 mL of ether and 25 mL of NaHCO$_3$ solution. The organic layer was washed two times with NaHCO$_3$ solution, dried (MgSO$_4$) and concentrated to an oil. Flash chromatography was performed on 80 g of silica gel packed, loaded and eluted with 3:7 ethyl acetate/hexane to provide 0.59 g (83%) of title alcohol as a colorless oil.

TLC Silica gel (3:7 ethyl acetate/hexane) R$_f$=0.60.

IR (film) 3339, 3027, 2932, 2859, 1603, 1452, 1385, 1231, 1181, 1057, 698 cm$^{-1}$.

$^1$H NMR (CDCl$_3$, 400 MHz) δ7.25, 7.15 (two m, 5H) 5.13 (t, 1H, J=6.8 Hz) 3.54 (t, 2H, J=6.4 Hz) 2.70 (t, 2H, J=7.7 Hz) 2.23 (t, 2H, J=7.7 Hz) 2.04 (q, 2H, J=7.3 Hz) 1.70 (s, 1H, OH) 1.65 (s, 3H) 1.55 (quint, 2H, J=7.7 Hz) ppm.

Mass Spec (CI—NH$_3$, + ions) m/e 222 (M+NH$_4$), 205 (M+H).

H. (E)-1-Iodo-5-methyl-7-phenyl-4-heptene

To a stirred solution of 0.59 g (2.89 mmol) of Part G alcohol and 0.66 mL (6.00 mmol) of triethylamine in 10 mL of methylene chloride at 0° C. was added 0.37 g (3.20 mmol) of methanesulfonyl chloride dropwise over 10 min. After 1 h at 0° C. the reaction was diluted with ether and washed with aqueous solutions of NH$_4$Cl, NaHCO$_3$, and brine. The organics were dried (Na$_2$SO$_4$) and concentrated under reduced pressure to provide the crude mesylate. The residual oil was dissolved in 25 mL of acetone and treated with 1.00 g (6.66 mmol) of NaI. The resulting solution was stirred at RT for 36 h and diluted with ether. The organics were washed with water, dried over MgSO$_4$, and concentrated to provide a yellow oil. Flash chromatography was performed on 100 g of silica gel packed, loaded and eluted with hexanes to provide 0.68 g (2.16 mmol, 100% overall yield) of title iodide as a colorless oil.

TLC Silica gel (hexane) R$_f$=0.27.

IR (film) 3061, 3027, 2932, 2857, 1603, 1495, 1452, 1204, 1165, 1030, 743, 698 cm$^{-1}$.

$^1$H NMR (CDCl$_3$, 400 MHz) δ7.25, 7.15 (two m, 5H) 5.03 (t, 1H, J=7.3 Hz) 3.05 (t, 2H, J=7.3 Hz) 2.70 (t, 2H, J=7.7 Hz) 2.28 (t, 2H, J=7.7 Hz) 2.06 (q, 2H, J=7.3 Hz) 1.80 (quint, 2H, J=7.3 Hz) 1.67 (s, 3H) ppm.

Mass Spec (CI—NH$_3$, + ions) m/e 332 (M+NH$_4$), 314 (M).

I. (E)-1-(Diethoxyphosphinyl)-6-methyl-8-phenyl-5-octenesulfonic acid, cyclohexyl ester To a suspension of 83 mg (3.44 mmol) of NaH in 7 mL of dry DMF at 0° C. under argon was added 1.25 g (4.00 mmol) of Example 1A Part B sulfonate over 15 min. to give a yellow solution. The reaction was allowed to warm to room temperature and stir for 0.5 h when 0.60 g (1.91 mmol) of Part H iodide was added in one portion. The reaction mixture was stirred for 18 h when it was quenched with saturated aq NH$_4$Cl solution and diluted with ether. The organic fraction was washed with water, brine, dried (Na$_2$SO$_4$) and evaporated to provide a crude yellow oil. Flash chromatography was performed on 75 g of silica gel eluted with 4:6 ethyl acetate/hexane to provide 0.76 g (79%) of title compound as a pale yellow oil.

TLC Silica gel (3:7 ethyl acetate/hexane) R$_f$=0.28.

IR (film) 3059, 3026, 2938, 2863, 1454, 1354, 1261, 1172, 1053, 1022, 927, 866 cm$^{-1}$.

$^1$H NMR (CDCl$_3$, 270 MHz) δ7.25, 7.15 (two m, 5H) 5.13 (t, 1H, J=7.3 Hz) 4.86 (m, 1H) 4.22 (m, 4H) 3.45 (dt, 1H, J=20.1, 6.5 Hz) 2.70 (t, 2H, J=7.3 Hz) 2.26 (t, 2H, J=7.8 Hz) 2.05 (m, 6H) 1.67 (m, 6H) 1.62 (s, 3H) 1.36 (t+m, 10H, J=7.0 Hz) ppm.

Mass Spec (CI—NH$_3$, + ions) m/e 518 (M+NH$_4$), 436 (M+NH$_4$-C$_6$H$_{10}$).

J. (E)-6-Methyl-8-phenyl-1-phosphono-5-octene-1-sulfonic acid, tripotassium salt To a solution of 0.76 g (1.52 mmol) of Part I compound and 10 mL of methanol in a sealable tube at 0° C. was added NH$_3$ (g) until the solution was saturated. The tube was sealed and placed in an oil bath at 60° C. for 24 h, at which point the tube was opened and the volatiles removed under reduced pressure. The remainder was dissolved in a 1:3 hexamethyldisiiazane/toluene solution and evaporated two times (2×10 mL) leaving a colorless viscous oil. The oil was dissolved in 7 mL of dry methylene chloride and treated with 1.48 mL (7.00 mmol) of hexamethyldisilazane and 1.00 mL (7.50 mmol) of bromotrimethylsilane. The reaction was allowed to stir at RT for 18 h when the solvent was evaporated and the residue pumped (≈0.5 mm pressure) for 0.5 h. The remainder was dissolved by adding 5 mL (5 mmol) of 1M KOH solution and stirring vigorously for ten min. The soapy solution was freeze dried to provide a white solid. The solid was purified by MPLC on a column of CHP20P gel (250 mL) eluting with water (150 mL) followed by a gradient created by the gradual addition of 500 mL of acetonitrile to a reservoir of 300 mL of water. Approximately 7 mL fractions were collected. Fractions 26 to 30 were pooled, the acetonitrile was removed under reduced pressure and the aqueous solution lyophilized to provide 0.45 g (63%) of title compound as a white lyophilate which was 98.5% pure by HPLC.

TLC Silica gel (6:3:1 n-propanol/conc. NH$_3$/water) R$_f$=0.17.

IR (KBr) 3418, 3063, 3027, 2934, 2863, 1663, 1454, 1383, 1196, 1111, 1086, 1047, 964, 698 cm$^{-1}$.

$^1$H NMR (CDCl$_3$, 400 MHz) δ7.25, 7.15 (two m, 5H) 5.15 (t, 1H, J=7.4 Hz) 2.77 (ddd, 1H, J=17.9, 7.5, 4.5 Hz) 2.64 (t, 2H, J=7.8 Hz) 2.20 (t, 2H, J=7.6 Hz) 1.97–1.65 (m, 4H) 1.57 (s, 3H) 1.46 (m, 2H) ppm.

Mass Spec (FAB, + ions) m/e 515 (M+K), 477 (M+H), 439 (M−K+2H).

Anal. Calc'd for C$_{15}$H$_{20}$O$_6$SPK$_3$+1.36 H$_2$O: C, 35.95; H, 4.57; P, 6.18; S, 6.40 Found: C, 36.26; H, 4.76; P, 5.84; S, 6.21.

EXAMPLE 37

(E,E)-7,11,15-Trimethyl-1-phosphono-6,10,14-hexadecatriene-1-sulfonic acid, tripotassium salt A. (E,E)-6,10,14-Trimethyl-5,9,13-pentadecatrienenitrile A solution of 4.78 g (13.30 mmol) of (E,E)-4-iodo-2,6,10-trimethyl-2,6,10-tetradecatriene (prepared in Example 1 Part C) and 2.59 g (39.80 mmol) potassium cyanide in an 8:1 mixture of ethanol/water was stirred at reflux overnight. The ethanol was removed under vacuum and the reaction was diluted with 200 mL ether and 50 mL water. The aqueous fraction was removed and the organics washed with water and brine. The combined aqueous fractions were back extracted with ether and the combined organics dried on sodium sulfate and concentrated to yield 3.00 g (87%) of title nitrile as a yellow oil. The compound was used without further purification.

TLC (Silica gel, 95:5 hexane/ethyl acetate) R$_f$=0.13.

MS (CI—NH$_3$+ ions) m/z 260 (M+H), 277 (M+NH$_4$).

IR (KBr) 2965, 2924, 2857, 2247, 1669, 1449, 1383, 1107, 833 cm$^{-1}$.

$^1$H NMR (CDCl$_3$, 400 MHz) δ5.07 (m, 3H) 2.31 (t, 2H, J=7.5 Hz) 2.15 (q, 2H, J=7.5 Hz) 2.03 (m, 8H) 1.71 (quint, 2H, J=7.5 Hz) 1.67 (s, 3H) 1.63 (s, 3H) 1.60 (s, 6H) ppm.

B. (E,E)-6,10,14-Trimethyl-5,9,13-pentadecatrienal

To a stirred solution of 1.50 g (5.79 mmol) of Part A nitrile in 6.0 mL tetrahydrofuran at 0° C. was added dropwise 5.80 mL (8.69 mmol) of 1.5N diisobutylaluminum hydride in toluene. After the addition was complete, the reaction was warmed to 50° C. in an oil bath for one hour. The reaction was quenched at 0° C. with 6.0 mL water, and diluted with 26 mL 1M tartaric acid and 15 mL ether. The mixture stirred at room temperature for 2½ hours, and was extracted with ether two times. The combined organics were washed with brine, dried over sodium sulfate, and concentrated to provide 1.50 g of title aldehyde as a yellow slurry which was used without further purification.

TLC (Silica gel, CH$_2$Cl$_2$) R$_f$=0.55.

$^1$H NMR (CDCl$_3$, 400 MHz) δ9.75 (s, 1H) 5.09 (m, 3H) 2.41 (dt, 2H, J=1.5, 7.3 Hz) 2.10–1.93 (m, 10H) 1.68 (s+m, 5H) 1.59 (s, 9H) ppm.

C. (E,E)-6,10,14-Trimethyl-5,9,13-pentadecatrien-1-ol

To stirred solution of 1.50 g (5.77 mmol) of Part B aldehyde in 15 mL methanol at 0° C. was added 330 mg (8.69 mmol) of sodium borohydride. After 15 minutes, the reaction was quenched with 5 mL ammonium chloride solution and partitioned between 100 mL ether and 50 mL ammonium chloride. The aqueous layer was removed and the organics were washed with brine, dried (sodium sulfate), and concentrated to 1.3 g of a yellow oil. The product was purified by flash chromatography on silica gel (150 g) packed, loaded, and eluted with 7:3 hexane/ethyl acetate. Pure fractions were concentrated to yield 0.80 g (45%) of title alcohol as a clear oil.

TLC (Silica gel 7:3 hexane/ethyl acetate) R$_f$=0.32.

MS (CI—NH$_3$, + ions) 265 (M+H), 282 (M+NH$_4$).

IR (CH$_2$Cl$_2$ film) 3331, 2928, 2859, 1451, 1383, 1061 cm$^{-1}$.

$^1$H NMR (CDCl$_3$, 400 MHz) δ5.10 (m, 3H) 3.63 (t, 2H, J=6.5 Hz) 2.08 (m, 4H) 2.00 (m, 6H) 1.68 (s, 3H) 1.59 (s, 9H) 1.55 (m, 2H) 1.40 (quint, 2H, J=6.5 Hz) ppm.

D. (E,E)-1-Iodo-6,10,14-trimethyl-5,9,13-pentadecatriene

To stirred solution of 0.78 g (2.95 mmol) of Part C alcohol in 10 mL methylene chloride at 0° C. was added 18 mg (5 mol %) of 4-dimethyl aminopyridine and 0.53 mL (3.83 mmol) of triethylamine followed by the dropwise addition of 0.35 mL (4.44 mmol) of methanesulfonyl chloride dissolved in 2.5 mL methylene chloride. The mixture was stirred at room temperature for 2 hours, when it was diluted with 100 mL ether and 25 mL water. The aqueous fraction was removed and the organics were washed with water and brine and dried (sodium sulfate). The product was concentrated to a yellow oil which was treated with 1.33 g (8.83 mmol) sodium iodide in 20 mL acetone at room temperature 16 hours and at 65° C. for two hours. The acetone was removed under vacuum and the orange residue dissolved in 80 mL hexane and 40 mL water. The aqueous layer was removed and the organics were washed with water, sodium sulfite (2×20 mL), brine, and concentrated to 0.75 g of a yellow oil. The crude product was purified by flash chromatography on silica gel (100 g) packed, loaded, and eluted with hexane. Pure fractions were combined and concentrated to yield 610 mg (55%) of title iodide as a clear oil.

TLC Silica gel, (hexane) R$_f$=0.16.

MS (CI—NH$_3$, + ions) 375 (M+H), 392 (M+NH$_4$).

IR (CH$_2$Cl$_2$ film) 2967, 2922, 2855, 1667, 1447, 1381, 1225, 1107 cm$^{-1}$.

$^1$H NMR (CDCl$_3$, 400 MHz) δ5.02 (m, 3H) 3.10 (t, 2H, J=7.0 Hz) 2.00 (m, 4H) 1.93 (m, 6H) 1.75 (quint, 2H, J=7.5 Hz) 1.60 (s, 3H) 1.52 (s, 9H) 1.37 (quint, 2H, J=7.5 Hz) ppm.

E. (E,E) -1-(Diethoxyphosphinyl) -7,11,15-trimethyl-6,10,14-hexadecatrienesulfonic acid, cyclohexyl ester To a stirred solution of 1.00 g (3.19 mmol) of Example 1A Part B sulfonate in 4.0 mL dimethylformamide at −20° C. was added 69 mg (2.88 mmol) of sodium hydride in one portion. The reaction was stirred at −20° C. for 20 minutes then at room temperature until gas evolution was completed (25 minutes), when 0.60 g (1.59 mmol) of Part D iodide in 2.0 mL dimethylformamide was added. The mixture was stirred for 20 hours, when it was quenched with 25 mL ammonium chloride and diluted with 75 mL ether. The aqueous fraction was removed, and the organics were washed with brine. The combined aqueous fractions were back extracted with ether and the combined organics were dried (sodium sulfate) and concentrated to 1.2 g of a yellow oil. The crude product was purified by flash chromatography on silica gel (100 g) packed, loaded, and eluded with 7:3 hexane/ethyl acetate. Pure fractions were combined and concentrated to yield 403 mg (45%) of title compound as a clear oil.

TLC (Silica gel 7:3 hexane/ethyl acetate) R$_f$=0.19.

$^1$H NMR (CDCl$_3$, 400 MHz) δ5.10 (m, 3H) 4.85 (m, 1H) 4.23 (m, 4H) 3.42 (dt, 1H, J=21, 6 Hz) 2.18–1.97 (m, 14H) 1.79–1.47 (m, 8H) 1.68 (s, 3H) 1.59 (s, 9H) 1.40–1.25 (m, 2H) 1.36 (t, 6H, J=7.5 Hz) ppm.

F. (E,E)-7,11,15-Trimethyl-1-phosphono-6,10,14-hexadecatriene-1-sulfonic acid, tripotassium salt A solution of 403 mg (0.72 mmol) of Part E triester in 10 mL of methanol in a sealable tube was saturated with ammonia gas at 0° C. The tube was sealed and heated at 75° C. for 20 hours. The tube was opened and the solution evaporated to a glassy oil which was evaporated from toluene two times. The residue was treated with a solution of 16:5 mL toluene/hexamethyldisilazane (HMDS) and evaporated (2×6.6 mL) before drying under high vacuum. The residue was dissolved in 4.5 mL of methylene chloride and treated sequentially with 0.76 mL (3.59 mmol) of HMDS and 0.57 mL (4.31 mmol) of trimethylsilyl bromide. The reaction was stirred at room temperature under argon for 48 hours, at which point the organics were removed under vacuum and the remainder was dissolved in 3.10 mL (3.1 mmol) of 1N KOH and lyophilized. The solid was purified by MPLC on a column of CHP20P gel (2.5 cm diameter×21 cm height), eluting with water (100 mL), followed by a gradient formed by the gradual addition of 400 mL acetonitrile to a reservoir of 350 mL water. Approximately 10 mL fractions were collected. Pure fractions were combined and concentrated to 316 mg (81%) of a glassy solid. The solid was triturated with acetone (3×2.0 mL) until a granular consistency was achieved, and dried under vacuum, yielding 263 mg (68%) of title compound as an off-white solid.

TLC (Silica gel, 7:2:1 n-propanol/ammonia/water) R$_f$=0.10.

MS (Ion Spray, − ions) 421 (M−3K+2H).

IR (KBr) 3457, 2965, 2926, 2857, 16559, 1624, 1451, 1400, 1383, 1213, 1173, 1140, 1090, 1044, 966, 885, 837, 785, 694, 644, 556 cm$^{-1}$.

$^1$H NMR (D$_2$O, 400 MHz) δ5.14 (t, 1H, J=6.6 Hz) 5.05 (m, 2H) 2.80 (dt, 1H, J=18, 6 Hz) 1.97 (m, 4H) 1.88 (m, 6H) 1.78 (m, 2H) 1.55 (s, 3H) 1.49 (s, 9H) 1.35–1.55 (m, 2H) 1.23 (m, 2H) ppm.

Anal. Calc'd for $C_{19}H_{32}O_6SPK_3 \cdot 1.21H_2O$: C, 40.85; H, 6.21; P, 5.54; S, 5.74. Found: C, 40.85; H, 6.32; P, 5.75; S, 5.60.

EXAMPLE 38

(all-E) -7,11,15-Trimethyl-1-phosphono-4-(3,7,11-trimethyl-2,6,10-dodecatrienyl)-6,10,14-hexadecatriene- 1-sulfonic acid, tripotassium salt A. (all-E)-Bis(3,7,11-trimethyl-2,6,10-dodecatrienyl)propanedioic acid, diethyl ester To a stirred solution of 6.57 g (41.10 mmol) of diethyl malonate in 80 mL dimethylformamide (DMF) at −25° C. under argon was added 2.17 g (90.30 mmol) of sodium hydride. The reaction was stirred for 30 minutes at −25° C. and room temperature for 30 minutes when a solution of 23.42 g (82.10 mmol) of farnesyl bromide in 20 mL of DMF was added. The reaction mixture was stirred for 15 hours, quenched with 100 mL ammonium chloride solution and diluted with 500 mL of a 1:1 hexane/ether mixture. The aqueous fraction was removed and the organics washed with brine, dried (sodium sulfate), and concentrated to yield 21.07 g of title compound as a yellow oil which was used without further purification.

TLC (Silica gel, 9:1 hexane/ethyl acetate) $R_f$=0.59.

$^1$H NMR (400 MHz, CDCl$_3$) δ5.08 (t, 4H, J=6.2 Hz) 4.98 (t, 2H, J=7.5 Hz) 4.16 (m, 4H) 2.60 (d, 4H, J=7.0 Hz) 2.01 (m, 20H) 1.68 (s, 6H) 1.60 (s+m, 19H) 1.23 (m, 6H) ppm.

B. (all-E)-5,9,13-Trimethyl-2-(3,7,11-trimethyl- 2,6,10-dodecatrienyl)-4,8,12-tetradecatrienoic acid, ethyl ester A solution of 21.07 g (37.00 mmol) of Part A compound, 0.66 mL (37.00 mmol) of water, and 3.14 g (74.10 mmol) of lithium chloride in 40 mL of methylsulfoxide was heated to 190° C. and stirred for 72 hours under argon. The reaction was treated with a 1:1 solution of hexane/ether and washed with water and brine. The organic fraction was dried (sodium sulfate), and concentrated to yield 18.00 g of title ester as a brown oil. The compound was used without further purification.

TLC (Silica gel, 9:1 hexane/ethyl acetate) $R_f$=0.73.

C. (all-E)-5,9,13-Trimethyl-2-(3,7,11-trimethyl-2,6,10-dodecatrienyl)-4,8,12-tetradecanrien-1-ol To a stirred solution of 18.00 g (36.20 mmol) of Part B compound in 250 mL ether at −70° C. under argon was added 1.37 g (36.20 mmol) of lithium aluminum hydride. The reaction was stirred at −70° C. for 1 hour, then at 0° C. for 4 hours. The reaction was quenched by the sequential addition of the following: a solution of 1.37 mL water in 28 mL of tetrahydrofuran (THF), 4.10 mL of a solution of 15% sodium hydroxide, a solution of 1.37 mL water in 28 mL of THF. The mixture was treated with 10 g of magnesium sulfate, filtered through celite and concentrated to yield 13.89 g of a dark yellow oil. The crude product was purified by flash Chromatography on silica gel (1000 g) packed, loaded, and eluted with 9:1 hexane/ethyl acetate. Pure fractions were combined and concentrated to yield 8.05 g (49% yield from farnesyl bromide) of title compound as a clear oil.

TLC (Silica gel, 9:1 hexane/ethyl acetate) $R_f$=0.15.

MS (CI, NH$_3$, + ions) 472 (M+NH$_4$), 455 (M+H).

IR (CHCl$_3$ film) 3351, 2967, 2918, 2857, 1447, 1383, 1090, 1030, 835, 735 cm$^{-1}$.

$^1$H NMR (400 MHz, CDCl$_3$) δ5.17 (t, 2H, J=7.5 Hz) 5.10 (m, 4H) 3.52 (d, 2H, J=5.5 Hz) 2.03 (m, 20H) 1.67 (s, 6H) 1.61 (s, 6H) 1.59 (s+m, 13H)ppm.

D. (all-E) -5,9,13-Trimethyl-2-(3,7,11-trimethyl- 2,6,10-dodecatrienyl)-4,8,12-tetradecatrien- 1-yl iodide To a stirred solution of 7.98 g (17.50 mmol) of Part C alcohol and 107 mg (2.5 mol %) of 4-dimethylaminopyridine in 50 mL methylene chloride at 0° C. was added 3.18 mL (22.80 mmol) of triethylamine followed by 1.50 mL (19.50 mmol) of methanesulfonyl chloride in 10.0 mL methylene chloride. The mixture was stirred at room temperature for 1 hour, when it was diluted with 150 mL ether and 50 mL water. The aqueous fraction was removed, the organic fraction was washed with brine, dried (sodium sulfate), and concentrated to 9.20 g of a yellow oil. The crude product was dissolved in 150 mL acetone and stirred with 7.89 g (52.60 mmol) of sodium iodide in the dark at 65° C. for 30 hours. The acetone was then removed under vacuum and the resulting orange residue dissolved in 400 mL hexane and 100 mL water. The aqueous fraction was removed and the organic fraction was washed with saturated sodium sulfite (3×50 mL) and brine, dried (sodium sulfate), and concentrated to leave 9.00 g of a yellow oil. The crude product was purified by flash chromatography on silica gel (100 g) packed, loaded, and eluted with 4 L of 100% hexane followed by 4 L of 1:99 ethyl acetate/hexane. Pure fractions were combined and concentrated to 7.91 g (80%) of title iodide as a clear oil.

TLC (Silica gel, 7:3 hexane/ethyl acetate) $R_f$=0.87.

MS (CI, NH$_3$, + ions) 582 (M+NH$_4$), 565 (M+H).

IR (CH$_2$Cl$_2$ film) 2967, 2917, 2855, 1443, 1383, 1235, 1202, 1152, 1107, 984, 833 cm$^{-1}$.

$^1$H NMR (400 MHz, CDCl$_3$) δ5.09 (m, 6H) 3.23 (d, 2H, J=5.0 Hz) 2.03 (m, 20H) 1.67 (s, 6H) 1.65 (s, 6H) 1.59 (s, 12H) 1.30 (m, 1H) ppm.

E. (all-E)-6,10,14-Trimethyl-3-(3,7,11-trimethyl- 2,6,10-dodecatrienyl)-5,9,13-pentadecatrienenitrile A stirred solution of 3.03 g (5.36 mmol) of Part D iodide and 0.80 g (16.10 mmol) of sodium cyanide in 30 mL of methylsulfoxide was heated to 45° C. for 44 hours. The mixture was then diluted with 200 mL of a 1:1 mixture of ether/hexane and washed with water and brine, dried (sodium sulfate) and concentrated to 2.30 g of a clear oil. The crude product was purified by flash chromatography on silica gel (300 g) packed, loaded, and eluted with 4:96 ethyl acetate/hexane. Pure fractions were combined and concentrated to yield 2.07 g (83%) of title compound as a clear oil.

TLC (Silica gel, 7:3 hexane/ethyl acetate) $R_f$=0.76.

MS (CI, NH$_3$, + ions) 481 (M+NH$_4$), 464 (M+H).

IR (CH$_2$Cl$_2$ film) 2967, 2918, 2855, 2245, 1669, 1445, 1383, 1107, 835, 594 cm$^{-1}$.

$^1$H NMR (400 MHz, CDCl$_3$) δ5.09 (m, 6H) 2.28 (d, 2H, J=5.5 Hz) 2.05 (m, 20H) 1.75 (m, 1H) 1.68 (s, 6H) 1.64 (s, 6H) 1.60 (s, 12H) ppm.

F. (all-E)-6,10,14-Trimethyl-3-(3,7,11-trimethyl-2,6,10-dodecatrienyl)-5,9,13-pentadecatrien-1-ol To a stirred solution of 4.70 g (10.10 mmol) of Part E nitrile in 10 mL of THF under argon at 0° C. was added 10.1 mL (15.2 mmol) of a 1.5M diisobutylaluminum hydride solution in toluene. The reaction was heated to 40° C. for three hours when it was cooled to 0° C. and quenched by the dropwise addition of 5 mL water. The mixture stirred at room temperature with 45 mL of 1M tartaric acid for two and a half hours, then was diluted with water (100 mL) and ether (400 mL). The aqueous fraction was removed and the organics washed with water and brine, dried (sodium sulfate), and concentrated to give 8.00 g of a clear oil.

The oil was dissolved in 20 mL of methanol and treated with 0.76 g (20.20 mmol) of sodium borohydride at 0° C. under argon for one hour. The reaction was quenched with 100 mL ammonium chloride and diluted with 300 mL ether. The aqueous fraction was removed and the organics washed with brine, dried (sodium sulfate), and concentrated to give 2.50 g of a yellow oil. The oil was purified by flash chromatography on silica gel (450 g) packed, loaded, and eluted with 9:1 hexane/ethyl acetate. Pure fractions were combined and concentrated to yield 1.85 g (46% based on 0.70 g of recovered Part D iodide starting material) of title alcohol as a clear oil.

TLC (Silica gel, CH$_2$Cl$_2$) R$_f$=0.24.

$^1$H NMR (270 MHz, CDCl$_3$) δ5.12 (m, 6H) 3.66 (t, 2H, J=7.0 Hz) 2.00 (m, 21H) 1.67 (s, 6H) 1.59 (s+m, 21H) ppm.

G. (all-E)-6,10,14-Trimethyl-3-(3,7,11-trimethyl-2,6,10-dodecatrienyl)-5,9,13-pentadecatrien-1-yl iodine To a stirred solution of 2.05 g (4.37 mmol) of Part F alcohol in 15 mL of THF at 0° C. under argon was added 0.65 g (9.61 mmol) of imidazole and 1.26 g (4.80 mmol) of triphenylphosphine, followed by the dropwise addition of 1.22 g (4.80 mmol) of iodine in 25 mL of THF. The mixture was stirred at room temperature for 45 minutes when it was diluted with hexane (200 mL) and water (20 mL). The aqueous fraction was removed and the organics were washed with saturated sodium sulfite and dried over sodium sulfate. The solution was absorbed onto 15 g of silica gel which was evaporated to dryness and loaded onto a column of 150 g of silica packed with hexane. The product was eluted with 3.5 L of hexane followed by 1 L of 1:9 ethyl acetate/hexane. Pure fractions were combined and concentrated to give 1.82 g (71%) of title iodide as a clear oil.

TLC (Silica gel, hexane) R$_f$=0.09.

MS (CI, NH$_3$, + ions) 596 (M+NH$_4$), 579 (M+H).

IR (CH$_2$Cl$_2$ film) 2967, 2922, 2855, 1667, 1447, 1383, 1225, 1202, 1107, 833 cm$^{-1}$.

$^1$H NMR (300 MHz, CDCl$_3$) δ5.12 (m, 6H) 3.22 (t, 2H, J=7.5 Hz) 2.00 (m, 20H) 1.80 (m, 2H) 1.73 (s, 6H) 1.62 (s+m, 19H) ppm.

H. (all-E)-1-(Diethoxyphosphinyl)-7,11,15-trimethyl-4-(3,7,11-trimethyl-2,6,10-dodecatrienyl)-6,10,14-hexadecatriene-1-sulfonic acid, cyclohexyl ester To a stirred solution of 0.76 g (2.42 mmol) of Example 1A Part B sulfonic acid, cyclohexyl ester in 2.0 mL of dimethylformamide (DMF) at 0° C. under argon was added 52 mg (2.18 mmol) of sodium hydride. After gas evolution subsided, the mixture was brought to room temperature and stirred for 20 minutes when 0.68 g (1.17 mmol) of Part G iodide in 1.5 mL of a 1:2 mixture of DMF/tetrahydrofuran was added. The mixture was stirred for 69 hours and quenched with 30 mL of ammonium chloride solution and diluted with 50 mL of ether. The aqueous fraction was removed and the organics were washed with brine. The combined aqueous fractions were back extracted with 25 mL of ether and the combined organics were dried (sodium sulfate) and concentrated to give 1.70 g of a yellow oil. The crude product was purified by flash chromatography on silica gel (100 g) packed and loaded with hexane, and eluted as with 1 L of hexane followed by 2 L of 7:3 hexane/ethyl acetate. Pure fractions were combined and concentrated to yield 0.19 g (21%) of title compound as a colorless oil.

TLC (Silica gel, 7:3 hexane/ethyl acetate) R$_f$=0.25.

MS (CI, NH$_3$, + ions) 711 (M−C$_6$H$_{10}$+NH$_3$), 683 (711−C$_2$H$_4$).

IR (neat) 2965, 2930, 2859, 1451, 1354, 1262, 1175, 1055, 1024, 972, 930, 866, 828, 801 cm$^{-1}$.

$^1$H NMR (400 MHz, CDCL$_3$) δ5.04 (m, 6H) 4.77 (m, 1H) 4.15 (m, 4H) 3.30 (dt, 1H, J=20.0, 6.0 Hz) 1.95 (m, 24H) 1.75–1.32 (m, 8H) 1.60 (s, 18H) 1.55 (s, 18H) 1.28 (t, 6H, J=7.5 Hz) ppm.

$^{13}$C NMR (100 MHz, CDCl$_3$) δ136.07 134.80 131.03 124.30 124.14 122.48 82.37 63.25 (two d, J=6 Hz) 60.64 (d, J=138 Hz) 39.85, 39.62 39.20 32.65 32.05 (d, J=5 Hz) 31.49 26.66 25.55 24.85 23.40 17.54 16.25 (d, J=5 Hz) 16.11, 15.87, ppm.

I. (all-E-)-7,11,15-Trimethyl-1-phosphono-4-(3,7,11-trimethyl-2,6,10-dodecatrienyl)-6,10,14-hexadecatriene-1-sulfonic acid, tripotassium salt To a solution of 190 mg (0.25 mmol) of Part H triester in 5 mL of methanol in a sealable tube was added ammonia gas at 0° C. until saturated. The tube was sealed and heated at 75° C. for 48 hours. The tube was opened and the solution evaporated to a glassy oil which was evaporated from toluene two times and dried under high vacuum, leaving an amber oil. The residue was dissolved in 3.5 mL of methylene chloride and treated sequentially with 0.33 mL (1.25 mmol) of bis(trimethylsilyl)trifluoroacetamide and 0.20 mL (1.50 mmol) of trimethylsilyl bromide. The reaction mixture was stirred at room temperature under argon for 48 hours, at which point the volatiles were removed under vacuum and the remainder was dissolved in 1.50 mL (1.50 mmol) of 1N KOH and lyophilized. The crude lyophilate was precipitated by dissolving the sample in 2 mL of water, warming to 50° C., treating the solution with 2 mL of acetone and placing the mixture in an ice bath for 0.5 h. The aqueous fraction was removed, the gummy solid was triturated with ether and dried under vacuum. The solid was dissolved in water and lyophilized to provide 89 mg (48%) of title compound as an off-white solid.

TLC (Silica gel, 7:2:1 n-propanol/ammonia/water) R$_f$=0.13.

MS (FAB, + ions) m/e 779 (M+K), 742 (M+H), 703 (M+2H−K).

IR (KBr) 3443, 2969, 2924, 2857, 1678, 1451, 1400, 1383, 1208, 1090, 1045, 968, 891, 835, 721 cm$^{-1}$.

$^1$H NMR (400 MHz, CDCl$_3$) δ5.14 (t, 2H, J=7.0 Hz) 5.00 (m, 4H) 2.75 (m, 1H) 1.90 (m, 22H) 1.58 (s+m, 6H) 1.54 (s, 6H) 1.50 (s, 6H) 1.48 (s, 6H) 1.40 (m, 1H) ppm.

Anal. Calc'd for C$_{34}$H$_{56}$O$_6$PSK$_3$·2.28H$_2$O·KOH: C, 48.71: H, 7.40; S, 3.82; P, 3.69; Found C, 48.71; H, 7.47; S, 4.05; P, 3.91.

EXAMPLE 39

(E,E)-4-Hydroxy-6,10,14-trimethyl-1-phosphono-5,9,13-pentadecatriene-1-sulfonic acid, tripotassium salt A. (E,E)-3,7,11-Trimethyl-2,6,10-dodecatrienal To a CH$_2$Cl$_2$ solution (15 mL) of oxalyl chloride (7.81 mL, 87.7 mmol) was added dimethyl sulfoxide (12.5 mL, 175.4 mmol) dropwise over 30 min at −60° C. The resulting clear solution was stirred at this temperature for 20 min. A solution of trans, trans- farnesol (Aldrich Chemical Co.) (15 g, 67.5 mmol) in CH$_2$Cl$_2$ (325 mL) was added dropwise over 15 min. The reaction mixture became cloudy white during addition. The heterogeneous reaction mixture was stirred at −60° C. for 30 min, whereupon triethylamine (56.4 mL, 405 mmol) was added dropwise over 10 min. The reaction mixture became thick. The reaction mixture was allowed to warm to RT over 1 h. Ethyl ether (800 mL) was added and the organic layer was washed with H$_2$O (500 mL), brine (500 mL) and dried over MgSO$_4$. Evaporation gave 15 g (100%) of title compound as a crude oil.

B. (E,E)-3-Hydroxy-5,9,13-trimethyl-4,8,12-tetradecatrienoic acid, 1,1-dimethylethyl ester n-Butyllithium solution (32.4 mL, 2.5M in THF, 81.0 mmol) was added dropwise to a solution diisopropylamine (11.35 mL, 81.0 mmol) in THF (20 mL) at 0° C. After stirring 15 min, the reaction solution was cooled to −78° C. tert-Butyl acetate (7.07 mL, 84.3 mmol) in THF (50 mL)

was added dropwise and stirring was continued for 30 min. A solution of Part A compound (15 g, 67.5 mmol) was added dropwise over 30 min and stirring was continued at −78° C. for 1 h. Water (100 mL) was added and reaction mixture was warmed to RT. The reaction mixture was diluted with ethyl acetate (500 mL) and the organic layer was washed with $H_2O$ (500 mL), brine (500 mL) and dried over $MgSO_4$. Evaporation gave a crude oil. Flash chromatography was performed on 1 kg silica gel, loaded and eluted with 10:90 ethyl acetate/hexane. The pure fractions were combined and evaporated to give 16.0 g (71%) of title compound as a yellowish oil.

C. (E,E)-5,9,13-Trimethyl-3-[[(1,1-dimethylethyl)dimethylsilyl]oxy]-4,8,12-tetradecatrienoic acid, 1,1-dimethylethyl ester tert-Butyldimethylsilyl chloride (2.96 g, 19.7 mmol) was added to a mixture of Part B compound (6.0 g, 17.9 mmol) and imidazole (1.58 g, 23.2 mmol) in DMF (50 mL) at RT. The reaction mixture was stirred at RT for 2 h, then partitioned between ethyl ether (800 mL) and $H_2O$ (500 mL). The aqueous layer was extracted with ethyl ether (200 mL). The combined organic layers were washed with $H_2O$ (2×500 mL), brine (2×500 mL) and dried over $MgSO_4$. Evaporation gave 8.01 g (100%) of title compound as a crude oil.

D. (E,E) -5,9,13-Trimethyl-3-[[(1,1-dimethylethyl)dimethylsilyl]oxy]-4,8,12-tetradecatrien-1-ol Diisobutylaluminum hydride solution (39.3 mL, 1M in toluene, 39.3 mmol) was added dropwise to a solution of Part C compound (8.0 g, 17.9 mmol) in toluene (70 mL) at 0° C. under argon. Stirring was continued for 1.5 h. Methanol (5 mL) was added until bubbling ceased. A 1M potassium sodium tartrate solution (300 mL) was added and vigrous stirring was begun. After a few minutes the reaction mixture gelatinized. Stirring was continued for 1 h. Ethyl acetate (500 mL) was added and the organic layer was washed with brine (500 mL), then dried over $MgSO_4$. Evaporation gave a pale yellow oil. Purification was performed by flash chromatography on 750 g silica gel, loaded and eluted with 10% ethyl acetate in hexane. Pure fractions were combined and evaporated to give 4.5 g (65%) of title compound as a colorless oil.

E. (E,E) -5,9,13-Trimethyl-3-[[(1,1-dimethylethyl)dimethylsilyl]oxy]-4,8,12-tetradecatrien-1-yl iodide To a mixture of Part D alcohol (4.50 g, 11.84 mmol), triphenylphosphine (3.40 g, 13.0 mmol) and imidazole (1.60 g, 23.7 mmol) in THF (30 mL), a solution of iodine (2.83 g, 13.0 mmol) in THF (5 mL) was added dropwise at RT. After stirring for 20 min, hexane (300 mL) was added to dilute the reaction mixture. The organic layer was washed with 10% sodium bisulfite (100 mL), saturated sodium bicarbonate (300 mL), brine (300 mL) and dried over $MgSO_4$. The filtrate was evaporated to a volume of 100 mL, silica gel (10 g) was added and evaporation was continued to dryness. Flash chromatography was performed on 500 g silica gel, loaded and eluted with 1:99 ethyl acetate/hexane. Pure fractions were combined and evaporated to give 5.2 g (90%) of title compound as a colorless oil.

F. (E,E)-1-(Diethoxyphosphinyl)-6,10,14-trimethyl- 4-[[(1,1-dimethylethyl)dimethylsilyl]oxy]- 5,9,13-pentadecatriene-1-sulfonic acid, cyclohexyl ester To a suspension of sodium hydride (0.51 g, 1.22 mmol) in DMF (12 mL) under argon, a solution of Example 1A Part B sulfonate (8.3 g, 26.53 mmol) in DMF (12 mL) was added dropwise over 10 min at 100° C. (ice bath). The ice bath was removed and the reaction mixture was stirred at RT until the reaction solution was clear. The reaction was recooled to 0° C., and a solution of Part E compound (5.2 g, 10.61 mmol) in DMF (12 mL) was added dropwise over 15 min. Stirring was continued for 2 h. The reaction mixture was warmed to RT and stirring was continued overnight. Diethyl ether (300 mL) was added to dilute reaction solution. The organic layer was washed with $H_2O$ (200 mL), brine (200 mL) and dried over $MgSO_4$. Evaporation gave a crude oil. Flash chromatography was performed on 450 g silica gel, loaded and eluted with 10:90 isopropanol/hexane. Pure fractions were combined and evaporated to give 4.8 g (70%) of title compound as a colorless oil.

G. (E,E)-1-(Diethoxyphosphinyl)-4-hydroxy-6,10,14-trimethyl-5,9,13-pentadecatriene-1-sulfonic acid, cyclohexyl ester A stock HF/pyridine(Py)/THF solution was prepared by combining commercial $HF_x \cdot p_y$ (2 mL) and dry pyridine (4 mL) in THF (14 mL).

Part F compound (4.8 g, 7.10 mmol) was dissolved in a stock solution of HF/Py/THF (200 mL) at RT. The reaction mixture was stirred at RT overnight. Ethyl acetate (500 mL) was added and the organic layer was washed with $H_2O$ (100 ML), 1N HCl (100 mL), saturated sodium bicarbonate (100 mL), brine (100 mL) and dried over MgSO4. Evaporation gave a crude oil. Flash chromatography was performed on 300 g silica gel, loaded and eluted with 1:1 ethyl acetate/hexane. Pure fractions were combined and evaporated to give 1.85 g (68%) of title compound as a colorless oil.

H. (E,E)-4-Hydroxy-6,10,14-trimethyl-1-phosphono- 5,9,13-pentadecatriene-1-sulfonic acid, tripotassium salt To a solution of Part G compound (1.00 g, 1.79 mmol) in methanol (20 mL) was bubbled anhydrous ammonia gas until the solution was saturated. Then the sealed tube containing the reaction mixture was heated in an oil bath (70° C.) overnight. The reaction mixture was evaporated to dryness. Purification was performed by chromatography on CHP20P gel (2.5×20 cm), loaded and eluted with water followed by gradual addition of $CH_3CN$ to a reservoir of water. The pure fractions were combined, evaporated and azeotroped with toluene. To a stirred solution of the resulting residue (780 mg, 1.57 mmol) and collidine (1.03 mL, 7.85 mmol) in dichloromethane (10 mL) at RT under argon was added bromotrimethylsilane (1.66 mL, 12.56 mmol). The mixture was stirred at RT for 20 h. The solvent was evaporated and the residue was pumped at high vacuum for 2 h. The residue was dissolved in 1M potassium hydroxide (10 mL, 10 mmol) and the reaction mixture was stirred for 2 h. The solution was lyophilized to give a white solid. The crude product was purified by chromatography on CHP20P gel (2.5×20 cm), loaded and eluted with water followed by gradual addition of $CH_3CN$ to a reservoir of water. The combined pure fractions were evaporated to remove $CH_3CN$ and the remaining aqueous solution was precipitated with acetone to provide 220 mg (30%) of title compound as a white solid.

IR (KBr) 2924, 1661, 1198, 1082, 964 $cm^{-1}$.

$^1H$ NMR ($D_2O$, 400 MHz) δ5.07–5.03 (m, 3H) 4.31–4.26 (m, 1H) 2.74 (m, 1H) 1.98–1.80 (m, 8H) 1.78–1.60 (m, 4H) 1.55 (s, 3H) 1.53 (s, 3H) 1.47 (s, 6H) ppm.

$^{13}C$ NMR ($D_2O$, 100 MHz) δ139.76,139.58 136.54 133.42 126.59, 126.52 124.56 68.78, 67.92 61.41 (dd, J=120 Hz) 38.99 38.94 37.09 (d, J=7 Hz) 25.97 24.98 24.55 17.07 16.02 15.36 ppm.

MS (FAB, + ions) m/z 521 [(M+H)–$H_2O$], 539 (M+H), 577 (M+K).

Anal. Calcd for $C_{18}H_{30}K_3O_7PS \cdot 1.0\ H_2O$: C, 38.83; H, 5.79; P, 5.56; S, 5.76 Found: C, 38.85; H, 5.84; P, 5.33; S, 5.57.

EXAMPLE 40

3-Phenoxy-α-phosphonobenzenebutanesulfonic acid, tripotassium salt

A. (E)-3-(3-Phenoxyphenyl)-2-propenoic acid, ethyl ester

Triethyl phosphonoacetate (6.5 mL, 32.8 mmol) was added dropwise to a suspension of sodium hydride (0.73 g, 30.2 mmol) in THF (40 mL) at 0° C. under argon. The ice bath was removed and the suspension was stirred at RT for 20 min, at which time a clear colorless solution resulted. The reaction solution was recooled to −78° C. and a solution of 3-phenoxybenzaldehyde (5.0 g, 25.2 mmol) in THF (10 mL) was added dropwise. The reaction mixture was stirred an −78° C. for 45 min. After warming to RT, the reaction was quenched with saturated ammonium chloride solution. Diethyl ether (200 mL) was added, the organic layer was washed with $H_2O$ (50 mL), brine (50 mL) and dried over $MgSO_4$. Evaporation gave 4.0 g of title ester (96%) as a colorless oil.

B. 3-Phenoxybenzenepropanoic acid, ethyl ester

A mixture of Part A ester (6.5 g, 24.3 mmol) and palladium on carbon (10%, 300 mg) in ethyl acetate (50 mL) was stirred under a hydrogen atmosphere (balloon) overnight at RT. The reaction mixture was filtered through Celite. Evaporation of filtrate gave a crude oil. Purification was performed by flash chromatography on 400 g silica gel, loaded and eluted with 10% ethyl acetate in hexane. Pure fractions were combined and evaporation gave 5.45 g of title ester (84%) as a colorless oil.

C. 3-Phenoxybenzenepropanol

Lithium aluminum hydride solution (20.5 mL, 1M in THF, 20.5 mmol) was added dropwise to a solution of Part B ester (5.45 g, 20.5 mmol) in THF (50 mL) at 0° C. under argon. Stirring was continued for 10 min. Ethyl acetate (5 mL) was added until bubbling ceased. Ethyl ether (300 mL) was added and the organic layer was washed with 1N HCl solution (2×150 mL), $H_2O$ (150 mL), saturated sodium bicarbonate (150 mL), and brine (150 mL), then dried over $MgSO_4$. Evaporation gave a pale yellow oil. Purification was performed by flash chromatography on 500 g silica gel, loaded and eluted with 15% ethyl acetate in hexane. Pure fractions were combined and evaporated to give 4.2 g of title alcohol (90%) as a colorless oil.

D. 1-(3-Iodopropyl)-3-phenoxybenzene

Iodine (1.80 g, 7.24 mmol) in THF (5 mL) was added to a mixture of Part C alcohol (1.5 g, 6.58 mmol), triphenylphosphine (1.90 g, 7.24 mmol) and imidazole (0.89 g, 13.2 mmol) in THF (15 mL). The reaction mixture was stirred at RT for 20 min, then diluted with hexane (200 ml). The organic layer was washed with 10% sodium bisulfite (50 mL), saturated sodium bicarbonate (50 mL), brine (50 mL) and dried over $MgSO_4$. The solvent was evaporated to 100 ml volume, 10 g silica gel was added and the mixture was evaporated to dryness. Flash chromatography was performed on 100 g silica gel, loaded and eluted with hexane. Pure fractions were combined and evaporated to give 1.70 g of title iodide (76%) as a colorless oil.

E. 3-Phenoxy-α-(diethoxyphosphinyl)benzenebutanesulfonic acid, cyclohexyl ester

To a stirred suspension of sodium hydride (241 mg, 10.1 mmol) in DMF (10 mL) at 0° C. under argon, Example 1A Part B sulfonate (3.95 g, 12.6 mmol) in DMF (4 mL) was added dropwise over 15 min. The ice bath was removed and the reaction mixture was stirred at RT for 30 min. The reaction mixture was recooled to 0° C. and a DMF solution (10 mL) of Part D iodide (1.7 g, 5.03 mmol) was added dropwise over 15 min. The mixture was stirred at 0° C. for 2 h. The ice bath was removed and the reaction mixture was stirred at RT overnight. The mixture was diluted with 300 ml of $Et_2O$ and washed with $H_2O$ (150 ml), brine (150 mL) and dried over $MgSO_4$. Evaporation gave a crude oil. Purification was performed by flash chromatography on 100 g silica gel, loaded and eluted with 25% ethyl acetate in hexane. The pure fractions were combined and evaporated to provide 1.5 g of title compound (57%) as a colorless oil.

F. 3-Phenoxy-α-phosphonobenzenebutanesulfonic acid, tripotassium salt

Ammonia gas was bubbled through a solution of Part E compound (1.20 g, 2.23 mmol) in methanol (20 mL) until the solution was saturated. The sealed tube was heated at 70° C. overnight. The reaction mixture was cooled to RT, evaporated to dryness and azeotroped with toluene. To a stirred solution of the resulting residue in dichloromethane (10 mL) at RT under argon was added bromotrimethylsilane (2.6 mL, 19.6 mmol). The mixture was stirred at RT for 20 h. The solvent was evaporated and the residue was pumped at high vacuum for 2 h. The residue was dissolved in 1M potassium hydroxide (10 mL, 10 mmol) and the reaction mixture was stirred for 2 h. The solution was lyophilized to give a white solid. The crude product was purified by chromatography on CHP20P gel (2.5×20 cm), loaded and eluted with water and followed by a gradient created by the gradual addition of $CH_3CN$ to a reservoir of water. The combined pure fractions were concentrated to about 5 mL volume then lyophilized to provide 780 mg (47%) of title compound as a white solid.

IR (KBr) 2957, 1613, 1595, 1489, 1250, 1202, 1074, 966 $cm^{-1}$ $^1H$ NMR $D_2O$, 400 MHz) δ7.29 (t, 2H, J=7.5 Hz) 7.21 (t, 1H, J=8.4 Hz) 7.07 (t, 1H, J=7.4 Hz) 6.99 (d, 1H, J=7.7 Hz) 6.95 (d, 2H, J=7.7 Hz) 6.86 (s, 1H) 6.76 (d, 1H, J=8.1 Hz) 2.76 (dt, 1H, J=6,18 Hz) 2.65–2.45 (m, 2H) 1.98–1.65 (m, 4H) ppm.

$^{13}C$ NMR ($D_2O$, 100 MHz) δ157.03, 156.87, 145.87, 130.24, 130.05, 124.05, 123.95, 119.09, 118.91, 116.11, 61.70, (d, J=120 Hz) 35.46, 31.38, (d, J=7 Hz) 19.67 ppm.

Mass Spec (FAB, + ions) m/z 463 (M-K+2H), 501 (M+H), 539 (M+K).

Anal. Calc'd for $C_{16}H_{16}K_3O_7PS$. 1.8 equiv $H_2O$: C, 36.05; H, 3.71; P, 5.81; S, 6.01. Found: C, 36.05; H, 3.97; P, 5.58; S, 6.06.

EXAMPLE 41

(E,E)-1-[Bis[(2,2-Dimethyl-1-oxopropoxy)methoxy]phosphinyl]-6,10,14-trimethyl-5,9,13-pentadecatriene-1-sulfonic acid, cyclohexyl ester A. 2,2-Dimethylpropanoic acid, iodomethyl ester Sodium iodide (dried) (15.0 g, 100 mmol) was added in one portion to a solution of 2,2-dimethylpropanoic acid, chloromethyl ester (10.0 g, 66.7 mmol) in dry acetonitrile (80 mL) at RT under argon. The heterogeneous reaction was stirred at RT for 6 h, then concentrated in vacuo. The residue was partitioned between toluene (150 mL) and 5% sodium bisulfite (40 mL). The organic layer was washed with 5% sodium bisulfite (40 mL) and water (20 mL), then dried over $MgSO_4$. Evaporation gave title iodide (12.1 g, 75%) as a pale yellow oil.

B. (E,E)-1-Phosphono-6,10,14-trimethylpentadecatriene-1-sulfonic acid, cyclohexyl ester, disilver salt Bromotrimethylsilane (1.45 mL, 11.0 mmol) was added dropwise to a solution of Example 1A Part C sulfonate (1.50 g, 2.75 mmol) and allyl trimethylsilane (4.36 mL, 27.5 mmol) in $CH_2Cl_2$ (5 mL) at RT under argon. The clear yellow reaction was stirred at RT for 52 h, concentrated in vacuo, then pumped at high vacuum overnight to give an orange oil.

The crude silyl ester prepared above was dissolved in 1N KOH (6.05 mL, 6.05 mmol) over 15 min, then added dropwise over 5 min to a solution of silver nitrate (1.17 g, 6.88 mmol) in water (100 mL) under argon in the dark (Al foil). The resultant tan suspension was stirred at RT for 10 min, then the reaction mixture was lyophilized to give a tan solid. The lyophilate was partitioned between toluene (50 mL) and water (50 mL). The aqueous layer was extracted with toluene (3×50 mL). The combined organic extracts were washed with water containing a few drops of brine (20 mL), then dried over $Na_2SO_4$. Evaporation followed by pumping under high vacuum for 30 min gave title compound (1.91 g, 99%) as a brown gum.

C. (E,E)-1-[Bis[(2,2-Dimethyl-1-oxo-propoxy) methoxy] phosphinyl-6,10,14-trimethyl- 5,9,13-pentadecatriene-1-sulfonic acid, cyclohexyl ester A solution of Part B compound (1.91 g, 2.71 mmol) in toluene (20 mL) was cooled to 0° C. under argon. A solution of Part A ester (1.66 g, 6.88 mmol) in toluene (5 mL) was added to the brown solution over 5 min. After 5 min at 0° C., a solid precipitated out of solution. The reaction was stirred an additional 15 min, then filtered through a 0.45 µm filter. The filtrate was concentrated in vacuo to give a pale yellow oil, which was purified by flash chromatography on silica gel (100 g) eluting with 15:85 EtOAc/hexane to provide title compound (1.34 g, 67%) as a colorless oil.

TLC (20:80 EtOAC/hexane): $R_f$=0.21

IR (neat) 2965, 2936, 1757, 1134, 959 cm$^{-1}$.

$^1$H NMR (CDCl$_3$, 400 MHz) δ5.74 (m, 4H) 5.10 (m, 3H) 4.85 (m, 1H) 3.57 (dt, 1H) 2.23–1.88 (m, 14H) 1.88–1.47 (m, 7H) including 1.68 (s, 3H) 1.60 (s, 9H) 1.47–1.13 (m, 3H) including 1.24 (s, 18H) ppm.

$^{13}$C NMR (CDCl$_3$, 100 MHz) δ176.69 176.63 136.14 134.91 131.12 124.33 124.10 122.96 83.17 82.30 (d, J=6 Hz) 82.09 (d, J=6 Hz) 60.30 (d, J=139 Hz) 39.68 38.66 32.60 27.95 (d, J=6 Hz) 27.49 26.78 26.71 26.66 26.44 25.61 24.84 23.32 17.60 16.04 15.90 ppm.

MS (CI, NH$_3$) m/z 736 (M+NH$_4$).

Anal. Calc'd for $C_{36}H_{63}O_{10}PS$: C, 60.15; H, 8.83; P, 4.31; S, 4.46. Found: C, 60.08; H, 9.03; P, 4.47; S, 4.18.

EXAMPLE 42

(E,E)-1-[Bis[(2,2-Dimethyl-1-oxopropoxy)methoxy]phosphinyl]-6,10,14-trimethyl-5,9,13-pentadecatriene-1-sulfonic acid, monopotassium salt Potassium acetate (403 mg, 4.11 mmol) was added to a solution of Example 41 compound (982 mg, 1.37 mmol) in 2,2,2-trifluoroethanol/water (10:1, 10 mL) at RT under argon. After dissolution, the clear colorless reaction was heated an 40° C. overnight (18 h), then concentrated in vacuo. The slightly colored oil was dissolved in EtOAc (30 mL) and washed with saturated KHCO$_3$ (2×5 mL) and half-saturated KCl (10 mL). The organic layer was dried over anhydrous KCl. Evaporation followed by pumping under high vacuum overnight gave title salt (893 mg, 97%) as a colorless oil.

TLC (10:90 MeOH/CH$_2$Cl$_2$) : $R_f$=0.18

IR (neat) 2969, 2920, 1755, 1248, 1136, 1005 cm$^{-1}$.

$^1$H NMR (DMSO, 400 MHz) δ5.59 (d, 2H, J=12.6 Hz) 5.56 (d, 2H, J=12.4 Hz) 5.08 (m, 3H) 2.98 (dt, 1H, J=6.2, 19.7 Hz) 2.08–1.68 (m, 12H) 1.63 (s, 3H) 1.56 (s, 9H) 1.55–1.45 (m, 2H) 1.17 (s, 9H) 1.16 (s, 9H) ppm.

$^{13}$C NMR (CD$_3$OD, 100 MHz) δ178.42 178.21 136.48 135.84 131.99 125.46 125.07 83.69 (d, J=5.9 Hz) 83.33 (d, J=5.9 Hz) 60.31 (d, J=138 Hz) 40.86 40.80 39.75 29.52 (d, J=7.4 Hz) 28.83 28.51 27.79 27.74 27.33 25.93 17.83 16.31 16.18 ppm.

MS (FAB, + ions) m/z 713 (M+K), 675 (M+H).

Anal. Calc'd for $C_{30}H_{52}KO_{10}PS$: C, 53.39; H, 7.77; P, 4.59; S, 4.75. Found: C, 53.30; H, 7.81; P, 4.84; S, 5.19.

EXAMPLE 43

α-Phosphono[1,1':4', 1"-terphenyl]-4"-butanesulfonic acid, tripotassium salt

A. 4-Aminobenzenepropanoic acid, ethyl ester

A 500 mL Parr hydrogenation vessel was charged with 12.36 g (55.9 mmol) of (E)-3-(4-nitrophenyl)- 2-propenoic acid, ethyl ester, 100 mL of absolute ethanol, 15 mL of concentrated hydrochloric acid and 0.75 g of 10% palladium-on-activated charcoal. The slurry was purged with nitrogen and then agitated under an initial pressure of 44.5 psi of hydrogen gas. After 16 h, 18.5 psi had been consumed. The flask was evacuated, purged again with nitrogen and the contents filtered through Celite and evaporated. The residue was dissolved in water and adjusted to pH 9 with solid sodium carbonate. The resulting mixture was extracted thrice with dichloromethane, and the combined organic extracts dried over Na$_2$SO$_4$, filtered and evaporated to provide 9.31 g, 86% of title compound as a yellow oil, sufficiently pure for use in subsequent reactions.

B. 4-Iodobenzenepropanoic acid, ethyl ester

To a stirred solution of 6.48 g (33.6 mmol) of Part A amine in 10 mL (120 mmol) of diiodomethane under nitrogen at room temperature was added 9 mL (67 mmol) of isoamyl nitrite over 10 min. The orange solution was stirred for 30 min and then heated to 80° C. for 2 h. The deep orange solution was diluted with ether and washed once with 2M HCl, once with water, once with saturated sodium bicarbonate solution and once with saturated sodium bisulfite solution. The organic phase was dried (MgSO$_4$) and evaporated. Purification by flash chromatography on silica gel (5×20 cm column) eluted with 3:2 hexanes/dichloromethane gave title iodide as a colorless oil, 8.65 g, 85% yield.

C. [1,1':4',1"-Terphenyl]-4-propanoic acid, ethyl ester

To a stirred solution of 1.17 g (5.0 mmol) of 4-bromobiphenyl in 10 mL of THF at −75° C. under argon was added 5.9 mL (10.0 mmol, 1,7M in pentane) of t-butyllithium dropwise over 15 min. After an additional 15 min, the blue-green solution was warmed to 0° C., stirred 30 min and a solution of 1.86 g (14 mmol) thrice-fused zinc chloride in 15, mL of THF was added. The resulting colorless, turbid solution was stirred for 1 h and then a solution of 1.00 g (3.3 mmol) of Part B iodide and 0.3 g (0.26 mmol) of tetrakis(triphenylphosphine)palladium(0) in 5 mL of THF was added. The reaction was stirred for 16 h, diluted with ether and washed once with 10% citric acid. The organic phase was dried (MgSO$_4$) and evaporated. Purification by flash chromatography on silica gel (5×15 cm column) eluted with 11:9 hexanes/dichloromethane gave title ester as an off-white solid, 1.07 g, 98% yield, mp 172°–174° C.

D. [1,1:4',1"-Terphenyl]-4-propanol

To a stirred solution of 1.00 g (3.0 mmol) of Part C ester in 5 mL of THF under nitrogen at room temperature was added 3 mL (3 mmol) of 1M lithium aluminium hydride in THF. The reaction was stirred for 1 h, quenched with brine and brought to pH 1 with 2N H$_2$SO$_4$. Extracted thrice with 100 mL portions of ethyl acetate. The organic extracts were combined, dried (MgSO$_4$) and evaporated to give title alcohol as gray flakes, mp 210°–212° C., 740 mg, 86% yield. The compound was used without further purification.

E. 4-(3-Iodopropyl) [1,1':4',1"-terphenyl]

To a stirred solution of 720 mg (2.50 mmol) of Part D title alcohol, 660 mg (2.51 mmol) of triphenylphosphine, and 375 mg (5.5 mmol) of imidazole in 20 mL of THF under argon at room temperature was added a solution of 640 mg (2.5 mmol) of iodine in 5 mL of THF, dropwise over 20 min. After addition was complete, the reaction was diluted with hexanes and washed once with saturated sodium bisulfite solution. The organic phase was dried (MgSO$_4$) and evaporated. Purification by flash chromatography on silica gel (5×10 cm column) eluted with CH$_2$Cl$_2$ gave title iodide as a white solid, 860 mg, 86% yield.

F. α-(Diethoxyphosphinyl) [1,1':4',1"-terphenyl]- 4-butanesulfonic acid, cyclohexyl ester To a stirred slurry of 145 mg (3.6 mmol, 60% mineral oil dispersion) of sodium hydride in 3 mL of DMF under argon at −10° C. was added a solution of 1.26 g (4.0 mmol) of Example 1A Part B sulfonate in 2 mL of DMF. After addition was complete, the reaction was warmed to room temperature and stirred for 30 min. To the resulting solution was added 800 mg (2.00 mmol) of Part E title iodide as a powdered solid. The reaction mixture was diluted with 1.5 mL of THF to form a turbid slurry. The reaction was stirred for 16 h, diluted with 100 mL of ether and washed once with 10% citric acid and thrice with water. The organic phase was dried (MgSO$_4$) and evaporated. Purification by flash chromatography on silica gel (5×15 cm column) eluted with 1:19 ether/dichloromethane gave title compound as a colorless oil, 620 mg, 53% yield.

G. α-Phosphono[1,1':4',1"-terphenyl]-4"-butanesulfonic acid, tripotassium salt

To a stirred solution of 590 mg (1 mmol) of Part F compound in 7 mL of dichloromethane under argon at room temperature was added 420 µL (3 mmol) of bromotrimethylsilane. After 24 h, the resulting clear solution was evaporated at 25° C. and the residue dissolved in 10 mL of THF. To this stirred solution was added 550 mg (3.3 mmol) of dried, finely ground potassium iodide and 5 mg (0.015 mmol) of 18-crown-6. The resulting slurry was heated to reflux for 24 h, evaporated and then stirred for 1 h with 6 mL (3 mmol) of 0.5M potassium hydroxide solution. The solution was lyophilized and then purified by MPLC (2.5×20 cm column of Mitsubishi Kasei Sepabeads CHP20P resin): 11.5 mL fractions, 7 mL/min flow rate, eluted with 140 mL water and then a gradient of 500 mL 3:2 acetonitrile/H$_2$O into 450 mL H$_2$O). Fractions 41–49 were collected and lyophilized to give title compound as a white solid, 480 mg, 78% yield.

IR (KBr pellet) 3407, 3092, 2932, 2864, 1634, 1485, 1198, 1078, 1049, 966 cm$^{-1}$.

$^1$H NMR (D$_2$O, 400 MHz) δ8.03 (br s, 6H) 7.93 (d, 2H, J=6.8 Hz) 7.80 (dd, 2H, J=6.9, 6.4 Hz) 7.71 (d, 4H, J=6.4 Hz) 2.97 (dt, 1H, J=6, 18 Hz) 2.21 (m, 2H) 2.21 (m, 4H) ppm.

Anal. Calc'd for C$_{22}$H$_{20}$K$_3$O$_6$PS.3.1 H$_2$O: C, 42.83; H, 4.29; P, 5.02; S, 5.20 Found: C, 42.83; H, 4.19; P, 5.03; S, 5.18.

MS (FAB, + ions) m/e 561 (M+H), 523 (M−K+2H), 485 (M−2K+3H).

EXAMPLE 44

4-(2-Methylphenoxy)-α-phosphonobenzenebutanesulfonic acid, tripotassium salt

A. 4-(2-Methylphenoxy)benzenepropanoic acid, ethyl ester

To a suspension of sodium hydride (155 mg, 6.44 mmol) in pyridine (25 mL) was added a solution of the iodide prepared as described in Example 43 Part B (696 mg, 6.44 mmol) in pyridine (2.5 mL) at 0° C. under argon. Stirring was continued until the solution was clear (15 min). The reaction was warmed to RT, and a solution of o-cresol (990 mg, 3.22 mmol) in pyridine (2.5 mL) was added to the reaction followed by copper bromide-dimethyl sulfide complex (2.0 g, 9.66 mmol). The reaction was refluxed for 2.5 h. The reaction was evaporated to dryness. Ethyl ether (200 mL) was added to dilute the reaction, and the organic layer was washed with 1N HCl (2×50 mL), water (2×50 mL), saturated sodium bicarbonate solution (50 mL), brine (50 mL) and dried over MgSO$_4$. Purification was performed by flash chromatography on 200 g silica gel, loaded and eluted with 10% ethyl acetate in hexane. Pure fractions were combined and evaporated to give title compound (650 mg, 72%) as a colorless oil.

B. 4-(2-Methylphenoxy)benzeneoropanol

Lithium aluminum hydride solution (2.32 mL, 1M in THF, 2.32 mmol) was added dropwise to a solution of Part A ester (650 mg, 2.32 mmol) in THF (50 mL) at 0° C. under argon. Stirring was continued for 10 min. Ethyl acetate (5 mL) was added to destroy excess lithium aluminum hydride (LAH). Ethyl ether (200 mL) was added and the organic layer was washed with 1N HCl solution (2×50 mL), H$_2$O (50 mL), saturated sodium bicarbonate solution (50 mL), and brine (50 mL), then dried over MgSO$_4$. Evaporation gave title compound (350 mg, 62%) as a colorless oil.

C. 1-(3-Iodopropyl)-4-(2-methylphenoxy)benzene

A solution of iodine (399 mg, 1.57 mmol) in THF (5 mL) was added to a mixture of Part B alcohol (345 mg, 1.43 mmol), triphenylphosphine (411 mg, 1.57 mmol) and imidazole (194 mg, 2.86 mmol) in THF (15 mL). The reaction mixture was stirred at RT for 10 min, then diluted with hexane (200 ml). The organic layer was washed with 10% sodium bisulfite (50 mL), saturated sodium bicarbonate (50 mL), brine (50 mL) and dried over MgSO$_4$. The solvent was evaporated to 100 ml volume, 6 g silica gel was added, and the mixture was evaporated to dryness. Flash chromatography was performed on 100 g silica gel, loaded and eluted with hexane. Pure fractions were combined and evaporated to give title iodide (400 mg, 76%) as a colorless oil.

D. α-(Diethoxyphosphinyl)-4-(2-methylphenoxy)benzenebutanesulfonic acid, cyclohexyl ester To a stirred suspension of sodium hydride (54.7 mg, 2.28 mmol) in DMF (5 mL) at 0° C. under argon, Example 1A Part B sulfonate (895 mg, 2.85 mmol) in DMF (2 mL) was added dropwise over 15 min. The ice bath was removed and the reaction mixture was stirred at RT for 30 min. The reaction mixture was recooled to 0° C. and a solution of Part C iodide (400 mg, 1.14 mmol) in DMF (2 mL) was added dropwise over 15 min. The mixture was stirred at 0° C. for 2 h. The ice bath was removed and the reaction mixture was stirred at RT overnight. The mixture was diluted with ethyl ether (150 mL) and washed with H$_2$O (50 ml), brine (50 mL) and dried over MgSO$_4$. Evaporation gave a crude oil. Purification was performed by flash chromatography on 150 g silica gel, loaded and eluted with 25% ethyl acetate in hexane. The pure fractions were combined and evaporated to provide title compound (450 mg, 73%) as a colorless oil.

E. 4-(2-Methylphenoxy)-α-phosphonobenzenebutanesulfonic acid, tripotassium salt

Ammonia gas was bubbled through a solution of Part D compound (450 mg, 0.84 mmol) in methanol (10 mL) until the solution was saturated. The sealed tube was heated at 70° C. overnight. The reaction mixture was cooled to RT, evaporated to dryness and azeotroped with toluene (2×20 mL). To a stirred solution of the resulting residue in dichloromethane (10 mL) at RT under argon was added bromotrimethylsilane (0.77 mL, 5.86 mmol). The mixture was stirred at RT for 20 h. The solvent was evaporated and the residue was pumped at high vacuum for 2 h. The residue was dissolved in 1M potassium hydroxide (5 mL, 5 mmol) and the reaction mixture was stirred for 2 h. The solution was lyophilized to give a white solid. The crude product was purified by chromatography on CHP20P gel (2.5×20 cm), loaded and eluted with water and followed by a gradient created by the gradual addition of $CH_3CN$ to a reservoir of water. The combined pure fractions were concentrated to about 5 mL volume then lyophilized to provide title compound (370 mg, 72%) as a white solid.

TLC (n-propanol/$NH_4OH$/$H_2O$=5:4:1) (silica gel) ($R_f$= 0.26)

IR (KBr) 2951, 2932, 1653, 1507, 1240, 1204, 1076, 966, 878 $cm^{-1}$ $^1$H NMR ($D_2O$, 400 MHz) δ7.22 (d, 1H, J=6.8 Hz) 7.14 (d, 2H, J=8.6 Hz) 7.10 (t, 1H, J=7.7 Hz) 7.03 (t, 1H, J=6.8 Hz) 6.84 (d, 1H, J=8.1 Hz) 6.74 (d, 2H, J=8.5 Hz) 2.78 (dt, 1H, J=5.3,18.0 Hz) 2.49 (m, 2H) 2.07 (s, 3H) 1.99–1.61 (m, 4H) ppm.

$^{13}$NMR ($D_2O$, 100 MHz) δ155.59 154.19 137.88 131.73 130.47 130.03 127.58 124.76 120.22 117.09 61.63 (d, J=118 Hz) 35.65 31.55 (d, J=8 Hz) 28.57 15.33 ppm.

MS (FAB, + ions) m/z 477 (M−K+2H), 515 (M+H), 553 (M+K).

Anal. Calcd for $C_{17}H_{18}K_3O_7PS$ 2.3 equiv $H_2O$: C, 36.72; H, 4.10; P, 5.57; S, 5.77. Found: C, 36.72; H, 3.91; P, 5.51; S, 5.54.

EXAMPLE 45

3-(3-Propylphenoxy)-α-phosphonobenzenebutanesulfonic acid, tripotassium salt

A. 3-Iodobenzenepropanoic acid, ethyl ester (1). (E)-3-(3-Nitrophenyl)-2-propenoic acid, ethyl ester A mixture of 3-nitrocinnamic acid (11.7 g, 60.6 mmol), concentrated sulfuric acid (0.16 mL, 3.03 mmol) and absolute ethanol (120 mL) was refluxed overnight. The reaction mixture was poured into ice water (400 mL). The mixture was extracted with ethyl ether (500 mL×2). The organic layer was washed with saturated sodium bicarbonate solution (100 mL×2), water (100 mL×2), brine (100 mL×2) and dried over magnesium sulfate. Evaporation gave title compound (12.0 g, 99%) as a colorless oil.

(2) 3-Aminobenzenepropanoic acid, ethyl ester

A Parr hydrogenation vessel was charged with Part (1) compound (12.0 g, 54.3 mmol), concentrated HCl (15 mL, 0.15 mmol), 10% palladium on carbon (750 mg) and absolute ethanol (75 mL). The slurry was purged with nitrogen and agitated under an initial pressure of 45 psi of hydrogen gas. After 16 h, the flask was evacuated and the contents filtered through Celite and evaporated. The residue was dissolved in water and adjusted to pH 9 with solid sodium carbonate. The resulting mixture was extracted with dichloromethane (250 mL×2). The combined extracts were evaporated to give the title compound (8.7 g, 86%) as an oil.

(3) 3-Iodobenzenepropanoic acid, ethyl ester

To a solution of Part (2) compound (7.2 g, 32 mmol) in diiodomethane (10.3 mL, 128 mmol) under argon at RT was added isoamyl nitrite (6.5 mL, 64 mmol) over 10 min. The brownish solution was stirred at RT for 40 min and then heated to 80° C. for 2 h. Ethyl ether (300 mL) was added to the reaction and the organic layer was washed with 1N hydrochloric acid (70 mL×2), water (70 mL), saturated sodium bicarbonate (70 mL×2), 10% sodium bisulfite solution (30 mL) and dried over magnesium sulfate. Purification was performed by flash chromatography on 800 g silica gel, loaded and eluted with 7% ethyl acetate in hexane. Pure fractions were combined and evaporated to give the title compound (4.1 g, 42%) as a colorless oil.

B. 3-Propylphenol (1) 3-(1-Propenyl)phenol

To a suspension of (ethyl)triphenylphosphonium bromide (35 g, 94.3 mmol) in THF (95 mL) was added potassium bis(trimethylsilyl)amide (180 ml, 0.5M in toluene, 90.2 mmol) dropwise. The reaction was stirred at 0° C. for 30 min, then a solution of 3-hydroxy-benzaldehyde (5 g, 41.0 mmol) in THF (5 mL) was added dropwise. After addition the reaction was stirred at 0° C. for 1 h. Ethyl ether (200 mL) was added to dilute the reaction. The organic layer was washed with water (50 mL×2), brine (50 mL×2) and dried over magnesium sulfate. Purification was performed by flash chromatography on 600 g silica gel, loaded and eluted with 10% ethyl acetate in hexane. Pure fractions were combined and evaporated to give the title compound (5.1 g, 93%) as a colorless oil.

(2) 3-Propylphenol

To a mixture of Part B (1) compound (3 g, 22.4 mmol) and 10% palladium on carbon (150 mg) in THF (25 mL) was connected a hydrogen balloon. Hydrogenation was maintained at RT overnight. The mixture of reaction was filtered through Celite. The resulting clear solution was evaporated to give the title compound (2.97 g, 100%) as a yellowish oil.

C. 3-(3-Propylphenoxy)benzenepropanoic acid, ethyl ester

To a suspension of sodium hydride (155 mg, 6.44 mmol) in pyridine (25 mL) was added a solution of Part B compound (1.5 g, 11.0 mmol) in pyridine (2.5 mL) at 0° C. under argon. Stirring was continued until the solution was clear (15 min). The reaction was warmed to RT, and a solution of Part A compound (2.5 g, 8.27 mmol) in pyridine (2.5 mL) was added to the reaction followed by copper bromide-dimethyl sulfide complex (2.27 g, 11.0 mmol). The reaction was refluxed for 24 h. The reaction was cooled to RT. The mixture of reaction was filtered and evaporated to dryness. Ethyl ether (250 mL) was added to the resulting residue, and the organic layer was washed with 1N HCl (2×50 mL), water (2×50 mL), saturated sodium bicarbonate solution (50 mL), brine (50 mL) and dried over $MgSO_4$. Purification was performed by flash chromatography on 200 g silica gel, loaded and eluted with 10% ethyl acetate in hexane. Pure fractions were combined and evaporated to give the title compound (1.68 g, 65%) as a colorless oil.

D. 3-(3-Propylphenoxy)benzenepropanol

Lithium aluminum hydride solution (5.29 mL, 1M in THF, 5.29 mmol) was added dropwise to a solution of Part C compound (1.65 g, 5.29 mmol) in THF (10 mL) at 0° C. under argon. Stirring was continued for 10 min. Ethyl acetate (5 mL) was added to destroy excess LAH. Ethyl ether (200 mL) was added and the organic layer was washed with 1N HCl solution (2×50 mL), $H_2O$ (50 mL), saturated sodium bicarbonate solution (50 mL), and brine (50 mL), then dried over $MgSO_4$. Evaporation gave the title compound (1.3 g, 91%) as a colorless oil.

E. 1-(3-Iodopropyl)-3-((3-propylphenoxy)benzene

A solution of iodine (1.35 g, 5.3 mmol) in THF (5 mL) was added to a mixture of Part D compound (1.3 g, 1.43 mmol), triphenylphosphine (1.39 g, 5.3 mmol) and imidazole (655 mg, 9.64 mmol) in THF (15 mL). The reaction mixture was stirred at RT for 10 min, then diluted with hexane (200 ml). The organic layer was washed with 10% sodium bisulfite (50 mL), saturated sodium bicarbonate (50 mL), brine (50 mL) and dried over $MgSO_4$. The solvent was evaporated to 100 mL volume, 6 g silica gel was added, and the mixture was evaporated to dryness. Flash chromatography was performed on 200 g silica gel, loaded and eluted with hexane. Pure fractions were combined and evaporated to give the title compound (1.6 g, 88%) as a colorless oil.

F. α-(Diethoxyphosphinyl)benzenebutanesulfonic acid, cyclohexyl ester

To a stirred suspension of sodium hydride (126 mg, 5.26 mmol) in DMF (5 mL) at 0° C. under argon, Example 1A Part B sulfonate (2.1 g, 6.58 mmol) in DMF (2 mL) was added dropwise over 15 min. The ice bath was removed and the reaction mixture was stirred am RT for 30 min. The reaction mixture was recooled to 0° C. and a solution of Part E compound (1.0 g, 2.63 mmol) in DMF (2 mL) was added dropwise over 15 min. The mixture was stirred at 0° C. for 2 h. The ice bath was removed and the reaction mixture was stirred at RT overnight. The mixture was diluted with ethyl ether (250 mL) and washed with $H_2O$ (50 ml), brine (50 mL) and dried over $MgSO_4$. Evaporation gave a crude oil. Purification was performed by flash chromatography on 150 g silica gel, loaded and eluted with 30% ethyl acetate in hexane. The pure fractions were combined and evaporated to provide the title compound (1.1 g, 74%) as a colorless oil.

G. 3-(3-Propylphenoxy)-α-phosphonobenzenebutanesulfonic acid, tripotassium salt

Ammonia gas was bubbled through a solution of Part F compound (800 mg, 2.19 mmol) in methanol (10 mL) until the solution was saturated. The sealed tube containing the reaction was heated at 70° C. overnight. The reaction mixture was cooled to RT, evaporated to dryness and azeotroped with toluene (2×20 mL). To a stirred solution of the resulting residue in dichloromethane (10 mL) at RT under argon was added bromotrimethylsilane (2.22 mL, 15.3 mmol). The mixture was stirred at RT for 20 h. The solvent was evaporated and the residue was pumped at high vacuum for 2 h. The residue was dissolved in 1M potassium hydroxide (8 mL, 8 mmol) and the reaction mixture was stirred for 2 h. The resulting clear solution was purified by chromatography on CHP20P gel (2.5×20 cm), loaded and eluted with water followed by a gradient created by the gradual addition of $CH_3CN$ to a reservoir of water. The combined pure fractions, were concentrated to about 5 mL volume then lyophilized to provide the title compound (500 mg, 42%) as a white solid.

IR (KBr) 2959, 2932, 1605, 1578, 1254, 1200, 1157, 1076, 966, 696 $cm^{-1}$ $^1$H NMR ($D_2O$, 400 MHz) δ7.21 (t, 2H, J=7.9 Hz) 6.99 (d, 1H, J=7.7 Hz) 6.93 (d, 1H, J=7.7 Hz) 6.86 (s, 1H) 6.81 (s, 1H) 6.77 (d, 1H, J=10.3 Hz) 6.74 (d, 1H, J=8.1) 2.77 (dt, 1H, J=6.0, 17.5 Hz) 2.51 (m, 2H) 2.44 (t, 2H, J=7.5 Hz) 1.99–1.63 (m, 4H) 1.45 (m, 2H) 0.74 (t, 3H, J=7.5 Hz,) ppm.

$^{13}$C NMR ($D_2O$, 100 MHz) δ156.99 156.95 145.96 145.80 130.28 129.97 124.05 124.01 119.22 118.97 116.17 116.02 61.50 (d, J=118 Hz) 37.16 35.40 31.22 28.55 23.98 13.02 ppm.

MS (FAB, + ions) m/z 505 (M–K+2H), 543 (M+H), 581 (M+K).

Anal. Calcd for $C_{19}H_{22}K_3O_7PS$ 1.7 equiv $H_2O$: C, 39.80; H, 4.47; P, 5.40; S, 5.59. Found: C, 39.85; H, 3.43; P, 5.25; S, 5.68.

EXAMPLE 46

6-Methyl-α-phosphonobenzeneoctanesulfonic acid, tripotassium salt

A. ε-Methylbenzeneheptanol

A solution of 1.43 g (7.00 mmol) of Example 36 Part G alcohol ((E)-5-methyl-7-phenyl-4-hepten-1-ol) in ethanol (100 mL) was stirred for 0.5 h with 0.5 g of 10% Pd/C and filtered through a pad of celite. The filtrate was treated with 6.30 g (100 mmol) of ammonium formate and 0.75 g of 10% Pd/C. The black suspension was stirred vigorously overnight and filtered through a pad of celite. The filtrate was concentrated leaving a colorless oil. The oil was diluted with ethyl acetate, washed with solutions of $NaHCO_3$ and brine, dried (MgSO4) and concentrated. The remainder was purified by flash chromatography performed on 150, g of silica gel eluted with 2:8 ethyl acetate/hexanes to provide 1.30 g (90%) of title alcohol as a colorless oil.

TLC Silica gel (3:7 ethyl acetate/hexanes) $R_f$=0.50.

IR (film) 3339, 3108, 3086, 3027, 2932, 2861, 1605, 1497, 1454, 1377, 1055, 746 $cm^{-1}$.

$^1$H NMR ($CDCl_3$, 400 MHz) δ7.25, 7.15 (two m, 5H) 3.55 (t, 2H, J=6.0 Hz) 2.60 (m, 2H) 2.20 (s, 1H, O—H) 1.70–1.05 (m, 9H) 0.90 (d, 3H, J=6.3 Hz) ppm.

Mass Spec (CI—$NH_3$, + ions) m/e 224 (M+$NH_4$).

B. (7-Iodo-3-methylheptyl)benzene

To a stirred solution of 1.00 g (4.85 mmol) of Part A alcohol, 1.52 g (5.82 mmol) of triphenylphosphine, and 0.49 g (7.27 mmol) of imidazole in 30 mL of THF under argon at room temperature was added a solution of 1.48 g (5.82 mmol) of iodine in 20 mL of THF, dropwise over 15 min. After the addition was complete, the reaction was diluted with 150 mL of ethyl acetate and washed with a saturated solution of $Na_2SO_3$. The organic phase was dried ($MgSO_4$) and concentrated. The residue was purified by flash chromatography on silica gel (100 g) eluted with 1 L of hexanes to give 1.30 g (85%) of title iodide as a colorless oil.

TLC Silica gel (hexane) $R_f$=0.40

IR (film) 3027, 2928, 2857, 1603, 1495, 1454, 1429, 1375, 1217, 1171, 1094, 1063, 1030 $cm^{-1}$.

$^1$H NMR ($CDCl_3$, 270 MHz) δ7.25, 7.15 (two m, 5H) 3.15 (t, 2H, J=7.0 Hz) 2.60 (m, 2H) 1.77 (quint, 2H, J=7.3 Hz) 1.60, 1.40, 1.15 (three m, 7H) 0.90 (d, 2H, J=6.0 Hz) ppm.

Mass Spec (CI—$NH_3$, + ions) m/e 334 (M+$NH_4$), 316 (M).

C. α-(Diethoxyphosphinyl)-5-methylbenzeneoctanesulfonic acid, cyclohexyl ester

To a suspension of 112 mg (4.69 mmol) of NaH in 7 mL of dry DMF at 0° C. under argon was added 1.80 g (5.73 mmol) of Example 1A Part B sulfonate over 15 min. to give a yellow solution. The reaction was allowed to warm to room temperature and stir for 0.5 h when 1.10 g (3.48 mmol) of Part B iodide was added in one portion. The reaction mixture was stirred for 18 h when it was quenched with saturated aq $NH_4Cl$ solution and diluted with ether. The organic fraction was washed with water, brine, dried ($Na_2SO_4$) and evaporated to provide a crude yellow oil. Flash chromatography was performed on 150 g of silica gel eluted with 4:6 ethyl acetate/hexane to provide 1.40 g (80%) of title compound as a pale yellow oil.

TLC Silica gel (4:6 ethyl acetate/hexane) $R_f$=0.28.

IR ($CH_2Cl_2$, film) 3027, 2934, 2863, 1454, 1354, 1260, 1173, 1053, 1024, 928, 866 $cm^{-1}$.

$^1$H NMR ($CDCl_3$, 270 MHz) δ7.25, 7.15 (two m, 5H) 4.86 (m, 1H) 4.22 (m, 4H) 3.45 (dt, 1H, J=19.5, 5.7 Hz) 2.60 (m 2H) 2.10 (m, 2H) 1.95 (m, 2H) 1.67, 1.40 (two m, 17H) 1.35 (t, 6H, J=7.0 Hz) 0.90 (d, 3H, J=7.0 Hz) ppm.

Mass Spec (CI—$NH_3$, + ions) m/e 520 (M+$NH_4$), 503 (M+H), 438 (M+$NH_4$-$C_6H_{10}$).

D. 6-Methyl-α-phosphonobenzeneoctanesulfonic acid, tripotassium salt

To a solution of 1.00 g (1.99 mmol) of Part C compound and 10 mL of methanol in a sealable tube at 0° C. was added 0.20 g (1.99 mmol) of KHCO$_3$. The tube was sealed and placed in an oil bath at 70° C. for 36 h, at which point the tube was opened and the volatiles removed under reduced pressure. The remainder was dissolved in toluene and evaporated two times (2×10 mL) leaving a colorless viscous oil. The oil was dissolved in 7 mL of dry methylene chloride and treated with 0.80 mL (6.00 mmol) of bromotrimethylsilane. The reaction was allowed to stir at RT for 18 h when the solvent was evaporated and the residue pumped (≈0.5 mm pressure) for 0.5 h. The remainder was dissolved by adding 4 mL (4 mmol) of 1M KOH solution and stirring vigorously for ten min. The soapy solution was purified by MPLC on a column of CHP20P gel (250 mL) eluting with water (150 mL) followed by a gradient created by the gradual addition of 500 mL of acetonitrile to a reservoir of 300 mL of water. Approximately 7 mL fractions were collected. Fractions #26 to 31 were pooled, the acetonitrile was removed under reduced pressure and the aqueous solution lyophilized to provide 0.90 g (94%) of title compound as a white lyophilate.

TLC Silica gel (6:3:1 n-propanol/conc. NH$_3$/water) $R_f$=0.17.

IR (KBr) 3427, 3065, 3027, 2926, 2859, 1636, 1497, 1377, 1209, 1148, 1084, 1044, 968, 698 cm$^{-1}$.

$^1$H NMR (D$_2$O, 400 MHz) δ7.25 (m, 4H) 7.10 (t, 1H, J=7.0 Hz) 2.77 (dt, 1H, J=17.0, 5.6 Hz) 2.50 (m, 2H) 1.77 (m, 2H) 1.55–1.00 (m, 9H) 0.75 (d, 3H, J=5.5 Hz) ppm.

Mass Spec (FAB, + ions) m/e 517 (M+K), 479 (M+H), 441 (M−K+2H).

Anal. Calc'd for C$_{15}$H$_{22}$O$_6$SPK$_3$+0.54 H$_2$O: C, 36.89; H, 4.76; P, 6.34; S, 6.56 Found: C, 36.59; H, 5.10; P, 6.01; S, 6.83.

EXAMPLE 47

3-(2-Butylphenoxy)-α-phosphonobenzenepropanesulfonic acid, tripotassium salt

A. Tetrahydro-2-phenoxy-2H-pyran

Phenol (10 g, 106 mmol) was dissolved in 3,4-dihydro-2H-pyran (29 mL, 318 mmol) and one drop concentrated HCl was added at RT. The reaction was stirred at RT overnight. Ethyl ether (500 mL) was added to dilute the reaction. The organic layer was washed with water (2×100 mL), saturated sodium bicarbonate (2×100 mL), brine (2×100 mL) and dried over MgSO$_4$. Evaporation gave title compound (17 g, 100%) as a colorless oil.

B. 2-(2-Butylphenoxy)tetrahydro-2H-pyran

To a solution of Part A compound (5 g, 31.3 mmol) in THF (69 mL) and ethyl ether (37 mL) was added dropwise a solution of 2.5M n-butyllithium in hexane (15.5 mL, 38.8 mmol) at 0° C. over 10 min. After an additional 30 min at 0° C., the reaction was allowed to warm to RT for 5 h. The reaction was recooled to 0° C. and iodobutane (7.55 mL, 66.4 mmol) was added. After 10 min at 0° C., the reaction was allowed to warm to RT and stirring was continued overnight. Ethyl ether (300 mL) was added to dilute the reaction, and the organic layer was washed with 1N HCl (2×50 mL), saturated sodium bicarbonate (2×50 mL), brine (2×50 mL) and dried over MgSO$_4$. Evaporation gave title compound (6.0 g, 89%) as a crude oil.

C. 2-Butylphenol

To a solution of Part B compound (6.0 g, 27.8 mmol) in dioxane (250 mL) was added 10% HCl solution (100 mL) at RT. The reaction was stirred at RT for 3.5 h. Ethyl ether (200 mL) was added to dilute the reaction. The organic layer was washed with saturated sodium bicarbonate solution (2×100 mL), brine (2×100 mL) and dried over MgSO$_4$. Purification was performed by flash chromatography on silica gel (500 g), loaded and eluted with 10% ethyl acetate in hexane. Pure fractions was combined and evaporated to give title compound (3.0 g, 70%) as a colorless oil.

D. 3-(2-Butylphenoxy)benzenepropanoic acid, ethyl ester

To a suspension of potassium hydride (572 mg, 14.3 mmol) [obtained by washing a 35 wt.% suspension of KH in mineral oil with hexane several times followed by evaporation of excess hexane] in pyridine (20 mL) was added a solution of Part C compound (2.2 g, 14.3 mmol) in pyridine (2.5 mL) at 0° C. under argon. Stirring was continued until the solution was clear (15 min). The reaction was warmed to RT, and a solution of Example 45 Part A iodide (2.9 g, 9.53 mmol) in pyridine (2.5 mL) was added to the reaction followed by copper bromidedimthyl sulfide complex (2.94 g, 14.3 mmol). The reaction was refluxed for 16 h. Ethyl ether (150 mL) was added to dilute the reaction. The resulting mixture was filtered through Celite, the filtrate was evaporated to dryness. Ethyl ether (200 mL) was added and the organic layer was washed with 1N HCl (2×50 mL), water (2×50 mL), 1N potassium hydroxide solution (2×50 mL), brine (50 mL) and dried over MgSO$_4$. Purification was performed by flash chromatography on 200 g silica gel, loaded and eluted with 7% ethyl acetate in hexane. Pure fractions were combined and evaporated to give title compound (1.2 g, 38%) as a colorless oil.

E. 3-(2-Butylphenoxy)benzenepropanol

Lithium aluminum hydride (LAH) solution (2.52 mL, 1M in THF, 2.52 mmol) was added dropwise to a solution of Part D compound (820 mg, 2.52 mmol) in THF (8 mL) at 0° C. under argon. Stirring was continued for 10 min. Methanol (5 mL) was added to destroy excess LAH. Ethyl ether (150 mL) was added and the organic layer was washed with 1N HCl solution (2×50 mL), H$_2$O (50 mL), saturated sodium bicarbonate solution (50 mL), and brine (50 mL), then dried over MgSO$_4$. Evaporation gave title compound (620 mg, 87%) as a colorless oil.

F. 1-(2-Butylphenoxy)-3-(3-iodopropyl)benzene

A solution of iodine (589 mg, 2.32 mmol) in THF (2 mL) was added to a mixture of Part E alcohol (600 mg, 2.11 mmol), triphenylphosphine (607 mg, 2.32 mmol) and imidazole (287 mg, 4.22 mmol) in THF (10 mL). The reaction mixture was stirred at RT for 10 min, then diluted with hexane (150 ml). The organic layer was washed with 10% sodium bisulfite (50 mL), saturated sodium bicarbonate (50 mL), brine (50 mL) and dried over MgSO$_4$. The solvent was evaporated to 100 ml volume, 5 g silica gel was added, and the mixture was evaporated to dryness. Flash chromatography was performed on 100 g silica gel, loaded and eluted with hexane. Pure fractions were combined and evaporated to give title compound (720 mg, 87%) as a colorless oil.

G. 3-(2-Butylphenoxy)-α-(diethoxyphosphinyl) benzenebutanesulfonic acid, cyclohexyl ester To a stirred suspension of sodium hydride (45.2 mg, 1.89 mmol) in DMF (2 mL) at 0° C. under argon, Example 1A Part B sulfonate (642 mg, 2.04 mmol) in DMF (2 mL) was added dropwise over 15 min. The ice bath was removed and the reaction mixture was stirred at RT for 30 min. The reaction mixture was recooled to 0° C. and a solution of Part F compound (620 mg, 1.57 mmol) in DMF (2 mL) was added dropwise over 15 min. The mixture was stirred at 0° C. for 2 h. The ice bath was removed and the reaction mixture was stirred at RT overnight. The mixture was diluted with ethyl ether (150 mL) and washed with H$_2$O (50 mL), brine (50 mL) and dried over MgSO$_4$. Evaporation gave a crude oil. Purification was performed by flash chromatography on 150 g silica gel, loaded and eluted with 25% ethyl acetate in hexane. The pure fractions were combined and evaporated to provide title compound (650 mg, 71%) as a colorless oil.

H. 3-(2-Butylphenoxy)-α-phosphonobenzenebutanesulfonic acid, tripotassium salt

Ammonia gas was bubbled through a solution of Part G compound (650 mg, 1.12 mmol) in methanol (10 mL) until the solution was saturated. The sealed tube was heated at 70° C. overnight. The reaction mixture was cooled to RT, evaporated to dryness and azeotroped with toluene (2×20 mL). To a stirred solution of the resulting residue in dichloromethane (10 mL) at RT under argon was added bromotrimethylsilane (1.10 mL, 7.84 mmol). The mixture was stirred at RT for 20 h. The solvent was evaporated and the residue was pumped at high vacuum for 2 h. The residue was dissolved in 1M potassium hydroxide (8 mL, 8 mmol) and the reaction mixture was stirred for 2 h. The solution was lyophilized to give a white solid. The crude product was purified by chromatography on CHP20P gel (2.5×20 cm), loaded and eluted with water and followed by a gradient created by the gradual addition of $CH_3CN$ to a reservoir of water. The combined pure fractions were concentrated to about 5 mL volume then lyophilized to provide title compound (350 mg, 56%) as a white solid.

IR (KBr) 2957, 2932, 1613, 1578, 1485, 1248, 1219, 1072, 964, 557 cm$^{-1}$.

$^1$H NMR (D$_2$O, 400 MHz) δ7.26 (d, 1H, J=6.4 Hz) 7.16 (t, 1H, J=8.4 Hz) 7.14 (t, 1H, J=8.5 Hz) 7.08 (t, 1H, J=6.8 Hz) 6.92 (d, 1H, J=7.3 Hz) 6.87 (d, 1H, J=8.2 Hz) 6.73 (s, 1H) 6.64 (d, 1H, J=8.2 Hz) 2.78 (dt, 1H, J=6.0, 17.6 Hz) 2.45 (2t, 4H, J=7.7 Hz) 1.99–1.61 (m, 4H) 1.40 (pentet, 2H, J=7.7 Hz) 1.13 (sextet, 2H, J=7.3 Hz) 0.69 (t, 3H, J=7.7 Hz) ppm.

$^{13}$C NMR (D$_2$O, 100 MHz) δ158.14 153.62 145.77 135.35 131.10 129.92 127.60 124.92 123.00 120.82 117.06 114.24 61.58 (d, J=120 Hz) 35.49 31.92 31.37 29.15 28.68 21.88 13.23 ppm.

MS (FAB, + ions) m/z 557 (M+H), 595 (M+K).

Anal. Calc'd for $C_{20}H_{24}K_3O_7PS$+1.8 equiv $H_2O$: C, 40.77; H, 4.72; P, 5.26; S, 5.44. Found: C, 40.84; H, 4.87; P, 5.10; S, 5.38.

EXAMPLE 48

(E,E)-1-Fluoro-6,10,14-trimethyl-1-phosphono-5,9,13-pentadecatriene-1-sulfonic acid, tripotassium salt A. (E,E)-1-(Diethoxyphosphinyl)-1-fluoro- 5,9,13-pentadecatriene-1-sulfonic acid, cyclohexyl ester To a suspension of 81 mg (2.0, mmol, 1.1 eq) of sodium hydride (as a 60% mineral oil dispersion) in 1 mL of THF at 0° C. was added a solution of 1.0 g (1.8 mmol, 1 eq) of Example 1A Part C compound in 3 mL of THF. The bubbling solution was warmed to RT and stirred for 30 min, then cooled to –78° C. A solution of 721 mg (2.3 mmol, 1.25 eq) of N-fluorobenzenesulfonimide in 2 mL of THF was added over 2 min and the reaction was stirred at –78° C. for 1 h, then warmed to RT and stirred for 2 h. The reaction was quenched by the addition of saturated ammonium chloride, then diluted with ether. The aqueous layer was extracted with ether and the combined organic solutions were stirred with 10% sodium thiosulfate for 30 min. The organic layer was washed with 10% KOH, dried and concentrated. Flash chromatography of the crude product on silica gel (75 g) eluding with 25% ethyl acetate in hexane afforded 674 mg (65%) of title compound as a clear colorless oil.

TLC Silica gel (10% ether in $CH_2Cl_2$) R$_f$=0.78.

B. (E,E)-1-Fluoro-6,10,14-trimethyl-1-phosphono- 5,9,13-pentadecatriene-1-sulfonic acid, tripotassium salt To a solution of 660 mg (1.2 mmol, 1 eq) of Part A compound in 10 mL of methanol at 0° C. in a thick-walled, sealable tube was bubbled ammonia until the solution was saturated. The reaction tube was then sealed and heated am 75° C. for 19 h. The reaction mixture was allowed to cool to RT and concentrated. The oily residue was coevaporated once with toluene, then with 10% hexamethyldisilazane in toluene (2×10 mL) to afford a clear oil.

To a solution of the oil in 5 mL of dry $CH_2Cl_2$ at RT was added 986 μL (4.7 mmol, 4 eq) of hexamethyldisilazane followed by 771 μL (5.8 mmol, 5 eq) of bromotrimethylsilane (TMSBr) dropwise over 1 min. After 22 h at RT, the reaction was concentrated and the resulting semisolid was placed on high vacuum (0.25 mm Hg) for 1 h. The residue was dissolved by adding 4.7 mL (4 eq) of 1M potassium hydroxide followed by 5 mL of water, frozen and lyophilized to afford an off-white lyophilate. The lyophilate was purified by MPLC on a column of CHP20P (2.5 cm×25 cm) eluting initially with 150 mL of water followed by a gradient formed by gradual addition of 400 mL of 50% acetonitrile in water to a reservoir containing 400 mL of water. Fractions containing pure product were pooled, concentrated, filtered, frozen and lyophilized. The lyophilate was dissolved in a minimum amount of water and concentrated. The resulting semisolid residue was triturated with acetone to afford, after high vacuum (0.025 mm Hg) removal of acetone remnants, 236 mg (60%) of a white solid.

TLC silica gel (5:4:1 n-Propanol:ammonium hydroxide-:water): R$_f$=0.43.

IR (KBr): 3426(br), 2969, 2926, 2857, 1663, 1451, 1213, 1101, 982 cm$^{-1}$.

$^1$H NMR (D$_2$O, 300 MHz): δ5.14 (t, J=7 Hz, 1H) 5.06 (t, J=7 Hz,1H) 5.04 (t, J=7 Hz, 1H) 2.07 (m, 2H) 1.90 (m, 10H) 1.54 (s, 3H) 1.50 (m, 2H) 1.49 (s, 3H) 1.46 (s, 6H) ppm.

$^{13}$C NMR (D$_2$O, 75.6 MHz): δ136.4 135.9 132.6 125.0 124.7 124.6 107.9 (dd, J$_{CF}$=211 Hz, J$_{cp}$=140 Hz) 39.4 39.3 34.0 (d, J$_{CF}$=211 Hz) 28.4 26.4 26.2 25.2 23.7 (t, J$_{CP}$=J$_{CF}$=3 Hz) 17.3 15.6 15.5 ppm.

$^{19}$F NMR (D$_2$O, 282.8 MHz): δ165.1 (ddd, J$_{PF}$=66 Hz, J$_{HF}$=23, 20 Hz) ppm.

$^{31}$P NMR (D$_2$O, 121.7 MHz): δ8.5 (d, J$_{FP}$=66 Hz) ppm.

Mass Spec (FAB, + ions): m/z 541 (M+H), 503 (M+2H–K).

Anal. Calcd for $C_{18}H_{29}O_6FPSK_3$+1.13 H$_2$O: C, 38.53; H, 5.62; S, 5.71; P, 5.52 Found: C, 38.53; H, 5.87; S, 5.40; P, 5.38.

EXAMPLE 49

(E,E)-1-[Bis[1-(1-Oxopropoxy)ethoxy]phosphinyl]-6,10, 14-trimethyl-5,9,13-pentadecatriene-1-sulfonic acid, monopotassium salt A. Propanoic acid, 1-chloroethyl ester To freshly fused zinc chloride (50 mg) was added $CH_2Cl_2$ (20 mL) followed by propionyl chloride (10.0 g, 108 mmol). The mixture was cooled to 10° C. and acetaldehyde (6.0 mL, 108 mmol) was added over 5 min. The brown reaction was allowed to warm to RT, then stirred at that temperature overnight. The reaction was diluted with $CH_2Cl_2$ (50 mL) and washed with 20% aqueous sodium acetate (20 mL). The organic layer was dried over MgSO$_4$ and evaporated to give a brown oil, which was distilled under high vacuum (0.5 torr) to give title compound (1.48 g, 10%) in the form of a clear, colorless liquid. bp 28°–31° C.

B. (E,E)-1-[Bis[1-(1-Oxopropoxy)ethoxy]phosphinyl]-6,10,14-trimethyl-5,9,13-pentadecatriene- 1-sulfonic acid, monopotassium salt A solution of Example 1B tripotassium salt (500 mg, 0.953 mmol) in water (3 mL) was added dropwise slowly via syringe pump at a rate of 0.24 mL/min to a solution of silver nitrate (586 mg, 3.44 mmol) in water (2 mL) at RT under argon. A white precipitate began to form immediately upon addition. The reaction was stirred at RT for 10 min, then filtered. The solid obtained was washed with water (2×2 mL) and diethyl ether (2 mL), then pumped under high vacuum for 7 h to give 567 mg of a silver salt in the form of a white solid.

To a suspension of the silver salt prepared above in $CH_2Cl_2$ (2 mL) under argon in the dark at RT was added 2,4,6-collidine (110 μL, 0.836 mmol) followed by a solution of Part A compound (568 mg, 4.18 mmol) in $CH_2Cl_2$ (1 mL). The reaction was stirred at RT for 6 h, filtered through Celite with the aid of $CH_2Cl_2$, then concentrated in vacuo to give an opaque oil. The crude material was dissolved in EtOAc (10 mL) and washed with 1N HCl (5×2 mL), saturated $KHCO_3$ (2×2 mL), and saturated KCl (2 mL), then dried over anhydrous KCl. Evaporation gave a pale yellow oil, which was chromatographed (2.5×20 cm CHP20P gel, 10 mL fractions, water elution followed by a gradient of acetonitrile in water). The product-containing fractions were combined and evaporated to give an opaque gum, which was dissolved in $CH_2Cl_2$ and dried over anhydrous KCl. Evaporation gave title compound (369 mg, 68%) as a colorless oil as a mixture of four diastereomers.

TLC (silica gel) (15:85 MeOH/$CH_2Cl_2$): $R_f$=0.42.

IR (neat) 2940, 2924, 1751, 1256, 1209, 1107, 1084, 1047, 978, 949 $cm^{-1}$.

$^1$H NMR (DMSO, 400 MHz) δ6.53 (m, 2H) 5.09 (m, 3H) 3.07–2.85 (m, 1H) 2.32 (m, 4H) 2.09–1.65 (m, 12H) 1.63 (s, 3H) 1.62–1.43 (m, 2H) 1.56 (s, 9H) 1.42 (m, 6H) 1.03 (m, 6H) ppm.

Mass Spec (FAB, + ions) m/z 685 (M+K).

Anal. Calcd for $C_{28}H_{48}KO_{10}PS$: C, 51.99; H, 7.48; P, 4.79; S, 4.96. Found: C, 51.69; H, 7.49; P, 4.44; S, 5.92.

The following additional examples may be prepared employing procedures see out hereinbefore including in the working Examples.

50. (E)-6-methyl-10-phenyl-1-phosphono-5-decene-1-sulfonic acid, tripotassium salt;

Mas Spec (FAB, + ions) m/z 519 (M+H), 481 (M+2H–K).

Anal. Calcd for $C_{18}H_{26}O_6SPK_3$+1.3 $H_2O$: C, 39.82; H, 5.33; P, 5.70; S, 5.90 Found: C, 39.82; H, 5.63; P, 5.49; S, 5.65.

51. (E)-9-cyclopentyl-6-methyl-1-phosphono-5-nonene-1-sulfonic acid, tripotassium salt;

Mass Spec (Ion Spray, + ions) m/z 445 (M–K+2H), 483 (M+H).

Anal. Calcd for $C_{15}H_{26}O_6SPK_3$+0.70 $H_2O$: C, 36.39; H, 5.57; P, 6.26; S, 6.48. Found: C, 36.60; H, 5.98; P, 5.92; S, 6.23.

52. α-phosphono-4α-methyl[1,1'-biphenyl]-4-butanesulfonic acid, tripotassium salt;

Mass Spec (electrospray, $CH_3CN$, $NH_3$, + ions) m/z 508 (M–3K+4H+3$CH_3CN$), 467 (M–3K+4H+2$CH_3CN$), 461 (M–K+2H), 443 (M–3K+3H+$NH_4$+$CH_3CN$), 426 (M–3K+4H+$CH_3CN$), 423 (M+H–2K), 402 (M–3K+3H+$NH_4$), 385 (M–3K+4H).

Anal. Calcd for $C_{17}H_{18}K_3O_6PS$+1.4 $H_2O$: C, 38.98; H, 4.00; P, 5.91; S, 6.12 Found: C, 39.32; H, 4.03; P, 6.12; S, 5.73.

53. α-phosphono-4-(3-propylphenoxy)benzene-butanesulfonic acid, tripotassium salt;

Mass Spec (FAB, + ions) m/z 429 (M+4H–3K), 467 (M+3H–2K), 505 (M+2H–K), 543 (M+H).

Anal. Calcd for $C_{19}H_{22}K_3O_7PS$+0.5 $H_2O$: C, 41.36; H, 4.20; P, 5.61; S, 5.81 Found: C, 41.17; H, 3.96; P, 5.40; S, 5.98.

54. 4'-ethyl-α-phosphono[1,1'-biphenyl]-4-butanesulfonic acid, tripotassium salt;

Mass Spec (FAB, + ions) m/z 551 (M+K), 513 (M+H), 475 (M–K+2H).

Anal. Calcd for $C_{18}H_{20}K_3O_6PS$+1.2 $H_2O$: C, 40.48; H, 4.22; P, 5.80; S, 6.00 Found: C, 40.17; H, 4.32; P, 5.97; S, 6.45.

55. 4'-chloro-α-phosphono[1,1'-biphenyl]-4-butanesulfonic acid, tripotassium salt;

Mass Spec (FAB, + ions) m/z 557/9 (M+K), 519/21 (M+H), 481/3 (M–K+2H).

Anal. Calcd for $C_{16}H_{15}ClK_3O_6PS$+0.75 $H_2O$: C, 36.10; H, 3.12; Cl, 6.66; P, 5.82; S, 6.02 Found: C, 35.88; H, 3.02; Cl, 6.88; P, 5.62; S, 6.42.

56. 14-methyl-1-phosphono-13-pentadecene-1-sulfonic acid, tripotassium salt;

Mass Spec (FAB, + ions) m/z 537 (M+K), 499 (M+H), 461 (M–K+2H).

Anal. Calcd for $C_{16}H_{30}O_6SPK_3$+2.3 $H_2O$: C, 35.63; H, 6.45; P, 5.74; S, 5.94 Found: C, 35.63; H, 6.27; P, 5.71; S, 6.14.

57. 4-(phenylthio)-α-phosphonobenzenebutane-sulfonic acid, tripotassium salt;

Mass Spec (FAB, + ions) m/z 441 (M+3H–2K), 479 (M+2H–K), 517 (M+H).

Anal. Calcd for $C_{16}H_{16}K_3O_6PS_2$+1.6 $H_2O$: C, 35.23; H, 3.55; P, 5.68; S, 11.76 Found: C, 34.89; H, 3.79; P, 5.46; S, 12.19.

58. α-phosphono-4-propylbenzeneoctanesulfonic acid, tripotassium salt;

Mass Spec (electrospray, + ions) m/z 427 [(M+3H–3K)+$NH_3$+$NH_4$], 448 [(M+2H–2K)+$NH_4$], 469 (M+2H–K).

Anal. Calcd for $C_{17}H_{26}K_3O_6PS$+1.0 $H_2O$: C, 38.91; H, 5.38; P, 5.90; S, 6.11 Found: C, 39.22; H, 5.27; P, 5.50; S, 6.14.

59. α-phosphono-3-(4-propylphenoxy)benzene-butanesulfonic acid, tripotassium salt;

Mass Spec (FAB, + ions) m/z 505 (M–K+2H), 543 (M+H), 581 (M+K).

Anal. Calcd for $C_{19}H_{22}K_3O_7PS$+1.4 $H_2O$: C, 40.18; H, 4.40; P, 5.45; S, 5.65 Found: C, 40.16; H, 4.72; P, 5.42; S, 6.06.

60. 4-[3-(2-methyl-1-propenyl)phenoxy]-α-phosphonobenzenebutanesulfonic acid, tripotassium salt;

Mass Spec (FAB, + ions) m/z 517 (M–K+2H), 555 (M+H), 593 (M+K).

Anal. Calcd for $C_{20}H_{22}K_3O_7PS$+1.0 $H_2O$: C, 41.94; H, 4.22; P, 5.42; S, 5.60 Found: C, 42.01; H, 4.10; P, 5.53; S, 5.57.

61. (10S)-10,14-dimethyl-1-phosphono-13-pentadecene-1-sulfonic acid, dipotassium salt;

Mass Spec (FAB, + ions) m/z 513 (M+H), 457 (M+2H–K), 437 (M+3H–2K).

Anal. Calcd for $C_{17}H_{33}O_6PSK_2$+2.0 $H_2O$: C, 39.98; H, 7.30; P, 6.06; S, 6.28 Found: C, 39.92; H, 6.99; P, 5.89; S, 6.27.

62. (E,E)-1-phosphono-3-[(3,7,11-trimethyl-2,6,10-dodecatrienyl)oxy]-1-propanesulfonic acid, tripotassium salt;

Mass Spec (FAB), + ions) m/z 577 (M+K), 539 (M+H).

Anal. Calcd for $C_{18}H_{30}O_7PSK_3$+1.25 $H_2O$: C, 38.51; H, 5.84; P, 5.52; S, 5.94 Found: C, 38.51; H. 5.95; P, 5.18; S, 5.52.

63. (E,E)-6,10,14-trimethyl-1-phosphono-5,9,13-pentadecatriene-1-sulfonic acid, 4-(methylthio)phenyl ester, dipotassium salt:

Mass Spec (FAB, + ions) m/z 645 (M+K), 607 (M+H).

Anal. Calcd for $C_{25}H_{37}O_6PS_2K_2$+4.6 $H_2O$: C, 43.53; H, 6.75; P, 4.49; S, 9.30 Found: C, 43.16; H, 6.25; P, 4.26; S, 9.53.

64.  4-(3-methylphenoxy)-α-phosphonobenzenebutanesulfonic acid, tripotassium salt;

Mass Spec (FAB, + ions) m/z 515 (M+H), 553 (M+K).

Anal. Calcd for $C_{17}H_{18}K_3O_7PS$+2.1 $H_2O$: C, 36.96; H, 4.05: P, 5.61: S, 5.80 Found: C, 36.94; H, 4.40; P, 5.49: S, 5.94.

65. (E,E)-1-[bis[[(cyclohexylacetyl)oxy]methoxy]phosphinyl]-6,10,14-trimethyl-5,9,13-pentadecatriene- 1-sulfonic acid, monopotassium salt;

Mass Spec (FAB, + ions) m/z 793 (M+K).

Anal. Calcd for $C_{36}H_{60}KO_{10}PS$: C, 57.27; H, 8.01; P, 4.10; S, 4.25 Found: C, 57.06; H, 8.03; P, 4.01; s, 4.56.

66. (E,E)-1-[bis[(benzoyloxy)methoxy]phosphinyl]-6,10,14-trimethyl-5,9,13-pentadecatriene-1-sulfonic acid, monopotassium salt;

Mass. Spec (FAB, + ions) m/z 753 (M+K).

Anal. Calcd for $C_{34}H_{44}PSO_{10}K$+0.53 $H_2O$: C, 56.37; H, 6.27; P, 4.28; S, 4.43 Found: C, 56.37; H, 6.32; P, 4.37; S, 4.32.

67.  4-(benzoylphenylamino)-α-phosphonobenzene-butanesulfonic acid, tripotassium salt;

Mass Spec (FAB, + ions) m/z 642 (M+K), 604 (M+H), 566 (M−K+2H).

Anal. Calcd for $C_{23}H_{21}NO_7SPK_3$+4.0 $H_2O$: C, 40.88; H, 4.33; N, 2.07; P, 4.58; S, 4.74 Found: C, 40.71; H, 4.28; N, 2.12; P, 4.76; S, 4.87.

68.  3-(benzoylphenylamino)-α-phosphonobenzene-butanesulfonic acid, tripotassium salt;

Mass Spec (FAB, + ions) m/z 642 (M+K), 604 (M+H), 566 (M−K+2H).

Anal. Calcd for $C_{23}H_{21}NO_7SPK_3$+2.50 $H_2O$: C, 42.58; H, 4.04; N, 2.16; P, 4.77; S, 4.94 Found: C, 42.73; H, 4.24; N, 2.47; P, 4.56; S, 4.88.

69.  4-(phenylamino)-α-phosphonobenzenebutanesulfonic acid, tripotassium salt;

Mass Spec (FAB, + ions) m/z 538 (M+K), 500 (M+H), 462 (M−K+2H).

Anal. Calcd for $C_{16}H_{17}NO_6SPK_3$+2.0 $H_2O$: C, 35.87; H, 3.95; N, 2.61; P, 5.78 Found: C, 36.08; H, 3.96; N, 2.47; P, 5.61.

70.  3-(phenylamino)-α-phosphonobenzenebunane-sulfonic acid, tripotassium salt;

Mass spec (FAB, + ions) m/z 538 (M+K), 500 (M+H), 462 (M−K+2H).

Anal. Calcd for $C_{16}H_{17}NO_6SPK_3$+1.0 $H_2O$: C, 37.12; H, 3.70; N, 2.71; P, 5.98; S, 6.19 Found: C, 36.97; H, 3.99; N, 2.47; P, 5.98; S, 6.14

71.  4-(phenylsulfinyl)-α-phosphonobenzenebutanesulfonic acid, tripotassium salt;

Mass Spec (FAB, + ions) m/z 457 (M−2K+3H), 495 (M−K+2H), 533 (M+H).

Anal. Calcd for $C_{16}H_{16}K_3O_7PS_2$+1.2 $H_2O$: C, 34.67; H, 3.35; P, 5.59; S, 11.57 Found: C, 34.68; H, 3.23; P, 5.27; S, 11.41

72.  4-(2-methylphenoxy)-α-phosphonobenzenebutanesulfonic acid, tripotassium salt;

Mass Spec (FAB, + ions) m/z 477 (M−K+2H), 515 (M+H), 553 (M+K).

Anal. Calcd for $C_{17}H_{18}K_3O_7PS$+2.3 $H_2O$: C, 36.72; H, 4.10; P, 5.57; S, 5.77 Found: C, 36.72; H, 3.91; P, 5.51; S, 5.54

73. 4-phenoxy-α-phosphonobenzenepentanesulfonic acid, tripotassium salt;

Mass Spec (FAB, + ions) m/z 476 (M−K+2H), 515 (M+H), 553 (M+K)

Anal. Calcd for $C_{17}H_{18}K_3O_7PS$+1.3 $H_2O$: C, 37.95; H, 3.86; P, 5.76; S, 5.96 Found: C, 38.15; H, 4.26; P, 5.63; S, 6.48

74.  4-(2-Fluorophenoxy)-α-phosphonobenzenebutanesulfonic acid, tripotassium salt;

Mass Spec (FAB, + ions) m/z 481 (M−K+2H), 519 (M+H) 557 (M+K).

Anal. Calcd for $C_{16}H_{15}FK_3O_7PS$+2.6 $H_2O$: C, 33.99; H, 3.60; P, 5.48; S, 5.67 Found: C, 34.14; H, 3.34; P, 5.53; S, 5.27

75.  4-(2-methoxyphenoxy)-α-phosphonobenzenebutanesulfonic acid, tripotassium salt;

Mass Spec (FAB, + ions) m/z 493 (M−K+2H), 531 (M+H), 569 (M+K).

Anal. Calcd for $C_{17}H_{18}K_3O_8PS$+2.6 $H_2O$: C, 35.36; H, 4.05; P, 5.36; S, 5.55 Found: C, 35.37; H, 3.81; P, 5.46; S, 5.47

76. (E,E)-1-[bis[[(1-oxoheptyl)oxy]methoxy]-phosphinyl]-6,10,14-trimethyl-5,9,13-pentadecatriene-1-sulfonic acid, monopotassium salt;

Mass Spec (FAB, + ions) m/z 769 (M+K), 731 (M+H).

Anal. Calcd for $C_{34}H_{60}PSO_{10}K$+0.06 $H_2O$: C, 55.79; H, 8.28; P, 4.23; S, 4.38 Found: C, 55.79; H, 8.38; P, 4.31; S, 4.00

77.  4-[(4-bromophenyl)thio]-α-phosphonobenzenebutanesulfonic acid, tripotassium salt;

Mass Spec HRMS (FAB, + ions) calcd for $C_{16}H_{17}{}^{79}BrK_2O_6PS_2$: 556.8662 (M−K+2H) Found: 556.8691

Anal. Calcd for $C_{16}H_{15}BrK_3O_6PS_2$+1.8 $H_2O$: C, 30.60; H, 2.99; P, 4.93; S, 10.21 Found: C, 30.89; H, 3.06; P, 4.54; S, 10.16

78.  4-(phenylsulfonyl)-α-phosphonobenzenebutanesulfonic acid, tripotassium salt;

Mass Spec (FAB, + ions) m/z 473 (M−2K+3H), 511 (M−K+2H), 549 (M+H), 587 (M+K).

Anal. Calcd for $C_{16}H_{16}K_3O_8PS_2$+2.6 $H_2O$: C, 32.27; H, 3.59; P, 5.20; S, 10.77 Found: C, 32.63; H, 3.54; P, 4,80; S, 9.55

79.  4-phenoxy-α-phosphonobenzenepropanesulfonic acid, tripotassium salt;

Mass Spec (FAB, + ions) m/z 449 (M−K+2H), 487 (M+H), 525 (M+K).

Anal. Calcd for $C_{15}H_{14}K_3O_7PS$+1.3 $H_2O$: C, 35.34; H, 3.28; P, 6.08; S, 6.29 Found: C, 35.34; H, 3.49; P, 5.92; S, 6.48

80.  6-methyl-9-phenyl-α-phosphono-5-nonene- 1-sulfonic acid, tripotassium salt;

Mass Spec (FAB, + ions) m/z 529 (M+K), 491 (M+H).

Anal. Calcd for $C_{16}H_{22}PSO_6K_3$+3.6 $H_2O$: C, 34,62; H, 5.29; P, 5.58; S, 5.78 Found: C, 34.29; H, 5.01; P, 5.60; S, 5.74

81. (E,E)-1-[bis[(2-methyl-1-oxopropoxy)methoxy]phosphinyl]- 6,10,14-trimethyl-5,9,13-pentadecatriene-1-sulfonic acid, monopotassium salt;

Mass Spec (FAB, + ions) m/z 685 (M+K).

Anal. Calcd for $C_{28}H_{48}PSO_{10}K$+1.0 $H_2O$: C, 50.54; H, 7.58; P, 4.51; S, 4.82 Found: C, 50.54; H, 7.47; P, 4.51; S, 4.85

82.  4-(2-butylphenoxy)-α-phosphonobenzenebutanesulfonic acid, tripotassium salt;

Mass Spec (FAB, + ions) m/z 519(M−K+2H), 557 (M+H), 595 (M+K).

Anal. Calcd for $C_{20}H_{24}K_3O_7PS$+1.3 $H_2O$: C, 41.36; H, 4.63; P, 5.33; S, 5.52 Found: C, 41.36; H, 4.98; P, 5.04; S, 5.54

83. (E)-6-methyl-7-(4-methylphenoxy)-1-phosphono-5-heptene-1-sulfonic acid, tripotassium salt;

Mass Spec (FAB, + ions) m/z 531 (M+K), 493 (M+H), 455 (M−K+2H).

Anal. Calcd for $C_{15}H_{20}O_7PSK_3+2.1\ H_2O$: C, 33.96; H, 4.60; P, 5.84; S, 6.04 Found: C, 34.34; H, 5.00; P, 6.11; S, 5.81

84. (E)-6-methyl-8-(4-methylphenyl)-1-phosphono-5-octenyl-1-sulfonic acid, tripotassium salt;

Mass Spec (FAB, + ions) m/z 529 (M+K), 491 (M+H), 453 (M−K+2H).

Anal. Calcd for $C_{16}H_{22}O_6PSK_3+1.74\ H_2O$: C, 36.82; H, 4.92; P, 5.93; S, 6.14 Found: C, 36.82; H, 5.35; P, 5.98; S, 6.11

85. (E)-6-methyl-7-(3-methylphenoxy)-1-phosphono-5-heptene-1-sulfonic acid, tripotassium salt;

Mass Spec (FAB, + ions) 531 (M+K), 493 (M+H), 455 (M−K+2H).

Anal. Calcd for $C_{15}H_{20}O_7PSK_3+0.85\ H_2O$: C, 35.47; H, 4.30; P, 6.10; S, 6.31 Found: C, 35.91; H, 4.73; P, 6.34; S, 6.42

86. 4-(1-naphthalenyl)-α-phosphonobenzenebutanesulfonic acid, tripotassium salt;

Mass Spec (FAB, + ions) m/z 535 (M+H), 497 (M−K+2H), 459 (M−2K+3H).

Anal. Calcd for $C_{20}H_{18}K_3O_6PS+2.24\ H_2O$: C, 41.77; H, 3.94; S, 5.58; P, 5.39 Found: C, 42.17; H, 4.38; S, 5.24; P, 5.50

87. 4-(2,6-dimethylphenoxy)-α-phosphonobenzenebutanesulfonic acid, tripotassium salt; Mass Spec (FAB, + ions) m/z 491 (M−K+2H), 529 (M+H), 567 (M+K).

Anal. Calcd for $C_{18}H_{20}K_3O_7PS+2.9\ H_2O$: C, 37.17; H, 4.48; P, 5.32; S, 5.51 Found: C, 37.17; H, 4.44; P, 5.12; S, 5.91

88. 3-(3-methylphenoxy)-α-phosphonobenzenebutanesulfonic acid, tripotassium salt;

Mass Spec (FAB, + ions) m/z 553 (M+K), 515 (M+H).

Anal. Calcd for $C_{17}H_{18}K_3O_7PS+1.5\ H_2O$: C, 37.69; H, 3.91: P, 5.72; S, 5.92 Found: C, 37.74; H, 3.92; P, 5.78; S, 6.24

89. (E)-6,10-dimethyl-1-phosphono-5,9-pentadecadiene-1-sulfonic acid, tripotassium salt;

Mass Spec (FAB, + ions) m/z 549 (M+K), 511 (M+H), 473 (M+2H−K).

Anal. Calcd for $C_{17}H_{30}O_6PSK_3+0.35\ H_2O$: C, 39.49; H, 5.98; P, 5.99; S, 6.20 Found: C, 39.51; H, 6.16; P, 5.17; S, 5.98

90. 4-(2-benzofuranyl)-α-phosphonobenzenebutanesulfonic acid, tripotassium salt;

Mass Spec m/z (FAB, + ions) 525 (M+H), 487 (M−K+2H), 449 (M−2K+3H).

Anal. Calcd for $C_{18}H_{16}K_3PO_7PS+4.5\ H_2O$: C, 35.66; H, 4.17; P, 5.11; S, 5.29 Found: C, 35.66; H, 4.18; P, 4.83; S, 4.95

91. α-phosphono-4'-propyl[1,1'-biphenyl]-4-pentanesulfonic acid, tripotassium salt;

Mass Spec (FAB, + ions) m/z 541 (M+H), 503 (M+2H−K), 465 (M+3H−2K).

Anal. Calcd for $C_{20}H_{24}O_6PSK_3+1.26\ H_2O$: C, 42.64; H, 4.47; P, 5.50; S, 5.69 Found: C, 42.64; H, 5.11; P, 5.20; S, 5.90

92. 3-(2-methylphenoxy)-α-phosphonobenzenebutanesulfonic acid, tripotassium salt;

Mass Spec (FAB, + ions) m/z 515 (M+H), 553 (M+K)

Anal. Calcd for $C_{17}H_{18}K_3O_7PS+1.7\ H_2O$: C, 37.45; H, 3.96; P, 5.68; S, 5.88 Found: C, 37.49; H, 4.07; P, 5.66; S, 6.00

93. α-[bis[(2,2-dimethyl-1-oxopropoxy)methoxy]phosphinyl]-3-phenoxybenzenebutanesulfonic acid, monopotassium salt;

Mass Spec (FAB, + ions) m/z 653 (M+H), 691 (M+K).

Anal. Calcd for $C_{28}H_{38}KO_{10}PS$: C, 51.52; H, 5.87; P, 4.75; S, 4.91 Found: C, 51.33; H, 5.62; P, 4.54; S, 4.75

94. 11-Phenyl-1-phosphono-1-undecanesulfonic acid, tripotassium salt;

Mass Spec (FAB, + ions) m/z 545 (M+K), 507 (M+H), 469 (M+2H−K).

Anal. Calcd for $C_{17}H_{26}K_3O_6PS+0.5\ H_2O$: C, 39.59; H, 5.28; P, 6.01; S, 6.22 Found: C, 39.61; H, 5.44; P, 5.77; S, 6.46

95. α-phosphonobenzeneoctanesulfonic acid, tripotassium salt;

Mass Spec (FAB, + ions) m/z 503 (M+K), 465 (M+H).

Anal. Calcd for $C_{14}H_{20}K_3O_6PS+2.2\ H_2O$: C, 33.34; H, 4.88; P, 6.14; S, 6.36 Found: C, 33.34; H, 4.94; P, 5.99; S, 6.17

96. 1-phosphono-7-(4-pentylphenoxy)-1-heptanesulfonic acid, tripotassium salt;

Mass Spec (ion spray, + ions) m/z 464 (M+4H−3K+CH$_3$CN), 461 (M+3H−2K), 423 (M+4H−3K).

Anal. Calcd for $C_{18}H_{28}K_3O_7PS+1.34\ H_2O$: C, 38.55; H, 5.51; P, 5.52; S, 5.72 Found: C, 38.55; H, 5.66; P, 5.11; S, 6.01

97. α-phosphono-3'-propyl[1,1'-biphenyl]-4-butanesulfonic acid, tripotassium salt;

Mass Spec (FAB, +ions) m/z 565 (M+K), 527 (M+H), 89 (M−K+2H), 451 (M−2K+3H)

Anal. Calcd for $C_{19}H_{22}O_6PSK_3+1.0\ H_2O$: C, 41.84; H, 4.45; S, 5.88; P, 5.68 Found: C, 41.84; H, 4.74; S, 6.14; P, 5.30

98. 4-(4-methylphenoxy)-α-phosphonobenzenebutanesulfonic acid, tripotassium salt;

Mass Spec (FAB, + ions) m/z 553 (M+K), 515 (M+H), 477 (M+2H−K)

Anal. Calcd for $C_{17}H_{18}K_3O_7PS+1.7\ H_2O$: C, 37.45; H, 3.96; P, 5.68; S, 5.88 Found: C, 37.38; H, 3.79; P, 5.38; S, 6.24

99. (E,E)-4,8,12-trimethyl-1-phosphono-3,7,11-tridecatriene-1-sulfonic acid, tripotassium salt;

Mass Spec (FAB, + ions) m/z 533 (M+K), 495 (M+H), 457 (M+2H−K)

Anal. Calcd for $C_{16}H_{26}PSO_6K_3+1.00\ H_2O$: C, 37.49; H, 5.50; P, 6.04; S, 6.25 Found: C, 37.40; H, 5.54; P, 6.08; S, 6.69

100. (E)-6-methyl-7-phenoxy-1-phosphono-5-heptenyl-1-sulfonic acid, tripotassium salt;

Mass Spec (FAB, + ions) m/z 517 (M+K), 479 (M+H), 441 (M−K+2H)

Anal. Calcd for $C_{14}H_{18}O_7PSK_3+2.0\ H_2O$: C, 32.67; H, 4.31; P, 6.02; S, 6.23 Found: C, 32.28; H, 4.25; P, 5.78; S, 6.11

101. (E)-6-methyl-7-(4-propylphenoxy)-1-phosphono-5-heptene-1-sulfonic acid, tripotassium salt;

Mass Spec (FAB, + ions) m/z 521 (M+H), 483 (M−K+2H), 445 (M−2K+3H)

Anal. Calcd for $C_{17}H_{25}O_7PSK_2+1.85\ H_2O$: C, 39.57; H, 5.61; P, 6.00; S, 6.21 Found: C, 39.18; H, 5.23; P, 6.14; S, 6.41

102. (E)-6-methyl-8-(3-methylphenyl)-1-phosphono-5-octenyl-1-sulfonic acid, tripotassium salt;

Mass Spec (FAB, + ions) m/z 529 (M+K), 491 (M+H), 453 (M−K+2H)

Anal. Calcd for $C_{16}H_{22}O_6PSK_3+1.03\ H_2O$: C, 37.74; H, 4.76; P, 6.08; S, 6.30 Found: C, 37.99; H, 5.21; P, 5.90; S, 6.60

103. (E)-6-methyl-1-phosphono-7-(3-propylphenoxy-5-heptene-1-sulfonic acid, tripotassium salt;

Mass Spec (FAB, + ions) m/z 521 (M+H), 483 (MK–K+2H), 445 (M–2K+3H), 407 (M–3K+4H)

Anal. Calcd for $C_{17}H_{24}O_7PSK_3+0.64\ H_2O$: C, 38.37; H, 4.79; P, 5.82; S, 6.02 Found: C, 38.37; H, 5.12; P, 5.83; S, 5.81

104. (E)-6-methyl-7-(2-methylphenoxy)-1-phosphono-5-heptene-1-sulfonic acid, tripotassium salt;

Mass Spec (FAB, + ions) m/z 531 (M+K), 493 (M+H), 455 (M–K+2H)

Anal. Calcd for $C_{15}H_{20}O_7PSK_3+1.46\ H_2O$: C, 34.72; H, 4.45; P, 5.97; S, 6.18 Found: C, 34.72; H, 4.90; P, 5.58; S, 5.92

105. (E,E)-6,10,14-trimethyl-1-phosphono-5,9-pentadecadiene-1-sulfonic acid, tripotassium salt;

Mass Spec (FAB, + ions) m/z 563 (M+K), 525 (M+H), 487 (M+2H–K)

Anal. Calcd for $C_{18}H_{32}O_6PSK_3+2.0\ H_2O$: C, 38.55; H, 6.47; P, 5.52; S, 5.72 Found: C, 38.93; H, 6.87; P, 5.62; S, 5.49

106. 4'-phenoxy-α-phosphono[1,1'-biphenyl]butanesulfonic acid, tripotassium salt;

Mass Spec (FAB, + ions) m/z 577 (M+H), 539 (MK+2H), 501 (M–2K+3H)

Anal. Calcd for $C_{22}H_{30}K_3O_7PS+1.6\ H_2O$: C, 43.64; H, 3.86; P, 5.11; S, 5.29 Found: C, 43.73; H, 3.97; P, 4.71; S, 5.30

107. α-phosphono-4'-propyl[1,'-biphenyl]-4-propanesulfonic acid, tripotassium salt Mass Spec (FAB, + ions) m/z 551 (M+K), 513 (M+H), 475 (M–K+2H)

Anal. Calcd for $C_{18}H_{20}K_3O_6PS+4.1\ H_2O$: C, 36.90; H, 4.84; P, 5.29; S, 5.47 Found: C, 36.90; H, 4.68; P, 5.05; S, 5.67

108. 3-(4-methylphenoxy)-α-phosphonobenzenebutanesulfonic acid, tripotassium salt;

Mass Spec (FAB, + ions) m/z 477 (M–K+2H), 515 (M+H), 553 (M+K)

Anal. Calcd for $C_{17}H_{18}K_3O_7PS+2.1\ H_2O$: C, 36.96; H, 4.05; P, 5.61; S, 5.80 Found: C, 37.27; H, 4.42; P, 5.43; S, 5.42

109. (E)-8-phenyl-1-phosphono-5-octene-1-sulfonic acid, tripotassium salt;

Mass spec (FAB, + ions) m/z 501 (M+K), 463 (M+H), 425 (M–K+2H)

Anal. Calcd for $C_{14}H_{18}O_6PSK_3+3.0\ H_2O$: C, 32.50; H, 4.69; P, 5.99; S, 6.20Found: C, 32.50; H, 4.73; P, 6.03; S, 6.40

110. 2'-methoxy-α-phosphono-4'-propyl[1,1'-biphenyl]-4-butanesulfonic acid, tripotassium salt;

Mass Spec (FAB, + ions) m/z 519 (M+2H–K), 481 (M+3H–2K)

Anal. Calcd for $C_{20}H_{24}K_3O_7PS+2.3\ H_2O$: C, 40.16; H, 4.82; P, 5.18; S, 5.36 Found: C, 40.14; H, 4.83; P, 4.79; S, 5.44

111. (E,E)-6,10-dimethyl-12-phenyl-1-phosphono-5,9-dodecadiene-1-sulfonic acid, tripotassium salt;

Mass Spec (FAB, + ions) m/z 583 (M+K), 545 (M+H), 507 (M+2H–K)

Anal. Calcd for $C_{20}H_{28}O_6PSK_3+0.8\ H_2O$: C, 42.96; H, 5.34; P, 5.54; S, 5.73 Found: C, 42.96; H, 5.74; P, 5.65; S, 5.72

112. (E)-6-methyl-7-(phenylthio)-1-phosphono-5-heptenyl-1-sulfonic acid, tripotassium salt;

Mass Spec (FAB, + ions) m/z 533 (M+K), 495 (M+H), 457 (M–K+2H), 419 (M–2K+3H)

Anal. Calcd for $C_{14}H_{18}O_6PS_2K_3+3.8\ H_2O$: C, 29.87; H, 4.58; P, 5.50; S, 11.39 Found: C, 29.87; H, 4.73; P, 5.48; S, 11.52

113. 3-phenoxy-α-phosphonobenzenepropanesulfonic acid, tripotassium salt;

Mass Spec (FAB, + ions) m/z 499 (M+2H–K), 487 (M+H), 525 (M+K)

Anal. Calcd for $C_{15}H_{14}K_3O_7PS+1.6\ H_2O$: C, 34.95; H, 3.36; P, 6.01; S, 6.22 Found: C, 34.91; H, 3.31; P, 5.93; S, 6.23

114. 2'-(methoxymethoxy)-α-phosphono-4'-propyl[1,1'-biphenyl]-4-butanesulfonic acid, tripotassium salt;

Mass Spec (FAB, + ions) m/z 625 (M+K), 586 (M+H), 549 (M+2H–K)

Anal. Calcd for $C_{21}H_{26}K_3O_8PS+2.4\ H_2O$: C, 40.03; H, 4.93; P, 4.92; S, 5.09 Found: C, 40.03; H, 5.03; P, 4.80; S, 5.42

115. 2'-hydroxy-α-phosphono-4'-propyl[1,1'-biphenyl]-4-butanesulfonic acid, tripotassium salt;

Mass Spec (FAB, + ions) m/z 581 (M+K), 543 (M+H), 467 (M+2H–K)

Anal. Calcd for $C_{19}H_{22}PSO_7K_3+2.7\ H_2O$: C, 38.59; H, 4.67; P, 5.24; S, 5.42 Found: C, 38.59; H, 4.58; P, 5.07; S, 5.56

116. α-phosphono-4'-(2-pyridinyl) [1,1'-biphenyl]-butanesulfonic acid, tripotassium salt;

Mass Spec (FAB, + ions) m/z 562 (M+H), 524 (M–K+2H), 486 (M–2K+3H)

Anal. Calcd for $C_{21}H_{19}NO_6PSK_3+2.5\ H_2O$: C, 41.57; H, 3.99; N, 2.31; P, 5.10; S, 5.28 Found: C, 41.48; H, 3.90; N, 2.40; P, 4.78; S, 5.27

117. (E)-6-methyl-7-phenyl-1-phosphono-5-heptane-1-sulfonic acid, tripotassium salt;

Mass Spec (FAB, + ions) m/z 501 (M+K), 463 (M+H), 425 (M–K+2H)

Anal. Calcd for $C_{14}H_{18}O_6PSK_3+2.9\ H_2O$: C, 32.67; H, 4.66; P, 6.02; S, 6.23 Found: C, 32.67; H, 4.63; P, 6.13; S, 6.02

118. α-fluoro-3-phenoxy-α-phosphonobenzenebutanesulfonic acid, tripotassium salt;

Mass Spec (FAB, + ions) m/z 519 (M+H), 481 (M+2H–K), 440 (M+3H–2K)

Anal. Calcd for $C_{16}H_{15}FO_7PSK_3+1.4\ H_2O$: C, 35.33; H, 3.30; P, 5.69; S, 5.89 Found: C, 35.73; H, 3.71; P, 5.77; S, 6.09

119. (E)-6methyl-8-(2-methylphenyl)-1-phosphono-5-octene-1-sulfonic acid, tripotassium salt;

Mass Spec (FAB, + ions) m/z 529 (M+K), 491 (M+H), 453 (M–K+2H)

Anal. Calcd for $C_{16}H_{22}PSO_6K_3+2.2\ H_2O$: C, 36.21; H, 5.02; P, 5.84; S, 6.04 Found: C, 36.29; H, 4.96; P, 5.44; S, 6.40

120. 3-(2-naphthalenyloxy)-α-phosphonobenzenebutanesulfonic acid, tripotassium salt;

Mass Spec (FAB, + ions) m/z 513 (M–K+2H), 551 (M+H), 589 (M+K)

Anal. Calcd for $C_{20}H_{18}K_3O_7PS+3.8\ H_2O$: C, 38.80; H, 4.17; P, 5.00; S, 5.18 Found: C, 38.69; H, 4.04; P, 5.10; S, 4.96

121. (E)-6-methyl-1-phosphono-8-(4-propylphenyl)-5-octene-1-sulfonic acid, tripotassium salt;

Mass Spec (FAB, + ions) m/z 557 (M+K), 519 (M+H), 481 (M÷K+2H)

Anal. Calcd for $C_{18}H_{26}PSO_6K_3+3.36\ mol\ H_2O$: C, 37.32; H, 5.69; P, 5.35; S, 5.53 Found: C, 37.32; H, 5.68; P, 5.46; S, 5.66

122. (E)-8-(3-methoxyphenyl)-6-methyl-1-phosphono-5-octene-1-sulfonic acid, tripotassium salt;

Mass Spec (FAB, + ions) m/z 545 (M+K), 507 (M+H), 469 (M−K+2H)

Anal. Calcd for $C_{16}H_{22}PSO_7K_3$+2.3 $H_2O$: C, 35.04; H, 4.90; P, 5.65; S, 5.85 Found: C, 35.04; H, 5.19; P, 5.54; S, 5.41

123. α-phosphono-4'-(1-piperidinyl) [1,1'-biphenyl]-4-butanesulfonic acid, tripotassium salt;

Mass Spec (FAB, + ions) m/z 606 (M+K), 568 (M+H), 530 (M−K+2H), 492 (M−2K+3H)

Anal. Calcd for $C_{21}H_{25}K_3NO_6PS$+2.7 $H_2O$: C, 40.92; H, 4.97; N, 2.27; P, 5.02; S, 5.20 Found: C, 40.93; H, 4.96; N, 2.00; P, 4.93; S, 5.53

124. ζ-methyl-α-phosphono-4-propylbenzeneoctanesulfonic acid, tripotassium salt;

Mass Spec (Electrospray, − ions) m/z 405(M−3K+2H)

Anal. Calcd for $C_{18}H_{28}O_6PSK_3$+1.92 $H_2O$:
C, 38.93; H, 5.78; P, 5.58; S, 5.77 Found: C, 38.93; H, 6.05; P, 5.45; S, 5.90

125. ζ,2-dimethyl-α-phosphonobenzeneoctanesulfonic acid, tripotassium salt;

Mass Spec (Electrospray, − ions) m/z 377 (M−3K+2H)

Anal. Calcd for $C_{16}H_{24}O_6PSK_3$+1.2 $H_2O$: C, 37.37; H, 5.17; P, 6.23; S, 6.02 Found: C, 37.87; H, 5.65; P, 6.10; S, 5.80

126. 3-(1-naphthalenyloxy)-α-phosphonobenzenebutanesulfonic acid, tripotassium salt;

Mass Spec (FAB, + ions) m/z 475 (M−2K+3H), 513 (M−K+2H), 551 (M+H), 589 (M+K)

Anal. Calcd for $C_{20}H_{18}K_3O_7PS$+2.5 $H_2O$: C, 40.32; H, 3.89; P, 5.20; S, 5.38 Found: C, 40.42; H, 4.17; P, 5.41; S, 5.09

127. 3-(cyclohexyloxy)-α-phosphonobenzenebutanesulfonic acid, tripotassium salt;

Mass Spec (FAB, + ions) m/z 545 (M+K), 507 (M+H), 469 (M−K+2H).

Anal. Calcd for $C_{16}H_{22}O_7PSK_3$+4.2 $H_2O$: C, 32.98; H, 5.27; P, 5.32; S, 5.50 Found: C, 32.98; H, 5.25; P, 5.65; S, 5.18.

128. 3-(3-ethylphenoxy)-α-phosphonobenzenebutanesulfonic acid, tripotassium salt;

Mass Spec (FAB, + ions) m/z 491 (M−K+2H), 529 (M+H), 567 (M+K).

Anal. Calcd for $C_{18}H_{20}K_3O_7PS$+1.6 $H_2O$: C, 38.78; H, 4.19; P, 5.56; S, 5.75 Found: C, 38.94; H, 4.47; P, 5.32; S, 5.31.

129. α-phosphono-3-[3-(trifluoromethyl)phenoxy]benzenebutanesulfonic acid, tripotassium salt;

Mass Spec (FAB, + ions) m/z 431 (M−K+2H), 569 (M+H), 607 (M+K)

Anal. Calcd for $C_{17}H_{15}F_3K_3O_7PS$+1.6 $H_2O$: C, 34.18; H, 3.07; F, 9.54; P, 5.18; S, 5.37 Found: C, 34.21; H, 3.15; F, 9.20; P, 5.02; S, 5.51

130. (E)-6-methyl-1-phosphono-8-[3-(trifluoromethyl)phenyl]-5-octene-1-sulfonic acid, tripotassium salt;

Mass Spec (Ion Spray, − ions) m/z 429 (M−3K+2H), 411 (M−3K+2H−$H_2O$).

Anal. Calcd for $C_{16}H_{19}F_3K_3PSO_6$+2.3 $H_2O$: C, 32.78; H, 4.06; P, 5.28; S, 5.47 Found: C, 32.78; H, 4.41; P, 5.55; S, 5.86.

131. 3-phenoxy-α-phosphonobenzenepentanesulfonic acid, tripotassium salt;

Mass Spec (FAB, + ions) m/z 477 (M+2H−K), 515 (M+H), 553 (M+K)

Anal. Calcd for $C_{17}H_{18}K_3O_7PS$+1.5 $H_2O$: C, 37.95; H, 3.86; P, 5.76; S, 5.96 Found: C, 37.95; H, 4.24; P, 5.56; S, 5.97.

132. 3-[2-(3-methylbutyl)phenoxy]-α-phosphonobenzenebutanesulfonic acid, tripotassium salt;

Mass Spec (FAB, +ion) m/z 533 (M−K+2H), 571 (M+H), 609 (M+K)

Anal. Calcd for $C_{21}H_{26}K_3O_7PS$+1.5 $H_2O$: C, 42.19; H, 4.89; P, 5.18; S, 5.36 Found: C, 42.33; H, 5.15; P, 4.96; S, 5.02.

133. 3-[2-(3-methyl-2-butenyl)phenoxy]-α-phosphonobenzenebutanesulfonic acid, tripotassium salt;

Mass Spec (FAB, +ion) m/z 569 (M+H), 607 (M+K)

Anal. Calcd for $C_{21}H_{24}K_3O_7PS^+$2-2 $H_2O$: C, 41.46; H, 4.71; P, 5.09; S, 5.27 Found: C, 41.64; H, 4.73; P, 5.11; S, 4.77.

134. α-[bis[1-(1-oxopropoxy)ethoxy]phos-, phinyl]-3-phenoxybenzenebutanesulfonic acid, monopotassium salt;

Mass Spec (FAB, + ions) 663 (M+K)

Anal. Calcd for $C_{26}H_{34}KO_{11}PS$: C, 49.99; H, 5.49; P, 4.96; S, 5.13 Found: C, 49.93; H, 5.54; P, 5.08; S, 5.44.

135. (E)-8-([1,1'-biphenyl]-4-yl)-6-methyl-1-phosphono-5-octene-1-sulfonic acid, tripotassium salt;

Mass Spec (FAB, + ions) m/e 591 (M+K), 553 (M+H), 515 (M−K+2H)

Anal. Calcd for $C_{21}H_{24}PSO_6K_3$+1.34 mol $H_2O$: C, 43.72; H, 4.66; P, 5.37; S, 5.56 Found: C, 43.72; H, 4.97; P, 5.31; S, 5.59.

136. 3-(2-cyclohexen-1-yloxy)-(α-phosphonobenzenebutanesulfonic acid, tripotassium salt;

Mass Spec (FAB, + ions) m/e 543 (M+K), 505 (M+H), 467 (M−K+2H)

Anal. Calcd for $C_{26}H_{20}O_7PSK_3$+5.22 $H_2O$: C, 32.10; H, 5.12; P, 5.17; S, 5.36 Found: C, 32.10; H, 4.84; P, 4.90; S, 5.71.

137. (E)-6-methyl-8-(2-naphthalenyl)-1-phosphono-5-octene-1-sulfonic acid, tripotassium salt;

Mass Spec (FAB, + ions) m/e 565 (M+K), 527 (M+H)

Anal. Calcd for $C_{19}H_{22}PSO_6K_3$+4.10 mol $H_2O$: C, 38.00; H, 5.07; P, 5.16; S, 5.34 Found: C, 38.39; H, 4.87; P, 5.31; S, 4.94.

138. 3-(phenylmethoxy)-α-phosphonobenzenebutanesulfonic acid, tripotassium salt;

Mass Spec 515 (M+H), 477 (M−K+2H), 439 (M−2K+3H)

Anal. Calcd for $C_{17}H_{18}O_7PSK_3$+3.5 $H_2O$: C, 35.34; H, 4.36; P, 5.36; S, 5.55 Found: C, 35.34; H, 4.40; P, 5.03; S, 5.26.

139. 6-([1,1'-biphenyl]-4-yl)-α-phosphono-3-pyridinebutanesulfonic acid, tripotassium salt;

Mass Spec (FAB, + ions) 600 (M+K), 562 (M+H), 524 (M−K+2H), 486 (M−2K+3H)

Anal. Calcd for $C_{21}H_{19}NO_6PSK_3$+2.3 $H_2O$: C, 41.82; H, 3.94; N, 2.32; P, 5.14; S, 5.32 Found: C, 42.21; H, 4.34; N, 2.30; P, 5.02; S, 5.34.

140. 3-(4-chlorophenoxy)-α-phosphonobenzenebutanesulfonic acid, tripotassium salt;

Mass Spec (FAB, + ions) m/z 573 (M+K), 535 (M+H), 497 (M−K+2H), 463 (M−K−Cl+3H)

Anal. Calcd for $C_{16}H_{15}ClO_7PS.3K$+0.89 $H_2O$: C, 34.87; H, 3.07; P, 5.62; S, 5.82; Cl, 6.43 Found: C, 35.28; H, 3.51; P, 5.48; S, 5.97; Cl, 6.25.

141. 3-(3-chlorophenoxy)-α-phosphonobenzenebutanesulfonic acid, tripotassium salt;

Mass Spec (FAB, +ion) m/z 459 (M−2K+3H), 497 (M−K+2H), 535 (M+H)

Anal. Calcd for $C_{16}H_{15}ClK_3O_7PS$+1.5 $H_2O$: C, 34.19; H, 3.23; P, 5.51; S, 5.70 Found: C, 34.23; H, 3.66; P, 5.25; S, 5.91.

142. (E)-6-methyl-1-phosphono-8-(2-pyridinyl)-5-octene-1-sulfonic acid, tripotassium salt;

Mass Spec (FAB, + ions) m/z 516 (M+K), 478 (M+H), 440 (M−K+2H)

Anal. Calcd for $C_{14}H_{19}NPSO_6K_3$+1.30 $H_2O$: C, 33.58; H, 4.34; N, 2.80; P, 6.19 S, 6.40 Found: C, 33.54; H, 4.41; N, 2.84; P, 6.05 S, 6.07

143. 2-methoxy-5-phenoxy-α-phosphonobenzenebutanoic acid, tripotassium salt;

Mass Spec (FAB, + ions) m/z 569 (M+K), 531 (M+H), 493 (M−K+2H), 455 (M−2K+3H)

Anal. Calcd for $C_{17}H_{18}K_3O_8PS$+1.2 $H_2O$: C, 36.94; H, 3.73; P, 5.60; S, 5.80 Found: C, 37.37; H, 4.17; P, 5.36; S, 5.38.

144. (E,E)-1-[bis[2-methyl-1-(1-oxopropoxy) propoxy]phosphinyl]-6,10,14-trimethyl-5,9,13-pentadecatriene-1-sulfonic acid, monopotassium salt;

Mass Spec (FAB, + ions) 703 (M+H), 741 (M+K)

Anal. Cald for $C_{32}H_{56}KO_{10}PS$: C, 54.68; H, 8.03; P, 4.41; S, 4.56 Found: C, 54.66; H, 8.07; P, 4.37; S, 4.37.

145. ζ-methyl-α-phosphono[1,1'-biphenyl]-4-octanesulfonic acid, tripotassium salt;

Mass Spec (FAB, + ions) m/e (M+K), 555 (M+H), 517 (M−K+2H)

Anal. Calcd for $C_{21}H_{26}PSO_6K_3$+2.47 mol $H_2O$: C, 42.09; H, 5.20; P, 5.17; S, 5.35 Found: C, 42.09; H, 5.18; P, 4.77; S, 5.02.

146. 4-(2-phenyl-5-pyridinyl)-α-phosphonobenzenebutanesulfonic acid, tripotassium salt;

Mass Spec (FAB, + ions) m/z 600 (M+K), 562 (M+H), 524 (M−K+2H)

Anal. Calcd for $C_{21}H_{19}NO_6PSK_3$+1.9 $H_2O$: C, 42.32; H, 3.86; N, 2.35; S, 5.38 P, 5.20 Found: C, 42.32; H, 4.21; N, 2.37; S, 5.27 P, 5.22.

147. α-[bis[1-(2,2-dimethyl-1-oxopropoxy)ethoxy]phinyl]- 3-phenoxybenzenebutanesulfonic acid, monopotassium salt;

Mass Spec (FAB, + ions) m/z 719 (M+K)

Anal. Calcd for $C_{30}H_{42}KO_{11}PS$+0.5 $H_2O$: C, 52.24; H, 5.28; P, 4.49; S, 4.65 Found: C, 52.42; H, 6.21; P, 4.65; S, 5.39.

148. 5-phenoxy-α-phosphono-2-thiophenebutanesulfonic acid, tripotassium salt;

Mass Spec (FAB, + ions) m/z 507 (M+H), 469 (M−K+2H), 431 (M−2K+3H)

Anal. Calcd for $C_{14}H_{14}O_7PS_2K_3$+2.04 $H_2O$: C, 30.95; H, 3.35; P, 5.70; S, 11.80 Found: C, 30.95; H, 3.37; P, 5.33; S, 11.99.

149. 3-[2-(2-methoxyethyl)phenoxy]-α-phosphonobenzenebutanesulfonic acid, tripotassium salt;

Mass Spec (FAB, + ions) m/z 597 (M+K), 559 (M+H), 543 (M−K+Na+H), 521 (M−K+2H), 483 (M−2K+3H)

Anal. Calcd for $C_{19}H_{22}O_8PS$.3K+1.15 $H_2O$: C, 39.38; H, 4.23; P, 5.34; S, 5.53 Found: C, 39.38; H, 4.51; P, 4.93; S, 5.34.

150. (E,E)-1-[bis [1-(benzoyloxy)ethoxy]phosphinyl]-6,10,14-trimethyl-5,9,13-pentadecatriene- 1-sulfonic acid, monopotassium salt;

Mass Spec (FAB, + ions) 781 (M+K)

Anal. Calcd for $C_{36}H_{48}KO_{10}PS$+0.3 $H_2O$: C, 57.80; H, 6.54; P, 4.14; S, 4.29 Found: C, 57.80; H, 6.43; P, 4.00; S, 3.23.

151. (E,E)-α-[bis[2-methyl-1-(1-oxopropoxy)propoxy]phosphinyl]-3-phenoxybenzenebutanesulfonic acid, monopotassium salt;

Mass Spec (FAB, + ions) m/z 719 (M+K)

Anal. Calcd for $C_{30}H_{42}KO_{11}PS$: C, 52.93; H, 6.22; P, 4.55; S, 4.71 Found: C, 52.86; H, 6.33; P, 4.28; S, 5.10.

152. 3-[2-(2-propenyl)phenoxy]-(α-phosphonobenzenebutanesulfonic acid, tripotassium salt;

Mass spec (FAB, +ion) m/z 465 (M−2K+3H), 503 (M−K+2H), 541 (M+H), 579 (M+K)

Anal. Calcd for $C_{19}H_{20}K_3O_7PS$+2.7 $H_2O$: C, 38.72; H, 4.34; P, 5.26; S, 5.44 Found: C, 38.79; H, 4.45; P, 5.00; S, 5.08.

153. 2-(methoxymethoxy)-5-phenoxy-α-phosphonobenzenebutanoic acid, tripotassium salt;

Mass Spec (FAB, + ions) m/z 599 (M+K), 561 (M+H), 523 (M−K+2H)

Anal. Calcd for $C_{18}H_{20}K_3O_9PS$+2.9 $H_2O$: C, 35.24; H, 4.25; P, 5.05; S, 5.23 Found: C, 35.24; H, 4.13; P, 4.84; S, 5.57.

154. α-phosphono-3-(2-pyridinyloxy)benzenebutanesulfonic acid, tripotassium salt;

Mass Spec m/z 540 (M+K), 502 (M+H), 464 (M−K+2H)

Anal. Calcd for $C_{15}H_{15}NO_7PSK_3$+2.63 $H_2O$: C, 32.82; H, 3.72; N, 2.55; P, 5.64; S, 5.84 Found: C, 32.87; H, 4.12; N, 2.50; P, 5.38; S, 6.22.

155. 3-[2-phenylmethyl)phenoxy]-α-phosphonobenzenebutanesulfonic acid, tripotassium salt;

Mass Spec 629 (M+K), 591 (M+H), 553 (M−K+2H), 515 (M−2K+3H)

Anal. Calcd for $C_{23}H_{22}K_3O_7PS$: C, 45.32; H, 3.98; N, 0.00; S, 5.26; P, 5.08 Found: C, 45.32; H, 4.25; N, 0.24; S, 5.54; P, 4.84.

156. δ-methyl-3-phenoxy-α-phosphonobenzenebutanesulfonic acid, tripotassium salt;

Mass Spec. (FAB, + ions) m/z 515 (M+H), 553 (M+K)

Anal. Calcd for $C_{17}H_{18}K_3O_7PS$+2.5 $H_2O$: C, 36.48; H, 4.14; P, 5.53; S, 5.73 Found: C, 36.50; H, 3.98; P, 5.37; S, 5.47.

157. 3-(3-fluorophenoxy)-α-phosphonobenzenebutanesulfonic acid, tripotassium salt;

Mass Spec (FAB, +ion) m/z 481 (M−K+2H), 519 (M+H), 557 (M+K)

Anal. Calcd for $C_{16}H_{15}FK_3O_7PS$.2.4 $H_2O$: C, 34.20; H, 3.55; P, 5.51; S, 5.71 Found: C, 34.21; H, 3.45; P, 5.36; S, 6.04.

158. 3-(4-fluorophenoxy)-α-phosphonobenzenebutanesulfonic acid, tripotassium salt;

Mass Spec (FAB, + ions) 557 (M+K), 519 (M+H), 481 (M−K+2H), 443 (M+2K+3H)

Anal. Calcd for $C_{16}H_{15}FO_7PSK_3$+2.0 $H_2O$: C, 34.65; H, 3..45; S, 5.78; P, 5.58; F, 3.43 Found: C, 34.92; H, 3.88; S, 6.12; P, 5.59; F, 3.48.

159. α-[bis[1-(2-methyl-1-oxopropoxy)ethoxy]phosphinyl]-3-phenoxybenzenebutanesulfonic acid, monopotassium salt;

Mass Spec (FAB, + ions) m/z 691 (M+K)

Anal. Calcd for $C_{28}H_{38}KO_{11}PS$: C, 51.52; H, 5.87; P, 4.75; S, 4.91 Found: C, 51.65; H, 5.93; P, 4.63; S, 5.89.

160. 4-(2-benzoxazolyl)-α-phosphinylbenzenebutanesulfonic acid, tripotassium salt;

Mass Spec (FAB, + ions) 526 (M+K), 488 (M+H), 450 (M−K+2H)

Anal. Calcd for $C_{17}H_{15}NO_7PSK_3$.2.22 $H_2O$: C, 36.10; H, 3.46; N, 2.48; S, 5.67; P, 5.48 Found: C, 35.98; H, 3.66; N, 2.60; S, 5.46; P, 5.53.

161. α-[bis[2-methyl-1-(2-methyl-1-oxo-propoxy)propoxy]phosphinyl]-3-phenoxybenzenebutanesulfonic acid, monopotassium salt;

Mass Spec (FAB, + ions) m/z 709 (M+K)

Anal. Calcd for $C_{32}H_{46}KO_{11}PS$: C, 54.22; H, 6.54; P, 4.37; S, 4.52 Found: C, 53.98; H, 6.57; P, 3.86; S, 5.31.

162. α-[bis[1-(1-oxopropoxy)propoxy]phosphinyl]-3-phenoxybenzenebutanesulfonic acid, monopotassium salt;

Mass Spec (FAB, + ions) m/z 691 (M+K)

Anal. Calcd for $C_{28}H_{38}KO_{11}PS$: C, 51.52; H, 5.87; P, 4.75; S, 4.91 Found: C, 51.75; H, 5.85; P, 4.54; S, 5.84.

163. 3-(3,4-dichlorophenoxy)-α-phosphonobenzenebutanesulfonic acid, tripotassium salt;

Mass Spec (FAB, +ion, for $^{35}$Cl) m/z 531 (M–K+2H), 569 (M+H), 607 (M+K), (Cl isotope pattern)

Anal. Calcd for $C_{16}H_{14}Cl_2K_3O_7PS·1.6\ H_2O$: C, 32.12; H, 2.90; P, 5.18; S, 5.36 Found: C, 32.10; H, 3.15; P, 5.16; S, 5.71.

164. 3-(2,3-dichlorophenoxy)-α-phosphonobenzenebutanesulfonic acid, tripotassium salt;

Mass Spec (FAB, +ion, for $^{35}$Cl) m/z 533 (M–K+2H), 569 (M+H), 607 (M+K), (Cl isotope pattern)

Anal. Calcd for $C_{16}H_{14}Cl_2O_7PS·2.2\ H_2O$: C, 31.55; H, 3.04; P, 5.09; S, 5.26 Found: C, 31.54; H, 3.17; P, 4.75; S, 5.51.

165. 3-(2-phenoxyphenoxy)-α-phosphonobenzenebutanesulfonic acid, tripotassium salt;

Mass Spec (FAB, +ion) m/z 555 (M–K+2H), 593 (M+H), 631 (M+K)

Anal. Calcd for $C_{22}H_{20}K_3O_8PS+1.8\ H_2O$: C, 42.27; H, 3.81; P, 4.95; S, 5.13 Found: C, 42.25; H, 3.91; P, 5.25; S, 4.88.

166. 3-(2-benzoylphenoxy)-α-phosphonobenzenesulfonic acid, tripotassium salt;

Mass Spec (FAB, +ion) m/z 567 (M–K+2H), 605 (M+H), 643 (M+K)

Anal. Calcd for $C_{23}H_{20}K_3O_8PS+3.1\ H_2O$: C, 41.82; H, 4.00; P, 4.69; S, 4.85 Found: c, 41.86; H, 3.88; P, 4.69; S, 4.86.

167. (Z)-6-methyl-8-phenyl-1-phosphono-5-octene-1-sulfonic acid, tripotassium salt;

Mass Spec (FAB, + ions) m/z 515, (M+K), 477 (M+H)

Anal. Calcd for $C_{15}H_{20}PSO_6K_3+1.8\ H_2O$: C, 35.36; H, 4.68; P, 6.08; S, 6.29 Found: C, 35.36; H, 4.67; P, 5.89; S, 6.00.

168. (E)-8-(2-fluorophenyl)-6-methyl-1-phosphono-5-octene-1-sulfonic acid, tripotassium salt;

Mass Spec (FAB, + ions) m/z 533 (M+K), 495 (M+H), 457 (M–K+2H)

Anal. Calcd for $C_{15}H_{19}FPSO_6K_3+3.50\ H_2O$: C, 32.35; H, 4.69; P, 5.56; S, 5.76 Found: C, 32.35; H, 4.69; P, 5.63; S, 5.76.

169. 3-(4-methoxyphenoxy)-α-phosphonobenzenebutanesulfonic acid, tripotassium salt;

Mass Spec (FAB, + ions) m/z 569 (M+K), 531 (M+H), 493 (M–K+2H), 455 (M–2K+3H)

Anal. Calcd for $C_{17}H_{18}O_8PS·3K +1.71\ H_2O$: C, 36.36; H, 3.85; P, 5.52; S, 5.71 Found: C, 36.78; H, 4.00; P, 5.13; S, 5.54.

170. 3-(3-methoxyphenoxy)-α-phosphonobenzenebutanesulfonic acid, tripotassium salt;

Mass Spec (FAB, +ion) m/z 531 (M+H), 569 (M–K)

Anal. Calcd for $C_{17}H_{18}K_3O_8PS+1.7\ H_2O$: C, 36.38; H, 3.84; P, 5.52; S, 5.71 Found: C, 36.43; H, 4.16; P, 5.43; S, 5.66.

171. 3-(2-propoxyphenoxy)-α-phosphonobenzenebutanoic acid, tripotassium salt;

Mass Spec (FAB, + ions) m/z 597 (M+K), 559 (M+H), 521 (M–K+2H)

Anal. Calcd for $C_{19}H_{22}K_3O_8PS+1.1\ H_2O$: C, 39.50; H, 4.21; P, 5.36; S, 5.55 Found: C, 39.50; H, 4.49; P, 5.09; S, 5.31.

172. α-phosphono-3-(2-propylphenoxy)benzenebutanesulfonic acid, tripotassium salt;

Mass Spec (FAB, +ion) m/z 505 (M–K+2H), 543 (M+H), 581 (M+K)

Anal. Calcd for $C_{19}H_{22}K_3O_7PS+2.0\ H_2O$: C, 39.43; H, 4.53; P, 5.35; S, 5.54 Found: C, 39.44: H, 4.42; P, 5.21; S, 5.85.

173. 3-[2-(2-ethoxymethyl)phenoxy]-α-phosphonobenzenebutanesulfonic acid, tripotassium salt;

Mass Spec (FAB, + ions) m/z 597 (M+K), 559 (M+H), 543 (M–K+Na+H), 521 (M–K+2H), 1041 (2M+K), 1079 (2M+2K–H), 1117 (2M+3K–2H)

Anal. Calcd for $C_{19}H_{22}O_8PS·3K+1.43\ H_2O$: C, 39.05; H0 4.29: P, 5.30; S, 5.49 Found: C, 39.05; H, 4.31; P, 5.11; S, 5.10.

EXAMPLE 174

α-[Bis[(2,2-Dimethyl-1-oxopropoxy)methoxy]phosphinyl]-3-phenoxybenzenebutanesulfonic acid, monopotassium salt A. α-[Bis[2,2-dimethyl-1-oxopropoxy)methoxy]phosphinyl]-3-phenoxybenzenebutanesulfonic acid, cyclohexyl ester Bromotrimethylsilane (3.61 g, 23.63 mmol, 4 eq.) was added dropwise to a solution of Example 40, Part E ester (3.10 g, 5.90 mmol) and allyltrimethylsilane (4.71 g, 41.3 mmol) in dichloromethane (20 mL) at RT under argon. The clear reaction mixture was stirred at RT for 48 h, concentrated and pumped at high vacuum for 4 h to give a colorless oil.

The crude silyl ester prepared above (3.55 g, ≈5.88 mmol) was dissolved in 1N KOH (12.7 mL, 12.7 mmol) over 10 min, then added slowly with vigorous stirring to a solution of silver nitrate (2.17 g, 12.76 mmol) in water (40 mL) under argon in the dark. The resulting white gum was diluted with 40 mL of water, extracted with toluene (4×75 mL) and dried over $Na_2SO_4$. The organics were filtered and concentrated to a thick gum. The gum was diluted with 80 mL of toluene, cooled to 0° C. and treated with 2,2-dimethylpropanoic acid, iodomethyl ester (3.87 g, 16.00 mmol) in 20 mL of toluene over 15 min. After 5 min. at 0° C., a solid precipitated out of the solution. The reaction was stirred an additional 0.5 h and warmed to room temperature. The mixture was stirred with Celite (4 g) for 6 min., filtered through a pad of Celite and concentrated to provide a yellow oil. The oil was purified by flash column chromatography on silica gel (200 g) eluting with (1.5 L) 20:80 ethyl acetate/hexane followed by (0.5 L) 40:60 ethyl acetate/hexane to provide 2.60 g (65%) of title compound as a colorless oil.

TLC Silica gel (3:7 ethyl acetate/hexanes) $R_f$=0.50.

B. α-[Bis[(2,2-Dimethyl-1-oxopropoxy)methoxy]phosphinyl]-3-phenoxybenzenebutanesulfonic acid, monopotassium salt To a mixture of 1.07 g (11.00 mmol) of KOAc in 40 mL of a 9:1 trifluoroethanol/water (v/v) solution was added 2.50 g (3.59 mmol) of Part A compound. After a homogeneous solution was obtained (≈15 min.), the solution was heated to 40° C. (bath temp.) for 20 h and the solvent removed under reduced pressure. The remainder was diluted with water (5 mL) and concentrated. The residue was diluted with ethyl acetate, washed with solutions of $KHCO_3$ (2×8 mL) and KCl (1×10 mL), dried over anhydrous KCl and evaporated to provide a pale yellow oil. The oil was diluted with 15 mL of water (a soapy slurry formed) and freeze dried to provide 2.02 g (86%) of title compound as a white lyophilate.

TLC Silica gel (1:9 methanol/dichloromethane) $R_f$=0.60.

IR (KBr) 3488, 3063, 2974, 1753, 1584, 1485, 1460, 1447, 1397, 1370, 1250, 1215, 1163, 1140, 1069, 1045, 1022, 1003, 963 cm$^{-1}$.

$^1$H NMR (DMSO, 300 MHz): δ7.33 (t, 2H, J=8.5 Hz) 7.25 (t, 1H, J=8.5 Hz) 7.15 (t, 1H, J=8.0 Hz) 6.93 (m, 3H) 6.80 (s, 1H) 6.75 (d, 1H, J=9.0 Hz) 5.45 (m, 4H) 3.15 (dt, 1H, J=19.0, 5.0 Hz) 2.50 (t, 2H, J=7.0 Hz) 1.90, 1.80 (two m, 4H) 1.10 (s, 3H, $H_{12}$) 1.55 (two s, 18H)ppm.

Mass Spec (FAB, + ions) m/z 691 (M+K), 615 (M−K+ 2H), 445 (M−C$_{12}$H$_{22}$O$_5$+K).

Anal. Calcd for C$_{28}$H$_{38}$O$_{11}$SPK: C, 51.52; H, 5.87; P, 4.75; S, 4.91 Found: C, 51.38; H, 5.93; P, 4.65; S, 4.90.

EXAMPLE 175

(S)-(−)-3-Phenoxy-α-phosphonobenzenebutanesulfonic acid, tripotassium salt

A. (1R,2R)-N,N'-Dimethyl-1,2-cyclohexanediamine

Preparation of the title compound was carried out as described by Hanessian, S. et. al. J. Amer. Chem. Soc. 1984, 106, 5754–5756, and Alexakis, A. et. al. J. Org. Chem. 1992, 57, 1224–237, Galsbol, F. et al., Acta Chem. Scand. 1972, 26, 3605 and Onuma, K. et. al., Bull. Chem. Soc. Jpn. 1980, 53, 2012.

[α$_{spec}$]$_D^{20}$=−150° CHCl$_3$, (C=1); Literature [α$_{spec}$]$_D^{20}$=−147°.

B. [3aR-(3aα,7aβ)]-Octahydro-1,2,3-trimethyl-1H-1,3,2-benzodiazaphosphole, 2-oxide To a solution of 4.0 g (28.1 mmol, 1 eq.) of Part A diamine and 7.92 mL (56.8 mmol, 2.02 eq) of triethylamine in 64 mL of benzene at RT was added a solution of 3.74 g (28.1 mmol, 1 eq.) of methylphosphonic dichloride in 40 mL of benzene over 40 minutes. The heterogeneous mixture was stirred for 90 minutes at RT and then filtered through a pad of Celite, rinsing well with ethyl acetate. Concentration of the organic solution afforded 5.67 g of a yellow oil. Flash chromatography of the oil on silica gel (100 g), eluting with 7% methanol in ethyl acetate, afforded 4.59 g (81%) of the title compound as a white solid, m.p. 61°–63° C.

TiC Silica gel (10% methanol in ethyl acetate): R$_f$ 0.12.

C. [3aR-(3aα,7aβ)]-Octahydro-1,3-dimethyl-2-[4-(3-phenoxyphenyl)butyl]-1H-1,3,2-benzodiazaphosohole, 2-oxide To a solution of 2.0 g (9.9 mmol, 1 eq.) of Part B compound in 15 mL of THF at −78° C. was added dropwise 4.4 mL (10.9 mmol, 1.1 eq.) of 2.5M n-BuLi in hexane. Addition of the alkyl lithium resulted in a gelatinous mixture to which 5 mL of THF was added. The resulting opaque white solution was stirred for 1 hour at −78° C. A solution of 3.8 g (11.9 mmol, 1.2 eq.) of 3-(3-phenoxyphenyl)propyliodide in 10 mL of THF was then added dropwise over 20 minutes. The reaction was stirred at −78° C. for 2 hours, 0° C. for 1 hour and RT for 19 hours. The reaction was quenched with methanol, diluted with ethyl acetate, washed with water and dried (Na$_2$SO$_4$). Concentration of the organic solution afforded 4.81 g of the crude product as a yellow oil. Flash chromatography of the oil on silica gel (200 g), eluting with 5% methanol in ethyl acetate, afforded 3.78 g (92%) of the title compound as a viscous yellow oil.

TLC Silica gel (10% methanol in ethyl acetate): R$_f$ 0.29.

D. [3aR-[2(R*),3aα,7aβ]]-1-[[(Dimethylamino) thioxomethyl]thio]-4-(3-phenoxyphenyl)butyl]octahydro-1,3-dimethyl-2-1H-1,3,2-benzodiazamhosphole, 2-oxide and E. [3aR-[2(S*),3aα,7β]]-1-[[(Dimethylamino) thioxomethyl]thio]-4-(3-phenoxyphenyl)butyl]octahydro-1,3-dimethyl-2-1-H-1,3,2-benzodiazaphosphole, 2-oxide To a solution of 3.7 g (8.97 mmol, 1 eq) of Part C compound in 60 mL of THF at −75° C. (internal temperature) was added dropwise 3.95 mL (9.87 mmol, 1.1 eq) of 2.5M n-BuLi in hexanes at a rate to keep temperature below −70° C. (15 min). The reaction was stirred at −75° C. for 2 h. The reaction was cooled to −90° C. (liquid nitrogen/ methanol slush) and 2.59 g (10.8 mmol, 1.2 eq) of tetramethylthiuram disulfide was added as a solid in small portions over 20 minutes. The reaction was stirred at −90° C. for 1 hour and then warmed to −70° C. (dry ice/methanol) and stirred for 2 hours. The reaction was quenched by the addition of methanol (5 mL), warmed to RT and diluted with ether. Concentration of the organic solution afforded 6.65 g of a yellow solid-oil mixture which contained title D α-(R) isomer and title E α-(S) isomer in a 1:3 ratio. Flash chromatography on silica gel (200 g), eluting with 2% methanol in ethyl acetate, afforded 0.807 g (17%) of title D α-(R) isomer and 2.66 g (56%) of title E α-(S) isomer, each with >99% d.e. as judged by $^{31}$P NMR.

$^{31}$P NMR(CDCl$_3$, 121 MHz, ref. to 10% H$_3$PO$_4$, 0 ppm): title D α-(R) isomer 41.6 ppm; title E α-(S) isomer 39.3 ppm.

TLC Silica gel (10% methanol in ethyl acetate): For title D α-(R) isomer R$_f$ 0.46; for title E α-(S) isomer R$_f$ 0.37.

(10.% methanol in t-Butyl methyl ether): For title D α-(R) isomer R$_f$ 0.45; for title E α-(S) isomer R$_f$ 0.33.

F. (S)-α-[[(Dimethylamino)thioxomethyl]thio]-3-phenoxybenzenebutanephosphonic acid To a solution of 1.95 g (3.67 mmol, 1 eq) of title E α-(S) isomer in 35 mL of acetonitrile was added 37 mL (110 mmol, 30 eq) of 3N hydrochloric acid. The homogeneous solution was stirred at RT for 13 hours. The reaction was concentrated and the residue was dissolved in 20 mL of water and evaporated. A column of Biorad AG-50W-X8 ion exchange resin, H$^+$ form (22 mL bed volume, 37 meq) was equilibrated initially with water (50 mL), followed by 50% aqueous isopropanol (50 mL). The residual oil was dissolved in 25 mL of 30% aqueous isopropanol and eluted slowly through the resin with 30% aqueous isopropanol followed by evaporation to afford 1.47 g (94%) of the title compound as a clear viscous oil.

[α$_{spec}$]$_D^{20}$+0.8° (c. 10, MeOH)

$^{31}$P NMR (CDCl$_3$, 121 MHz, ref. to 10% H$_3$PO$_4$, 0 ppm): 30.5 ppm.

TLC Silica gel (6:3:1 n-propanol:ammonium hydroxide:water): R$_f$ 0.59.

G. (S)-(−)-3-Phenoxy-α-phosphonobenzenebutanesulfonic acid tripotassium salt

To 1.44 g (3.39 mmol, 1 eq) of Part F α-(S) isomer was added 12 mL of acetic acid and mixture was allowed to stir to effect complete dissolution. A white precipitate formed after 15 minutes. To the heterogeneous reaction was added 1.35 mL of formic acid followed after 5 minutes by 2.08 mL (20.3 mmol, 6 eq) of 30% hydrogen peroxide in water (exothermic:internal temperature increased to 38° C.). The reaction became cloudy after 30 sec and a yellow precipitate became visible within 1 min. The reaction was monitored by reverse phase HPLC. After 7 h, excess peroxide was decomposed by the slow addition of 622 µL (8.48 mmol, 2.5 eq) of dimethyl sulfide (exothermic:internal temperature increased to 40° C.). The reaction was diluted with water, filtered and concentrated. The residue was dissolved in water (25 mL), concentrated, then redissolved in water (10 mL) and the pH of the resulting solution (pH ≈1.95) was brought to pH 12 with 1N potassium hydroxide (12 mL). The basic solution was lyophilized. The lyophilate was dissolved in water and chromatographed on CHP-20P gel (2.5 cm×25 cm) eluting initially with water (1 L) followed by 10% CH$_3$CN in water. Fractions containing product were analyzed by HPLC, then pooled and concentrated to afford a clear waxy residue which was dissolved in water, filtered and lyophilized to afford 1.42 g (82%) of the title compound as a white lyophilate.

TLC Silica gel (6:3:1 n-propanol:ammonium hydroxide:water): R$_f$ 0.21.

$[\alpha_{spec}]_D^{20}$ –9.9° (c. 0.97 H$_2$O)

Chiral HPLC analysis of enantiomeric excess was performed on a ChromTech α-acid glycoprotein (α$_1$-AGP) column, eluted with 85% 0.1M KH$_2$PO$_4$, 15% CH$_3$CN, pH 4.6, in isocratic mode.

For this sample:

ret. time 10.3 min, 99.65% (S)-isomer ret. time 18.8 min, 0.35% (R)-isomer therefore 99.3% enantiomeric excess.

$^1$H NMR (D$_2$O, 300 MHz, ref. to HOD, 4.65 ppm): δ7.25 (dt, J=8,1 Hz, 2H) 7.17 (t, J=7 Hz,1H) 7.02 (t, J=7 Hz,1H) 6.92 (m, 3H) 6.81 (s, 1H) 6.72 (dd, J=8, 2 Hz, 1H) 2.74 (ddt, J=18, 5, 4 Hz, 1H) 2.45 (m, 2H) 1.88–1.62 (m, 4H) ppm.

MS (FAB, + ions): m/z 539 (M+K), 501 (M+H), 463 (M–K +2H).

Anal. Calcd. for C$_{16}$H$_{16}$O$_7$PSK$_3$+0.75 H$_2$O: C, 37.38; H, 3.43; P, 6.02; S, 6.24. Found: C, 37.37; H, 3.44; P, 5.86; S, 6.08

EXAMPLE 176

(R)-(+)-3-Phenoxy-α-phosphonobenzenebutanesulfonic acid, tripotassium salt

A. (R)-α-[[(Dimethylamino)thioxomethyl]thio]- 3-phenoxybenzenebutanephosphonic acid To a solution of 0.32 g (0.60 mmol, 1 eq) of Example 175 Part D α-(R)-isomer in 12 mL of acetonitrile was added 18 mL (18 mmol, 30 eq) of 1N hydrochloric acid. The initially opaque, milky white solution became homogeneous after 2 min and was stirred at RT for 14 h. The reaction was concentrated and the residue was dissolved in methanol and passed through a column of Biorad AG-50W-X8 ion exchange resin, H$^+$ form (60 mL bed volume, 102 meq) which has been equilibrated with water (50 mL), 0.1N HCl (100 mL), water (100 mL pH of eluant ~7) and 10% methanol in water prior to use. The column was eluted with methanol to afford 0.18 g (72%) of title compound as a clear viscous oil.

$[\alpha_{spec}]_D^{20}$ –2.3° (c. 2.6, MeOH)

$^{31}$P NMR (CD$_3$OD, 121 MHz, ref. to 10% H$_3$PO$_4$, 0 ppm): 24.2 ppm.

TLC Silica gel (6:3:1 n-propanol:ammonium hydroxide:water): R$_f$ 0.56

B. (R)-(+)-3-Phenoxy-α-phosphonobenzenebutanesulfonic acid, tripotassium salt

To a solution of 0.18 g (0.59 mmol, 1 eq) of Part A compound in 40 mL of 98% formic acid was added 2.16 mL (21.2 mmol, 50 eq) of 30% hydrogen peroxide in water. The reaction became cloudy after 0.5 min and a precipitate formed after ~1 min. After 45 min, the reaction was concentrated and the residue was dissolved in water. The solution was cooled to 0° C. and the excess peroxide was decomposed by the slow addition of 25 mL of 1N potassium sulfite. The solution was again concentrated and the residue was coevaporated twice with water. The residue was dissolved in 10 mL of water and the pH of the solution (pH ~3) was brought to pH 12 with 1N potassium hydroxide. The solution was then chromatographed on CHP-20P gel (2.5 cm×25 cm) eluting with water. Fractions containing pure product were pooled and concentrated to afford a clear waxy residue which was dissolved in water, filtered and lyophilized to afford 132 mg (56%) of title compound as a white lyophilate.

TLC Silica gel (6:3:1 n-propanol:ammonium hydroxide:water): R$_f$ 0.21.

$[\alpha_{spec}]_D^{20}$ +9.5° (c. 0.89 H$_2$O)

Chiral HPLC analysis of enantiomeric excess was performed on a ChromTech α-acid glycoprotein (α$_1$-AGP) column, eluted with 85% 0.1M KH$_2$PO$_4$, 15% CH$_3$CN, pH 4.6 in an isocratic mode.

For this sample:

ret. time 17.8 min, 97.77% (R)-enantiomer ret. time 10.9 min, 2.23% (S)-enantiomer therefore 95.5% enantiomeric excess.

$^1$H NMR (D$_2$O, 300 MHz, ref. to HOD, 4.65 ppm): δ7.25 (t, J=8 Hz, 2H) 7.17 (t, J=7 Hz, 1H) 7.03 (t, J=7 Hz, 1H) 6.92 (m, 3H) 6.81 (s, 1H) 6.72 (dd, J=8, 2 Hz, 1H) 2.72 (ddt, J=18, 5, 4 Hz, 1H) 2.47 (m, 2H) 1.95–1.56 (m, 4H) ppm.

IR (KBr): 3412 (br), 3071, 2936, 2866, 1661, 1489, 1204, 1076, 966 cm$^{-1}$.

MS (FAB, + ions): m/z 539 (M+K), 501 (M+H), 463 (M–K+2H).

Anal. Calcd for C$_{16}$H$_{16}$O$_7$PSK$_3$+3.33 H$_2$O: C, 34.28; H, 4.07; P, 5.52; S, 5.72 Found: C, 34.28; H, 3.99; P, 5.14; S, 5.79.

EXAMPLE 177

[3aR-[2(R*),3aα, 7a β]]-[1-[[(Dimethylamino)thioxomethyl]thio]-4-(3-phenoxyphenyl)butyl]octahydro-1,3-dimethyl-2-1H-1,3,2-benzodiazaphosphole, 2-oxide and

[3aR-[2(S*), 3aα, 7aβ]]-[1-[[(Dimethylamino)thioxomethyl]thio]-4-(3-phenoxyphenyl)butyl]-octahydro-1,3-dimethyl-2-1H-1,3,2-benzodiazaphosphole, 2-oxide A. [3aR-(3aR, 7aβ)]-2-[[[(Dimethylamino)thioxomethyl]thio]]octahydro-1,3-dimethyl- 1H-1,3,2-benzodiazaphosphole, 2-oxide To a stirred solution of 502 mg (2.48 mmol) of Example 175 Part B compound in 10 mL of THF under argon at –78° C. was added 1.09 mL (2.73 mmol) of a 2.5N solution of n-butyllithium in hexanes dropwise over 10 minutes. After stirring at –78° C. for one hour, 87 mg (2.73 mmol) of sulfur was added via a solid addition tube, and temperature of the reaction was raised to –20° C. over 1 hour. The reaction mixture was treated with 0.93 mL (6.69 mmol) of triethylamine and 276 mg (2.23 mmol) of dimethylthiocarbamoyl chloride at –20° C., stirred for 5 minutes, then allowed to warm to room temperature. The mixture was diluted with ether and washed with water. The aqueous layer was back extracted with ether and the organics were combined, dried and concentrated to afford 558 mg of an oil. The crude product was purified by flash chromatography on silica gel (50 g) eluted with 96:4 ethyl acetate/methanol. Pure fractions were combined and concentrated to yield 337 mg (47%) of title compound as a clear oil.

TLC (Silica gel, 9:1 ethyl acetate/methanol) R$_f$=0.35.

MS (CI, + ions) 332 (M+H).

$^{31}$P NMR (CDCl$_3$, 121 MHz) 37.7 ppm.

B. 3aR-[2(R*),3aα, 7aβ]]-[1-[[(Dimethylamino) thioxomethyl]thio]-4-(3-phenoxyphenyl) butyl]octahydro-1,3-dimethyl-2-1H-1,3,2-benzodiazaphosphole, 2-oxide To a stirred solution of 89 mg (0.28 mmol) of Part A compound in 1 mL of THF under argon at –78° C. was added 122 µL (0.31 mmol) of a 2.5N solution of n-butyllithium in hexanes dropwise over 10 minutes. After 90 minutes at –78° C., 0.096 mL (0.55 mmol) of hexamethylphosphoramide was added, followed by 98 mg (0.30 mmol) of 3-(3-phenoxyphenyl)propyliodide in 1 mL of THF. After 28 hours at –78° C., the reaction was quenched with methanol and allowed to reach room temperature. The mixture was concentrated, then dissolved in ether and washed with water and brine, dried over sodium sulfate, and concentrated to afford 129 mg of a yellow oil. The crude product was purified by flash chromatography on silica gel (15 g) eluted with 98:2 ethyl acetate/methanol. Fractions (#11-19) containing pure material were combined and concentrated to yield 50 mg (34%) of title α-(R) isomer as a clear oil.

TLC (Silica gel, 9:1 ethyl acetate/methanol) $R_f$=0.45.

C. [3aR-[2(S*),3aα, 7aβ]]-[1-[[(Dimethylamino) thioxomethyl]thio]-4-(3-phenoxyphenyl) butyl]octahydro-1,3-dimethyl-2-1H- 1,3,2-benzodiazaphosphole, 2-oxide Fractions #21–30 were combined and concentrated to provide 10 mg (7%) of title isomer as a clear oil.

TLC (Silica gel, 9:1 ethyl acetate/methanol) $R_f$=0.39.

MS (CI, + ions) 532 (M+H).

$^{31}$P NMR (CDCl$_3$, 121 MHz) 39.3 ppm.

The Parts B and C compounds may then be separated and subjected to acid hydrolysis and then oxidation and salt formation as described in Example 175 to form the title compound of Examples 175 and 176.

EXAMPLE 178

[3aR-[2(R*),3aα, 7a β]]-[1-[[(Dimethylamino)thioxomethyl]thio]-4-(3-phenoxyphenyl)butyl]octahydro-1,3-dimethyl-2-1H-1,3,2-benzodiazaphosphole, 2-oxide A. [3aR-(3aα, 7aβ)]-Octahydro-1,3-dimethyl-1H-1,3,2-benzodiazaphosphole, 2-oxide To a stirred solution of 497 mg (3.49 mmol) of Example 175 Part A (R,R)-diamine and 1.07 mL (7,89 mmol) of triethylamine in 25 mL of tetrahydrofuran (THF) under argon at −78° C. was added dropwise over 5 minutes 335 μL (3.84 mmol) of phosphorus trichloride. The cloudy solution was allowed to warm to room temperature and was filtered under argon through a pad of celite and magnesium sulfate. The filtrate was chilled to −78° C. under argon and treated with 536 μL of triethylamine and 63 μL (3.49 mmol) of water. The mixture was allowed to warm to room temperature and was filtered under argon through a pad of celite and magnesium sulfate and concentrated to provide 544 mg (82%) of title compound as a yellow oil.

$^{31}$P NMR (CDCl$_3$, 121 MHz) δ 27.3 ppm.

B. [3aR-[2(R*), 3aα, 7aβ)]-Octahydro-1,3-dimethyl-2-[4-(3-phenoxyphenyl)-1-[(trimethylsilyl)oxy]butyl]-1H-1,3,2-benzodiazaphosphole, 2-oxide C. [3aR-[2(S*),3aα, 7aβ)]-Octahydro-1,3-dimethyl-2-[4-(3-phenoxyphenyl)-1-[(trimethylsilyl)oxy]butyl]-1H-1,3,2-benzodiazaphosphole, 2-oxide A solution of 544 mg (2.89 mmol) of Part A compound and 534 mg (2.22 mmol) of 3-phenoxybenzenebutanal (Example 180 Part B) in 5 mL of methylene chloride under argon was treated with 814 μL (3.33 mmol) of bis[trimethylsilyl] acetamide at room temperature and stirred for 17 hours. The reaction was quenched with water and extracted with methylene chloride (3×35 mL). The combined organics were washed with brine, dried (sodium sulfate), and concentrated to provide 875 mg of a yellow oil. The crude product mixture was purified by flash chromatography on silica gel (80 g) eluted with 2 L of 9:1 hexane/acetone followed by 2 L of 85:15 hexane/acetone and 1.5 L of 8:2 hexane/acetone. Fractions containing the more polar α-(R) isomer (title B) were combined and concentrated to yield 135 mg (14%) of title B compound as a clear oil.

TLC Silica gel (1:1 hexane/acetone) $R_f$=0.29.

$^{31}$P NMR (CDCl$_3$, 121 MHz) δ41.1 ppm.

Fractions #85–96 were combined and concentrated to yield 112 mg (12%) of the pure Part C α-(S)isomer.

TLC Silica gel (1:1 hexane/acetone) $R_f$=0.31.

$^{31}$P NMR (CDCl$_3$, 121 MHz) δ27.3 ppm.

D. [3aR-[2(R*), 3aα, 7aβ)]-Octahydro-2-[1-hydroxy-4-(3-phenoxyphenyl)butyl]-2,3-dimethyl- 1H-1,3,2-benzodiazaphosphole, 2-oxide To a stirred solution of 125 mg (0.20 mmol) of Part B isomer in 1 mL of THF was added 0.29 mL (0.29 mmol) of a 1.0N solution of tetrabutylammonium fluoride in THF. After stirring for three hours at room temperature, the mixture was diluted with ether, washed with saturated sodium bicarbonate, brine, dried (sodium sulfate), and concentrated to provide 104 mg of a white solid. The crude product was purified by flash chromatography on silica gel (15 g) eluted with 97.5:2.5 ethyl acetate/methanol. Clean fractions (#41–71) were combined and concentrated to yield 100 mg (93%) of title compound as a white solid. m.p. 122°–125° C.

TLC Silica gel (1:1hexane/acetone) $R_f$=0.44.

$^{31}$P NMR (CDCl$_3$, 121 MHz) δ41.1 ppm.

E. [3aR-[2(R*), 3aα, 7aβ)]-[1-[[(Dimethylamino) thioxomethyl]thio]-4-(3-phenoxyphenyl) butyl]octahydro-1,3-dimethyl-2-1H-1,3,2-benzodiazaphosphole, 2-oxide To a stirred suspension of 56 mg (0.13 mmol) of Part D compound, 30 mg (0.09 mmol) of dimethyldithiocarbamic acid, zinc salt, and 47 mg (0.18 mmol) of triphenylphosphine in 1 mL of THF at 0° C. under argon was added a solution of 52 μL (0.27 mmol) of diisopropyl azodicarboxylate in 0.5 mL of THF over fifteen minutes. The reaction was stirred at room temperature for 45 hours, then diluted with ether and quenched with water. The organics were washed with brine, dried (sodium sulfate), and concentrated to provide 150 mg of an oil. The crude product was purified by flash chromatography on silica gel (15 g) eluded with ethyl acetate. Pure fractions were combined and concentrated to yield 15 mg (21%) of title compound as a film, the α(R)-isomer.

TLC Silica gel (1:1 hexane/acetone) $R_f$=0.20. Note: This is identical to Example 175 Part D compound and is the precursor to the Example 176 compound.

MS (C.I, + ions) 532 (M+H).

$^{31}$P NMR (CDCl$_3$, 121 MHz) δ41.2 ppm.

EXAMPLE 179

(S)-(−)-3-Phenoxy-α-phosphonobenzenebutanesulfonic acid, tripotassium salt

A. [3aR-(3aα, 7aβ)]-2-Chlorooctahydro-1,3-dimethyl-1H-1,3,2-benzodiazaphosphole, 2-oxide A solution of 4.72 g (33.20 mmol) of Example 175 Part A diamine and 12.63 g (125.0 mmol) of triethylamine in 50 mL of toluene at 0° C. was treated with 5.00 g (33.20 mmol) of phosphorus oxychloride dropwise over 15 min. The reaction mixture was stirred for 10 min. at 0° C. and warmed to RT. After 3 h the solids were filtered off and the filtrate concentrated to a slurry. The slurry was purified by flash chromatography (100 g of silica gel) eluting with 15:85 acetone/toluene to provide 6.50 g (88%) of title chloride as a low melting solid.

TLC Silica gel (1:4 acetone/toluene) $R_f$=0.30.

$^{1}$H NMR (CDCl$_3$, 300 MHz): δ2.85 (td, 1H, J=10.8, 3.0 Hz) 2.67 (d, 3H, J=10.0 Hz) 2.55 (d+m, 4H, J=18.0 Hz) 2.05 (m, 2H) 1.85 (m, 2H) 1.35 (m, 4H) ppm.

$^{13}$C NMR (CDCl$_3$, 75.6 MHz): δ63.5 (d, J=7.0 Hz) 62.5 (d, J=10.0 Hz) 28.0 27.5 (d, J=7.0 Hz) 27.0 (d, J=7.0 Hz) 24.0 23.9 ppm.

$^{31}$P NMR (CDCl$_3$, 121.7 MHz): δ36.6 ppm

B. [3aR-(3aα, 7aβ)]-Octahydro-1,3-dimethyl-1H-1,3,2-benzodiazaphosphole-2-methanesulfonic acid, ethyl ester, 2-oxide To a rapidly stirred solution of 6.20 g (50.0 mmol) of ethyl methanesulfonate in 150 mL of THF at −73 °C. (internal temperature) was added 20 mL (50 mmol) of 2.5M n-butyllithium dropwise over 20 min (The internal temperature was not allowed to rise above −69° C. throughout the addition of n-BuLi). After an additional 30 min., 5.56 g (25.0 mmol) of freshly prepared Part A chloride in 25 mL of THF was added at a rate to keep the solution temperature below −69° C. The reaction mixture was stirred for 0.3 h at −73° C. and for 3 h at −30° C. The reaction mixture was poured into 250 mL of a rapidly stirring mixture of 1:1 saturated aqueous $NaHCO_3$ solution/ethyl acetate. The mixture was partitioned between ethyl acetate and water (3×75 mL). The organic extracts were dried ($Na_2SO_4$) and concentrated to an oil. The oil was purified by flash chromatography (200 g silica gel) eluting with methylene chloride (600 mL) followed by 93:7 dichloromethane/isopropanol (1000 mL) to provide 6.60 g (85%) of title compound as a low melting solid.

TLC Silica gel (1:9 2-propanol/dichloromethane) $R_f$=0.58.

IR (KBr) 2947, 2878, 1478, 1451, 1348, 1258, 1236, 1215, 1165, 1123, 1026, 1005, 918 $cm^{-1}$.

Mass Spec (CI—$NH_3$, + ions) m/e 638 (2M+$NH_4$), 621 (2M+H), 328 (M+$NH_4$), 311 (M+H).

Anal. Calc'd for $C_{11}H_{23}N_2O_4PS$: C, 42.57; H, 7.47; N, 9.03; P, 9.89; S, 10.33 Found: C, 42.95; H, 7.55; N, 9.10; P, 9.81; S, 10.59.

$[\alpha]_D^{20}$=−79° $CHCl_3$, (c=1)

$^1$H NMR ($CDCl_3$, 300 MHz): δ4.35 (q, 2H, J=6.9 Hz) 3.82 (t, 1H, J=14.1 Hz) 3.73 (t, 1H, J=15.0 Hz) 2.93 (td, 1H, J=9.0, 2.0 Hz) 2.80 (td, 1H, J=9.0, 2.0 Hz) 2.67 (d, 3H, J=8.0 Hz) 2.63 (d, 3H, J=8.0 Hz) 2.05 (m, 2H) 1.85 (m, 2H) 1.40 (t, 3H, J=7.0 Hz) 1.30 (m, 4H) ppm.

$^{13}$C NMR ($CDCl_3$, 75.6 MHz): δ67.0 64.3 (d, J=6.8 Hz) 62.8 (d, J=9.0 Hz) 46.3 (d, J=102.0 Hz) 28.7 (d, J=2.0 Hz) 27.8 (d, J=10.5 Hz) 27.7 (d, J=8.3 Hz) 27.4 (d, J=4.5 Hz) 24.0 23.9 ppm.

$^{31}$P NMR ($CDCl_3$, 121.7 MHz): δ26.7 ppm

C. [3aR-(3aα, 7aβ)]-Octahydro-1,3-dimethyl-1H-1,3,2-benzodiazaphosphole-2-methanesulfonic acid, tetrabutylammonium salt, 2-oxide A suspension of 5.00 g (16.12 mmol) of Part B compound and 6.02 g (16.29 mmol) of tetrabutylammonium iodide in 30 mL of anhydrous THF at RT was stirred for 10 min. at 0° C. and warmed to RT. After 30 h the clear solution was concentrated to a thick oil. The oil was dried under vacuum (0.009 mm Hg) overnight. The honey-like oil was used without further purification.

$^1$H NMR ($CD_3OD$, 300 MHz): δ3.55 (t, 1H, J=14.1 Hz) 3.50 (t, 1H, J=14.1 Hz) 3.30 (m, 8H) 3.00 (m, 1H) 2.67 (m, 1H) 2.62 (d, 3H, J=10.0 Hz) 2.58 (d, 3H, J=10.0 Hz) 2.05 ($t_{br}$, 2H, J=10.0 Hz) 1.85 (m, 2H) 1.70 (m, 8H) 1.40 (m, 12H) 1.05 (t, 12H, J=8.0 Hz) ppm.

$^{13}$C NMR ($CDCl_3$, 75.6 MHz): δ64.1 (d, J=6 Hz) 63.0 (d, J=6.8 Hz) 58.6 48.4 (d, J=107 Hz) 29.0 (d, J=2.0 Hz) 28.9 (d, J=4.5 Hz) 27.9 (d, J=10 Hz) 24.2 (d, J=18 Hz) 24.0 23.9 19.6 13.6 ppm.

$^{31}$P NMR ($CD_3OD$, 121.7 MHz): δ35.4 ppm

Mass Spec (FAB, + ions) m/e 242 ($Bu_4N$).

Mass Spec (high res., FAB, − ions)

Calcd for $C_9H_{18}O_4N_2PS$: 281.0725 Found: 281.0717

$[\alpha]_D^{20}$=−33.8° $CH_3OH$ (c=1)

D. (S)-(−)-3-Phenoxy-α-phosphonobenzenebutanesulfonic acid, tripotassium salt

To a slurry of 3.29 g (6.29 mmol) of Part C compound in 20 mL of dry THF at −90° C. (internal temperature) under argon was added 3.0 mL (7.50 mmol) of 2.5M n-BuLi in hexanes to give a yellow solution. After 0.5 h at −90° C. the solution was treated with 2.10 g (6.29 mmol) of 3-(3-phenoxyphenyl)propyl iodide in 6 mL of THF at such at rate to keep the internal temperature below −85° C. The reaction mixture was stirred at −90° C. for 3 h when it was gradually warmed to −74° C. overnight. The mixture was quenched with 360 uL of acetic acid in 3 mL of THF and allowed to warm to RT. The mixture was concentrated and acidified with 12 mL of 2M HCl solution (24 mmol). The reaction mass was extracted with hexane, the aqueous layer was heated to 80° C. for 3 hours and then diluted with 2-propanol until a clear solution resulted. After heating an additional hour the solvent was evaporated and the residue pumped (=0.5 mm pressure) for 0.5 h. The remainder was dissolved in 30 mL (30 mmol) of 1M KOH solution and freeze dried to provide a cream colored solid. The solid was diluted with water and eluted through 24 g of AG50X8 (63 meq, $K^+$ form) ion exchange resin. Final purification was accomplished by MPLC on a column of CHP20P gel (125 mL) eluting with water (200 mL) followed by a gradient created by the gradual addition of 500 mL of acetonitrile to a reservoir of 500 mL of water. Approximately 10 mL fractions were collected. Pure fractions were pooled, the acetonitrile was removed under reduced pressure and the aqueous solution lyophilized to provide 1.48 g (47%) of title compound as a white lyophilate.

TLC Silica gel (6:3:1 propanol/ammonium hydroxide/water) $R_f$=0.2

Chiral HPLC analysis of enantiomeric excess was performed on a ChromTech α-acid glycoprotein (α1-AGP) column: isocratic 85% 0.1M $KH_2PO_4$/15% $CH_3CN$, (pH 4.6) in isocratic mode.

For this sample title compound (S)-isomer: retention time ≈10.3 min. 94%

Example 176 compound (R)-isomer: retention time ≈19.0 min. 6%

Therefore, the enantiomeric excess is 88%.

Anal. Calc'd for $C_{16}H_{16}O_7PSK_3$+2.2 $H_2O$: C, 35.54; H, 3.81; P, 5.73; S, 5.93 Found: C, 35.54; H, 3.98; P, 5.42; S, 6.30.

EXAMPLE 180

(R)-(+)-3-Phenoxy-α-phosphonobenzenebutanesulfonic acid, tripotassium salt

A. 4-(3-Phenoxyphenyl)butyl alcohol

A (1) 3-Phenoxybenzyl alcohol

Sodium borohydride (961 mg, 25.3 mmol) was added in one portion to a solution of 3-phenoxybenzaldehyde (10.0 g, 50.5 mmol) in methanol (150 mL) at RT under argon. Once the bubbling ceased, the reaction was stirred at RT for 5 min, then adjusted to pH 6 with glacial acetic acid (about 1 mL). The reaction was concentrated in vacuo to give a residue, which was partitioned between EtOAc (200 mL) and saturated $NaHCO_3$ (50 mL). The organic layer was washed with water and brine (50 mL each), then dried over $MgSO_4$. Evaporation gave title compound (10.1 g, 100%) as a tan oil.

A (2) 3-Phenoxybenzylbromide

Phosphorus tribromide solution (11.0 mL, 1M in $CH_2Cl_2$, 11.0 mmol) was added over 5 min to a solution of Part 1(A) alcohol (2.00 g, 10.0 mmol) in $CH_2Cl_2$ (30 mL) under argon at RT. The yellow reaction was stirred at RT for 10 min, diluted with $CH_2Cl_2$ (100 mL), and washed with saturated $NaHCO_3$ (2×30 mL). The organic layer was dried over MgSO$_4$. Evaporation gave a pale yellow oil, which was purified by flash chromatography on silica gel (75 g) eluting with 10:90 CH$_2$Cl$_2$/hexane to provide title bromide (1.57 g, 60%) as a yellow oil.

A (3) 4-(3-Phenoxyphenylbutyl alcohol

A Grignard solution of ClMg (CH$_2$)$_3$OMgCl (19.2 mL, 0.6M in THF, 11.5 mmol) was added to a mixture of Part A(2) bromide (1.51 g, 5.74 mmol) and copper(I) iodide (11 mg, 0.057 mmol) in THF (10 mL) at 0° C. under argon over a period of 5 min. The dark green reaction was stirred at 0° C. for 30 min, then quenched by dropwise addition of 2-propanol (2 mL). The reaction was diluted with diethyl ether (100 mL) and washed with 1N KHSO$_4$ (2×50 mL). The aqueous layers were back-extracted with diethyl ether (20 mL). The combined organic layers were dried over MgSO$_4$. Evaporation gave a pale yellow oil, which was purified by flash chromotography on silica gel (100 g) eluting with 30:70 EtOAc/hexane to provide title alcohol (1.10 g, 79%) as a colorless oil.

B. 3-Phenoxybenzenebutanal

To a stirred solution of 3.4 mL (48.6 mmol) of methyl sulfoxide in 50 mL of CH$_2$Cl$_2$ under argon at –78° C. was added 3.9 mL (44.5 mmol) of oxalyl chloride dropwise over 5 min. The reaction was stirred at –78° C. for 0.5 h at which time 9.8 g (40.4 mmol) of Part A alcohol in 15 mL of CH$_2$Cl$_2$ was added dropwise. The reaction was stirred at –78° C. for 20 min, warmed to –30° C. for 5 min, cooled back down to –78° C. and treated with 22.6 mL (162 mmol) of triethylamine. The reaction gradually warmed to –20° C. and was quenched with 150 mL of water. The mixture was diluted with a 1:1 mixture of hexanes/ethyl acetate and the layers were separated. The organics were dried over Na$_2$SO$_4$ and evaporated to dryness to provide 8.8 g (91%) of title compound as a pale yellow oil.

TLC Silica gel (70:30 hexanes/ethyl acetate) R$_f$=0.40.

C. 4,6-Dimethyl-2-[3-(3-phenoxyphenyl)propyl]- 1,3-dioxane

To a solution of 5.6 g (23.33 mmol) of Part B aldehyde in 25 mL of benzene was added 2.4 g (23.33 mmol) of (2S, 4S)-(+)-pentanediol and a 50 mg (0.36 mol) of p-toluenesulfonic acid. The reaction was refluxed for 2 h using a Dean-Stark trap for the azeotropic removal of water. The reaction was diluted with ethyl acetate, washed with sat. NaHCO$_3$ solution, water, dried over MgSO$_4$ and evaporated to provide a crude yellow oil. Flash chromatography was performed on 300 g of silica gel eluting with 90:10 hexanes/ethyl acetate. Pure product fractions were combined and evaporated to provide 5.5 g (72%) of title compound as a colorless oil.

TLC Silica gel (90:10 hexanes/ethyl acetate) R$_f$=0.21.
[α]$_D^{20}$–13.1° (c=1, CH$_2$Cl$_2$)
MS (CI—NH$_3$, + ions) m/e 344 (M+NH$_4$), 326 (M).

D. [R-[R*[R*(R*)]]]-α-(3-Hydroxy-1-methylbutoxy)-3-phenoxybenzenebutanephosphonic acid, diethyl ester (Yokomatsu, T., Shibuya, S., Tetrahedron *Asymmetry* 1992, 3, 377-8).

To a solution of 2.9 mL (16.87 mmol) of triethyl phosphite in 7 mL of CH$_2$Cl$_2$ at –78° C. under argon was added dropwise 1.5 mL (13.50 mmol) of titanium (IV) chloride. The resulting orange solution was stirred at –78° C. for 0.5 h at which time 2.2 g (6.75 mmol) of Part C compound in 5 mL of CH$_2$Cl$_2$ was added dropwise over 0.5 h (internal temperature of the reaction maintained at –68° C.). The reaction was stirred for 48 h at –78° C. at which time the reaction was poured into 200 mL of a 1:1 mixture of NaHCO$_3$/ethyl acetate and extracted. The organics were washed with water, brine, dried (MgSO$_4$) and evaporated to provide 2.0 g of a crude oil. Flash chromatography was performed on 200 g of silica gel eluting with 4:1 dichloromethane/acetone. Pure product fractions were pooled and evaporated to provide 1.5 g (48%) of title compound as a colorless oil.

TLC Silica gel (4:1 dichloromethane/acetone) R$_f$=0.24.
[α]$_D^{20}$+15.8 (c=1 CH$_2$Cl$_2$)
IR (Film, CH$_2$Cl$_2$) 3410, 3040, 2969, 2870, 1584, 1487, 1447, 1385, 1250, 1215, 1163, 1047 cm$^{-1}$.
$^{31}$P NMR (CDCl$_3$, 121 MHz, ref. to 10% H$_3$PO$_4$, 0 ppm): 24.20 ppm.
HRMS (EI, + ions) m/z Calculated for C$_{25}$H$_{37}$O$_6$P: M$^+$464.2328 Found: 464.2316

E. (R)-α-Hydroxy-3-phenoxybenzenebutanephosonic acid, diethyl ester

To a solution of 3 mL (6.00 mmol) of 2.0M oxalyl chloride in CH$_2$Cl$_2$ in 3.5 mL of CH$_2$Cl$_2$, under argon at –70° C., was added dropwise 535 μL (7.54 mmol) of DMSO (exothermic). This mixture was stirred at –70° C. for 15 min at which time 1.4 g (3.02 mmol) of Part D compound in 5 mL of CH$_2$Cl$_2$ was added dropwise. The reaction was stirred at –70° C. for 1 h, treated with 1.7 mL of triethylamine and allowed to warm to RT. The reaction was quenched with water and diluted with a 1:1 mixture of hexanes/ethyl acetate. The organics were dried (MgSO$_4$) and evaporated to provide 1.4 g of a crude oil. The crude oil was treated with 14 mL of dioxane, 70 mg (0.37 mmol, 5%) of p-toluenesulfonic acid, 1.4 mL of water and refluxed for 0.5 h then cooled to RT. The mixture was diluted with a 1:1 mixture of water/NaHCO$_3$ and extracted 3 times with CH$_2$Cl$_2$. The organics were dried (MgSO$_4$) and evaporated to provide 1.2 g of a pale yellow oil. Flash chromatography was performed on 100 g of silica gel eluding with 4:1 dichloromethane/acetone. Pure product fractions were combined and evaporated to provide 690 mg (60%) of title compound as a colorless oil.

[α]$_D^{20}$–5.9° (c=1, CHCl$_3$)
TLC Silica gel (4:1 dichloromethane/acetone) R$_f$=0.23.
IR (Film, CH$_2$Cl$_2$) 3306, 2982, 1584, 1485, 1445, 1385, 1250, 1215, 1163, 1142, 1096, 1051, 1026, 966 cm$^{-1}$.
$^1$H (300 MHz, CDCl$_3$): δ7.30–6.70 (m, 9H) 4.15 (m, 4H) 3.95 (m, 1H) 3.87 (m, 1H) 2.61 (m, 2H) 1.95 (m, 1H) 1.70 (m, 3H) 1.30 (t, 6H, J=7.1 Hz) ppm.
$^{13}$C NMR (75 MHz, CDCl$_3$) δ157.2, 157.0, 144.1, 129.6, 129.4, 123.3, 122.9, 118.9, 118.6, 116.2, 67.5 (d, J=161 Hz), 62.6 (d, J=6.8 Hz), 62.4 (d, J=6.8 Hz), 35.2, 30.8, 27.2 (d, J=12.8 Hz), 16.4 (d, J=4.5 Hz) ppm.
$^{31}$P NMR (121 MHz, CDCl$_3$, ref. to 10% H$_3$PO$_4$, 0 ppm): 25.28 ppm.
HRMS (FAB, + ions) m/z Calculated for C$_{20}$H$_{28}$O$_5$P: (M+H)$^+$=379.1675 FOUND: 379.1692
Anal. Calcd. for C$_{20}$H$_{27}$PO$_5$+0.50 mol H$_2$O. Effective MW=387.40. C, 62.00; H, 7.28; P, 7.99 Found: C, 62.00; H, 7.05; P, 8.13.

F. (R)-α-[[(Dimethylamino)thioxomethyl]thio]- 3-phenoxybenzenebutaneohosphonic acid To a stirred slurry of 415 mg (1.10 mmol) of Part E compound, 585 mg (2.23 mmol) of triphenylphosphine and 252 mg (0.82 mmol) of dimethyldithiocarbamic acid, zinc salt, in 3 mL of THF at 0° C. under argon was added 446 mg (2.21 mmol) of diisopropyl diazodicarboxylate in 2 mL of THF over the course of 20 minutes. The resulting light yellow solution was allowed to warm to room temperature and stirred for 16 hours. The reaction mixture was then evaporated and immediately purified by flash chromatography (5×15 cm column, eluting with 1:3 ether/dichloromethane). Fractions containing both the product and an impurity were collected, concentrated and re-chromatographed (5×15 cm column, 85:15 ethyl acetate/hexane). The resulting yellow oil still contained ca. 8–10% of diisopropyl dicarbazide as an impurity. The yield of title compound was 490 mg (82% of 91% pure material).

$[\alpha]_D^{20}$=24.5° (c=0.99, CHCl$_3$)

G. (R)-(+)-3-Phenoxy-α-phosphonobenzenebutanesulfonic acid, tripotassium salt

To a stirred solution of 410 mg (0.851 mmol) of Part F compound in 3 mL of CH$_2$Cl$_2$ at room temperature under argon was added 0.7 mL (5.3 mmol) of bromotrimethylsilane. The nearly colorless solution was stirred for 16 hours and then evaporated at less than 25° C. The residue was dissolved in 10 mL of dry methanol and stirred for 1 hour. Re-evaporation gave 358 mg (99%) of the diacid as a colorless glass.

To a solution of 0.326 g (0.77 mmol, 1 eq) of the diacid in 50 mL of 98% formic acid was added 4.2 mL (38 mmol, 50 eq) of 30% hydrogen peroxide in water. The reaction became cloudy after 0.5 min and a precipitate formed after ~2 min. After 1 h, the reaction was cooled to 0° C. and the excess peroxide was decomposed by the slow addition of 40 mL of 1N potassium sulfite. The solution was concentrated and the residue was coevaporated twice with water. The residue was dissolved in 10 mL of water and the pH of the solution (pH ~3) was brought to pH 12 with 1N potassium hydroxide. The solution was then chromatographed on CHP-20P gel (2.5 cm×25 cm) eluting with water. Fractions containing product were analyzed by HPLC, then pooled and concentrated to afford a clear waxy residue which was dissolved in water, filtered and lyophilized to afford 201 mg (48%) of title compound.

TLC Silica gel (6:3:1 n-propanol:ammonium hydroxide:water): $R_f$ 0.21.

Chiral HPLC analysis of enantiomeric excess was performed on a ChromTech α-acid glycoprotein ($\alpha_1$-AGP) column, eluted with 85% 0.1M KH$_2$PO$_4$, 15% CH$_3$CN, pH 4.6 in isocratic mode.

For title compound: ret. time 18.5 min, 98.95% (R)-enantiomer ret. time 11.2 min, 1.05% (S)-enantiomer therefore 97.9% enantiomeric excess of the (R)-isomer.

Anal. Calc'd for C$_{16}$H$_{16}$O$_7$PSK$_3$+2.5 H$_2$O: C, 35.19; H, 3.88; P, 5.67; S, 5.87 Found: C, 35.19; H, 3.54; P, 5.32; S, 6.27.

EXAMPLE 181

(S)-(−)-3-Phenoxy-α-phosphonobenzenebutanesulfonic acid, 1-adamantanamine (1:2) salt A sample of the (R)-(−)-trisalt (94:6, (S):(R)) prepared in Example 179 (70 mg, 0.14 mmol) was stirred with 3 g of Ag50-X8 ion exchange resin (7.5 meq, H* form) for 1 h in 5 mL of water and 3 mL of methanol. The mixture was slowly eluted through an additional column of Ag50-X8 ion exchange resin (1 g, 2.5 meq, H$^+$ form) with 1:1 methanol/water. Approximately 3 mL fractions were collected. Fractions #2 to 7 were pooled, the methanol was removed under reduced pressure and the aqueous solution lyophilized to provide 54 mg (100%) of the free acid form of the title salt as a thin film.

The free acid (54 mg, 0.14 mmol) in 3 mL of a 1:1 methanol/water solution was treated with 39 mg (0.28 mmol, 2 eq) of adamantanamine and the mixture stirred for 0.5 h. The mixture was concentrated to a white solid. The solid was recystallized from hot water and 2-propanol. The white granules were collected to yield 79 mg (85 %) of title salt as a 97:3 mixture of (S):(R) enantiomers. The recrystallization procedure was repeated to provide 66 mg (85 %) of title salt, as a white solid, mp 248°–252° C. The two recystalizations from hot 2-propanol/water improved the ratio of (S):(R) enantiomers from 94:6 to 98:2 determined by HPLC as described on the α-acid glycoprotein column.

TLC Silica gel (6:3:1 n-propanol/conc. ammonia/water) $R_f$=0.30.

IR (KBr) 3426, 3086, 3065, 3036, 2915, 2855, 1609, 1582, 1485, 1233, 1215, 1175, 1022, 882 cm$^{-1}$.

$^1$H NMR (CD$_3$OD, 400 MHz): δ7.30 (t, 2H, J=8.1 Hz) 7.20 (t, 1H, J=8.0 Hz) 7.07 (t, 1H, J=6.2 Hz) 6.95 (m, 3H) 6.86 (s, 1H) 6.73 (dd, 1H, J=8.5, 2.5 Hz) 3.05 (dt, 1H, J=18.0, 6.2 Hz) 2.65 (m, 2H) 2.15 (s+m, 8H) 2.00 (m, 2H) 1.90 (s, 12H) 1.75 (d, 6H, J=12.0 Hz) 1.68 (d, 6H, J=12.0 Hz) ppm.

Mass Spec (FAB, + ions) m/e 689 (M+H); (FAB, − ions) m/e 385 (M−2 (C$_9$H$_{17}$N)+H).

Anal. Calc'd for C$_{36}$H$_{53}$O$_7$N$_2$PS+1.00 H$_2$O: C, 61.17; H, 7.84; N, 3.96; P, 4.38; S, 4.54. Found: C, 61.26; H, 7.90; N, 4.00; P, 4.27; S, 4.74.

Regeneration of Metal Salt

Title salt (60 mg, 0.08 mmol) was stirred with 1.5 mL of Ag50-X8 ion exchange resin (2.5 meq, K$^+$ form) for 2 h in 3 mL of water and 1 mL of methanol (pH=7). The mixture was slowly eluted through an additional column of Ag50-X8 ion exchange resin (1.5 mL, 2.5 meq, K$^+$ form) with 1:1 methanol/water. Product containing fractions were pooled, the methanol was removed under reduced pressure and the aqueous solution lyophilized to provide 38 mg (95 %) of the tripotassium salt as a white lyophilate.

Chiral HPLC analyis of enantiomeric excess was performed on a ChromTech α-acid glycoprotein (α1-AGP) column eluted with isocratic 85% 0.1M KH$_2$PO$_4$, 15% CH$_3$CN, pH 4.6.

For this sample,

Example 181 (S)-isomer: retention time ≈9.5 min. 98%

Example 180 (R)-isomer: retention time ≈19.0 min. 2%, therefore a 96% enantiomeric excess of the (S)-isomer.

EXAMPLE 182

(S)-(−)-3-Phenoxy-α-phosphonobenzenebutanesulfonic acid, (S)-α-methylbenzylamine (1:2) salt A sample of the (−)-isomer (Example 175) (70 mg, 0.14 mmol) was stirred with 3 g of Ag50-X8 ion exchange resin (7.5 meq, H$^+$ form) for 1 h in 5 mL of water and 3 mL of methanol. The mixture was slowly eluted through an additional column of Ag50-X8 ion exchange resin (1 g, 2.5 meq, H+ form) with 1:1 methanol/water. Approximately 3 mL fractions were collected. Fractions #2 to 7 were pooled, the methanol was removed under reduced pressure and the aqueous solution lyophilized to provide 54 mg (100%) of the free acid form of the title salt as a thin film. The free acid was used without further characterization.

The free acid in 3 mL of a 1:1 methanol/water solution was treated with 36 uL (0.21 mmol, 2 eq) of (S)-(−)-α-methylbenzylamine under argon. The mixture was stirred for 0.5 h and concentrated to an oil. Recrystallization from 3 mL of hot acetonitrile and 3 drops of water followed by slow evaporation to dryness provided 60 mg (73%) of title diamine salt as needles. mp 160°–163° C.

$[\alpha]_D^{20}$=−8.0° (methanol, c=1)

IR (KBr) 3447, 3050, 3038, 2938, 2762, 1613, 1582, 1566, 1489, 1242, 1213, 1182, 1163, 1072, 1044, 1022, 924, 702 cm$^{-1}$.

Mass Spec (FAB, + ions) m/e 629 (M+H); (FAB, − ions) m/e 385 (M−2(C$_8$H$_{11}$N)+H).

¹H NMR (3:1 DMSO:CD₃OD, 300 MHz): δ7.58–7.30 (m, 12H) 7.25 (t, 1H, J=8.0 Hz) 7.10 (t, 1H, J=8.0 Hz) 7.00 (d, 3H, J=9.0 Hz) 6.85 (m, 1H) 6.75 (dd, 1H, J=7.0, 2.0 Hz) 4.40 (q, 2H, J=6.5 Hz) 2.80 (dt, 1H, J=19.0, 5.8 Hz) 2.57 (m, 2H) 1.80 (m, 4H) 1.55 (d, 6H, J=6.5 Hz) ppm.

The needles were subjected to X-ray crystallographic studies, which demonstrated that the (−)-isomer had the (S)-stereochemistry at the α-carbon.

EXAMPLE 183

(S)-α-[Bis[(2,2-dimethyl-1-oxopropoxy)methoxy]phosphinyl]-3-phenoxybenzenebutanesulfonic acid, monopotassium salt A. (S)-3-Phenoxy-α-phosphonobenzenebutanesulfonic acid, trisilver salt A solution of Example 175 product (1.66 g, 3.32 mmol) in water (17 mL) was added over 30 min via syringe pump to a vigorously stirred solution of silver nitrate (2.02 g, 11.9 mmol) in water (17 mL) under argon at RT in the dark. A white precipitate resulted immediately upon addition. Following addition, additional water (5 mL) was added to aid stirring, and the thick slurry was stirred vigorously at RT for 15 min then filtered through a porosity D (10–20 μm) glass fritted funnel. The solid was washed with water (2×40 mL) and diethyl ether (2×40 mL) then air-dried for 15 min. The product was further dried by pumping under high vacuum in the dark overnight to give title compound (2.28 g, 97%) as a beige solid.

B. (S)-α-[Bis[(2,2-dimethyl-1-oxopropoxy)methoxy]phosphinyl]-3-phenoxybenzenebutanesulfonic acid, monopotassium salt A suspension of Part A compound (2.12 g, 3.00 mmol) and activated 4A molecular sieves (2.1 g) in $CH_2Cl_2$ (25 mL) was stirred at RT in the dark under argon for 45 min. Anhydrous anisole (1.6 mL, 15.0 mmol) was added and the reaction was placed in a 20° C. water bath. To the suspension was added a solution of 2,2-dimethylpropanoic acid, iodomethyl ester (2.18 g, 9.00 mmol) in $CH_2Cl_2$ (5 mL) dropwise slowly over 15 min via syringe pump ensuring that the reaction temperature remained below 30° C. The reaction turned bright yellow during addition. The heterogeneous reaction was stirred vigorously at RT in the dark for 40 min, then filtered through Celite with the aid of $CH_2Cl_2$ (200 mL). Evaporation of the filtrate gave 3.3 g of the crude triester α-[bis[(2,2-dimethyl-1-oxopropoxy)methoxy]phosphinyl]-3-phenoxybenzenebutanesulfonic acid, (2,2-dimethyl-1-oxopropoxy)methyl ester as a yellow liquid.

The crude triester was dissolved in $CH_3CN$/water (4:1, 40 mL) to give an opaque solution containing a small amount of yellow precipitate. The reaction was stirred at RT and progress of the solvolysis was monitored by ¹H NMR (disappearance of the t-BuCO₂CH₂— sulfonate signal at 5.8 ppm [in d₆-DMSO]). When no sulfonate ester remained (8 h) the reaction was partitioned between EtOAc (150 mL) and saturated KCl (20 mL). The resultant biphasic mixture was filtered to remove she yellow precipitate. The organic layer was washed with 1M potassium phosphate (pH=6.0, 2×20 mL) and saturated KCl (5 mL), then dried over anhydrous KCl. Evaporation followed by pumping under high vacuum for 1.5 h gave 2.0 g of a colorless oil.

CHP20P gel was stirred with 0.5M potassium phosphate buffer (pH=5.0, 1000 mL) for 4 h, then packed (5×25 cm column) and flushed with water (500 mL). The column was equilibrated with 5:95 $CH_3CN$/water (1.5 L).

The crude product was dissolved in $CH_3CN$ (5 mL), then water (10 mL) was added. The solution was adjusted to pH 5.0 with 1M potassium phosphate buffer (pH=7.0). The product solution was chromatographed on CHP20P gel prepared above (25 mL fractions), eluted with 5:95 $CH_3CN$/$H_2O$ (250 mL) followed by a gradient created by the gradual addition of 80:20 $CH_3CN$/$H_2O$ (1200 mL) to a reservoir of 5:95 $CH_3CN$/$H_2O$ (1200 mL)). Fractions 55–62 were combined and concentrated to a volume of 100 mL consisting almost entirely of water. The aqueous solution (pH=3.2) was adjusted slowly to pH=5.0 with 1M potassium phosphate (pH=7.0), then concentrated to dryness. The resultant residue was dissolved in $CH_3CN$/$H_2O$ (1:4, 10 mL) and lyophilized to give title compound (1.12 g, 57%) as a white lyophilate.

TLC (silica gel) (10:90 MeOH/$CH_2Cl_2$) $R_f$ 0.25

Chiral purity was determined by HPLC on a Chrom Tech α-acid glycoprotein column, with isocratic elution of 10 mM $KH_2PO_4$/iPrOH/MeOH buffer (78:16:6). This sample was 99.2% (S)-isomer (retention time=23.5 min) and 0.8% (R)-isomer (retention time=17.0 min) and therefore had a 98.4% enantiomeric excess favoring the (S)-isomer.

IR (KBr) 2974, 1755, 1584, 1485, 1250, 1215, 1140, 1024, 1003, 963 cm⁻¹.

MS (FAB, + ions) 653 (M+H), 691 (M+K)

Anal. Calcd. for $C_{28}H_{38}KO_{11}PS$+0.60 $KH_2PO_4$: C, 45.69; H, 5.38; P, 6.75 Found: C, 45.64; H, 5.43; P, 7.12.

¹H NMR (300 MHz, DMSO): δ7.38 (t, 2H, J=8.0 Hz) 7.27 (t, 1H, J=7.8 Hz) 7.12 (t, 1H, J=7.4 Hz) 7.00 (d, 2H, J=7.7 Hz) 6.96 (d, 1H, J=7.9 Hz) 6.83 (t, 1H, J=1.8 Hz) 6.78 (dd, 1H, J=2.2 Hz, 7.8 Hz) 5.56 (m, 4H) 3.03 (dt, 1H, J=5.6 Hz, 19.5 Hz) 2.50 (m, 2H, buried under DMSO signal) 2.02–1.70 (m, 4H) 1.15 (s, 9H) 1.13 (s, 9H) ppm.

¹P NMR (122 MHz, 5:3 DMSO/D₂O): δ23.45 0.07 ($KH_2PO_4$) ppm.

The compounds of Examples 42, 93, 174, 175 and 183 are particularly preferred.

What is claimed is:

1. A method for forming an enantiomer of a phosphonosulfonate compound having the structure

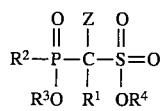

wherein $R^2$ is $OR^5$, $R^3$ and $R^5$ represents an alkali metal ion;

$R^4$ is an alkali metal ion;

$R^1$ is a lipophilic group containing at least 7 carbons;

Z is H, halogen, lower alkyl or lower alkenyl, by any of the following processes: A) which comprises providing a methylphosphondiamide compound of the structure

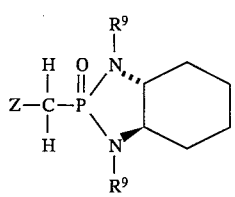

wherein $R^9$ is alkyl or arylalkyl, treating the above diamide with a metalating agent to form an anion of the diamide, alkylating the anion of the diamide by treating with a halide of the structure

R¹X where X is I, Cl, Br, tosylate, or $CF_3SO_3$—, to form the alkylated compound

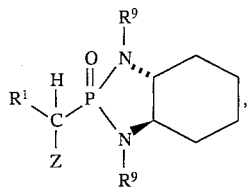

treating the above alkylated diamide with a metalating agent to form the metalated alkylated compound, subjecting the metalated alkylated compound to sulfuration with tetramethylthiuram disulfide, to form a mixture of isomers of the structures

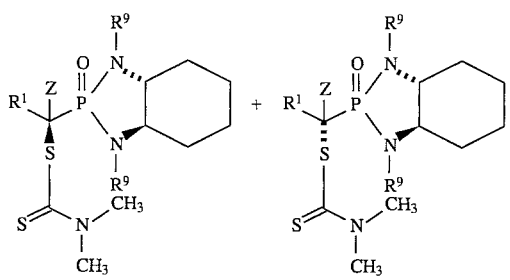

separating the isomers into the α-(S) isomer and α-(R) isomer, treating the desired isomer with an acid to form the desired diacid

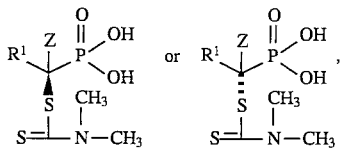

treating the diacid with an oxidizing agent and then with base to form the desired enantiomer

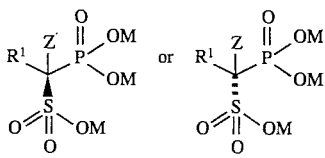

where M is an alkali metal;

or B) forming an enantiomer of said phosphonosulfonate compound, which comprises providing a methylphosphondiamide of the structure

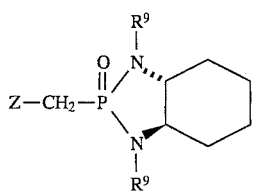

wherein $R^9$ is alkyl or arylalkyl, treating the above diamide with a metalating agent to form the corresponding anion salt, treating the anion salt with sulfur and a dialkylthiocarbamoyl halide to form a dithiocarbamoylate of the structure

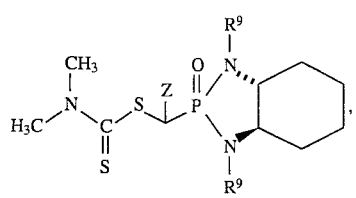

treating the dithiocarbamoylate with a metalating agent to form the corresponding metalated compound, treating the so-formed metalated compound with an alkylating agent

R¹X to form a mixture of isomers of the structure

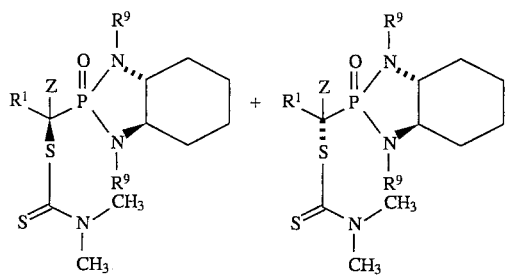

separating the isomers, treating the desired isomer with an acid to form the desired diacid

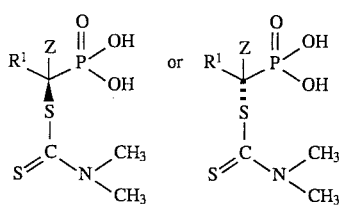

treating the desired diacid with an oxidizing agent and then with base to form the desired enantiomer

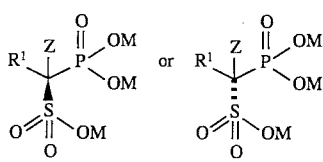

where M is an alkali metal;

or C) forming an enantiomer of said phosphonosulfonate compound, which comprises providing a phosphorous diamide of the structure

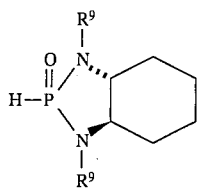

wherein $R^9$ is alkyl, aryl or arylalkyl,
treating the diamide with an aldehyde of the structure $R^1$—CHO and a silylating compound to form a mixture of protected isomers of the structures

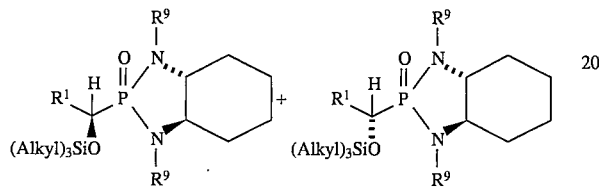

separating the isomers,
reacting the desired isomer with a fluoride source to form a deprotected compound of the structure

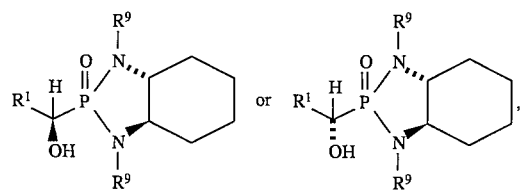

treating either deprotected isomer with dimethyldithiocarbamic acid, zinc salt and triphenylphosphine and diisopropylazodicarboxylate (DIAD) to form the isomer

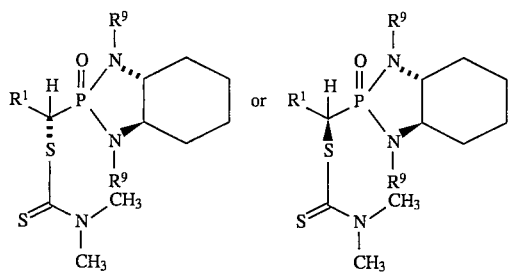

treating the desired isomer with an acid to form the desired diacid

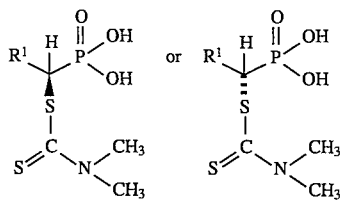

treating the desired diacid with an oxidizing agent and then with base to form the desired enantiomer

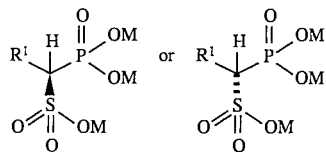

where M is an alkali metal;
or D) forming an enantiomer of said phosphonosulfonate compound, which comprises providing a phosphorous diamide of the structure

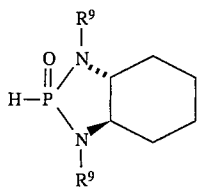

wherein $R^9$ is alkyl or arylalkyl, treating the diamide with an aldehyde of the structure $R^1$—CHO and a base including a fluoride source to form a mixture of isomers of deprotected compound of the structures

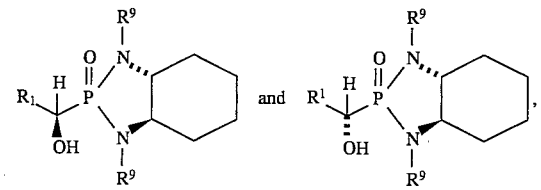

separating the isomers,
treating either deprotected isomer with dimethyldithiocarbamic acid, zinc salt, triphenyl-phosphine and DIAD to form the isomer

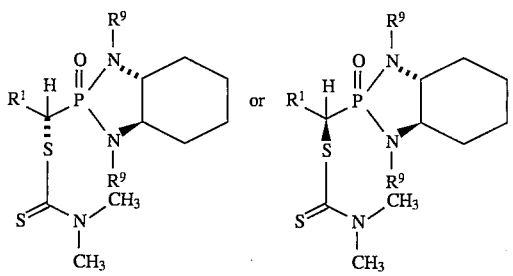

treating the desired isomer with an acid to form the desired diacid

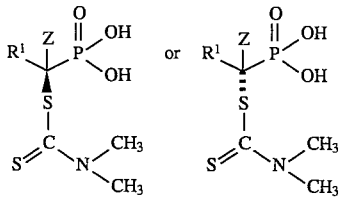

treating the desired diacid with an oxidizing agent and then with base to form the desired enantiomer

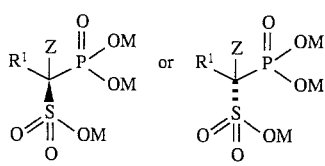

where M is an alkali metal;

or E) forming an enantiomer of said phosphonosulfonate compound, which comprises providing an acid chloride of the structure

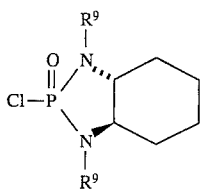

reacting the acid chloride with the metalated anion

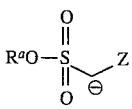

(where $R^a$ is alkyl or cycloalkyl) to form

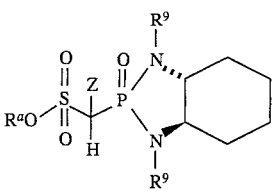

treating the product with $(alkyl)_4N^{\oplus}I^{\ominus}$ to form the corresponding ammonium compound

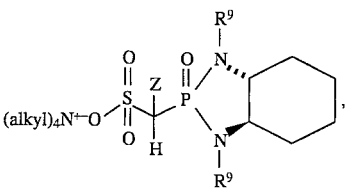

treating the above dealkylated compound with a metalating agent and then with an alkylating agent $R^1X$ to form the alkylated compound

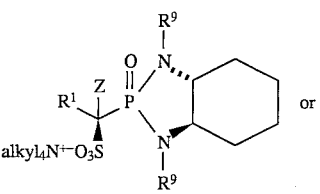

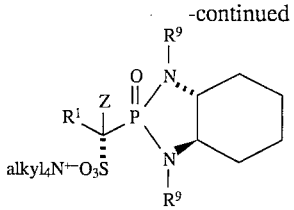

treating the desired isomer with an acid and then with an ion exchange resin to form the desired enantiomer

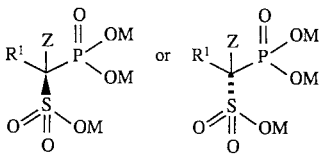

where M is an alkali metal;

or F) forming an enantiomer of said phosphonsulfonate compound, which comprises treating an aldehyde of the structure $R^1CHO$ where $R^1$ is as defined in claim 1 with an (S,S)-diol

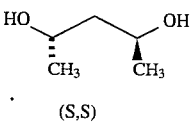

(S,S)

in the presence of an acid catalyst to form the acetal of the structure

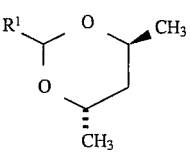

treating the acetal with a trialkylphos-phite in the presence of titanium tetrachloride to form the alcohol

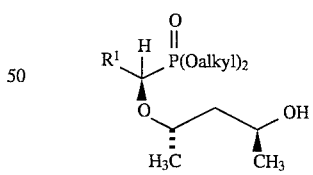

treating the above alcohol with an oxidizing agent to form a compound of the structure

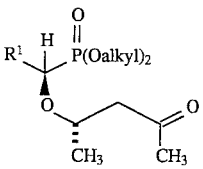

treating the above with p-toluenesulfonic acid in the presence of dioxane to form the diester

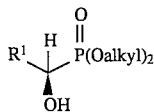

treating the above diester with triphenyl phosphine, dimethyldithiocarbamic acid, zinc salt and diisopropyl azodicarboxylate to form

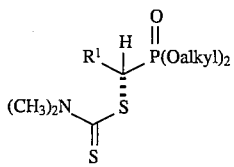

treating the above diester with a bromotrimethylsilane to form the diacid

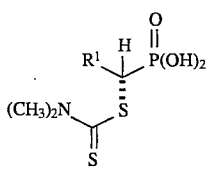

treating the diacid with an oxidizing agent and then with a strong base to form the desired enantiomer

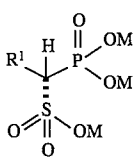

where M is an alkali metal.

2. The method as defined in claim 1 part A) or part E) wherein the final product is the (S)-enantiomer when Z is H

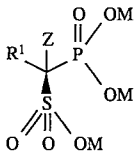

and as defined in claim 1 part B) or part F) wherein the final product is the (R)-enantiomer when Z is H

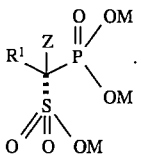

3. A method for forming an enantiomer of a phosphonosulfonate compound having the structure

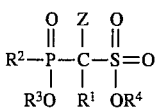

wherein
$R^2$ is $OR^5$, $R^3$ and $R^5$ represent an alkali metal ion $R^4$ is an alkali metal ion;

$R^1$ is a lipophilic group containing at least 7 carbons;

Z is H, halogen, lower alkyl or lower alkenyl, by any of the following processes: A) which comprises providing a methylphosphondiamide compound of the structure

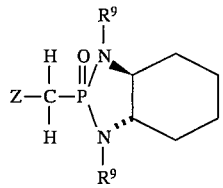    A wherein $R^9$ is alkyl or arylalkyl, treating the above diamide with a metalating agent to form an anion of the diamide, alkylating the anion of the diamide by treating with a halide of the structure $R^1X$ where X is I, Cl, Br, tosylate, or $CF_3SO_3$—, to form the alkylated compound

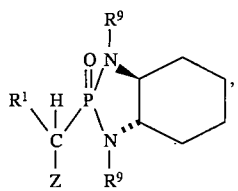, treating the above alkylated diamide with a metalating agent to form the metalated alkylated compound, subjecting the metalated alkylated compound to sulfuration with tetramethylthiuram disulfide, to form a mixture of isomers of the structures

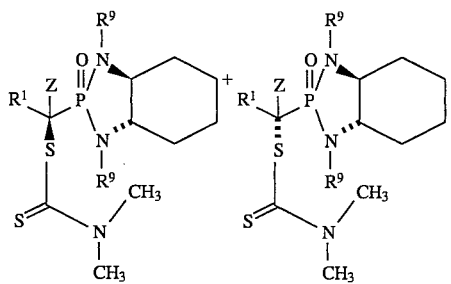

separating the isomers into the α-(S) isomer and isomer, treating the desired isomer with an acid to form the desired diacid

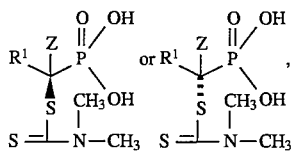

treating the diacid with an oxidizing agent and then with base to form the desired enantiomer

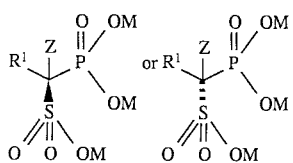

where M is an alkali metal;

or B) forming an enantiomer of said phosphonosulfonate compound, which comprises providing a methylphosphondiamide of the structure

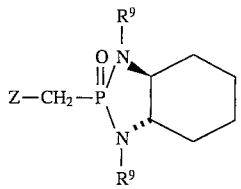

wherein $R^9$ is alkyl or arylalkyl, treating the above diamide with a metalating agent to form the corresponding anion salt, treating the anion salt with sulfur and a dialkylthiocarbamoyl halide to form a dithiocar-bamoylate of the structure

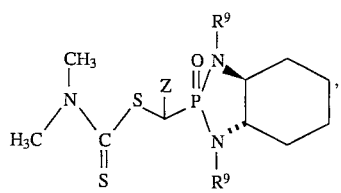

treating the dithiocarbamoylate with a metalating agent to form the corresponding metalated compound, treating the so-formed metalated compound with an alkylating agent $R^1X$ to form a mixture of isomers of the structure

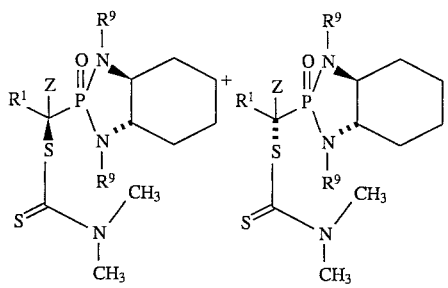

separating the isomers, treating the desired isomer with an acid to form the desired diacid

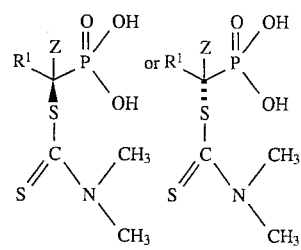

treating the desired diacid with an oxidizing agent and then with base to form the desired enantiomer

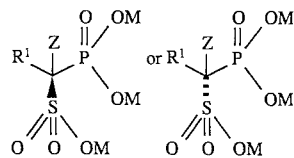

where M is an alkali metal;

or C) forming an enantiomer of said phosphonosulfonate compound, which comprises providing a phosphorous diamide of the structure

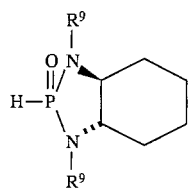

wherein $R^9$ is alkyl, aryl or arylalkyl, treating the diamide with an aldehyde of the structure $R^1$—CHO and a silylating compound to form a mixture of protected isomers of the structures

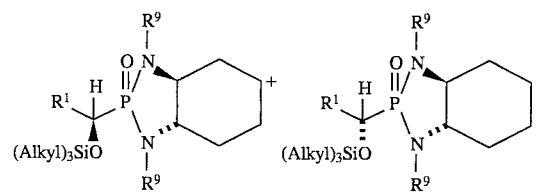

separating the isomers, reacting the desired isomer with a fluoride source to form a deprotected compound of the structure

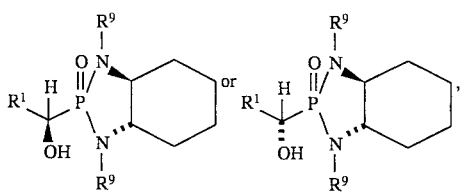

treating either deprotected isomer with dimethyldithiocarbamic acid, zinc salt and triphenylphosphine and diisopropylazodicarboxylate (DIAD) to form the isomer

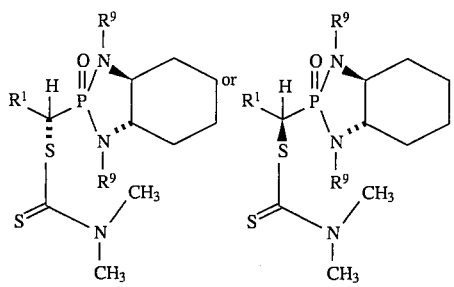

treating the desired isomer with an acid to form the desired diacid

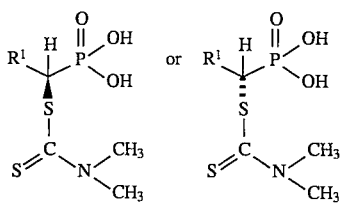

treating the desired diacid with an oxidizing agent and then with base to form the desired enantiomer

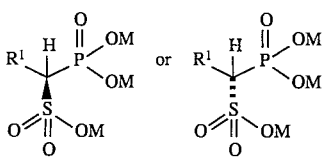

where M is an alkali metal;

or D) forming an enantiomer of said phosphonosulfonate compound, which comprises providing a phosphorous diamide of the structure

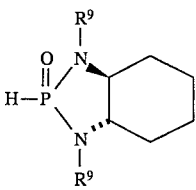

wherein $R^9$ is alkyl or arylalkyl, treating the diamide with an aldehyde of the structure

and a base including a fluoride source to form a mixture of isomers of deprotected compound of the structures

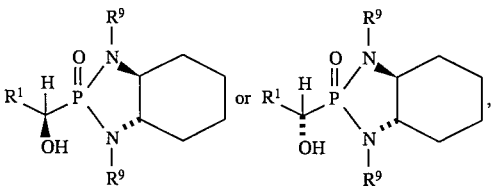

separating the isomers, treating either deprotected isomer with dimethyldithiocarbamic acid, zinc salt, triphenyl-phosphine and DIAD to form the isomer

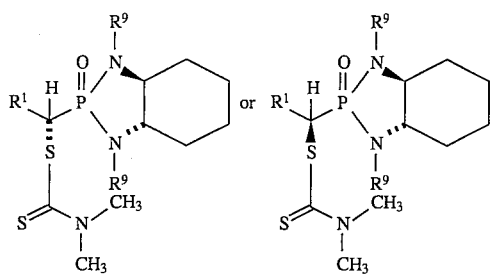

treating the desired isomer with an acid to form the desired diacid

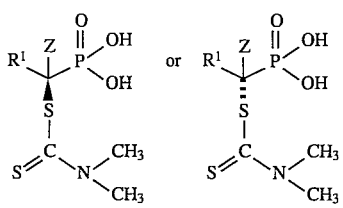

treating the desired diacid with an oxidizing agent and then with base to form the desired enantiomer

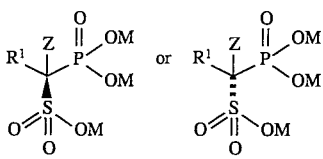

where M is an alkali metal;

or E) forming an enantiomer of said phosphonosulfonate compound, which comprises providing an acid chloride of the structure

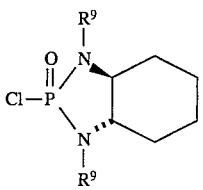

reacting the acid chloride with the metalated anion

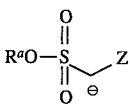

(where $R^a$ is alkyl or cycloalkyl) to form

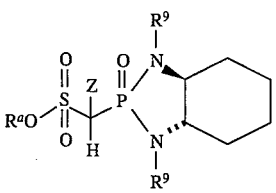

treating the above reaction product with $(alkyl)_4 N^\oplus I^\ominus$ agent to form the corresponding ammonium compound

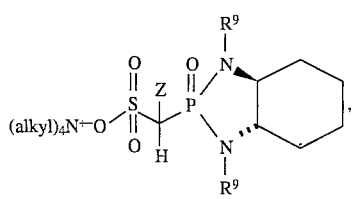

treating the above de alkylated compound with a metalating agent and then with an alkylating agent

R¹X to form the alkylated compound

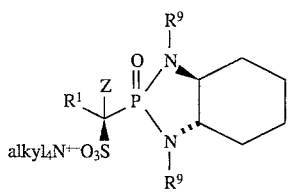

or

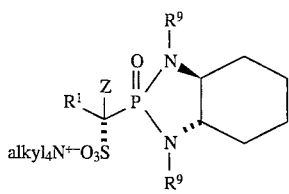

treating the desired isomer with an acid and then with an ion exchange resin to form the desired enantiomer

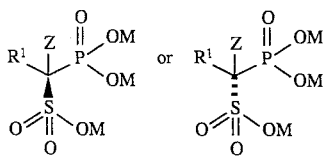

where M is an Alkali metal;

or F) forming an enantiomer of said phosphonosulfonate compound, which comprises treating an aldehyde of the structure

R¹CHO where $R^1$ is as defined in claim 1, with an (R,R)-diol

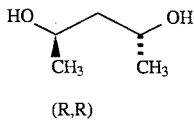

(R,R)

in the presence of an acid catalyst to form the acetal of the structure

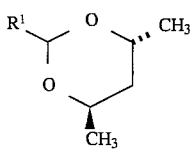

treating the acetal with a trialkylphos-phite in the presence of titanium tetrachloride to form the alcohol

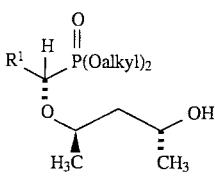

treating the above alcohol with an oxidizing agent to form a compound of the structure

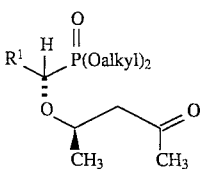

treating the above with p-toluenesulfonic acid in the presence of dioxane to form the diester

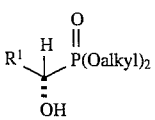

treating the above diester with triphenyl phosphine, dimethyldithiocarbamic acid, zinc salt and diisopropyl azodicarboxylate to form

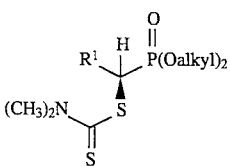

treating the above diester with a bromotrimethylsilane to form the diacid

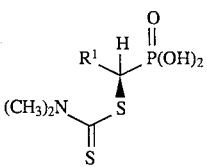

treating the diacid with an oxidizing agent and then with a strong base to form the desired enantiomer

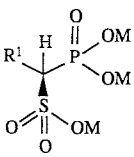

where m is a Alkali metal.

4. The method as defined in claim 3 part A) or part E) wherein the final product is the (R)-enantiomer when Z is H

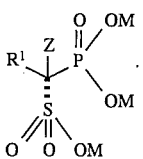

5. The method as defined in claim 1 part B) or part F) wherein the final product is the (S)-enantiomer when Z is H

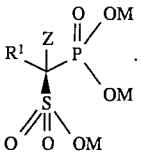

6. The method as defined in claim 1 wherein $R^1$ is alkyl containing 7 to 25 carbons in the chain; alkenyl containing from 7 to 25 carbon atoms in the chain and from 1 to 6 double bonds; alkynyl containing 1 to 6 triple bonds; mixed alkenyl-alkynyl containing 1 to 5 double bonds and 1 to 5 triple bonds; or aryl; and where in the above groups alkenyl, alkynyl and/or aryl may be substituted or unsubstituted; cycloheteroalkyl linked through a carbon on the ring or a heteroatom; cycloalkyl; heteroarylalkyl; cycloalkylalkyl; heteroaryl; cycloheteroalkylalkyl; alkyl; or a group of the structure

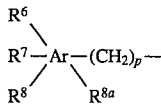

wherein Ar is aryl or heteroaryl, and Ar may include one to three additional rings fused to Ar, and wherein $(CH_2)_p$ contains from 1 to 15 carbons in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy containing 2 to 40 carbons, hydroxy, halogen, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, heteroaryl, cycloalkyl, cycloalkylalkyl, Ar-alkyl, ArO, Ar-amino, Ar, Ar-thio, Ar-sulfinyl, Ar-sulfonyl, cyano, Ar-carbonyloxy, or Ar-carbonylamino.

7. The method as defined in claim 3 wherein $R^1$ is alkyl containing 7 to 25 carbons in the chain; alkenyl containing from 7 to 25 carbon atoms in the chain and from 1 to 6 double bonds; alkynyl containing 1 to 6 triple bonds; mixed alkenyl-alkynyl containing 1 to 5 double bonds and 1 to 5 triple bonds; or aryl; and where in the above groups alkenyl, alkynyl and/or aryl may be substituted or unsubstituted; cycloheteroalkyl linked through a carbon on the ring or a heteroatom; cycloalkyl; heteroarylalkyl; cycloalkylalkyl; heteroaryl; cycloheteroalkylalkyl; or a group of the structure

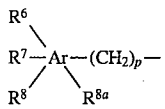

wherein Ar is aryl or heteroaryl, and Ar may include one to three additional rings fused to Ar, and wherein $(CH_2)_p$ contains from 1 to 15 carbons in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons alkynyloxy containing 2 to 40 carbons, hydroxy, halogen, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, heteroaryl, cycloalkyl, cycloalkylalkyl, Ar-alkyl, ArO, Ar-amino, Ar, Ar-thio, Ar-sulfinyl, Ar-sulfonyl, cyano, Ar-carbonyloxy, or Ar-carbonylamino.

8. The method as defined in claim 6 where in the final product $R^1$ is

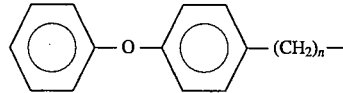

wherein n is 2, 3 or 4.

9. The method as defined in claim 8 where in $R^1$, n is 3.

10. The method as defined in claim 7 where in the final product $R^1$ is

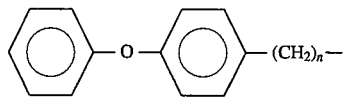

wherein n is 2, 3 or 4.

11. The method as defined in claim 10 where in $R^1$, n is 3.

* * * * *

UNITED STATES PATENT AND TRADEMARK OFFICE
CERTIFICATE OF CORRECTION

PATENT NO. : 5,567,841
DATED : October 22, 1996
INVENTOR(S) : David R. Magnin et al It is certified that error appears in the above-identified patent and that said Letters Patent is hereby corrected as shown below:

In the claims Col. 184, line 55, after "and" and before "isomer" please insert --α-(R)--.

Signed and Sealed this

Fifteenth Day of July, 1997

*Attest:*

BRUCE LEHMAN

*Attesting Officer*     *Commissioner of Patents and Trademarks*